United States Patent
Strum et al.

(10) Patent No.: US 10,376,519 B2
(45) Date of Patent: Aug. 13, 2019

(54) TRICYCLIC LACTAMS FOR USE IN HSPC-SPARING TREATMENTS FOR RB-POSITIVE ABNORMAL CELLULAR PROLIFERATION

(71) Applicant: G1 Therapeutics, Inc., Research Triangle Park, NC (US)

(72) Inventors: Jay Copeland Strum, Hillsborough, NC (US); John Emerson Bisi, Apex, NC (US); Patrick Joseph Roberts, Durham, NC (US); Ricky D. Gaston, Kalamazoo, MI (US); Robert C. Gadwood, Portage, MI (US)

(73) Assignee: G1 Therapeutics, Inc., Research Triangle Park, NC (US)

( * ) Notice: Subject to any disclaimer, the term of this patent is extended or adjusted under 35 U.S.C. 154(b) by 0 days.

(21) Appl. No.: 15/665,071

(22) Filed: Jul. 31, 2017

(65) Prior Publication Data

US 2017/0333440 A1    Nov. 23, 2017

Related U.S. Application Data

(63) Continuation of application No. 14/690,180, filed on Apr. 17, 2015, now Pat. No. 9,717,735.

(60) Provisional application No. 61/980,895, filed on Apr. 17, 2014, provisional application No. 61/980,939, filed on Apr. 17, 2014, provisional application No. 61/980,918, filed on Apr. 17, 2014, provisional application No. 61/980,883, filed on Apr. 17, 2014.

(51) Int. Cl.
| | |
|---|---|
| *C07D 487/14* | (2006.01) |
| *C07D 487/20* | (2006.01) |
| *C07D 471/20* | (2006.01) |
| *A61K 31/5377* | (2006.01) |
| *A61K 45/06* | (2006.01) |
| *A61K 31/527* | (2006.01) |
| *A61K 31/519* | (2006.01) |

(52) U.S. Cl.
CPC ........ *A61K 31/5377* (2013.01); *A61K 31/519* (2013.01); *A61K 31/527* (2013.01); *A61K 45/06* (2013.01); *C07D 487/14* (2013.01); *C07D 487/20* (2013.01); *C07D 471/20* (2013.01)

(58) Field of Classification Search
CPC ... C07D 487/14; C07D 487/20; C07D 471/20
See application file for complete search history.

(56) References Cited

U.S. PATENT DOCUMENTS

| | | |
|---|---|---|
| 5,591,855 A | 1/1997 | Hudkins et al. |
| 5,628,984 A | 5/1997 | Boucher |
| 6,291,504 B1 | 9/2001 | Nugiel et al. |
| 6,369,086 B1 | 4/2002 | Davis |
| 6,610,684 B2 | 8/2003 | Zaharevitz et al. |
| 6,667,346 B2 | 12/2003 | Reddy et al. |
| 6,936,612 B2 | 8/2005 | Barvian et al. |
| 6,962,993 B2 | 11/2005 | Blumenkopf et al. |
| 6,982,277 B2 | 1/2006 | Gudkov et al. |
| 7,208,489 B2 | 4/2007 | Barvian et al. |
| 7,345,171 B2 | 3/2008 | Beylin et al. |
| 7,482,354 B2 | 1/2009 | Traquandi et al. |
| 8,598,186 B2 | 12/2013 | Tavares et al. |
| 8,598,197 B2 | 12/2013 | Tavares et al. |
| 8,691,830 B2 | 4/2014 | Tavares et al. |
| 8,822,683 B2 | 9/2014 | Tavares et al. |
| 8,829,012 B2 | 9/2014 | Tavares et al. |
| 9,102,682 B2 | 8/2015 | Tavares et al. |
| 9,260,442 B2 | 1/2016 | Tavares |
| 2002/0042412 A1 | 4/2002 | Zaharevitz et al. |
| 2003/0069430 A1 | 4/2003 | Davis et al. |
| 2003/0073668 A1 | 4/2003 | Booth et al. |
| 2003/0224522 A1 | 12/2003 | de Jong et al. |
| 2003/0229026 A1 | 12/2003 | Al-Awar et al. |
| 2004/0006074 A1 | 1/2004 | Kelley et al. |
| 2004/0048915 A1 | 3/2004 | Engler et al. |
| 2004/0236084 A1 | 11/2004 | Biwersi et al. |
| 2005/0222163 A1 | 10/2005 | Eck et al. |
| 2007/0027147 A1 | 2/2007 | Hayama et al. |
| 2007/0179118 A1 | 8/2007 | Barvian et al. |
| 2007/0212736 A1 | 9/2007 | Chen-Kiang et al. |
| 2007/0270362 A1 | 11/2007 | Harlan et al. |
| 2008/0085890 A1 | 4/2008 | Tsou et al. |
| 2008/0161355 A1 | 7/2008 | Curry et al. |
| 2008/0182853 A1 | 7/2008 | Kruman et al. |
| 2011/0224221 A1 | 9/2011 | Sharpless et al. |
| 2011/0224227 A1 | 9/2011 | Sharpless et al. |
| 2012/0100100 A1 | 4/2012 | Sharpless et al. |
| 2013/0289031 A1 | 10/2013 | Sanofi |

(Continued)

FOREIGN PATENT DOCUMENTS

| | | |
|---|---|---|
| CA | 2656290 | 1/2008 |
| CN | 1278794 | 1/2001 |

(Continued)

OTHER PUBLICATIONS

U.S. Appl. No. 14/982,443, Tavares.

(Continued)

*Primary Examiner* — Samira J Jean-Louis
(74) *Attorney, Agent, or Firm* — Knowles Intellectual Property Strategies, LLC

(57) ABSTRACT

This invention is in the area of tricyclic lactam compounds for and methods of treating selected Rb-positive cancers and other Rb-positive abnormal cellular proliferative disorders while minimizing the deleterious effects on healthy cells, for example healthy Hematopoietic Stem Cells and Progenitor Cells (HSPCs), associated with current treatment modalities. In one aspect, treatment of select Rb-positive cancers is disclosed using specific compounds disclosed herein. In certain embodiments, the compounds described herein act as selective cyclin-dependent kinase 4/6 (CDK 4/6) inhibitors when administered to subjects.

10 Claims, 22 Drawing Sheets

(56) References Cited

U.S. PATENT DOCUMENTS

| | | |
|---|---|---|
| 2014/0107114 A1 | 4/2014 | Kim et al. |
| 2014/0271460 A1 | 9/2014 | Strum et al. |
| 2014/0271466 A1 | 9/2014 | Strum et al. |
| 2014/0274896 A1 | 9/2014 | Strum et al. |
| 2014/0275066 A1 | 9/2014 | Strum et al. |
| 2014/0275067 A1 | 9/2014 | Strum et al. |
| 2015/0246925 A1 | 9/2015 | Tavares et al. |
| 2015/0246926 A1 | 9/2015 | Tavares et al. |
| 2015/0297606 A1 | 10/2015 | Strum et al. |
| 2015/0297607 A1 | 10/2015 | Strum et al. |
| 2015/0297608 A1 | 10/2015 | Strum et al. |
| 2016/0045509 A1 | 2/2016 | Strum et al. |

FOREIGN PATENT DOCUMENTS

| | | |
|---|---|---|
| CN | 1379668 | 11/2002 |
| JP | 2001-517652 | 10/2001 |
| JP | 2005-519909 | 7/2005 |
| JP | 2007-530425 | 11/2007 |
| JP | 2007-530654 | 11/2007 |
| WO | WO 1998/033798 | 8/1998 |
| WO | WO 1999/015500 | 4/1999 |
| WO | WO 2001/012188 | 2/2001 |
| WO | WO 2002/044174 | 6/2002 |
| WO | WO 2003/062236 A1 | 7/2003 |
| WO | WO 2005/005426 | 1/2005 |
| WO | WO 2005/040166 A1 | 5/2005 |
| WO | WO 2005/052147 | 6/2005 |
| WO | WO 2005/094830 | 10/2005 |
| WO | WO 2005/105213 A2 | 11/2005 |
| WO | WO 2006/074985 | 7/2006 |
| WO | WO 2006/127587 | 11/2006 |
| WO | WO 2007/025090 | 3/2007 |
| WO | WO 2007/048847 A2 | 5/2007 |
| WO | WO 2007/065820 | 6/2007 |
| WO | WO 2007/124252 A2 | 11/2007 |
| WO | WO 2008/005538 | 1/2008 |
| WO | WO 2008/079933 | 7/2008 |
| WO | WO 2009/003003 A2 | 12/2008 |
| WO | WO 2009/061345 | 5/2009 |
| WO | WO 2009/085185 A1 | 7/2009 |
| WO | WO 2010/012777 A1 | 2/2010 |
| WO | WO 2010/020675 A1 | 2/2010 |
| WO | WO 2010/039997 A2 | 4/2010 |
| WO | WO 2010/051127 A2 | 5/2010 |
| WO | WO 2010/132725 A2 | 11/2010 |
| WO | WO 2011/101409 | 8/2011 |
| WO | WO 2011/103485 A1 | 8/2011 |
| WO | WO 2012/068381 A2 | 5/2012 |
| WO | WO 2012/061156 | 10/2012 |
| WO | WO 2013/148748 A1 | 10/2013 |
| WO | WO 2013/163239 A1 | 10/2013 |
| WO | WO 2014/144326 A1 | 9/2014 |
| WO | WO 2014/144596 A2 | 9/2014 |
| WO | WO 2014/144740 A2 | 9/2014 |
| WO | WO 2014/144847 A2 | 9/2014 |
| WO | WO 2014/168975 A1 | 10/2014 |
| WO | WO 2015/061407 A1 | 4/2015 |
| WO | WO 2015/161283 A1 | 10/2015 |
| WO | WO 2015/161285 A1 | 10/2015 |
| WO | WO 2015/161287 A1 | 10/2015 |
| WO | WO 2015/161288 A1 | 10/2015 |
| WO | WO 2016/040848 A1 | 3/2016 |
| WO | WO 2016/040858 A1 | 3/2016 |

OTHER PUBLICATIONS

U.S. Appl. No. 15/015070, Strum et al.
WO PCT/US16/16468.
An, H. X. et al. "Gene amplification and overexpression of CDK4 in sporadic breast carcinomas is associated with high tumor cell proliferation" American Journal of Pathology, 1999; 154: 113-118.
Anderson, M. S. and J. A. Bluestone "The NOD mouse: a model of immune dysregulation" Annu Rev Immunol, 2005; 23: 447-485.
Barginear, M. F. and D. R. Budman "Trastuzumab-DM1: A review of the novel immuno-conjugate for HER2-overexpressing breast cancel" The Open Breast Cancer Journal, 2009; 1: 25-30.
Baughn, L. B. et al. "A novel orally active small molecule potently induces G1 arrest in primary myeloma cells and prevents tumor growth by specific inhibition of cyclin-dependent kinase 4/6" Cancer Res, Aug. 1, 2006; 66(15): 7661-7667.
Berge et al. "Pharmaceutical Salts" J. Pharm. Sci., 1977; 66(1): 1-19.
Bernhard, E. J. et al. "Reducing the radiation-induced G2 delay causes HeLa cells to undergo apoptosis instead of mitotic death" Int J Radiat Biol., May 1996; 69(5): 575-584.
Blagosklonny, M. V. and A. B. Pardee "Exploiting cancer cell cycling for selective protection of normal cells" Cancer Res, Jun. 1, 2001; 61(11): 4301-4305.
Brookes et al. "INK4a-deficient human diploid fibroblasts are resistant to RAS-induced senescence" EMBO J., Jun. 17, 2002; 21(12): 2936-2945.
Bucher, N. and C. D. Britten "G2 checkpoint abrogation and checkpoint kinase-1 targeting in the treatment of cancer" Br J Cancer, Feb. 12, 2008; 98(3): 523-528.
Burdelya et al. "An agonist of toll-like receptor 5 has radioprotective activity in mouse and primate models" Science, Apr. 11, 2008; 320(5873): 226-230.
Casi, G. and D. Neri "Antibody-drug conjugates: basic concepts, examples and future perspectives" Journal of Controlled Release, 2012; 161(2): 422-428.
Chari, R.V. "Targeted cancer therapy: conferring specificity to cytotoxic drugs" Accounts of Chemical Research, 2008; 41(1): 98-107.
Chen, X. et al. "Protection of normal proliferating cells against chemotherapy by staurosporine-mediated, selective, and reversible G1 arrest" J Natl Cancer Inst., Dec. 20, 2000; 92(24): 1999-2008.
Chin et al. "Cooperative effects of INK4a and ras in melanoma susceptibility in vivo" Genes & Development, 1997; 11: 2822-2834.
Chu et al. "Discovery of [4-Amino-2-(1-methanesulfonylpiperidin-4-ylamino)pyrimidin-5-yl](2,3-difluoro-6-methoxyphenyl)methanone (R547), a potent and selective cyclin-dependent kinase inhibitor with significant in vivo antitumor activity" J Med Chem, Nov. 2, 2006; 49(22): 6549-6560.
Curtin et al. "Distinct Sets of Genetic Alterations in Melanoma" N Engl J Med 2005; 353: 2135-2147.
Daniotti et al. "BRAF alterations are associated with complex mutational profiles in malignant melanoma" Oncogene, 2004; 23: 5968-5977.
Davis, S. T. et al. "Prevention of chemotherapy-induced alopecia in rats by CDK inhibitors" Science, Jan. 5, 2001; 291(5501): 134-137.
Davis, S.T. et al. "Retraction" Science, Dec. 20, 2002; 298(5602): 2327.
Davis, T. A. et al. "Genistein induces radioprotection by hematopoietic stem cell quiescence" Int J Radiat Biol, Sep. 2008; 84(9): 713-726.
Decker et al. "Expression of Cyclin E in resting and activated B-chronic lymphocytic leukemia cells: cyclin E/cdk2 as protential therapeutic target" British Journal of Hematology, Jan. 13, 2004, 125, 141-148.
Dickson, M. A. and G. K. Schwartz "Development of cell-cycle inhibitors for cancer therapy" Curr Oncol, Mar. 2009; 16(2): 36-43.
Dickson, Mark, et al. "Phase II Trial of the CDK4 Inhibitor PD0332991 in Patients With Advanced CDK4-Amplified Well-Differentiated or Dedifferentiated Liposarcoma." J Clin Oncol. Jun. 1, 2013; 31(16):2024-2028.
Diehl, J. A. "Cycling to Cancer with Cyclin D1" Cancer Biology and Therapy, 2002; 1(3): 226-231.
El-Diery, W. S. "Meeting report: The international conference on tumor progression and therapeutic resistance" Cancer Res, Jun. 1, 2005; 65(11): 4475-4484.
Elkind, M.M. and H. Sutton "Radiation response of mammalian cells grown in culture. 1. Repair of x-ray damage in surviving Chinese hamster cells" Radiat Res., 1960; 13: 556-593.
Elkind, M.M. and H. Sutton "X-ray damage and recovery in mammalian cells in culture" Nature, 1959; 184: 1293-1295.

(56) References Cited

OTHER PUBLICATIONS

Engler et al. "Novel, potent and selective cyclin D1/CDK4 inhibitors: indolo [6,7-a]pyrrolo[3,4-c]carbazoles" Bioorg Med Chem Lett, Jul. 21, 2003; 13(14): 2261-2267.
Finn et al. "PD 0332991, a selective cyclin D kinase 4/6 inhibitor, preferentially inhibits proliferation of luminal estrogen receptor-positive human breast cancer cell lines in vitro" Breast Cancer Research, Oct. 29, 2009; 11(5): R77.
Finn et al. "Results of a randomized phase 2 study of PD 0332991, a cyclin-dependent kinase (CDK) 4/6 inhibitor, in combination with letrozole vs letrozole alone for first-line treatment of ER+/HER2- advanced breast cancer (BC)" Cancer Res, 2012; 72(24 Suppl): Abstract nr S1-6.
Firer, M. A. and G. J. Gellerman Targeted drug delivery for cancer therapy: the other side of antibodies, J. Hematol. Oncol., 2012; 5: 70. [retrieved from http://www.jhoonline.org/content/5/1/70 on Jul. 16, 2014].
Franken et al. "Clonogenic assay of cells in vitro" Nature Protocols, 2006; 1: 2315-2319.
Fry, D. W. et al. "Specific inhibition of cyclin-dependent kinase 4/6 by PD 0332991 and associated antitumor activity in human tumor xenografts" Mol Cancer Ther., Nov. 2004; 3(11): 1427-1438.
Goldberg et al. "Pyrazinoindolone inhibitors of MAPKAP-K2" Bioogranic & Medicinal Chemistry Letters, Dec. 23, 2007, 18, 938-941.
Guillard et al., "Synthesis and biological evaluations of new pyrrolo[2,3-b]pyrimidine as SDI analogs" Heterocyles, 2008, vol. 75(5), pp. 1163-1189.
Guo et al. "Staurosporine modulates radiosensitivity and radiation-induced apoptosis in U937 cells" Int J Radiat Biol., Feb. 2006; 82(2): 97-109.
Hallahan, D. E. et al. "Inhibition of protein kinases sensitizes human tumor cells to ionizing radiation" Radiat Res., Mar. 1992; 129(3): 345-350.
Hara, E. et al. "Regulation of p16CDKN2 expression and its implications for cell immortalization and senescence" Mol Cell Biol, Mar. 1996; 16(3): 859-867.
Herodin, F. et al. "Short-term injection of antiapoptotic cytokine combinations soon after lethal gamma-irradiation promotes survival" Blood, Apr. 1, 2003; 101(7): 2609-2616.
Hershman, D et al. "Acute myeloid leukemia or myelodysplastic syndrome following use of granulocyte colony-stimulating factors during breast cancer adjuvant chemotherapy" J Natl Cancer Inst, Feb. 7, 2007; 99(3): 196-205.
Hibbs, M. L. et al. "Multiple defects in the immune system of Lyn-deficient mice, culminating in autoimmune disease" Cell, Oct. 20, 1995; 83(2): 301-311.
Hirose, Y. et al. "Abrogation of the Chk1-mediated G(2) checkpoint pathway potentiates temozolomide-induced toxicity in a p53-independent manner in human glioblastoma cells" Cancer Res, Aug. 1, 2001; 61(15): 5843-5849.
Honma, T. et al. "A novel approach for the development of selective Cdk4 inhibitors: library design based on locations of Cdk4 specific amino acid residues" J Med Chem, Dec. 20, 2001; 44(26): 4628-4640.
Honma, T. et al. "Structure-based generation of a new class of potent Cdk4 inhibitors: new de novo design strategy and library design" J Med Chem, Dec. 20, 2001; 44(26): 4615-4627.
Humphreys, B.D. et al. "Intrinsic epithelial cells repair the kidney after injury" Cell Stem Cell, 2008; 2: 284-291.
Humphreys, B.D. et al. "Repair of injured proximal tubule does not involve specialized progenitors" Proc Natl Acad Sci USA, 2011; 108: 9226-9231.
Ikuta, M. et al. "Crystallographic approach to identification of cyclin-dependent kinase 4 (CDK4)-specific inhibitors by using CDK4 mimic CDK2 protein" J Biol Chem, Jul. 20, 2001; 276(29): 27548-27554.
Johnson, D. G. and C. L. Walker "Cyclins and Cell Cycle Checkpoints" Annual Review of Pharmacology and Toxicology, Apr. 1999; 39: 295-312.

Johnson, N. and G. Shapiro "Cyclin-dependent kinase 4/6 inhibition in cancer therapy" Cell Cycle, Nov. 1, 2012; 11(21): 3913-3918.
Johnson, S.M., et al. "Mitigation of hematologic radiation toxicity in mice through pharmacological quiescence induced by CDK4/6 inhibition" J Clin Invest, Jul. 2010; 120(7): 2528-2536.
Karaman, M. W. et al. "A quantitative analysis of kinase inhibitor selectivity" Nat Biotechnol., Jan. 2008; 26(1): 127-132.
Khuri, F. R. "Weighing the hazards of erythropoiesis stimulation in patients with cancer" N Engl J Med, Jun. 14, 2007; 356(24): 2445-2448.
Kiel et al. "SLAM Family Receptors Distinguish Hematopoietic Stem and Progenitor Cells and Reveal Endothelial Niches for Stem Cells" Cell, 2005; 121: 1109-1121.
Kim, S. et al. "Enhancement of radiation effects by flavopiridol in uterine cervix cancer cells" Cancer Res Treat, Jun. 2005; 37(3): 191-195.
Knockaert et al. "Pharmacological inhibitors of cyclin-dependent kinases" Trends Pharmacol Sci, Sep. 2002; 23(9): 417-425.
Kubo, et al. "The p16 status of tumor cell lines identifies small molecule inhibitors specific for cyclin-dependent kinase 4" Clin Cancer Res, 1999; 5: 4279-4286.
Lambert, J. M. Drug-conjugated antibodies for the treatment of cancer British Journal of Clinical Pharmacology, 2013; 76(2): 248-262.
Landis, M.W. et al. Cyclin D1-dependent kinase activity in murine development and mammary tumorigenesis. Cancer Cell, 2006; 9: 13-22.
Laredo, J. et al. "Effect of the protein kinase C inhibitor staurosporine on chemosensitivity to daunorubicin of normal and leukemic fresh myeloid cells" Blood, Jul. 1, 1994; 84(1): 229-237.
Le Deley et al. "Anthracyclines, Mitoxantrone, Radiotherapy, and Granulocyte Colony-Stimulating Factor: Risk Factors for Leukemia and Myelodysplastic Syndrome After Breast Cancel" J Clin Oncol, 2007; 25: 292-300.
Little, J.B. "Repair of sub-lethal and potentially lethal radiation damage in plateau phase cultures of human cells" Nature, 1969; 224(5221): 804-806.
Lohmann and Gallie "Retinoblastoma" Gene Reviews (2000), retrieved from http://www.ncbi.nlm.nih.gov/books/NBK1452/ on Jul. 10, 2014.
Lopus, M. Antibody-DM1 conjugates as cancer therapeutics, Cancer Letters, 2011; 307(2): 113-118.
Luo, Y. et al. "Blocking Chk1 expression induces apoptosis and abrogates the G2 checkpoint mechanism" Neoplasia, Sep.-Oct. 2001; 3(5): 411-419.
Malumbres, M. and M. Barbacid "Cell cycle, CDKs and cancer: a changing paradigm" Nature Reviews Cancer, Mar. 2009; 9(3): 153-166.
Malumbres, M. and M. Barbacid "Mammalian cyclin-dependent kinases" Trends Biochem. Sci., Nov. 2005; 30(11): 630-641.
McInnes, C. "Progress in the evaluation of CDK inhibitors as anti-tumor agents" Drug Discov Today, Oct. 2008; 13(19-20): 875-881.
Meng et al. "Ionizing Radiation and Busulfan Induce Premature Senescence in Murine Bone Marrow Hematopoietic Cells" Cancer Res, 2003; 63: 5414-5419.
Menu, E. et al. "A novel therapeutic combination using PD 0332991 and bortezomib: study in the 5T33MM myeloma model" Cancer Res, Jul. 15, 2008; 68(14): 5519-5523.
Michaud, Karine et al. "Pharmacologic inhibition of cdk4/6 arrests the growth of glioblastoma multiforme intracranial xenografts" Cancer Res, Apr. 15, 2011; 70: 3228-3238.
Morgan, D.O. "Cyclin-dependent Kinases. Engines, Clocks, and Microprocessors" Annual Review of Cell and Developmental Biology, 1997; 13: 261-291.
Na Nakorn et al. "Myeloerythroid-restricted progenitors are sufficient to confer radioprotection and provide the majority of day 8 CFU-S" J Clin Invest, 2002; 109: 1579-1585.
Newland, A. M. "Brentuximab vedotin: a CD30-directed antibody-cytotoxic drug conjugate" Pharmacotherapy, Jan. 2013; 33(1): 93-104.
O'Dwyer, et al. "A phase I dose escalation trial of a daily oral CDK 4/6 inhibitor PD-0332991" J Clin Oncol, 2007; 25(18S): 3550. [Abstract].

(56) References Cited

OTHER PUBLICATIONS

Ojeda, F. et al. "Role of protein kinase-C in thymocyte apoptosis induced by irradiation" Int J Radiat Biol., May 1992; 61(5): 663-667.
Parsam et al. "A comprehensive, sensitive and economical approach for the detection of mutations in the RB1 gene in retinoblastoma" Journal of Genetics, Dec. 2009; 88(4): 517-527.
Passegué et al. "Global analysis of proliferation and cell cycle gene expression in the regulation of hematopoietic stem and progenitor cell fates" J Exp Med, 2005; 202: 1599-1611.
Pawlik, T. M. and K. Keyomarsi "Role of cell cycle in mediating sensitivity to radiotherapy" Int J Radiat Oncol Biol Phys, Jul. 15, 2004; 59(4): 928-942.
Presser, Armin and Antje Hüfner "Trimethylsilyldiazomethane—A Mild and Efficient Reagent for the Methylation of Carboxylic Acids and Alcohols in Natural Products" Monatshefte für Chemie, 2004; 135(8): 1015-1022.
Ramsey, M. R. et al. "Expression of p16Ink4a compensates for p18Ink4c loss in cyclin-dependent kinase 4/6-dependent tumors and tissues" Cancer Res, May 15, 2007; 67(10): 4732-4741.
Reddy, H. K. et al. "Cyclin-dependent kinase 4 expression is essential for neu-induced breast tumorigenesis" Cancer Research, 2005; 65: 10174-10178.
Roberts et al. "Multiple Roles of Cyclin-Dependent Kinase 4/6 Inhibitors in Cancer Therapy" JNCI, 2012; 104(6):476-487.
Ruas et al. "CDK4 and CDK6 Delay Senescence by Kinase-Dependent and p16INK4a-Independent Mechanisms" Molecular and Cellular Biology, Jun. 2007; 27(12): 4273-4282.
Samady, L. et al. "Activation of CDK4 gene expression in human breast cancer cells by the Brn-3b POU family transcription factor" Cancer Biology & Therapy, 2004; 3: 317-323.
Sanchez-Martinez, C. et al. "Aryl[a]pyrrolo[3,4-c]carbazoles as selective cyclin D1-CDK4 inhibitors" Bioorg Med Chem Lett, Nov. 3, 2003; 13(21): 3835-3839.
Sanchez-Martinez, C. et al. "Studies on cyclin-dependent kinase inhibitors: indolo-[2,3-a]pyrrolo[3,4-c]carbazoles versus bis-indolylmaleimides" Bioorg Med Chem Lett, Nov. 3, 2003; 13(21): 3841-3846.
Sapra, P. and B. Shor "Monoclonal antibody-based therapies in cancer: advances and challenges" Pharmacology & Therapeutics, 2013; 138(3): 452-469.
Sarkar et al. "Nonsolvent Application of Ionic Liquids: Organo-Catalysis by 1-Alkyl-3-methylimidazolium Cation Based Room-Temperature Ionic Liquids for Chemoselective N-tert-Butyloxycarbonylation of Amines and the Influence of the C-2 Hydrogen on Catalytic Efficiency" Journal of Organic Chemistry, 2011; 76(17): 7132-7140.
Schliemann, C. and D. Neri "Antibody-based targeting of the tumor vasculature" Biochimica et Biophysica Acta, 2007; 1776(2): 175-192.
Schmidt, M. and Z. Fan "Protection against chemotherapy-induced cytotoxicity by cyclin-dependent kinase inhibitors (CKI) in CKI-responsive cells" Oncogene, Sep. 27, 2001; 20(43): 6164-6171.
Schönauer, K. and E. Zibral "Reactions with organophosphorus compounds, 50.: Trimethylsilylethoxymethylene triphenylphosphorane, a novel reagent for the homologation of carbonyl compounds." Tetrahedron Letters, 1983; 24: 573-576.
Schwartz, G.K. et al. "Phase I study of PD 0332991, a cyclin-dependent kinase inhibitor, administered in 3-week cycles (Schedule 2/1)" Br J Cancer, Jun. 7, 2011; 104(12): 1862-1868.
Seed, T. M. "Radiation protectants: current status and future prospects" Health Phys, Nov. 2005; 89(5): 531-545.
Sharma, P.S. et al. "Inhibitors of cyclin dependent kinases: useful targets for cancer treatment" Curr.Cancer Drug Targets, Feb. 2008; 8(1): 53-75.
Sharpless et al. "Both products of the mouse Ink4a/Arf locus suppress melanoma formation in vivo" Oncogene, Aug. 7, 2003; 22(32): 5055-5059.
Sherr, C. J., "Cancer Cell Cycles" Science, Dec. 6, 1996; 274(5293): 1672-1677.

Shields et al. "Lack of Extracellular Signal-Regulated Kinase Mitogen-Activated Protein Kinase Signaling Shows a New Type of Melanoma" Cancer Res, 2007; 67: 1502-1512.
Shimamura, T. et al. "Identification of potent 5-pyrimidinyl-2-aminothiazole CDK4, 6 inhibitors with significant selectivity over CDK1, 2, 5, 7, and 9" Bioorg Med Chem Lett., Jul. 15, 2006; 16(14): 3751-3754.
Sinclair, W.K. and R.A. Morton "X-ray sensitivity during the cell generation cycle of cultured Chinese hamster cells" Radiat Res., Nov. 1966; 29(3): 450-474.
Soni, R. et al. "Selective in vivo and in vitro effects of a small molecule inhibitor of cyclin-dependent kinase 4" J Natl Cancer Inst, Mar. 21, 2001; 93(6): 436-446.
Stone, S. et al. "Reversible, p16-mediated cell cycle arrest as protection from chemotherapy" Cancer Research, Jul. 15, 1996; 56(14): 3199-3202.
Sun, Y. et al. "Antibody-drug conjugates as targeted cancer therapeutics" Acta Pharmaceutica Sinica, 2009; 44(9): 943-952.
Takano, Y. et al. Cyclin D1 overexpression in invasive breast cancers: correlation with cyclin-dependent kinase 4 and oestrogen receptor overexpression, and lack of correlation with mitotic activity Journal of Cancer Research and Clinical Oncology, 1999; 125: 505-512.
Teicher, B. A. and R. V. Chari "Antibody conjugate therapeutics: challenges and potential" Clinical Cancer Research, 2011; 17(20): 6389-6397.
Terasima, T. and Li Tolmach "X-ray sensitivity and DNA synthesis in synchronous populations of HeLa cells" Science, 1963, 140: 490-492.
Teyssier, F. et al. "Cell cycle regulation after exposure to ionizing radiation" Bull Cancer., Apr. 1999; 86(4): 345-357. [Abstract].
Toogood, P. L. et al. "Discovery of a potent and selective inhibitor of cyclin-dependent kinase 4/6" J.Med Chem, Apr. 7, 2005; 48(7): 2388-2406.
Tsou, H. R. et al. "4-(Phenylaminomethylene)isoquinoline-1,3(2H,4H)-diones as potent and selective inhibitors of the cyclin-dependent kinase 4 (CDK4)" J Med Chem, Jun. 26, 2008; 51(12): 3507-3525.
Tsou, H. R. et al. "Discovery of 4-(benzylaminomethylene)isoquinoline-1,3-(2H,4H)-diones and 4-[(pyridylmethyl)aminomethylene]isoquinoline-1,3-(2H,4H)-diones as potent and selective inhibitors of the cyclin-dependent kinase 4" J Med Chem, Apr. 23, 2009; 52(8): 2289-2310.
Tu, S. et al. "New potential inhibitors of cyclin-dependent kinase 4: design and synthesis of pyrido [2,3-d]pyrimidine derivatives under microwave irradiation" Bioorg Med Chem Lett, Jul. 1, 20061; 16(13): 3578-3581.
Uckun, F. M. et al. "In vivo radioprotective effects of recombinant human granulocyte colony-stimulating factor in lethally irradiated mice" Blood, Feb. 1, 1990; 75(3): 638-645.
Vanderwel, S.N. et al. "Pyrido[2,3-d]pyrimidin-7-ones as specific inhibitors of cyclin-dependent kinase 4" J Med Chem., Apr. 7, 2005; 48(7): 2371-2387.
Vlachakis, D. and S. Kossida "Antibody Drug Conjugate bioinformatics: drug delivery through the letterbox" Comput. Math. Methods Med., 2013; 2013: 282398. Published online on Jun. 19, 2013. [retrieved from http://dx.doi.org/10.1155/2013/282398 on Jul. 16, 2014].
Walker et al. "Virtually 100% of melanoma cell lines harbor alterations at the DNA level within CDKN2A, CDKN2B, or one of their downstream targets" Genes Chromosomes & Cancer, 1998; 22: 157-163.
Wang et al. "Loss of p21 increases sensitivity to ionizing radiation and delays the onset of lymphoma in atm-deficient mice" Proc Natl Acad Sci, USA, 1997; 94: 14590-14595.
Wang, R. H. et al. "Protein kinase inhibitor staurosporine enhances cytotoxicity of antitumor drugs to cancer cells" Yao Xue Xue Bao, 1996; 31(6): 411-415. [Abstract].
Weiss and Landauer "History and development of radiation-protective agents" International Journal of Radiation Biology, Jul. 2009; 85: 539-573.
White, J.D. et al. "Transformations of Quinic Acid. Asymmetric Synthesis and Absolute Configuration of Mycosporin I and Mycosporingly" Journal of Organic Chemistry, 1995, 60(12): 3600-3611.

(56) References Cited

OTHER PUBLICATIONS

Wilson et al. "Hematopoietic Stem Cells Reversibly Switch from Dormancy to Self-Renewal during Homeostasis and Repair" Cell, 2008; 135: 1118-1129.
Yu, Q. et al. "Requirement for CDK4 kinase function in breast cancel" Cancer Cell, 2006; 9: 23-32.
Yu, Q. et al. "Specific protection against breast cancers by cyclin D1 ablation" Nature, 2001; 411: 1017-1021.
Zhang, W. et al. "Sensitization of C6 glioma cells to radiation by staurosporine, a potent protein kinase C inhibitor" J Neurooncol., Jan. 1993; 15(1): 1-7.
Zhu, G. et al. "Synthesis, structure-activity relationship, and biological studies of indolocarbazoles as potent cyclin D1-CDK4 inhibitors" J Med Chem., May 22, 2003; 46(11): 2027-2030.
Zhu, G. et al. "Synthesis of quinolinyl/isoquinolinyl[a]pyrrolo [3,4-c] carbazoles as cyclin D1/CDK4 inhibitors" Bioorg Med Chem Lett, Apr. 7, 2003; 13(7): 1231-1235.

TRICYCLIC LACTAMS FOR USE IN HSPC-SPARING TREATMENTS FOR RB-POSITIVE ABNORMAL CELLULAR PROLIFERATION

RELATED APPLICATIONS

This application is a continuation of U.S. application Ser. No. 14/690,180, filed Apr. 17, 2015, which claims the benefit of provisional U.S. Application No. 61/980,883, filed Apr. 17, 2014, provisional U.S. Application No. 61/980,895, filed Apr. 17, 2014, provisional U.S. Application No. 61/980,918, filed Apr. 17, 2014, and provisional U.S. Application No. 61/980,939, filed Apr. 17, 2014, which are hereby incorporated by reference for all purposes.

GOVERNMENT INTEREST

The U.S. Government has rights in this invention by virtue of support under Grant No. 5R44A1084284 awarded by the National Institute of Allergy and Infectious Diseases.

FIELD

This invention is in the area of tricyclic lactam compounds for and methods of treating selected Rb-positive cancers and other Rb-positive abnormal cellular proliferative disorders while minimizing the deleterious effects on healthy cells, for example healthy Hematopoietic Stem Cells and Progenitor Cells (HSPCs), associated with current treatment modalities.

BACKGROUND

The regulation of the cell cycle is governed and controlled by specific proteins, which are activated and deactivated mainly through phosphorylation/dephosphorylation processes in a precisely timed manner. The key proteins that coordinate the initiation, progression, and completion of cell-cycle program are cyclin dependent kinases (CDKs). Cyclin-dependent kinases belong to the serine-threonine protein kinase family. They are heterodimeric complexes composed of a catalytic kinase subunit and a regulatory cyclin subunit. CDK activity is controlled by association with their corresponding regulatory subunits (cyclins) and CDK inhibitor proteins (Cip & Kip proteins, INK4s), by their phosphorylation state, and by ubiquitin-mediated proteolytic degradation (see D. G. Johnson, C. L. Walker, Annu. Rev. Pharmacol. Toxicol 39 (1999) 295-312; D. O. Morgan, Annu. Rev. Cell Dev. Biol. 13 (1997) 261-291; C. J. Sherr, Science 274 (1996) 1672-1677; T. Shimamura et al., Bioorg. Med. Chem. Lett. 16 (2006) 3751-3754).

There are four CDKs that are significantly involved in cellular proliferation: CDK1, which predominantly regulates the transition from G2 to M phase, and CDK2, CDK4, and CDK6, which regulate the transition from G1 to S phase (Malumbres M, Barbacid M. Cell cycle, CDKs and cancer: a changing paradigm. Nat. Rev. Cancer 2009; 9(3):153-166). In early to mid G1 phase, when the cell is responsive to mitogenic stimuli, activation of CDK4-cyclin D and CDK6-cyclin D induces phosphorylation of the retinoblastoma protein (pRb). Phosphorylation of pRb releases the transcription factor E2F, which enters the nucleus to activate transcription of other cyclins which promote further progression of the cell cycle (see J. A. Diehl, Cancer Biol. Ther. 1 (2002) 226-231; C. J. Sherr, Cell 73 (1993) 1059-1065). CDK4 and CDK6 are closely related proteins with basically indistinguishable biochemical properties (see M. Malumbres, M. Barbacid, Trends Biochem. Sci. 30 (2005) 630-641).

A number of CDK 4/6 inhibitors have been identified, including specific pyrido[2,3-d]pyrimidines, 2-anilinopyrimidines, diaryl ureas, benzoyl-2,4-diaminothiazoles, indolo[6,7-a]pyrrolo[3,4-c]carbazoles, and oxindoles (see P. S. Sharma, R. Sharma, R. Tyagi, Curr. Cancer Drug Targets 8 (2008) 53-75). WO 03/062236 identifies a series of 2-(pyridin-2-ylamino-pyrido[2,3]pyrimidin-7-ones for the treatment of Rb positive cancers that show selectivity for CDK4/6, including 6-acetyl-8-cyclopentyl-5-methyl-2-(5-piperazin-1-yl-pyridin-2-ylammino)-8H-pyrido-[2,3-d]-pyrimidin-7-one (palbociclib). The clinical trial studies have reported rates of Grade 3/4 neutropenia and leukopenia with the use of palbociclib, resulting in 71% of patients requiring a dose interruption and 35% requiring a dose reduction; and adverse events leading to 10% of the discontinuations (see Finn, Abstract S1-6, SABCS 2012). These side effects may be caused by the undesirable pharmacokinetics of palbociclib, which has a relatively long $T_{1/2}$ of roughly 26.7 hours, resulting in an accumulative concentration build-up of the CDK4/6 inhibitor and a persistent quiescence of HPSC replication.

VanderWel et al. describe an iodine-containing pyrido[2,3-d]pyrimidine-7-one (CKIA) as a potent and selective CDK4 inhibitor (see VanderWel et al., J. Med. Chem. 48 (2005) 2371-2387).

WO 99/15500 filed by Glaxo Group Ltd discloses protein kinase and serine/threonine kinase inhibitors.

WO 2010/020675 filed by Novartis A G describes pyrrolopyrimidine compounds as CDK inhibitors. WO 2011/101409 also filed by Novartis describes pyrrolopyrimidines with CDK 4/6 inhibitory activity.

WO 2005/052147 filed by Novartis and WO 2006/074985 filed by Janssen Pharma disclose additional CDK4 inhibitors.

US 2007/0179118 filed by Barvian et al. teaches the use of CDK4 inhibitors to treat inflammation.

U.S. Patent Publication 2011/0224227 to Sharpless et al. describes the use of certain CDK4/6 inhibitors, such as PD0332991 and 2BrIC (see Zhu, et al., J. Med. Chem., 46 (11) 2027-2030 (2003); PCT/US2009/059281) to reduce or prevent the effects of cytotoxic compounds on HSPCs in a subject undergoing chemotherapeutic treatments. See also U.S. Patent Publication 2012/0100100.

U.S. Patent Publication 2011/0224221 to Sharpless et al. describes the use of certain CDK4/6 inhibitors, such as PD0332991 and 2BrIC (see Zhu, et al., J. Med. Chem., 46 (11) 2027-2030 (2003); PCT/US2009/059281) to reduce or prevent the deleterious effects of ionizing radiation on HSPCs in a subject exposed to radiation. See also U.S. Patent Publication 2012/0100100.

Stone, et al., Cancer Research 56, 3199-3202 (Jul. 1, 1996) describes reversible, p16-mediated cell cycle arrest as protection from chemotherapy.

WO 2012/061156 filed by Tavares and assigned to G1 Therapeutics describes CDK inhibitors (see also, U.S. Pat. Nos. 8,829,012, 8,822,683, 8,598,186, 8,691,830, and 8,598,197, all assigned to G1 Therapeutics), describe CDK Inhibitors having the basic core structure:

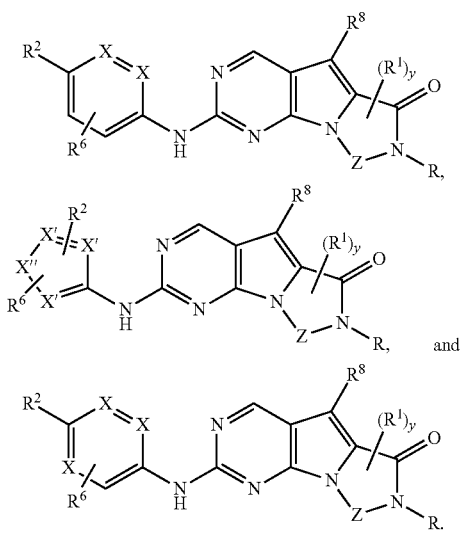

WO 2013/148748 filed by Tavares and assigned to G1 Therapeutics describes Lactam Kinase inhibitors having the basic core structures:

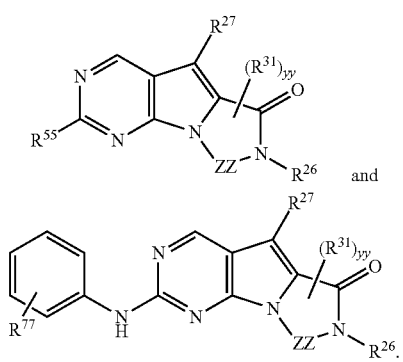

U.S. Patent Publication 2014/0275066 and 2014/0275067, assigned to G1 Therapeutics, describes the use of CDK4/6 inhibitors such as 2'-((5-(4-methylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one for the protection of healthy hematopoietic stem and progenitor cells in a subject receiving a DNA-damaging chemotherapeutic agent for the treatment of a Rb-negative tumors.

U.S. Patent Publication 2014/0274896, assigned to G1 Therapeutics, describes the use of CDK4/6 inhibitors such as 2'-((5-(4-methylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one for the protection of healthy hematopoietic stem and progenitor cells in a subject exposed to ionizing radiation.

U.S. Patent Publication 2014/0271466, assigned to G1 Therapeutics, describes the use of CDK4/6 inhibitors such as 2'-((5-(4-methylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one for use as an antineoplastic for the treatment of a Rb-positive proliferative disorders.

U.S. Patent Publication 2014/0271460, assigned to G1 Therapeutics, describes the use of CDK4/6 inhibitors such as 2'-((5-(4-methylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one for use an antineoplastic for the treatment of a T- or B-cell disorder, for example a leukemia.

While selective CDK4/6 inhibitors are generally designed to target CDK4/6-replication dependent cancers, the very fact that they inhibit CDK4/6 activity may also result in deleterious effects to CDK4/6-dependent healthy cells, for example their growth inhibition. CDK4/6 activity is necessary for the production of healthy blood cells by the bone marrow, as healthy hematopoietic stem and progenitor cells (HSPCs) require the activity of CDK4/6 for proliferation (see Roberts et al. Multiple Roles of Cyclin-Dependent Kinase 4/6 Inhibitors in Cancer Therapy. JNCI 2012; 104 (6):476-487). Healthy hematopoietic stem cells give rise to progenitor cells which in turn give rise to all the differentiated components of blood as shown in FIG. 1 (e.g., lymphocytes, erythrocytes, platelets, granulocytes, monocytes). Healthy hematopoietic cells display a gradient dependency on CDK4/6 activity for proliferation during myeloid/erythroid differentiation (see Johnson et al. Mitigation of hematological radiation toxicity in mice through pharmacological quiescence induced by CDK4/6 inhibition. J Clin. Invest. 2010; 120(7): 2528-2536). Accordingly, the least differentiated cells (e.g., healthy hematopoietic stem cells (HSCs), multi-potent progenitors (MPPs), and common myeloid progenitors (CMP)) appear to be the most dependent on CDK4/6 activity for proliferation, and therefore the most deleteriously affected by the use of a CDK4/6 inhibitor to treat a CDK4/6 replication dependent cancer or other proliferative disorder.

Accordingly, there is an ongoing need for CDK4/6 inhibitor compounds, methods, and regimes to treat patients with select Rb-positive cancers and abnormal cellular proliferative disorders while minimizing the treatment's effect on healthy cells such as HSPCs.

SUMMARY OF THE INVENTION

Tricyclic lactam compounds, methods, and compositions are provided to treat select Rb-positive abnormal cellular proliferation including an Rb-positive cancer while minimizing the treatment's deleterious effects on healthy cells, such as healthy HSPCs and other CDK4/6-replication dependent healthy cells by administration of an effective amount of a compound described herein.

In one embodiment of the invention, a compound is selected from the compounds of Formula I, II, III, IV, V, or VI as described herein, or a pharmaceutically acceptable composition, salt, isotopic analog, or prodrug thereof. In one non-limiting example, a compound can be selected from the compounds of Table 1 below, or a pharmaceutically acceptable composition, salt, isotopic analog, or prodrug thereof.

In one embodiment, the Rb-positive cancer can be Rb-positive adenocarcinoma. The Rb-positive cancer can be Rb-positive adenocarcinoma of the colon. The Rb-positive cancer can also be Rb-positive adenocarcinoma of the rectum.

Alternatively, the Rb-positive cancer can be Rb-positive anaplastic astrocytoma.

The Rb-positive cancer can be Rb-positive breast cancer. In one embodiment, the Rb-positive cancer is Rb-positive estrogen-receptor positive, HER2-negative advanced breast cancer. Alternatively, the Rb-positive cancer can be Rb-positive estrogen receptor-negative breast cancer. The Rb-positive cancer can be Rb-positive estrogen receptor positive breast cancer. The Rb-positive cancer can be Rb-positive late-line metastatic breast cancer. The Rb-positive cancer can be Rb-positive luminal A breast cancer. The Rb-positive cancer can be Rb-positive luminal B breast cancer. The Rb-positive cancer can be Rb-positive Her2-negative breast cancer or Rb-positive HER2-positive breast cancer. The Rb-positive cancer is Rb-positive male breast cancer. In one embodiment, the Rb-positive cancer is Rb-positive progesterone receptor-negative breast cancer. The Rb-positive cancer can be Rb-positive progesterone receptor-positive breast cancer. The Rb-positive cancer can be Rb-positive recurrent breast cancer. In one embodiment, the Rb-positive cancer is Rb-positive stage IV breast cancers. In one embodiment, the Rb-positive cancer is Rb-positive advanced HER2-positive breast cancer.

The Rb-positive cancer can be Rb-positive bronchial cancer. The Rb-positive cancer can be Rb-positive colon cancer. The Rb-positive cancer can be Rb-positive recurrent colon cancer. The Rb-positive cancer can be Rb-positive stage IV colon cancers. In one embodiment, the Rb-positive cancer is Rb-positive colorectal cancer.

In one embodiment, the Rb-positive cancer is Rb-positive endometrial cancer.

The Rb-positive cancer can be Rb-positive extragonadal seminoma. The Rb-positive cancer can be Rb-positive stage III extragonadal seminoma. The Rb-positive cancer can be Rb-positive stage IV extragonadal seminoma.

The Rb-positive cancer can be Rb-positive germ cell cancer. The Rb-positive cancer can be Rb-positive central nervous system germ cell tumor. The Rb-positive cancer can be Rb-positive familial testicular germ cell tumor. The Rb-positive cancer can be Rb-positive recurrent gonadal germ cell tumor. The Rb-positive cancer can be Rb-positive recurrent extragonadal non-seminomatous germ cell tumor. The Rb-positive cancer can be Rb-positive extragonadal seminomatous germ cell tumor. The Rb-positive cancer can be Rb-positive recurrent malignant testicular germ cell tumors. The Rb-positive cancer can be Rb-positive recurrent ovarian germ cell tumors. The Rb-positive cancer can be Rb-positive stage III malignant testicular germ cell tumors. The Rb-positive cancer can be Rb-positive stage III ovarian germ cell tumors. The Rb-positive cancer can be Rb-positive stage IV ovarian germ cell tumors. The Rb-positive cancer can be Rb-positive stage III extragonadal non-seminomatous germ cell tumors. The Rb-positive cancer can be Rb-positive stage IV extragonadal non-seminomatous germ cell tumors. In one embodiment, the Rb-positive cancer is Rb-positive germ cell cancer. In one embodiment, the Rb-positive cancer is Rb-positive cisplatin-refractory, unrespectable germ cell cancer.

In one embodiment, the Rb-positive cancer is Rb-positive glioblastoma.

In one embodiment, the Rb-positive cancer is Rb-positive liver cancer. The Rb-positive cancer can be Rb-positive hepatocellular cancer.

The Rb-positive cancer can be Rb-positive lung cancer. In one embodiment, the Rb-positive cancer is Rb-positive non-small cell lung cancer. In one embodiment, the Rb-positive cancer is Rb-positive KRAS mutant non-small cell lung cancer.

The Rb-positive cancer can be Rb-positive melanoma. In one embodiment, the Rb-positive cancer is Rb-positive recurrent melanomas. In one embodiment, the Rb-positive cancer is Rb-positive stage IV melanomas.

The Rb-positive cancer can be Rb-positive ovarian cancer. In one embodiment, the Rb-positive cancer is Rb-positive ovarian epithelial carcinoma.

The Rb-positive cancer can be Rb-positive pancreatic cancer.

The Rb-positive cancer can be Rb-positive prostate cancer.

In one embodiment, the Rb-positive cancer is Rb-positive rectal cancer. The Rb-positive cancer can be Rb-positive recurrent rectal cancer. The Rb-positive cancer can be Rb-positive stage IV rectal cancers.

The Rb-positive cancer can be Rb-positive sarcoma. The Rb-positive cancer can be Rb-positive gliosarcoma. The Rb-positive cancer can be Rb-positive liposarcoma. The Rb-positive cancer can be Rb-positive fibrosarcoma. The Rb-positive cancer can be Rb-positive myxosarcoma. In one embodiment, the Rb-positive cancer can be Rb-positive chondrosarcoma. The Rb-positive cancer can be Rb-positive osteosarcoma.

The Rb-positive cancer can be Rb-positive malignant fibrous histiocytoma. The Rb-positive cancer can be Rb-positive hemangiosarcoma. The Rb-positive cancer can be Rb-positive angiosarcoma. The Rb-positive cancer can be Rb-positive lymphangiosarcoma. The Rb-positive cancer can be Rb-positive mesothelioma. The Rb-positive cancer can be Rb-positive leiomyosarcoma. The Rb-positive cancer can be Rb-positive rhabdomyosarcoma. The Rb-positive cancer can be Rb-positive meningioma. The Rb-positive cancer can be Rb-positive schwannoma.

In one embodiment, the Rb-positive cancer is Rb-positive pheochromocytoma. The Rb-positive cancer can be Rb-positive Islet cell carcinoma. The Rb-positive cancer can be Rb-positive carcinoid. The Rb-positive cancer can be Rb-positive paraganglioma.

In one embodiment, the Rb-positive cancer is Rb-positive squamous cell carcinoma. The Rb-positive cancer can be Rb-positive adenocarcinoma. The Rb-positive cancer can be Rb-positive hepatocellular carcinoma. The Rb-positive cancer can be Rb-positive renal cell carcinoma. The Rb-positive cancer can be Rb-positive cholangiocarcinoma.

The Rb-positive cancer can be Rb-positive refractory solid tumors.

The Rb-positive cancer can be Rb-positive neuroblastoma.

The Rb-positive cancer can be Rb-positive medulloblastoma.

In one embodiment, the Rb-positive cancer is a Teratoma. The Rb-positive cancer can be Rb-positive ovarian immature teratoma. The Rb-positive cancer can be Rb-positive ovarian mature teratoma. The Rb-positive cancer can be an Rb-positive ovarian specialized teratoma. The Rb-positive cancer can be Rb-positive testicular immature teratoma. The Rb-positive cancer can be Rb-positive testicular mature teratoma. The Rb-positive cancer can be Rb-positive teratoma. The Rb-positive cancer can be Rb-positive ovarian monodermal teratoma.

The Rb-positive cancer can be Rb-positive testicular cancer.

In one embodiment, the Rb-positive cancer is Rb-positive vaginal cancer.

In one embodiment, the Rb-positive cancer is selected from an Rb-positive carcinoma, sarcoma, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers.

In one embodiment, the subject is suffering from an Rb-positive abnormal cellular proliferation disorder. In one embodiment, the Rb-positive abnormal cellular proliferation disorder is non-cancerous.

In one embodiment, a compound described herein, when used to treat a select Rb-positive cellular proliferation disorder, such as a cancer, allows for a rapid reentry of healthy cells into the normal cell-cycle and a fast reconstitution of damaged tissue and progeny cells such as hematological cells. Non-limiting examples of active compounds are described in Table 1, or a pharmaceutically acceptable composition, salt, isotopic analog, or prodrug thereof as provided below.

In one embodiment of the invention, a compound described herein can be administered in a concerted regimen with another agent such as a non-DNA-damaging, targeted anti-neoplastic agent or a hematopoietic growth factor agent for beneficial, additive, or synergistic effect against the abnormal cellular proliferation. It has been recently reported that the untimely administration of hematopoietic growth factors can have serious side effects. For example, the use of the EPO family of growth factors has been associated with arterial hypertension, cerebral convulsions, hypertensive encephalopathy, thromboembolism, iron deficiency, influenza like syndromes and venous thrombosis. The G-CSF family of growth factors has been associated with spleen enlargement and rupture, respiratory distress syndrome, allergic reactions and sickle cell complications. By combining the administration of a compound described herein and methods of the present invention with the timely administration of hematopoietic growth factors, for example, at the time point wherein the affected cells are no longer under growth arrest, it is possible for the health care practitioner to decrease the amount of the growth factor to minimize the unwanted adverse effects while achieving the desired therapeutic benefit. In one embodiment, the growth factor is administered upon cessation of the effect of the inhibitory effect of the compound on the CDK4/6 replication dependent healthy cells, for example HSPCs.

In one embodiment, the use of a compound or method described herein is combined with the use of a hematopoietic growth factor including, but not limited to, granulocyte colony stimulating factor (G-CSF), granulocyte-macrophage colony stimulating factor (GM-CSF), thrombopoietin, interleukin (IL)-12, steel factor, and erythropoietin (EPO), or a derivative thereof. In one embodiment, the tricylic lactam is administered prior to administration of the hematopoietic growth factor. In one embodiment, the hematopoietic growth factor administration is timed so that the tricyclic lactam's effect on HSPCs has dissipated.

In one embodiment, the use of a compound described herein is combined in a therapeutic regime with at least one other chemotherapeutic agent, and can be one that does, or in certain embodiments does not, rely on proliferation or advancement through the cell-cycle for anti-proliferative activity. Such agent may include, but is not limited to, tamoxifen, midazolam, letrozole, bortezomib, anastrozole, goserelin, an mTOR inhibitor, a PI3 kinase inhibitors, dual mTOR-PI3K inhibitors, MEK inhibitors, RAS inhibitors, ALK inhibitors, HSP inhibitors (for example, HSP70 and HSP 90 inhibitors, or a combination thereof). Examples of mTOR inhibitors include but are not limited to rapamycin and its analogs, everolimus (Afinitor), temsirolimus, ridaforolimus, sirolimus, and deforolimus. Examples of PI3 kinase inhibitors include but are not limited to Wortmannin, demethoxyviridin, perifosine, idelalisib, PX-866, IPI-145, BAY 80-6946, BEZ235, RP6503, TGR 1202 (RP5264), MLN1117 (INK1117), Pictilisib, Buparlisib, SAR245408 (XL147), SAR245409 (XL765), Palomid 529, ZSTK474, PWT33597, RP6530, CUDC-907, and AEZS-136. Examples of MEK inhibitors include but are not limited to Tametinib, Selumetinib, MEK162, GDC-0973 (XL518), and PD0325901. Examples of RAS inhibitors include but are not limited to Reolysin and siG12D LODER. Examples of ALK inhibitors include but are not limited to Crizotinib, AP26113, and LDK378. HSP inhibitors include but are not limited to Geldanamycin or 17-N-Allylamino-17-demethoxygeldanamycin (17AAG), and Radicicol.

In certain embodiments, a compound described herein is administered to the subject prior to treatment with another chemotherapeutic agent, during treatment with another chemotherapeutic agent, after administration of another chemotherapeutic agent, or a combination thereof. In one embodiment, a compound described herein is administered to the subject less than about 24 hours, 20 hours, 16 hours, 12 hours, 8 hours, 4 hours, 2 hours, 1 hour, or ½ hour or less prior to treatment with another chemotherapeutic agent in order to sensitize the Rb-positive cancer to the chemotherapeutic agent's effects.

In one embodiment, a compound described herein is administered in a manner that allows the drug facile access to the blood stream, for example via intravenous injection or sublingual, intraaortal, or other efficient blood-stream accessing route. In one embodiment, a compound described herein is administered in an orally administrable formulation. In other embodiments, a compound described herein is administered via topical, transdermal, or other desired administrative routes.

In one embodiment, a compound described herein is administered to the subject less than about 24 hours, 20 hours, 16 hours, 12 hours, 8 hours, 4 hours, 2 hours, 1 hour, or ½ hour or less prior to treatment with the hematopoietic growth factor. In one embodiment, the compound is administered up to 4 hours prior to treatment with the hematopoietic growth factor or other chemotherapeutic agent.

The use of a compound as described herein in a therapeutic regime targeting CDK4/6-replication dependent cancers can result in reduced anemia, reduced lymphopenia, reduced thrombocytopenia, or reduced neutropenia compared to that typically expected after, common after, or associated with treatment with currently available antineoplastic chemotherapeutic agents. The use of the compounds as described herein may result in a faster recovery from bone marrow suppression associated with long-term use of CDK4/6 inhibitors, such as myelosuppression, anemia, lymphopenia, thrombocytopenia, or neutropenia, following the cessation of use of the CDK4/6 inhibitor. In some embodiments, the use of a compound as described herein results in reduced bone marrow suppression associated with long-term use of CDK4/6 inhibitors, such as myelosuppression, anemia, lymphopenia, leukopenia, thrombocytopenia, or granulocytopenias such as neutropenia.

In some embodiments, the subject or host is a mammal, including a human. The compound can be administered to the subject by any desired route, including intravenous, sublingual, buccal, oral, intraaortal, topical, intranasal, parenteral, transdermal, systemic, intramuscular, or via inhalation.

In summary, the present invention includes the following features:

A) Tricyclic lactam compounds, methods, and compositions as chemotherapeutics which minimize the deleterious effects on CDK4/6 replication dependent healthy cells, for example hematopoietic stem and progenitor cells (HSPCs), in a subject undergoing treatment for a select Rb-positive cancer, comprising administering an effective amount of a tricyclic lactam compound of Formula I, II, III, IV, V, or VI, including a compound selected from Table 1 as described herein;

B) Tricyclic lactam compounds, methods, and compositions as chemotherapeutics which minimize the deleterious effects on CDK4/6 replication dependent healthy cells in a subject, the method comprising administering to a subject with an Rb-positive abnormal cellular proliferative disorder an effective amount of a tricyclic lactam compound of Formula I, II, III, IV, V, or VI, including a compound selected from Table 1 as described herein.

C) A compound as described herein, or a pharmaceutically acceptable composition, salt, isotopic analog, or prodrug thereof, for use as a chemotherapeutic in the treatment of an Rb-positive abnormal cellular proliferation disorder, including Rb-positive cancers;

D) A compound as described herein, or a pharmaceutically acceptable composition, salt, isotopic analog, and prodrug thereof, for use as a chemotherapeutic regimen for the treatment of an Rb-positive abnormal cellular proliferation disorder, including Rb-positive cancers, which minimizes the deleterious effects on CDK4/6-replication dependent healthy cells, for example HSPCs or renal cells;

E) A compound as described herein, or a pharmaceutically acceptable composition, salt, isotopic analog, and prodrug thereof, for use in combination with hematopoietic growth factors in a subject undergoing a therapeutic regime to treat an Rb-positive abnormal cellular proliferation disorder, including Rb-positive cancers;

F) Compounds as described herein, or a pharmaceutically acceptable composition, salt, isotopic analog, or prodrug thereof, for use in combination with a second chemotherapeutic agent in a subject undergoing a therapeutic regime to treat an Rb-positive abnormal cellular proliferation disorder, including Rb-positive cancers;

G) Use of a compound described herein, or a pharmaceutically acceptable composition, salt, isotopic analog, or prodrug thereof, in the manufacture of a medicament for use as a chemotherapeutic to treat a subject with an Rb-positive abnormal cellular proliferation disorder, including Rb-positive cancers;

H) Use of a compound described herein, or a pharmaceutically acceptable composition, salts, isotopic analog, or prodrug thereof, in the manufacture of a medicament for use as chemotherapeutic to treat a subject with an Rb-positive cellular proliferation disorder, including a Rb-positive cancer that, when exposed to a CDK4/6 inhibitor, is growth arrested or growth inhibited;

I) Processes for the preparation of therapeutic products that contain an effective amount of a compound described herein, for use in the treatment of a subject having an Rb-positive abnormal cellular proliferation disorder, such as cancer, and;

J) A method for manufacturing a medicament selected from the compounds described herein intended for therapeutic use as a chemotherapeutic on the treatment of an Rb-positive, abnormal cellular proliferation disorder, such as a cancer.

DETAILED DESCRIPTION OF THE INVENTION

Figure 1:
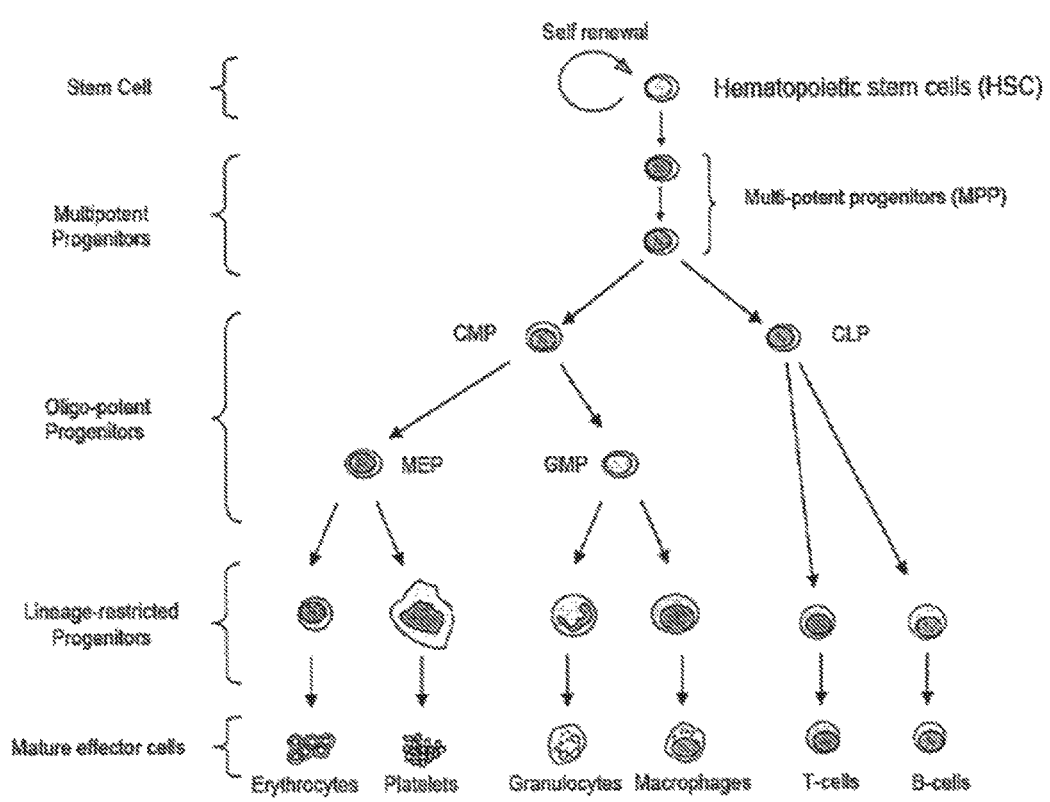
FIG. 1 is a schematic drawing of hematopoiesis showing the hierarchical proliferation of healthy hematopoietic stem cells (HSC) and healthy hematopoietic progenitor cells with increasing differentiation upon proliferation.

Tricyclic lactam compounds, methods, and compositions are provided as chemotherapeutics for the treatment of select Rb-positive cancers which minimize or reduce the deleterious effects on CDK4/6 replication dependent healthy cells, such as hematopoietic stem cells and/or progenitor cells (HSPCs) in subjects, typically humans.

Definitions

Unless otherwise stated, the following terms used in this application, including the specification and claims, have the definitions given below. As used in the specification and the appended claims, the singular forms "a," "an" and "the" include plural referents unless the context clearly dictates otherwise. Definition of standard chemistry terms may be found in reference works, including Carey and Sundberg (2007) *Advanced Organic Chemistry 5th Ed.* Vols. A and B, Springer Science+Business Media LLC, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology. Conventional methods of organic chemistry include those included in *March's Advanced Organic Chemistry: Reactions, Mechanisms, and Structure, 6th Edition*, M. B. Smith and J. March, John Wiley & Sons, Inc., Hoboken, N.J., 2007.

The term "alkyl," either alone or within other terms such as "haloalkyl" and "alkylamino," embraces linear or branched radicals having one to about twelve carbon atoms. "Lower alkyl" radicals have one to about six carbon atoms. Examples of such radicals include methyl, ethyl, n-propyl, isopropyl, n-butyl, isobutyl, sec-butyl, tert-butyl, pentyl, isoamyl, hexyl and the like. The term "alkylene" embraces bridging divalent linear and branched alkyl radicals. Examples include methylene, ethylene, propylene, isopropylene and the like.

The term "alkenyl" embraces linear or branched radicals having at least one carbon-carbon double bond of two to about twelve carbon atoms. "Lower alkenyl" radicals having two to about six carbon atoms. Examples of alkenyl radicals include ethenyl, propenyl, allyl, propenyl, butenyl and 4-methylbutenyl. The terms "alkenyl" and "lower alkenyl," embrace radicals having "cis" and "trans" orientations, or alternatively, "E" and "Z" orientations.

The term "alkynyl" denotes linear or branched radicals having at least one carbon-carbon triple bond and having two to about twelve carbon atoms. "Lower alkynyl" radicals having two to about six carbon atoms. Examples of such radicals include propargyl, butynyl, and the like.

Alkyl, alkenyl, and alkynyl radicals may be optionally substituted with one or more functional groups such as halo, hydroxy, nitro, amino, cyano, haloalkyl, aryl, heteroaryl, heterocyclo and the like.

The term "alkylamino" embraces "N-alkylamino" and "N,N-dialkylamino" where amino groups are independently substituted with one alkyl radical and with two alkyl radicals, respectively. "Lower alkylamino" radicals have one or two alkyl radicals of one to six carbon atoms attached to a nitrogen atom. Suitable alkylamino radicals may be mono or dialkylamino such as N-methylamino, N-ethylamino, N.N-dimethylamino, N,N-diethylamino and the like.

The term "halo" means halogens such as fluorine, chlorine, bromine or iodine atoms.

The term "haloalkyl" embraces radicals wherein any one or more of the alkyl carbon atoms is substituted with one or more halo as defined above. Examples include monohaloalkyl, dihaloalkyl and polyhaloalkyl radicals including perhaloalkyl. A monohaloalkyl radical, for one example, may have an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means an alkyl radical having all hydrogen atoms replaced with fluoro atoms. Examples include trifluoromethyl and pentafluoroethyl.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 or more substituents such as lower alkyl, hydroxyl, halo, haloalkyl, nitro, cyano, alkoxy, lower alkylamino, and the like. An aryl group may be optionally substituted with one or more functional groups such as halo, hydroxy, nitro, amino, cyano, haloalkyl, aryl, heteroaryl, heterocyclo and the like.

The term "heterocyclyl" (or "heterocyclo") embraces saturated, and partially saturated heteroatom-containing ring radicals, where the heteroatoms may be selected from nitrogen, sulfur and oxygen. Heterocyclic rings comprise monocyclic 6-8 membered rings, as well as 5-16 membered bicyclic ring systems (which can include bridged fused and spiro-fused bicyclic ring systems). It does not include rings containing —O—O—.—O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino, lower alkylamino, and the like.

Examples of saturated heterocyclo groups include saturated 3- to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl, dihydrothiazolyl, and the like.

Particular examples of partially saturated and saturated heterocyclo groups include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1Hλ'-benzo[d]isothiazol-6-yl, dihydropyranyl, dihydrofuryl and dihydrothiazolyl, and the like.

Heterocyclo groups also includes radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl].

The term "heteroaryl" denotes aryl ring systems that contain one or more heteroatoms selected from the group O, N and S, wherein the ring nitrogen and sulfur atom(s) are optionally oxidized, and nitrogen atom(s) are optionally quarternized. Examples include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, IH-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term "heteroarylalkyl" denotes alkyl radicals substituted with a heteroaryl group. Examples include pyridylmethyl and thienylethyl.

The term "sulfonyl", whether used alone or linked to other terms such as alkylsulfonyl, denotes respectively divalent radicals —SO$_2$—.

The terms "carboxy" or "carboxyl", whether used alone or with other terms, such as "carboxyalkyl", denotes —C(O)—OH.

The term "carbonyl", whether used alone or with other terms, such as "aminocarbonyl", denotes —C(O)—.

The term "aminocarbonyl" denotes an amide group of the Formula —C(O)—NH$_2$.

The terms "heterocycloalkyl" embrace heterocyclic-substituted alkyl radicals. Examples include piperidylmethyl and morpholinylethyl.

The term "arylalkyl" embraces aryl-substituted alkyl radicals. Examples include benzyl, diphenylmethyl and phenylethyl. The aryl in said aralkyl may be additionally substituted with halo, alkyl, alkoxy, halkoalkyl and haloalkoxy.

The term "cycloalkyl" includes saturated carbocyclic groups of 3 to 10 carbons. Lower cycloalkyl groups include $C_3$-$C_6$ rings. Examples include cyclopentyl, cyclopropyl, and cyclohexyl. Cycloalkyl groups may be optionally substituted with one or more functional groups such as halo, hydroxy, nitro, amino, cyano, haloalkyl, aryl, heteroaryl, heterocyclo and the like.

The term "cycloalkylalkyl" embraces cycloalkyl-substituted alkyl radicals. "Lower cycloalkylalkyl" radicals are cycloalkyl radicals attached to alkyl radicals having one to six carbon atoms. Examples of include cyclohexylmethyl. The cycloalkyl in said radicals may be additionally substituted with halo, alkyl, alkoxy and hydroxy.

The term "cycloalkenyl" includes carbocyclic groups having one or more carbon-carbon double bonds including "cycloalkyldienyl" compounds. Examples include cyclopentenyl, cyclopentadienyl, cyclohexenyl and cycloheptadienyl.

The term "comprising" is meant to be open ended, including the indicated component but not excluding other elements.

The term "oxo" as used herein contemplates an oxygen atom attached with a double bond.

The term "nitro" as used herein contemplates —$NO_2$.

The term "cyano" as used herein contemplates —CN.

As used herein, the term "prodrug" means a compound which when administered to a host in vivo is converted into the parent drug. As used herein, the term "parent drug" means any of the presently described chemical compounds that are useful to treat any of the disorders described herein, or to control or improve the underlying cause or symptoms associated with any physiological or pathological disorder described herein in a host, typically a human. Prodrugs can be used to achieve any desired effect, including to enhance properties of the parent drug or to improve the pharmaceutic or pharmacokinetic properties of the parent. Prodrug strategies exist which provide choices in modulating the conditions for in vivo generation of the parent drug, all of which are deemed included herein. Nonlimiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others.

Throughout the specification and claims, a given chemical formula or name shall encompass all optical and stereoisomers, as well as racemic mixtures where such isomers and mixtures exist, unless otherwise noted.

The current invention is directed to an HSPC-sparing strategy during the treatment of Rb-positive proliferation disorders. According, as used herein, the term "HSPCs" is meant to describe healthy hematopoietic stem and/or hematopoietic progenitor cells, as opposed to diseased HSPCs or cells of related hematological origin. HSPCs include hematopoietic stem cells, such as long term hematopoietic stem cells (LT-HSCs) and short term hematopoietic stem cells (ST-HSCs), and hematopoietic progenitor cells, including multipotent progenitors (MPPs), common myeloid progenitors (CMPs), common lymphoid progenitors (CLPs), granulocyte-monocyte progenitors (GMPs) and megakaryocyte-erythroid progenitors (MEPs).

In some embodiments, a CDK4/6-replication dependent healthy cell is a hematopoietic stem progenitor cell. In some embodiments, the CDK4/6-replication dependent healthy cell may be a cell in a non-hematopoietic tissue, such as, but not limited to, the liver, kidney, pancreas, brain, lung, adrenals, intestine, gut, stomach, skin, auditory system, bone, bladder, ovaries, uterus, testicles, gallbladder, thyroid, heart, pancreatic islets, blood vessels, and the like.

The term "selective CDK4/6 inhibitor" used in the context of the compounds described herein includes compounds that inhibit CDK4 activity, CDK6 activity, or both CDK4 and CDK6 activity at an $IC_{50}$ molar concentration at least about 500, or 1000, or 1500, or 1800, or 2000, or 5000, or 10,000 times less than the $IC_{50}$ molar concentration necessary to inhibit to the same degree of CDK2 activity in a standard phosphorylation assay.

As used herein the term "chemotherapy" or "chemotherapeutic agent" refers to treatment with a cytostatic or cytotoxic agent (i.e., a compound) to reduce or eliminate the growth or proliferation of undesirable cells, for example cancer cells. Thus, as used herein, "chemotherapy" or "chemotherapeutic agent" refers to a cytotoxic or cytostatic agent used to treat a proliferative disorder, for example cancer.

By "induces G1-arrest" is meant that the inhibitor compound induces a quiescent state in a substantial portion of a cell population at the G1 phase of the cell cycle.

By "hematological deficiency" is meant reduced hematological cell lineage counts or the insufficient production of blood cells (i.e., myelodysplasia) and/or lymphocytes (i.e., lymphopenia, the reduction in the number of circulating lymphocytes, such as B- and T-cells). Hematological deficiency can be observed, for example, as myelosuppression in form of anemia, reduction in platelet count (i.e., thrombocytopenia), reduction in white blood cell count (i.e., leukopenia), or the reduction in granulocytes (e.g., neutropenia).

By "synchronous reentry into the cell cycle" is meant that CDK4/6-replication dependent healthy cells, for example HSPCs, in G1-arrest due to the effect of a tricyclic lactam compound reenter the cell-cycle within relatively the same collective timeframe or at relatively the same rate upon dissipation of the compound's effect. Comparatively, by "asynchronous reentry into the cell cycle" is meant that the healthy cells, for example HSPCs, in G1 arrest reenter the cell-cycle within relatively different collective timeframes or at relatively different rates upon dissipation of the compound's effect, such as PD0332991.

By "off-cycle" or "drug holiday" is meant a time period during which the subject is not administered or exposed to a chemotherapeutic. For example, in a treatment regime wherein the subject is administered the chemotherapeutic for 21 straight days and is not administered the chemotherapeutic for 7 days, and the regime is repeated a number of times, the 7 day period of non-administration is considered the "off-cycle" or "drug holiday." Off-cycle and drug holiday may also refer to an interruption in a treatment regime wherein the subject is not administered the chemotherapeutic for a time due to a deleterious side effect, for example, myelosuppression.

The subject treated is typically a human subject, although it is to be understood the methods described herein are effective with respect to other animals, such as mammals and vertebrate species. More particularly, the term subject can include animals used in assays such as those used in preclinical testing including but not limited to mice, rats, monkeys, dogs, pigs and rabbits; as well as domesticated swine (pigs and hogs), ruminants, equine, poultry, felines, bovines, murines, canines, and the like.

Active Compounds

In one embodiment, the invention is directed to compounds or the use of such compounds of Formula I, II, III, IV, or V:

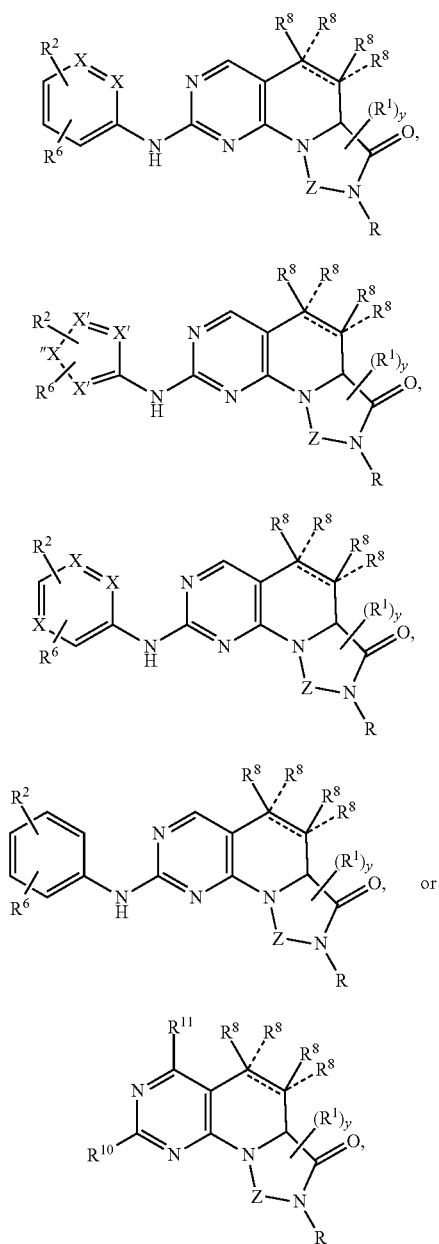

or a pharmaceutically acceptable salt thereof;
wherein:
Z is —$(CH_2)_x$— wherein x is 1, 2, 3 or 4 or —O—$(CH_2)_z$— wherein z is 2, 3 or 4;
each X is independently CH or N;
each X' is independently CH or N;
X" is independently $CH_2$, S or NH, arranged such that the moiety is a stable 5-membered ring; R, $R^8$, and $R^{11}$ are independently H, $C_1$-$C_3$alkyl or haloalkyl, cycloalkyl or cycloalkyl containing one or more heteroatoms selected from N, O or S; -(alkylene)$_m$-$C_3$-$C_8$ cycloalkyl, -(alkylene)$_m$-aryl, -(alkylene)$_m$-heterocyclo, -(alkylene)$_m$-heteroaryl, -(alkylene)$_m$—$NR^3R^4$, -(alkylene)$_m$-C(O)—$NR^3R^4$; -(alkylene)$_m$-O—$R^5$, -(alkylene)$_m$-S(O)$_n$—$R^5$, or -(alkylene)$_m$-S(O)$_n$—$NR^3R^4$ any of which may be optionally independently substituted with one or more $R^x$ groups as allowed by valence, and wherein two $R^x$ groups bound to the same or adjacent atoms may optionally combine to form a ring;

each $R^1$ is independently aryl, alkyl, cycloalkyl or haloalkyl, wherein each of said alkyl, cycloalkyl and haloalkyl groups optionally includes O or N heteroatoms in place of a carbon in the chain and two $R^1$'s on adjacent ring atoms or on the same ring atom together with the ring atom(s) to which they are attached optionally form a 3-8-membered cycle;

y is 0, 1, 2, 3 or 4;

$R^2$ is -(alkylene)$_m$-heterocyclo, -(alkylene)$_m$-heteroaryl, -(alkylene)$_m$$NR^3R^4$, -(alkylene)$_m$-C(O)—$NR^3R^4$; -(alkylene)$_m$-C(O)—O-alkyl; -(alkylene)$_m$-O—$R^5$, -(alkylene)$_m$- S(O)$_n$—$R^5$, or -(alkylene)$_m$-S(O)$_n$—$NR^3R^4$ any of which may be optionally independently substituted with one or more $R^x$ groups as allowed by valence, and wherein two $R^x$ groups bound to the same or adjacent atom may optionally combine to form a ring and wherein m is 0, 1 or 2 and n is 0, 1 or 2;

$R^3$ and $R^4$ at each occurrence are independently:
(i) hydrogen or
(ii) alkyl, cycloalkyl, heterocyclo, aryl, heteroaryl, cycloalkylalkyl, heterocycloalkyl, arylalkyl, or heteroarylalkyl any of which may be optionally independently substituted with one or more $R^x$ groups as allowed by valence, and wherein two $R^x$ groups bound to the same or adjacent atom may optionally combine to form a ring; or $R^3$ and $R^4$ together with the nitrogen atom to which they are attached may combine to form a heterocyclo ring optionally independently substituted with one or more $R^x$ groups as allowed by valence, and wherein two $R^x$ groups bound to the same or adjacent atom may optionally combine to form a ring;

$R^5$ and $R^{5*}$ at each occurrence is:
(i) hydrogen or
(ii) alkyl, alkenyl, alkynyl, cycloalkyl, heterocyclo, aryl, heteroaryl, cycloalkylalkyl, heterocycloalkyl, arylalkyl, or heteroarylalkyl any of which may be optionally independently substituted with one or more $R^x$ groups as allowed by valence;

$R^x$ at each occurrence is independently, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)$_m$-$OR^5$, -(alkylene)$_m$-O-alkylene-$OR^5$, -(alkylene)$_m$-S(O)$_n$—$R^5$, -(alkylene)$_m$-$NR^3R^4$, -(alkylene)$_m$-CN, -(alkylene)$_m$-C(O)—$R^5$, -(alkylene)$_m$-C(S)—$R^5$, -(alkylene)$_m$-C(O)—$OR^5$, -(alkylene)$_m$-O—C(O)—$R^5$, -(alkylene)$_m$-C(S)—$OR^5$, -(alkylene)$_m$-C(O)-(alkylene)$_m$-$NR^3R^4$, -(alkylene)$_m$-C(S)—$NR^3R^4$, -(alkylene)$_m$-N($R^3$)—C(O)—$NR^3R^4$, -(alkylene)$_m$-N($R^3$)—C(S)—$NR^3R^4$, -(alkylene)$_m$-N($R^3$)—C(O)—$R^5$, -(alkylene)$_m$-N($R^3$)—C(S)—$R^5$, -(alkylene)$_m$-O—C(O)—$NR^3R^4$, -(alkylene)$_m$-O—C(S)—$NR^3R^4$, -(alkylene)$_m$-$SO_2$—$NR^3R^4$, -(alkylene)$_m$-N($R^3$)—$SO_2$—$R^5$, -(alkylene)$_m$-N($R^3$)—$SO_2$—$NR^3R^4$, -(alkylene)$_m$-N($R^3$)—C(O)—$OR^5$) -(alkylene)$_m$-N($R^3$)—C(S)—$OR^5$, or -(alkylene)$_m$-N($R^3$)—$SO_2$—$R^5$; wherein:

said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more -(alkylene)$_m$-CN, -(alkylene)$_m$-OR$^{5*}$, -(alkylene)$_m$-S(O)$_n$—R$^{5*}$, -(alkylene)$_m$-NR$^{3*}$R$^{4*}$, -(alkylene)$_m$-C(O)—R$^{5*}$, -(alkylene)$_m$-C(=S)R$^{5*}$, -(alkylene)$_m$-C(=O)O R$^{5*}$, -(alkylene)$_m$-OC(=O) R$^{5*}$, -(alkylene)$_m$-C(S)—OR$^{5*}$, -(alkylene)$_m$-C(O)—NR$^{3*}$R$^{4*}$, -(alkylene)$_m$-C(S)—NR$^{3*}$R$^{4*}$, -(alkylene)$_m$-N(R$^{3*}$)—C(O)—NR$^{3*}$R$^{4*}$, -(alkylene)$_m$-N(R$^{3*}$)—C(S)—NR$^{3*}$R$^{4*}$, -(alkylene)$_m$-N(R$^{3*}$)—C(O)—R$^{5*}$, -(alkylene)$_m$-N(R$^{3*}$)—C(S)—R$^{5*}$, -(alkylene)$_m$-O—C(O)—NR$^{3*}$R$^{4*}$, -(alkylene)$_m$-O—C(S)—NR$^{3*}$R$^{4*}$, -(alkylene)$_m$-SO$_2$—NR$^{3*}$R$^{4*}$, -(alkylene)$_m$-N(R$^{3*}$)—SO$_2$—R$^{5*}$, -(alkylene)$_m$-N(R$^{3*}$)—SO$_2$—NR$^{3*}$R$^{4*}$, -(alkylene)$_m$-N(R$^{3*}$)—C(O)—OR$^{5*}$, -(alkylene)$_m$-N(R$^{3*}$)—C(S)—OR$^{5*}$, or -(alkylene)$_m$-N(R$^{3*}$)—SO$_2$—R$^{5*}$, n is 0, 1 or 2, and m is 0, 1 or 2;

R$^{3*}$ and R$^{4*}$ at each occurrence are independently:
  (i) hydrogen or
  (ii) alkyl, alkenyl, alkynyl cycloalkyl, heterocyclo, aryl, heteroaryl, cycloalkylalkyl, heterocycloalkyl, arylalkyl, or heteroarylalkyl any of which may be optionally independently substituted with one or more R$^x$ groups as allowed by valence; or R$^{3*}$ and R$^{4*}$ together with the nitrogen atom to which they are attached may combine to form a heterocyclo ring optionally independently substituted with one or more R$^x$ groups as allowed by valence; and R$^6$ is H or lower alkyl, -(alkylene)$_m$-heterocyclo, -(alkylene)$_m$-heteroaryl, -(alkylene)$_m$-NR$^3$R$^4$, -(alkylene)$_m$-C(O)—NR$^3$R$^4$; -(alkylene)$_m$-O—R$^5$, -(alkylene)$_m$-S(O)$_n$—R$^5$, or -(alkylene)$_m$-S(O)$_n$—NR$^3$R$^4$ any of which may be optionally independently substituted with one or more R$^x$ groups as allowed by valence, and wherein two R$^x$ groups bound to the same or adjacent atoms may optionally combine to form a ring; and R$^6$ is (i) NHR$^A$, wherein R$^A$ is unsubstituted or substituted C$_1$-C$_8$ alkyl, cycloalkylalkyl, or -TT-RR, C$_1$-C$_8$ cycloalkyl or cycloalkyl containing one or more heteroatoms selected from N, O, and S; TT is an unsubstituted or substituted C$_1$-C$_8$ alkyl or C$_3$-C$_8$ cycloalkyl linker; and RR is a hydroxyl, unsubstituted or substituted C$_1$-C$_6$ alkoxy, amino, unsubstituted or substituted C$_1$-C$_6$ alkylamino, unsubstituted or substituted di-C$_1$-C$_6$ alkylamino, unsubstituted or substituted C$_6$-C$_{10}$ aryl, unsubstituted or substituted heteroaryl comprising one or two 5- or 6-member rings and 1-4 heteroatoms selected from N, O and S, unsubstituted or substituted C$_3$-C$_{10}$ carbocycle, or unsubstituted or substituted heterocycle comprising one or two 5- or 6-member rings and 1-4 heteroatoms selected from N, O and S; or (ii) —C(O)—R$^{12}$ or —C(O)O—R$^{13}$, wherein R$^{12}$ is NHR$^A$ or R$^A$ and R$^{13}$ is R$^A$;

when compounds comprise a double bond in the 6-membered ring fused to the pyrimidine ring, two R$^8$ groups are present and are as defined above;

when compounds do not comprise a double bond in the 6-membered ring fused to the pyrimidine ring, four R$^8$ groups are present and are as defined above;

or a pharmaceutically acceptable salt, prodrug or isotopic variant, for example, partially or fully deuterated form thereof.

In one embodiment, two R$^8$ groups bonded to the same carbon can form an exocyclic double bond. In another embodiment, two R$^8$ groups bonded to the same carbon can form a carbonyl group.

In one embodiment, the invention is directed to compounds or the use of such compounds of Formula VI:

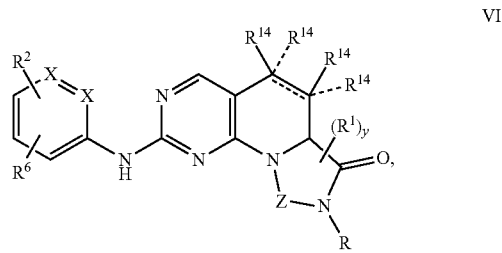

VI wherein R, R$^2$, R$^3$, R$^4$, R$^5$, R$^6$, R$^x$, Z, m, n, and y are as defined above;

each R$^{14}$ is independently H, C$_1$-C$_3$alkyl (including methyl) or haloalkyl, cycloalkyl or cycloalkyl containing one or more heteroatoms selected from N, O or S; -(alkylene)$_m$-C$_3$-C$_8$ cycloalkyl, -(alkylene)$_m$-aryl, -(alkylene)$_m$-heterocyclo, -(alkylene)$_m$-heteroaryl, -(alkylene)$_m$-NR$^3$R$^4$, -(alkylene)$_m$-C(O)—NR$^3$R$^4$; -(alkylene)$_m$-O—R$^5$, -(alkylene)$_m$-S(O)$_n$—R$^5$, or -(alkylene)$_m$-S(O)$_n$—NR$^3$R$^4$ any of which may be optionally independently substituted with one or more R$^x$ groups as allowed by valence, and wherein two R$^x$ groups bound to the same or adjacent atoms may optionally combine to form a ring;

or two R$^{14}$ groups bonded to the same carbon can form an exocyclic double bond;

or two R$^{14}$ groups bonded to the same carbon can form a carbonyl group; and when the compound of Formula VI has a double bond, as indicated by the (----), in the 6-membered ring fused to the pyrimidine ring, two R$^{14}$ groups are present as allowed for in Formula VI above; or when the compound of Formula VI does not include a double bond, as indicated by the (----), in the 6-membered ring fused to the pyrimidine ring, four R$^{14}$ groups are present as allowed for in Formula VI above;

or a pharmaceutically acceptable salt, prodrug or isotopic variant, for example, partially or fully deuterated form thereof.

In an alternative embodiment, the invention is directed to compounds or the use of such compounds of Formula I, II, III, IV, or V:

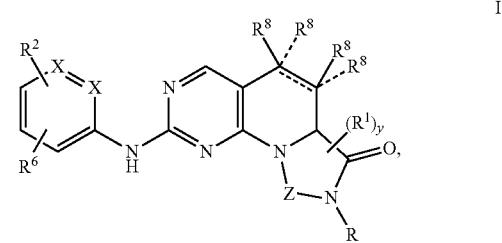

I

-continued

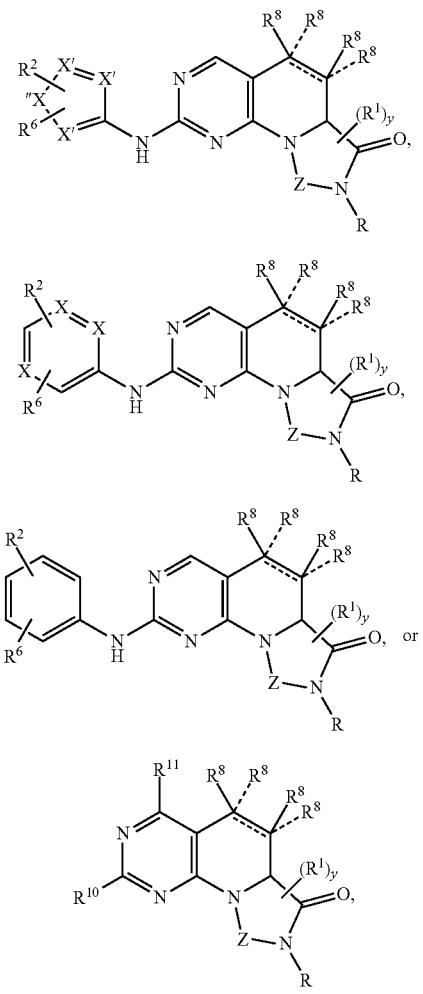

or a pharmaceutically acceptable salt thereof;
wherein:
Z is —(CH$_2$)$_x$— wherein x is 1, 2, 3 or 4 or —O—(CH$_2$)$_z$— wherein z is 2, 3 or 4;
each X is independently CH or N;
each X' is independently CH or N;
X" is independently CH$_2$, S or NH, arranged such that the moiety is a stable 5-membered ring; R, R$^8$, and R$^{11}$ are independently H, C$_1$-C$_3$alkyl (including methyl) or haloalkyl, cycloalkyl or cycloalkyl containing one or more heteroatoms selected from N, O or S; -(alkylene)$_m$-C$_3$-C$_8$ cycloalkyl, -(alkylene)$_m$-aryl, -(alkylene)$_m$-heterocyclo, -(alkylene)$_m$-heteroaryl, -(alkylene)$_m$-NR$^3$R$^4$, -(alkylene)$_m$-C(O)—NR$^3$R$^4$; -(alkylene)$_m$-O—R$^5$, -(alkylene)$_m$-S(O)$_n$—R$^5$, or -(alkylene)$_m$-S(O)$_n$—NR$^3$R$^4$ any of which, other than heterocyclo, may be optionally independently substituted with one or more R$^x$ groups as allowed by valance, and wherein two R$^x$ groups bound to the same or adjacent atoms may optionally combine to form a ring;
each leis independently aryl, alkyl, cycloalkyl or haloalkyl, wherein each of said alkyl, cycloalkyl and haloalkyl groups optionally includes O or N heteroatoms in place of a carbon in the chain and two R$^1$'s on adjacent ring atoms or on the same ring atom together with the ring atom(s) to which they are attached optionally form a 3-8-membered cycle;
y is 0, 1, 2, 3 or 4;
R$^2$ is -(alkylene)$_m$-heterocyclo, -(alkylene)$_m$-heteroaryl, -(alkylene)$_m$-NR$^3$R$^4$, -(alkylene)$_m$-C(O)—NR$^3$R$^4$; -(alkylene)$_m$-C(O)—O-alkyl; -(alkylene)$_m$-O—R$^5$, -(alkylene)$_m$-S(O)$_n$—R$^5$, or -(alkylene)$_m$-S(O)$_n$—NR$^3$R$^4$ any of which, other than heterocyclo, may be optionally independently substituted with one or more R$^x$ groups as allowed by valance, and wherein two R$^x$ groups bound to the same or adjacent atom may optionally combine to form a ring and wherein m is 0, 1, or 2 and n is 0, 1 or 2;
wherein heterocyclo may be optionally independently substituted with 1 to 3 R$^x$ groups as allowed by valance, and wherein two R$^x$ groups bound to the same or adjacent atom may optionally combine to form a ring;
R$^3$ and R$^4$ at each occurrence are independently:
(i) hydrogen or
(ii) alkyl, cycloalkyl, heterocyclo, aryl, heteroaryl, cycloalkylalkyl, heterocycloalkyl, arylalkyl, or heteroarylalkyl any of which, other than heterocyclo, may be optionally independently substituted with one or more R$^x$ groups as allowed by valance, and wherein two R$^x$ groups bound to the same or adjacent atom may optionally combine to form a ring; or R$^3$ and R$^4$ together with the nitrogen atom to which they are attached may combine to form a heterocyclo ring optionally independently substituted with one or more R$^x$ groups as allowed by valance, and wherein two R$^x$ groups bound to the same or adjacent atom may optionally combine to form a ring;
R$^5$ and R$^{5*}$ at each occurrence is:
(i) hydrogen or
(ii) alkyl, alkenyl, alkynyl, cycloalkyl, heterocyclo, aryl, heteroaryl, cycloalkylalkyl, heterocycloalkyl, arylalkyl, or heteroarylalkyl any of which, other than heterocyclo, may be optionally independently substituted with one or more R$^x$ groups as allowed by valance;
R$^x$ at each occurrence is independently, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)$_m$-OR$^5$, -(alkylene)$_m$-O-alkylene-OR$^5$, -(alkylene)$_m$-S(O)$_n$—R$^5$, -(alkylene)$_m$-NR$^3$R$^4$, -(alkylene)$_m$-CN, -(alkylene)$_m$-C(O)—R$^5$, -(alkylene)$_m$-C(S)—R$^5$, -(alkylene)$_m$-C(O)—OR$^5$, -(alkylene)$_m$-O—C(O)—R$^5$, -(alkylene)$_m$-C(S)—OR$^5$, -(alkylene)$_m$-C(O)-(alkylene)$_m$-NR$^3$R$^4$, -(alkylene)$_m$-C(S)—NR$^3$R$^4$, -(alkylene)$_m$-N(R$^3$)—C(O)—NR$^3$R$^4$, -(alkylene)$_m$-N(R$^3$)—C(S)—NR$^3$R$^4$, -(alkylene)$_m$-N(R$^3$)—C(O)—R$^5$, -(alkylene)$_m$-N(R$^3$)—C(S)—R$^5$, -(alkylene)$_m$-O—C(O)—NR$^3$R$^4$, -(alkylene)$_m$-O—C(S)—NR$^3$R$^4$, -(alkylene)$_m$-SO$_2$—NR$^3$R$^4$, -(alkylene)$_m$-N(R$^3$)—SO$_2$—R$^5$, -(alkylene)$_m$-N(R$^3$)—SO$_2$—NR$^3$R$^4$, -(alkylene)$_m$-N(R$^3$)—C(O)—OR$^5$, -(alkylene)$_m$-N(R$^3$)—C(S)—OR$^5$, or -(alkylene)$_m$-N(R$^3$)—SO$_2$—R$^5$; wherein: said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups, any of which, other than heterocyclo, may be further independently substituted with one or more -(alkylene)$_m$-CN, -(alkylene)$_m$-OR$^{5*}$, -(alkylene)$_m$-S(O)$_m$—R$^{5*}$, -(alkylene)$_m$-NR$^{3*}$R$^{4*}$, -(alkylene)$_m$-C(O)—R$^{5*}$, -(alkylene)$_m$-C(=S)R$^{5*}$, -(alkylene)$_m$-C(=O)OR$^{5*}$, -(alkylene)$_m$-OC(=O)R$^{5*}$, -(alkylene)$_m$-C(S)—OR$^{5*}$, -(alkylene)$_m$-C(O)—NR$^{3*}$R$^{4*}$, -(alkylene)$_m$-C(S)—NR$^{3*}$R$^{4*}$, -(alkylene)$_m$-N(R$^{3*}$)—C(O)—NR$^{3*}$R$^{4*}$, -(alkylene)$_m$-N(R$^{3*}$)—C(S)—NR$^{3*}$R$^{4*}$, -(alkylene)$_m$-N(R$^{3*}$)—C(O)—R$^{5*}$, -(alkylene)$_m$-N(R$^{3*}$)—C(S)—R$^{5*}$, -(alkylene)$_m$—O—C(O)—NR$^3$*R$^4$*, -(alkylene)$_m$-O—C(S)—NR$^3$*R$^4$*, -(alkylene)$_m$-SO$_2$—NR$^3$*R$^4$*, -(alkylene)$_m$-N(R$^3$*)—SO$_2$—R$^5$*,   -(alkylene)$_m$-N(R$^3$*)—SO$_2$—NR$^3$*R$^4$*,   -(alkylene)$_m$-N(R$^3$*)—C(O)—OR$^5$*, -(alkylene)$_m$-N(R$^3$*)—C(S)—OR$^5$*, or -(alkylene)$_m$-N(R$^3$*)—SO$_2$—R$^5$*, and wherein heterocycle may be further independently substituted with one to three substitutions selected from -(alkylene)$_m$-CN,   -(alkylene)$_m$-OR$^5$*,   -(alkylene)$_m$-S(O)$_n$—R$^5$*, -(alkylene)$_m$-NR$^3$*R$^4$*, -(alkylene)$_m$-C(O)—R$^5$*, -(alkylene)$_m$-C(=S)R$^5$*, -(alkylene)$_m$-C(=O)OR$^5$*, -(alkylene)$_m$-OC(=O)R$^5$*, -(alkylene)$_m$-C(S)—OR$^5$*,   -(alkylene)$_m$-C(O)—NR$^3$*R$^4$*, -(alkylene)$_m$-C(S)—NR$^3$*R$^4$*, -(alkylene)$_m$-N(R$^3$*)—C(O)—NR$^3$*R$^4$*,   -(alkylene)$_m$-N(R$^3$*)—C(S)—NR$^3$*R$^4$*, -(alkylene)$_m$-N(R$^3$*)—C(O)—R$^5$*, -(alkylene)$_m$-N(R$^3$*)—C(S)—R$^5$*, -(alkylene)$_m$-O—C(O)—NR$^3$*R$^4$*,   -(alkylene)$_m$-O—C(S)—NR$^3$*R$^4$*, -(alkylene)$_m$-SO$_2$—NR$^3$*R$^4$*, -(alkylene)$_m$-N(R$^3$*)—SO$_2$—R$^5$*,   -(alkylene)$_m$-N(R$^3$*)—SO$_2$—NR$^3$*R$^4$*, -(alkylene)$_m$-N(R$^3$*)—C(O)—OR$_5$*,   -(alkylene)$_m$-N(R$^3$*)—C(S)—OR$^5$*, or -(alkylene)$_m$-N(R$^3$*)—SO$_2$—R$^5$*;

n is 0, 1 or 2, and m is 0, 1; or 2 and

R$^3$* and R$^4$* at each occurrence are independently:
(i) hydrogen or
(ii) alkyl, alkenyl, alkynyl, cycloalkyl, heterocyclo, aryl, heteroaryl, cycloalkylalkyl, heterocycloalkyl, arylalkyl, or heteroarylalkyl any of which, other than heterocyclo, may be optionally independently substituted with one or more R$^x$ groups as allowed by valance; or R$^3$* and R$^4$* together with the nitrogen atom to which they are attached may combine to form a heterocyclo ring optionally independently substituted with one or more R$^x$ groups as allowed by valance;

R$^6$ is H, absent, or lower alkyl, -(alkylene)$_m$-heterocyclo, -(alkylene)$_m$-heteroaryl, -(alkylene)$_m$-NR$^3$R$^4$, -(alkylene)$_m$-C(O)—NR$^3$R$^4$; -(alkylene)$_m$-O—R$^5$, -(alkylene)$_m$-S(O)$_n$—R$^5$, or -(alkylene)$_m$-S(O)$_n$—NR$^3$R$^4$ any of which, other than heterocyclo, may be optionally independently substituted with one or more R$^x$ groups as allowed by valence, and wherein two R$^x$ groups bound to the same or adjacent atoms may optionally combine to form a ring; and R$^{10}$ is (i) NHR$^A$, wherein R$^A$ is unsubstituted or substituted C$_1$-C$_8$ alkyl, cycloalkylalkyl, or -TT-RR, C$_1$-C$_8$ cycloalkyl or cycloalkyl containing one or more heteroatoms selected from N, O, and S; TT is an unsubstituted or substituted C$_1$-C$_8$ alkyl or C$_3$-C$_8$ cycloalkyl linker; and RR is a hydroxyl, unsubstituted or substituted C$_1$-C$_6$ alkoxy, amino, unsubstituted or substituted C$_1$-C$_6$ alkylamino, unsubstituted or substituted di-C$_1$-C$_6$ alkylamino, unsubstituted or substituted C$_6$-C$_{10}$ aryl, unsubstituted or substituted heteroaryl comprising one or two 5- or 6-member rings and 1-4 heteroatoms selected from N, O and S, unsubstituted or substituted C$_3$-C$_{10}$ carbocycle, or unsubstituted or substituted heterocycle comprising one or two 5- or 6-member rings and 1-4 heteroatoms selected from N, O and S; or (ii) —C(O)—R$^{12}$ or —C(O)O—R$^{13}$, wherein R$^{12}$ is NHR$^A$ or R$^A$ and R$^{13}$ is R$^A$;

when the compound of Formula I, II, III, IV, or V has a double bond, as indicated by the (----), in the 6-membered ring fused to the pyrimidine ring, two R$^8$ groups are present as allowed for in Formula I, II, III, IV, or V above; or when the compound of Formula I, II, III, IV, or V does not include a double bond, as indicated by the (----), in the 6-membered ring fused to the pyrimidine ring, four R$^8$ groups are present as allowed for in Formula I, II, III, IV, or V above;

wherein each heteroaryl is an aryl ring system that contains one or more heteroatoms selected from the group O, N and S, wherein the ring nitrogen and sulfur atom(s) are optionally oxidized, and nitrogen atom(s) are optionally quarternized;

wherein each aryl is a carbocyclic aromatic system containing one or two rings, wherein such rings may be attached together in a fused manner, and wherein each aryl may have 1 or more R$^x$ substituents;

wherein each heterocyclo is a saturated or partially saturated heteroatom-containing ring radical, where the heteroatoms may be selected from nitrogen, sulfur and oxygen, wherein each heterocyclo is a monocyclic 6-8 membered ring or a 5-16 membered bicyclic ring system, and wherein each heterocyclo may have 1 to 3 R$^x$ substituents;

or a pharmaceutically acceptable salt, prodrug or isotopic variant, for example, partially or fully deuterated form thereof.

In an alternative embodiment, the term "aryl" means a carbocyclic aromatic system containing one or two rings wherein such rings may have be attached together in a fused manner, which may have 1 or more substituents selected from lower alkyl, hydroxyl, halo, haloalkyl, nitro, cyano, alkoxy and lower alkylamino, In an alternative embodiment, the term "heterocyclyl" or "heterocyclo" means a saturated or partially saturated heteroatom-containing ring radical, where the heteroatoms may be selected from nitrogen, sulfur and oxygen, which may have 1 to 3 substituents selected from hydroxyl, Boc, halo, haloalkyl, cyano, lower alkyl, lower aralkyl, oxo, lower alkoxy, amino and lower alkylamino, wherein the heterocyclic ring is a monocyclic 6-8 membered rings, or a 5-16 membered bicyclic ring systems which can include bridged fused and spiro-fused bicyclic ring systems, and which does not include rings containing —O—O—. —O—S— or —S—S— portion.

In an alternative embodiment, the term "heteroaryl" means an aryl ring system that contains one or more heteroatoms selected from the group O, N and S, wherein the ring nitrogen and sulfur atom(s) are optionally oxidized, and nitrogen atom(s) are optionally quarternized;

In one embodiment, two R$^8$ groups bonded to the same carbon can form an exocyclic double bond. In another embodiment, two R$^8$ groups bonded to the same carbon can form a carbonyl group.

In an alternative embodiment, the invention is directed to compounds or the use of such compounds of Formula VI:

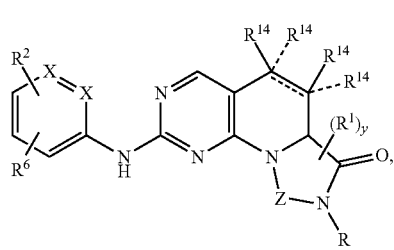

VI wherein R, R$^2$, R$^3$, R$^4$, R$^5$, R$^6$, R$^x$, Z, m, n, and y are as defined above;

each $R^{14}$ is independently H, $C_1$-$C_3$alkyl (including methyl) or haloalkyl, cycloalkyl or cycloalkyl containing one or more heteroatoms selected from N, O or S; -(alkylene)$_m$-$C_3$-$C_8$ cycloalkyl, -(alkylene)$_m$-aryl, -(alkylene)$_m$-heterocyclo, -(alkylene)$_m$-heteroaryl, -(alkylene)$_m$-NR$^3$R$^4$, -(alkylene)$_m$-C(O)—NR$^3$R$^4$; -(alkylene)$_m$-O—R$^5$, -(alkylene)$_m$-S(O)$_n$—R$^5$, or -(alkylene)$_m$-S(O)$_n$—NR$^3$R$^4$ any of which, other than heterocyclo, may be optionally independently substituted with one or more R$^x$ groups as allowed by valence, and wherein two R$^x$ groups bound to the same or adjacent atoms may optionally combine to form a ring;

or two $R^{14}$ groups bonded to the same carbon can form an exocyclic double bond;

or two $R^{14}$ groups bonded to the same carbon can form a carbonyl group; and when the compound of Formula VI has a double bond, as indicated by the (----), in the 6-membered ring fused to the pyrimidine ring, two $R^{14}$ groups are present as allowed for in Formula VI above; or when the compound of Formula VI does not include a double bond, as indicated by the (----), in the 6-membered ring fused to the pyrimidine ring, four $R^{14}$ groups are present as allowed for in Formula VI above;

wherein each heteroaryl is an aryl ring system that contains one or more heteroatoms selected from the group O, N and S, wherein the ring nitrogen and sulfur atom(s) are optionally oxidized, and nitrogen atom(s) are optionally quarternized;

wherein each aryl is a carbocyclic aromatic system containing one or two rings, wherein such rings may be attached together in a fused manner, and wherein each aryl may have 1 or more R$^x$ substituents;

wherein each heterocyclo is a saturated or partially saturated heteroatom-containing ring radical, where the heteroatoms may be selected from nitrogen, sulfur and oxygen, wherein each heterocyclo is a monocyclic 6-8 membered ring or a 5-16 membered bicyclic ring system, and wherein each heterocyclo may have 1 to 3 R$^x$ substituents;

or a pharmaceutically acceptable salt, prodrug or isotopic variant, for example, partially or fully deuterated form thereof.

In some aspects, the compound is of Formula I or Formula II and $R^6$ is absent.

In some aspects, the compound is of Formula III:

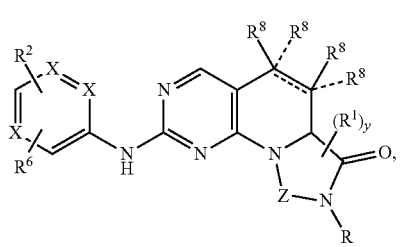

III and the variables are as defined for compounds of Formulae I and II and pharmaceutically acceptable salts thereof.

In some aspects, R$^x$ is not further substituted.

In some aspects, $R^2$ is -(alkylene)$_m$-heterocyclo, -(alkylene)$_m$-heteroaryl, -(alkylene)$_m$-NR$^3$R$^4$, -(alkylene)$_m$-C(O)—NR$^3$R$^4$; -(alkylene)$_m$-O—R$^5$, -(alkylene)$_m$-S(O)$_n$—R$^5$, or -(alkylene)$_m$-S(O)$_n$—NR$^3$R$^4$ any of which may be optionally independently substituted with one or more R$^x$ groups as allowed by valence, and wherein two R$^x$ groups bound to the same or adjacent atom may optionally combine to form a ring and wherein m is 0 or 1 and n is 0, 1 or 2.

In some aspects, $R^8$ is hydrogen or $C_1$-$C_3$alkyl.

In some aspects, R is hydrogen or $C_1$-$C_3$alkyl.

In some aspects, $R^2$ is -(alkylene)$_m$-heterocyclo, -(alkylene)$_m$-NR$^3$R$^4$, -(alkylene)$_m$-C(O)—NR$^3$R$^4$, -(alkylene)$_m$-C(O)—O-alkyl or -(alkylene)$_m$-OR$^5$ any of which may be optionally independently substituted with one or more R$^x$ groups as allowed by valence, and wherein two R$^x$ groups bound to the same or adjacent atom may optionally combine to form a ring.

In some aspects, $R^2$ is -(alkylene)$_m$-heterocyclo, -(alkylene)$_m$-NR$^3$R$^4$, -(alkylene)$_m$-C(O)—NR$^3$R$^4$, -(alkylene)$_m$-C(O)—O-alkyl or -(alkylene)$_m$-OR$^5$ without further substitution.

In some aspects, m in $R^2$ is 1. In a further aspect, the alkylene in $R^2$ is methylene.

In some aspects, $R^2$ is

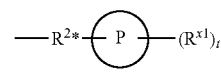

wherein:

R$^{2*}$ is a bond, alkylene, -(alkylene)$_m$-O-(alkylene)$_m$-, -(alkylene)$_m$-C(O)-(alkylene)$_m$-, -(alkylene)$_m$-S(O)$_2$-(alkylene)$_m$- or -(alkylene)$_m$-NH-(alkylene)$_m$- wherein each m is independently 0 or 1;

P is a 4- to 8-membered mono- or bicyclic saturated heterocyclyl group; each R$^{x1}$ is independently -(alkylene)$_m$-(C(O))$_m$-(alkylene)$_m$-(N(R$^N$))$_m$-(alkyl)$_m$ wherein each m is independently 0 or 1 provided at least one m is 1, —(C(O))—O-alkyl, -(alkylene)$_m$-cycloalkyl wherein m is 0 or 1, —N(R$^N$)-cycloalkyl, —C(O)-cycloalkyl, -(alkylene)$_m$-heterocyclyl wherein m is 0 or 1, or —N(R$^N$)-heterocyclyl, —C(O)-heterocyclyl, —S(O)$_2$-(alkylene)$_m$ wherein m is 1 or 2, wherein:

R$^N$ is H, $C_1$ to $C_4$ alkyl or $C_1$ to $C_6$ heteroalkyl, and wherein two R$^{x1}$ can, together with the atoms to which they attach on P, which may be the same atom, form a ring; and t is 0, 1 or 2.

In some aspects, each R$^{x1}$ is only optionally substituted by unsubstituted alkyl, halogen or hydroxy.

In some aspects, R$^{x1}$ is hydrogen or unsubstituted $C_1$-$C_4$ alkyl.

In some aspects, at least one R$^{x1}$ is -(alkylene)$_m$-heterocyclyl wherein m is 0 or 1.

In some aspects, $R^2$ is

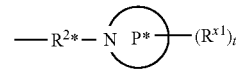

wherein P* is a 4- to 8-membered mono- or bicyclic saturated heterocyclyl group.

In some aspects, $R^2$ is

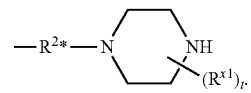

In some aspects, $R^2$ is

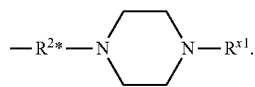

In some aspects, $R^2$ is

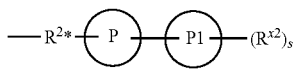

wherein:
$R^{2*}$ is a bond, alkylene, -(alkylene)$_m$-O-(alkylene)$_m$-, -(alkylene)$_m$-C(O)-(alkylene)$_m$-, -(alkylene)$_m$-S(O)$_2$-(alkylene)$_m$- or -(alkylene)$_m$-NH-(alkylene)$_m$- wherein each m is independently 0 or 1;

P is a 4- to 8-membered mono- or bicyclic saturated heterocyclyl group;

P1 is a 4- to 6-membered monocyclic saturated heterocyclyl group; each $R^{x2}$ is independently hydrogen or alkyl; and s is 0, 1 or 2.

In some aspects, $R^2$ is

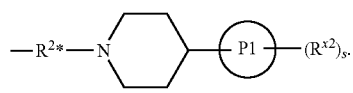

In some aspects, P1 includes at least one nitrogen.

In some aspects, any alkylene in $R^{2*}$ in any previous aspect is not further substituted.

Figure 2:
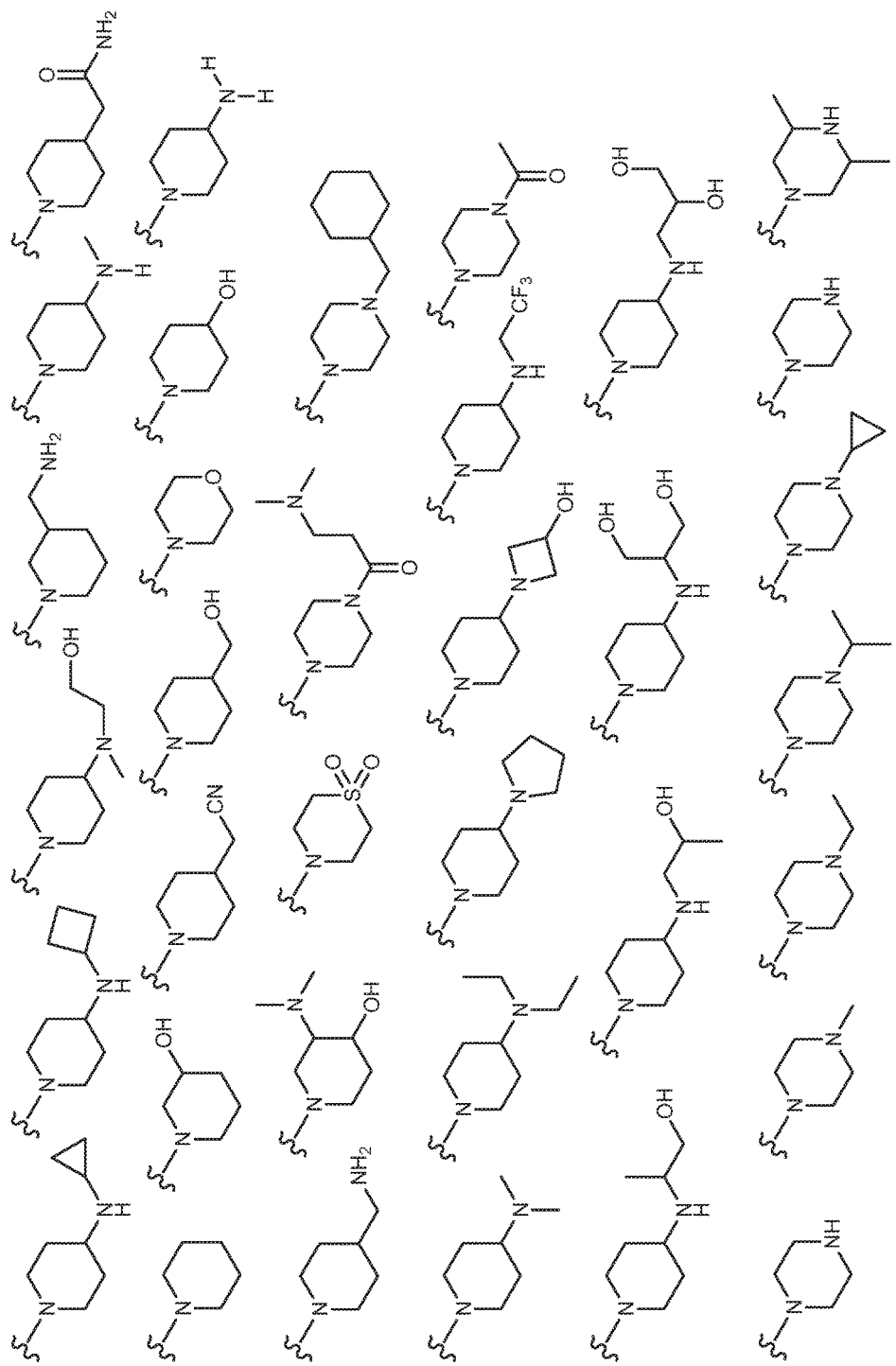
FIGS. 2-4 illustrate several exemplary embodiments of $R^2$ of the compounds of the invention.
Figure 3:
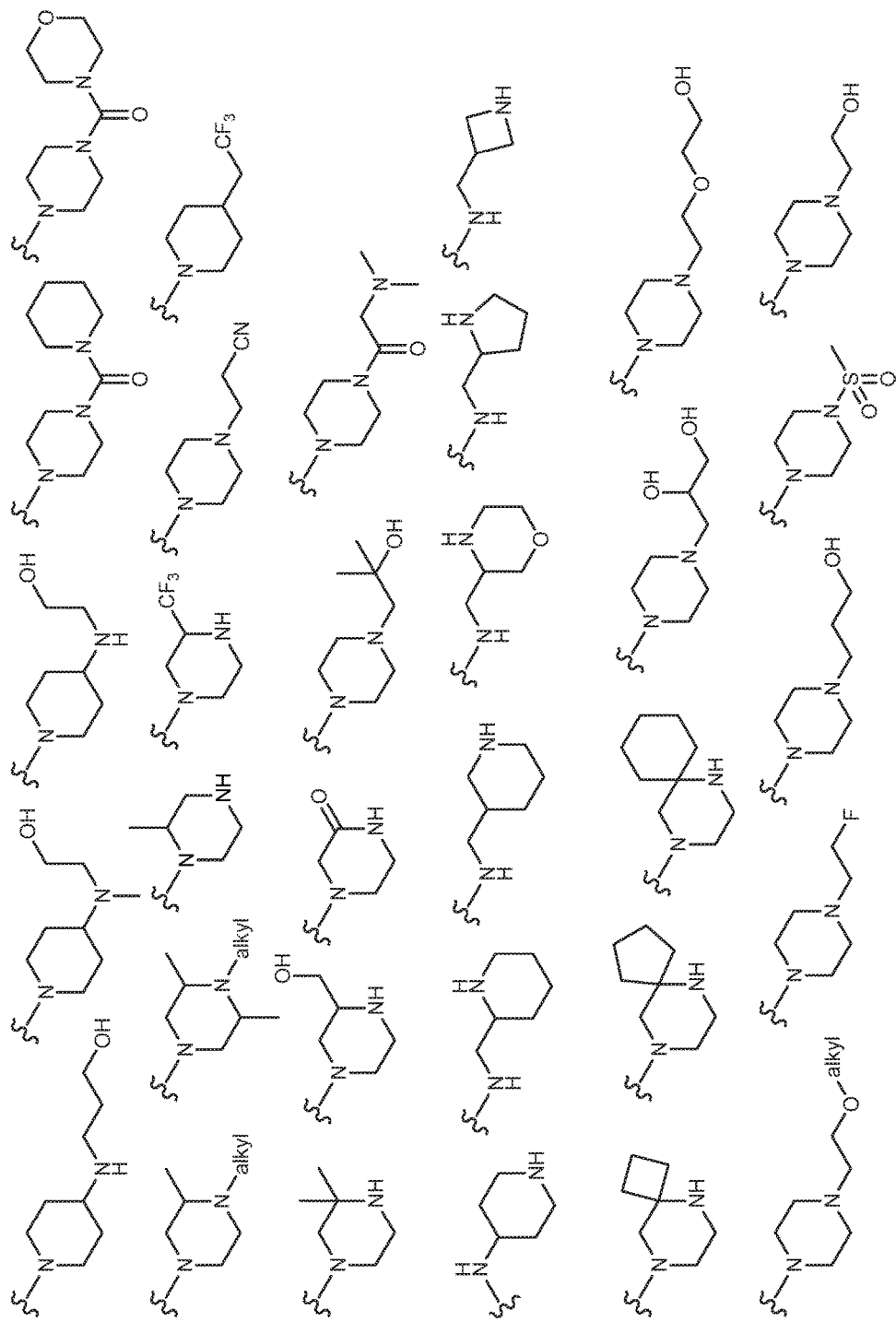
Figure 4:
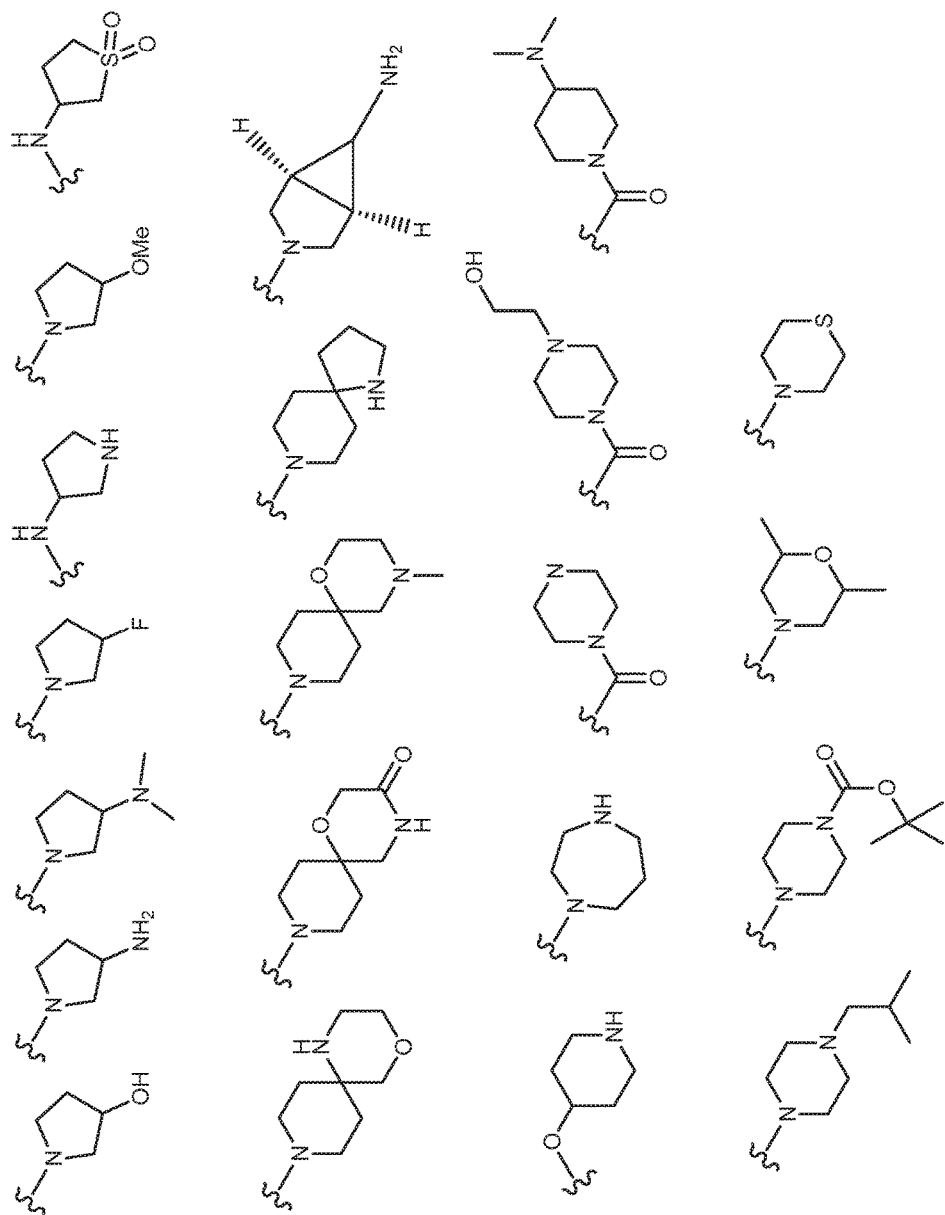
Figure 5A:
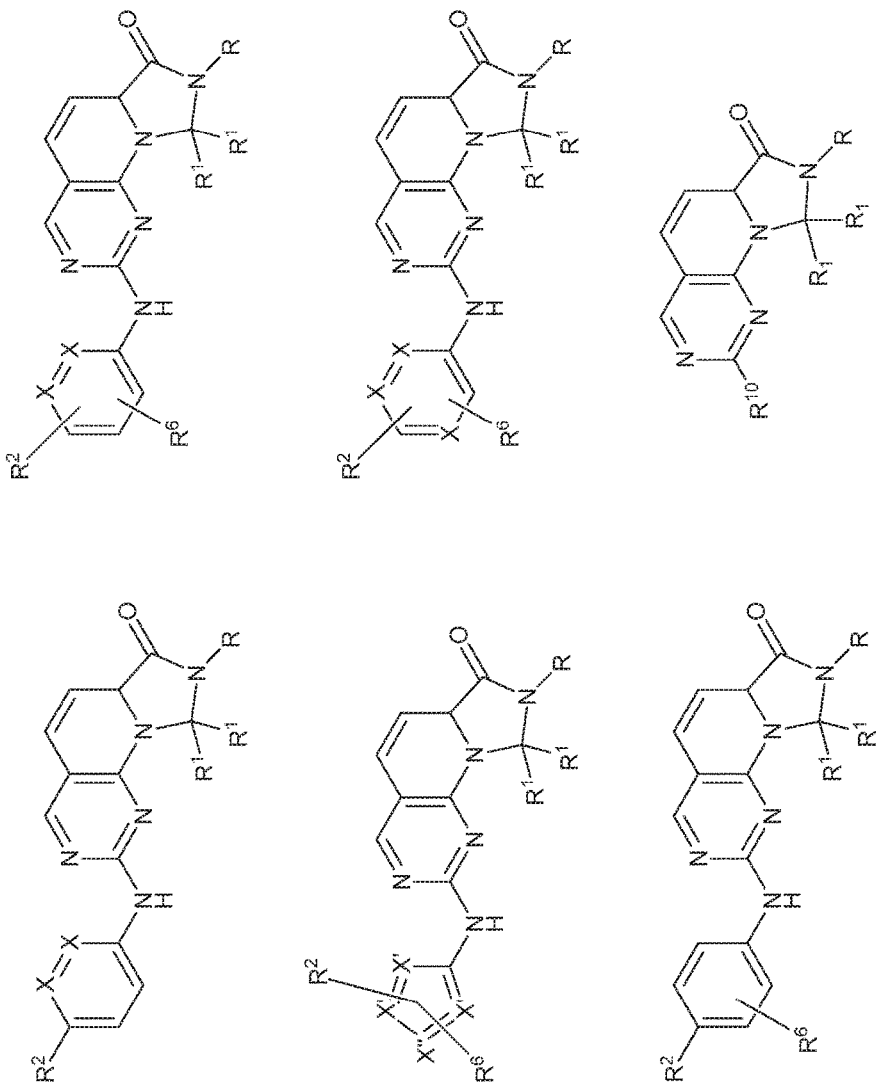
FIGS. 5A-5C, 6A-6D, 7A-7C, 8A-8B, and 9A-9F illustrate several exemplary embodiments of the core structure of the compounds of the invention.
Figure 5B:
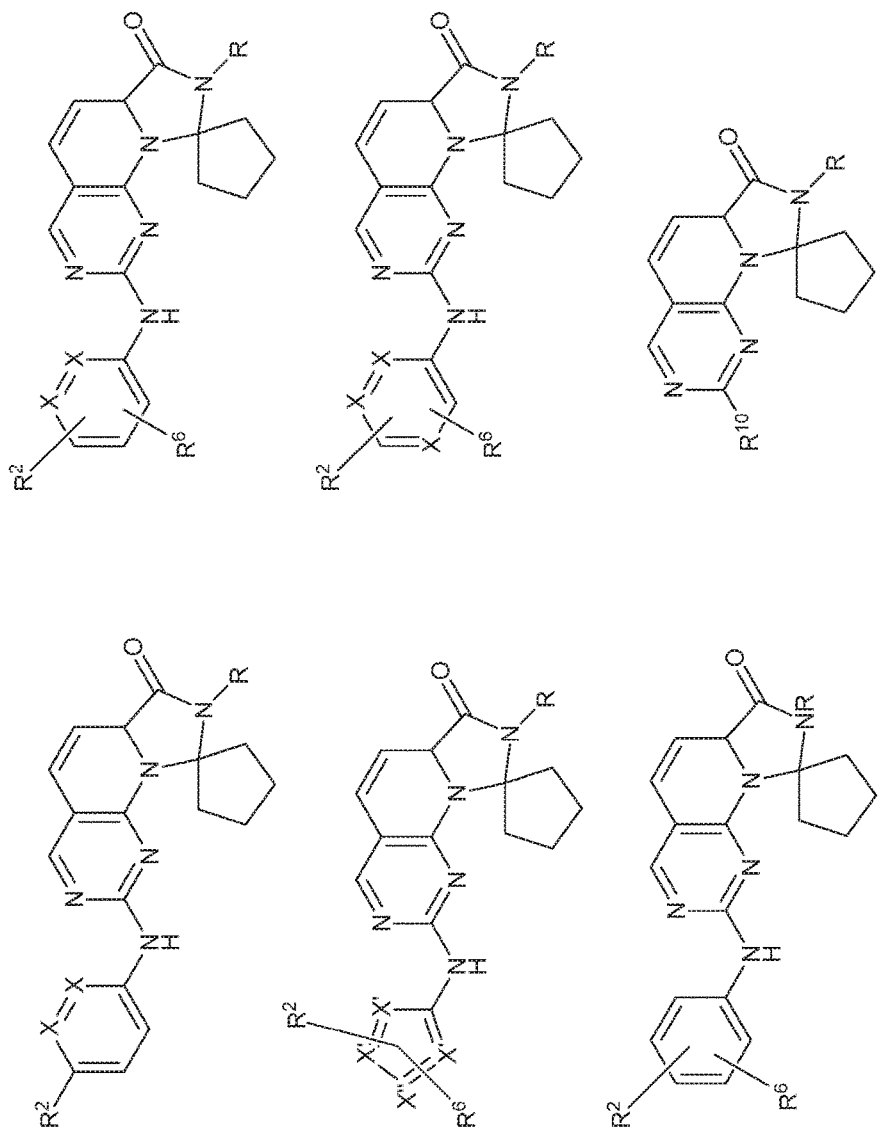
Figure 5C:
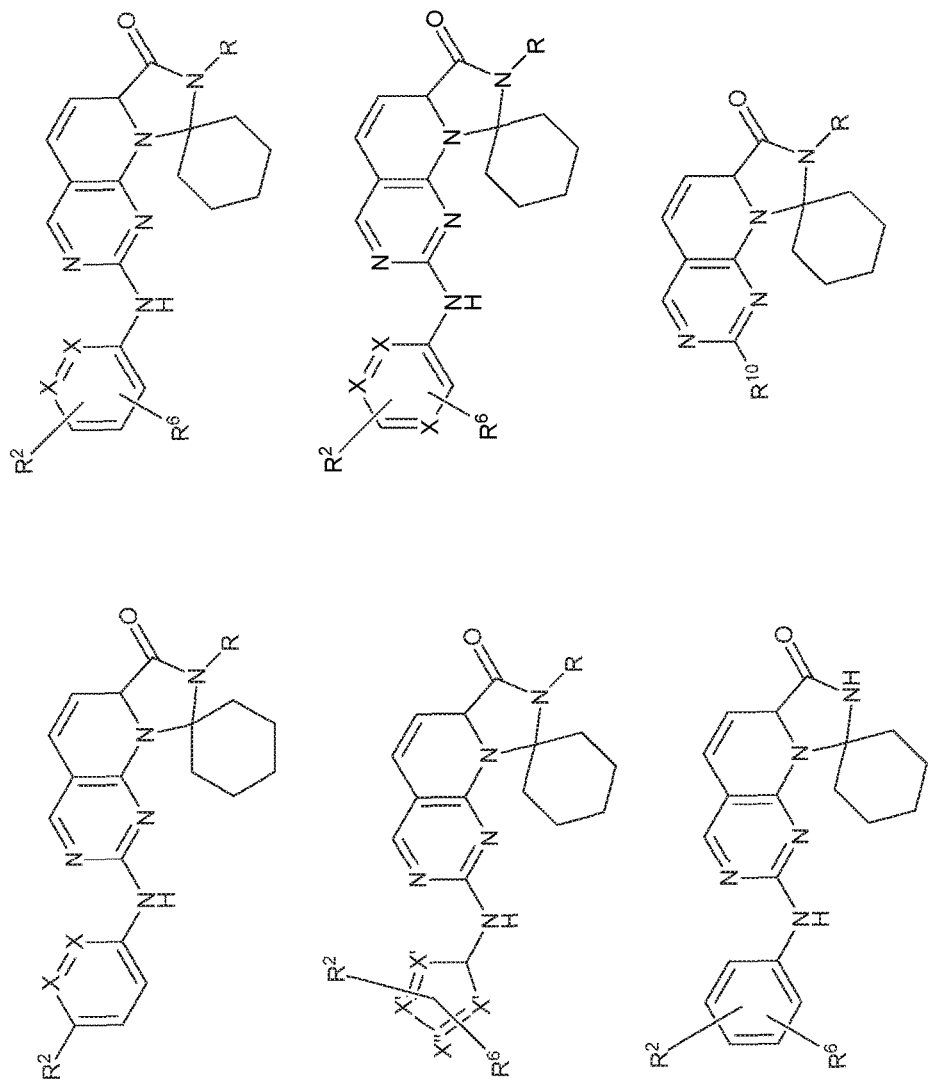
Figure 6A:
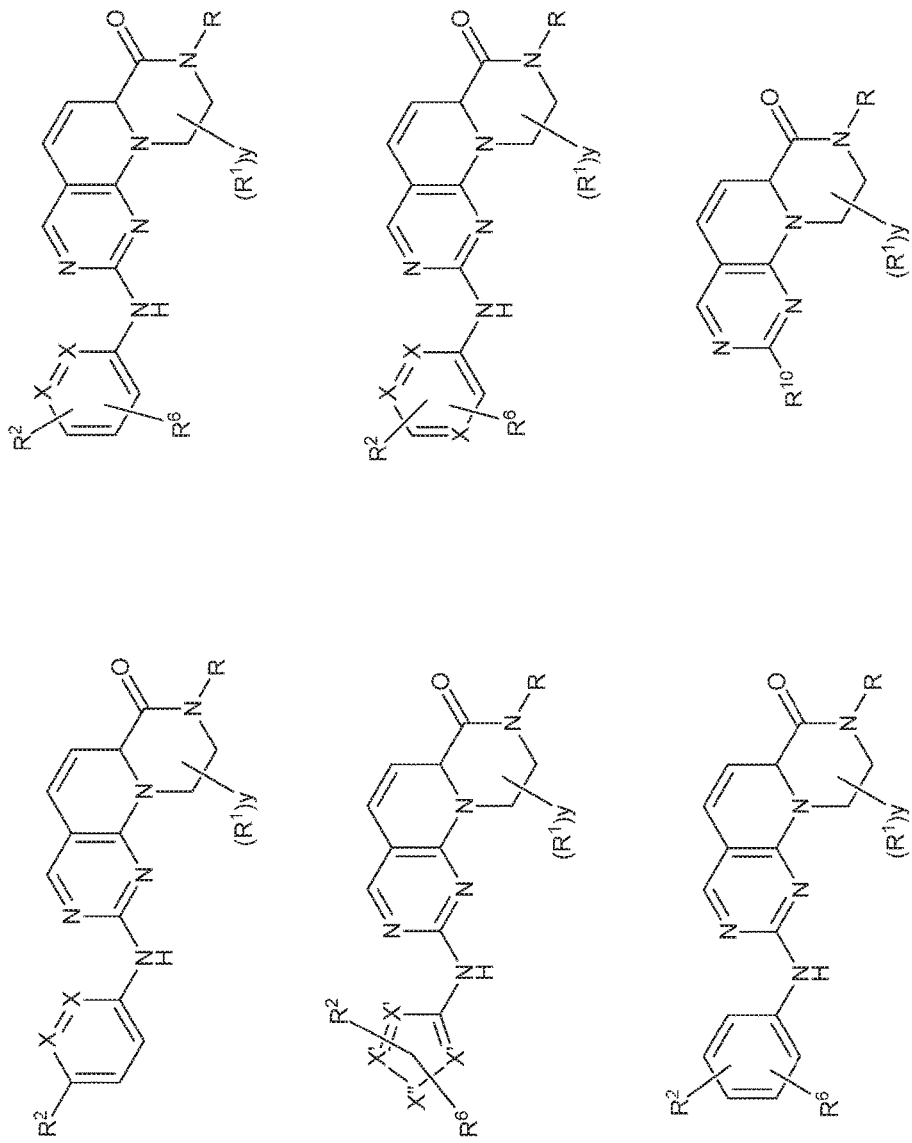
Figure 6B:
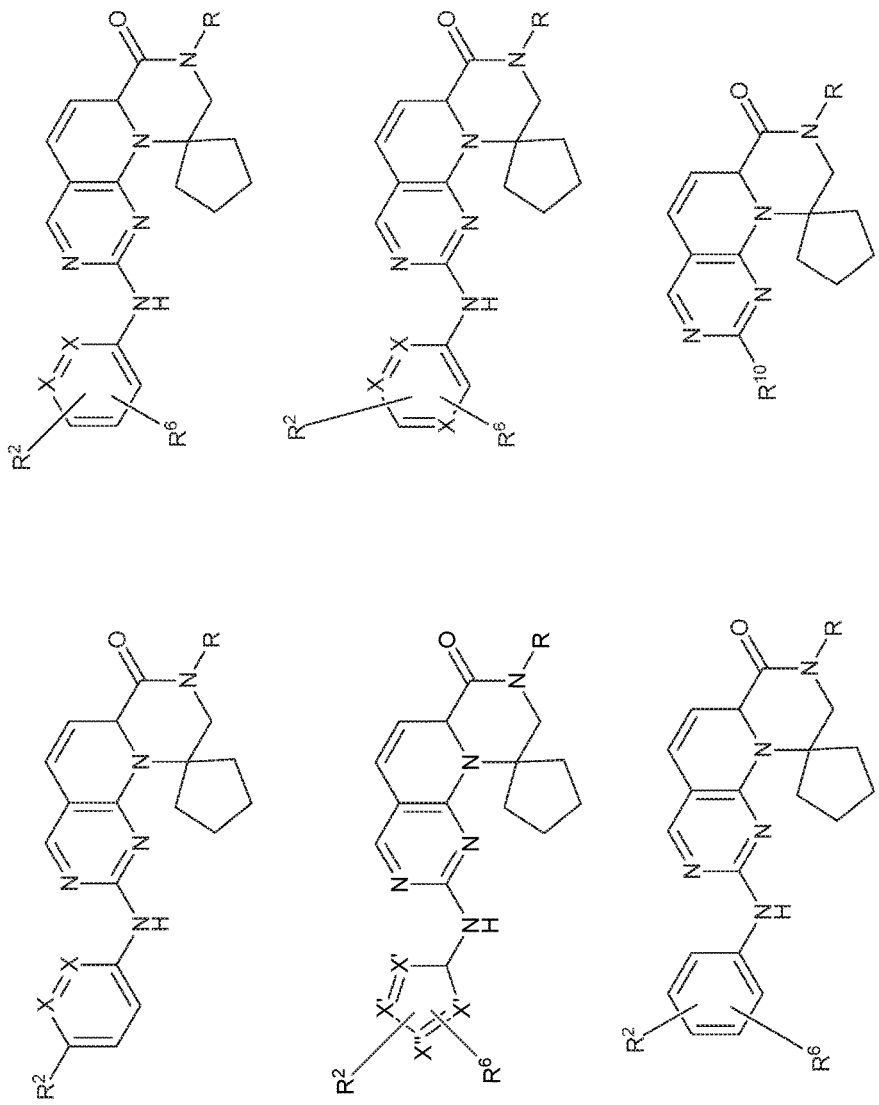
Figure 6C:
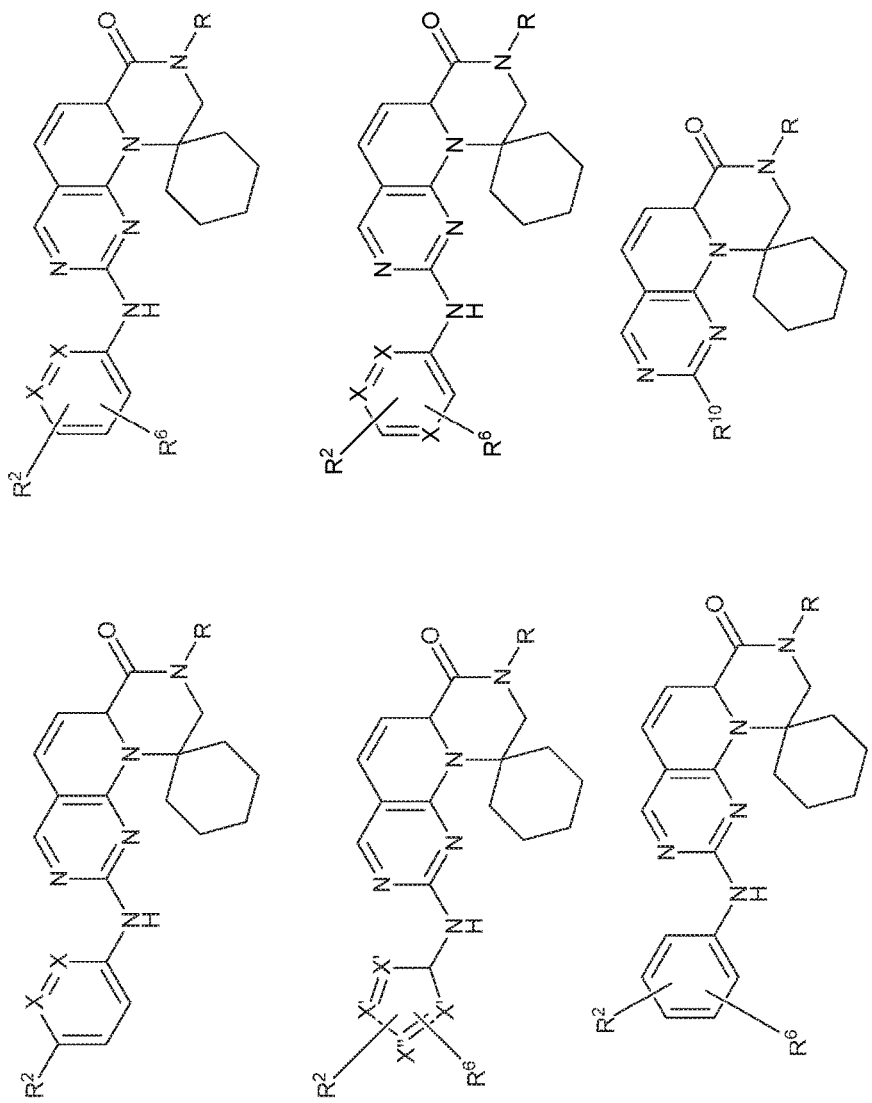
Figure 6D:
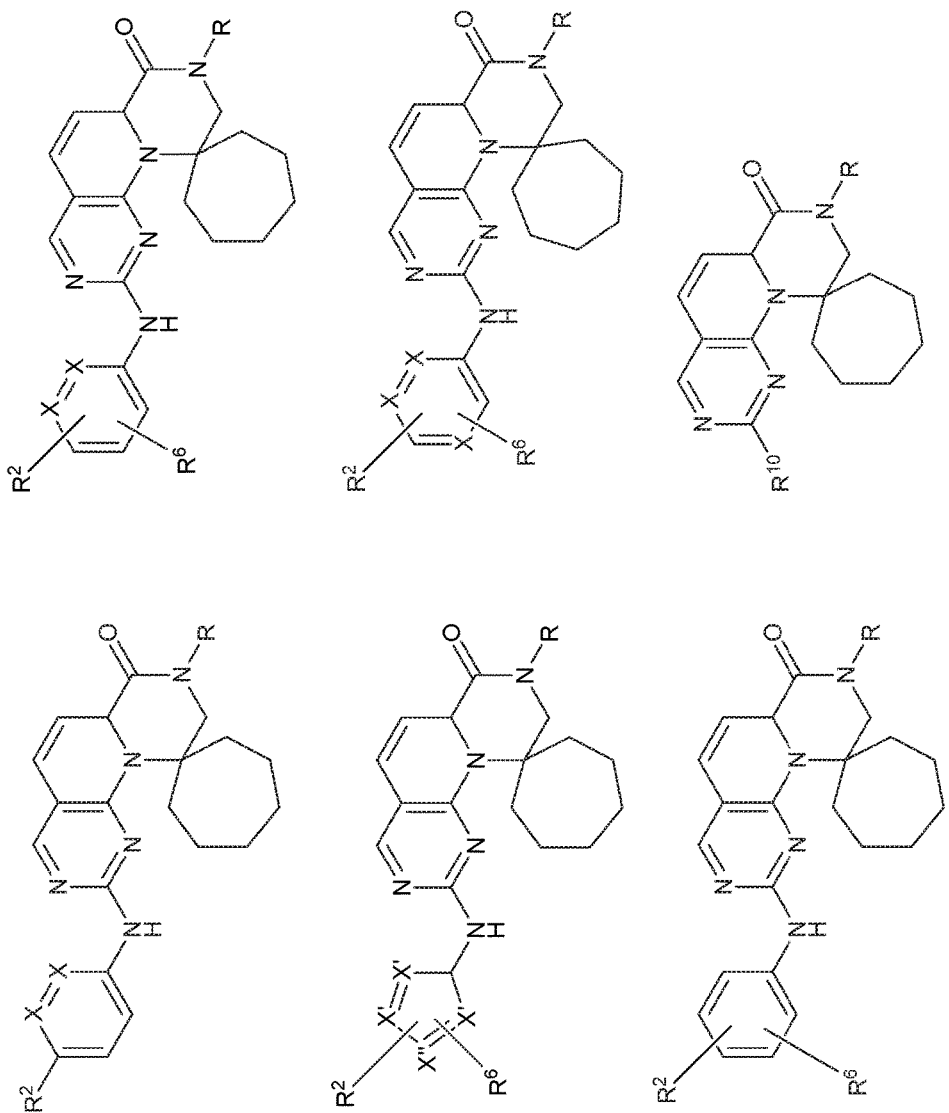
Figure 7A:
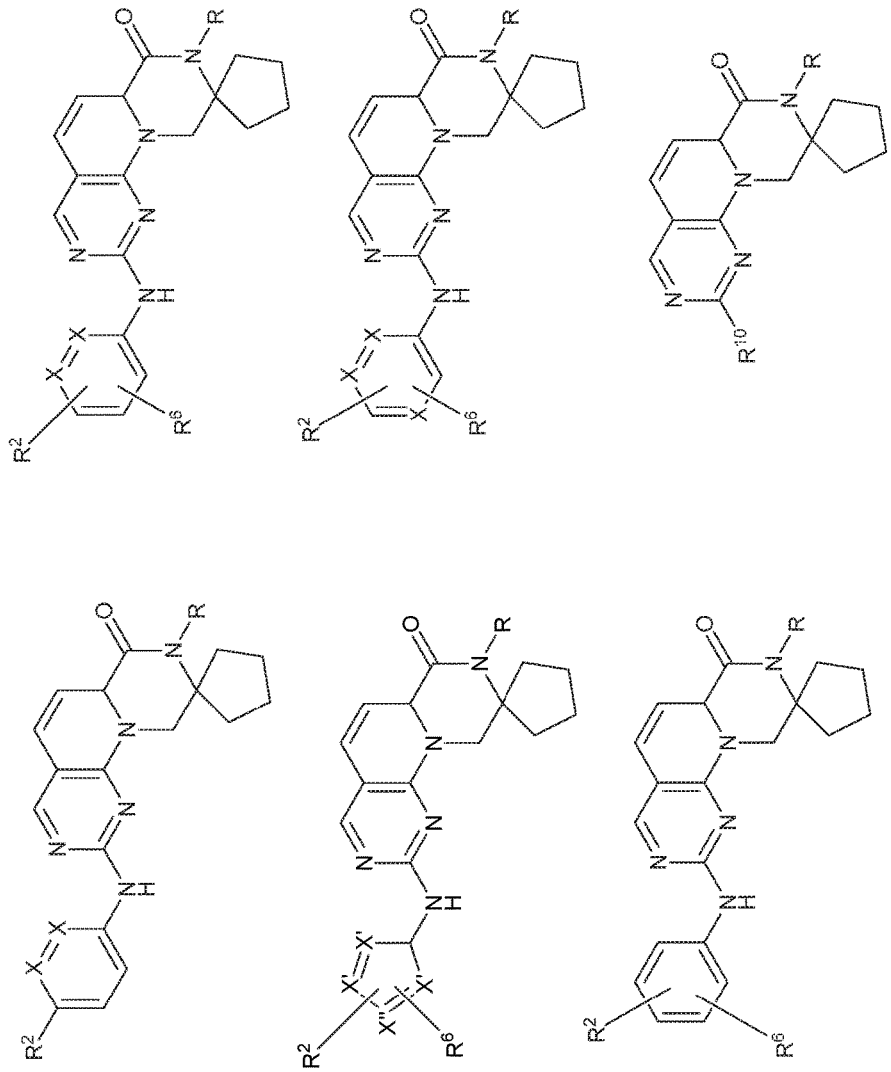
Figure 7B:
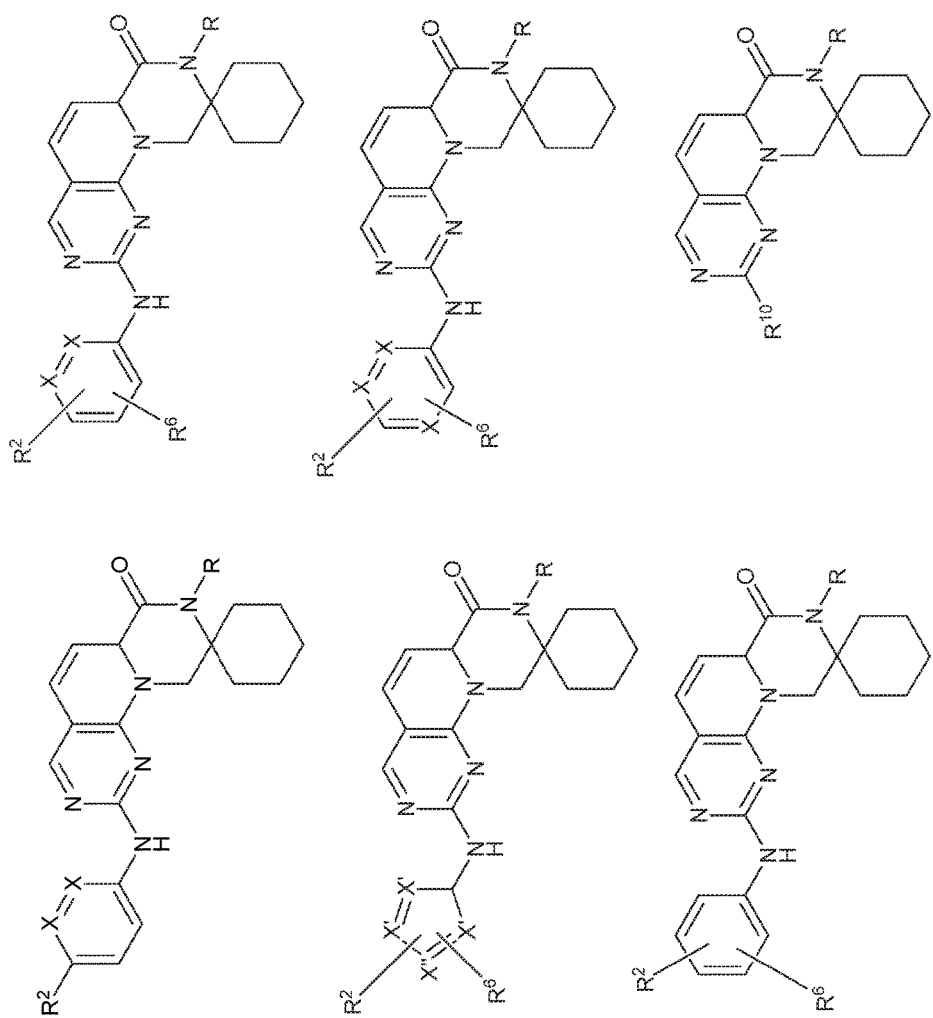
Figure 7C:
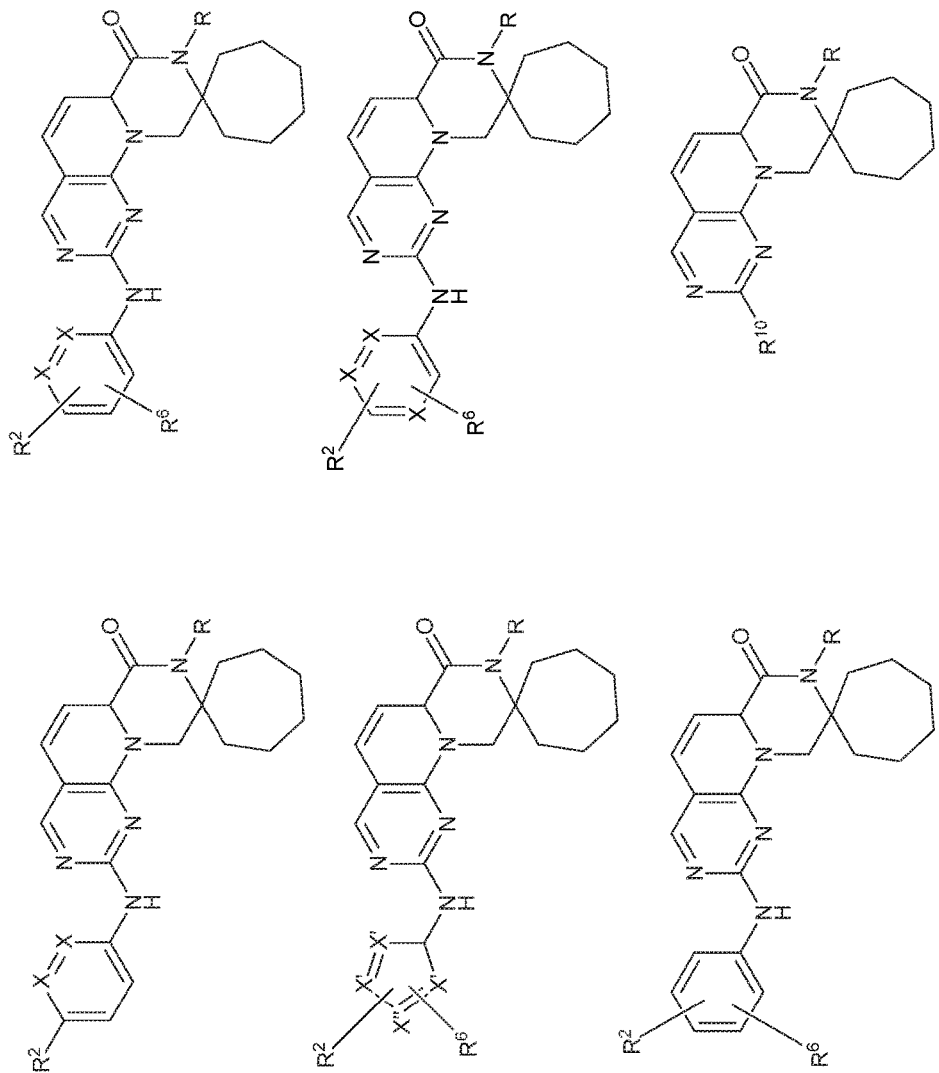
Figure 8A:
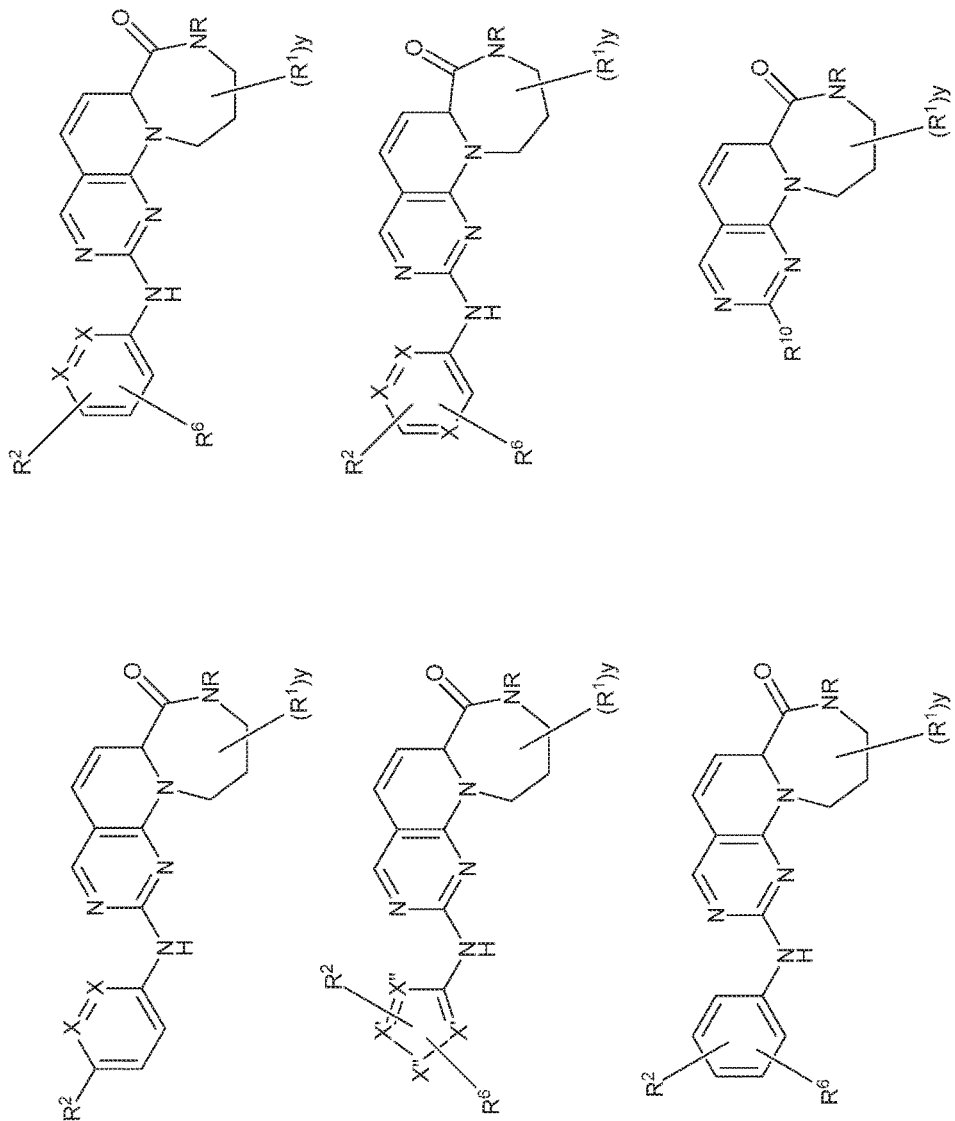
Figure 8B:
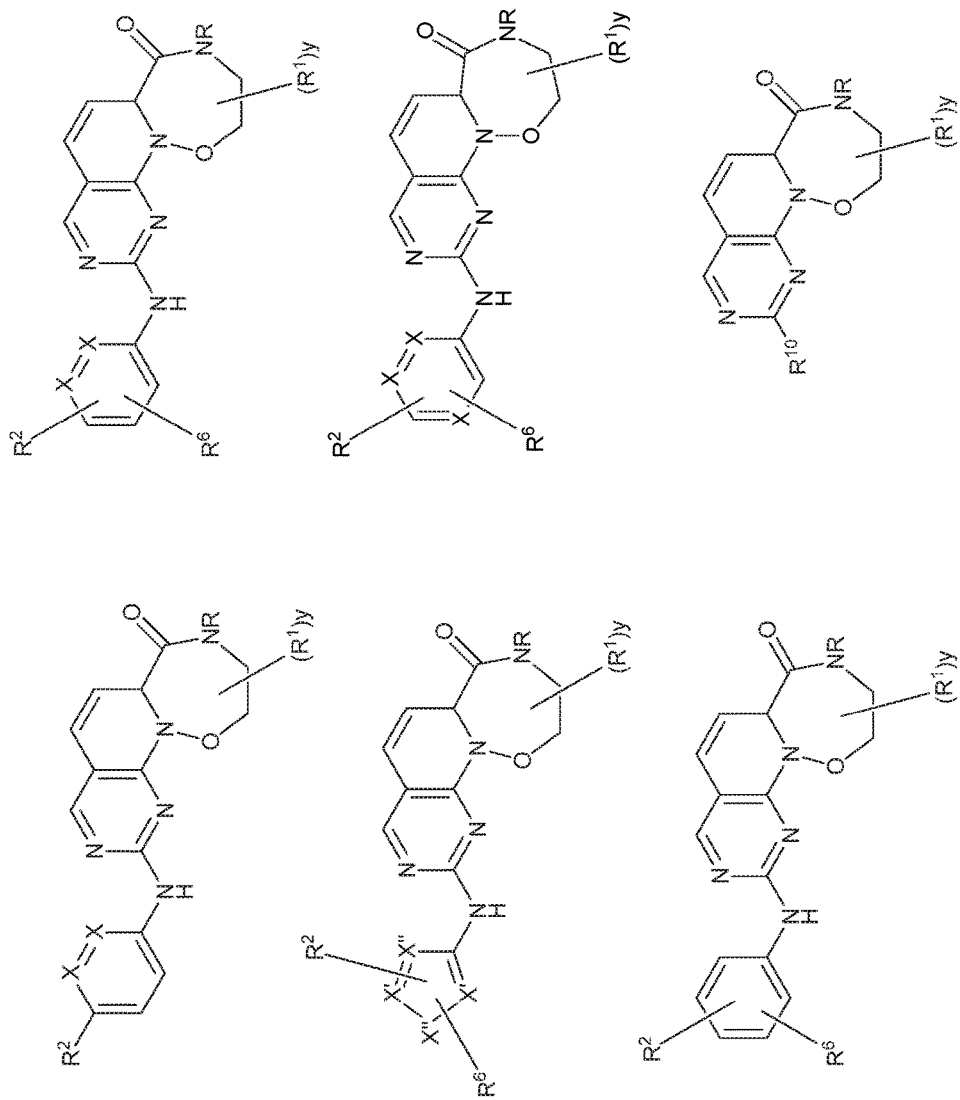
Figure 9A:
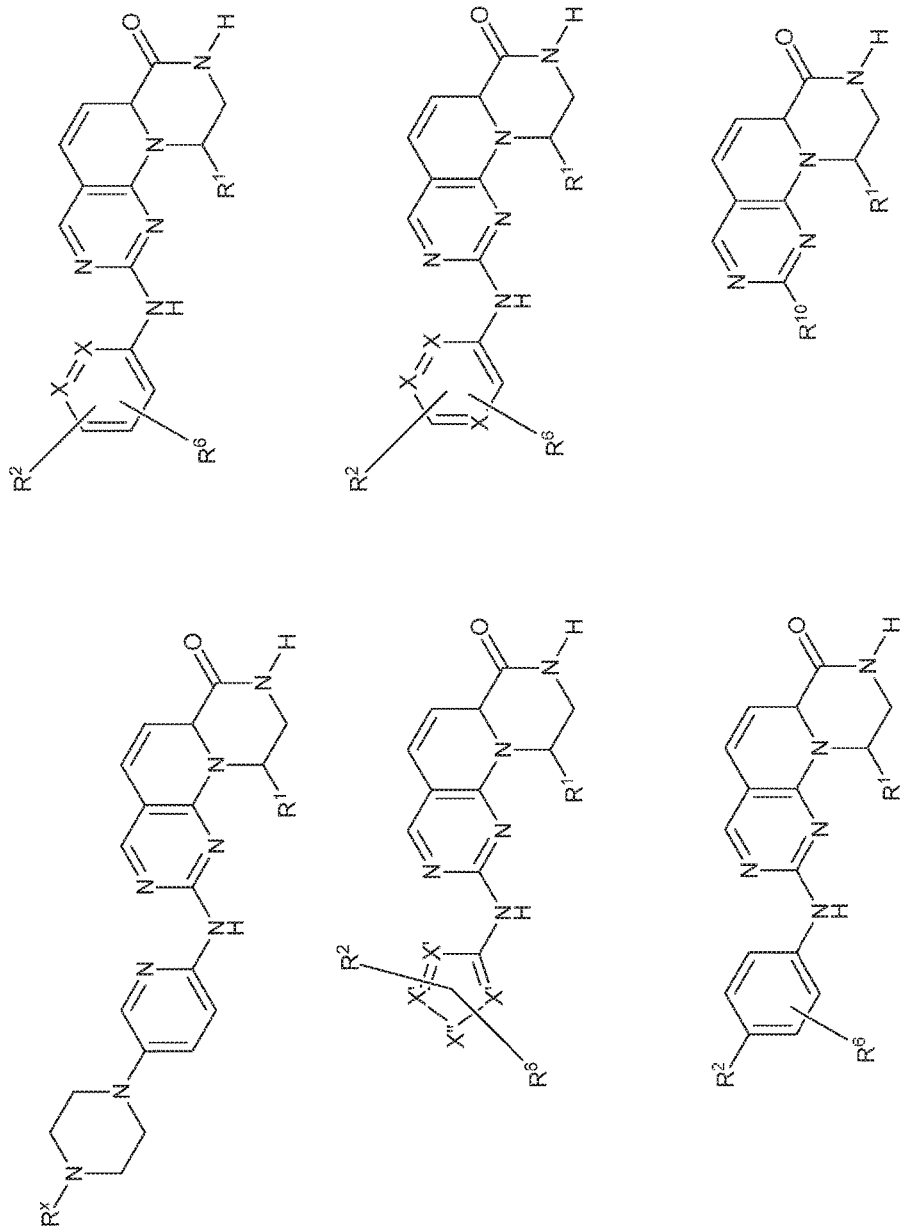
Figure 9B:
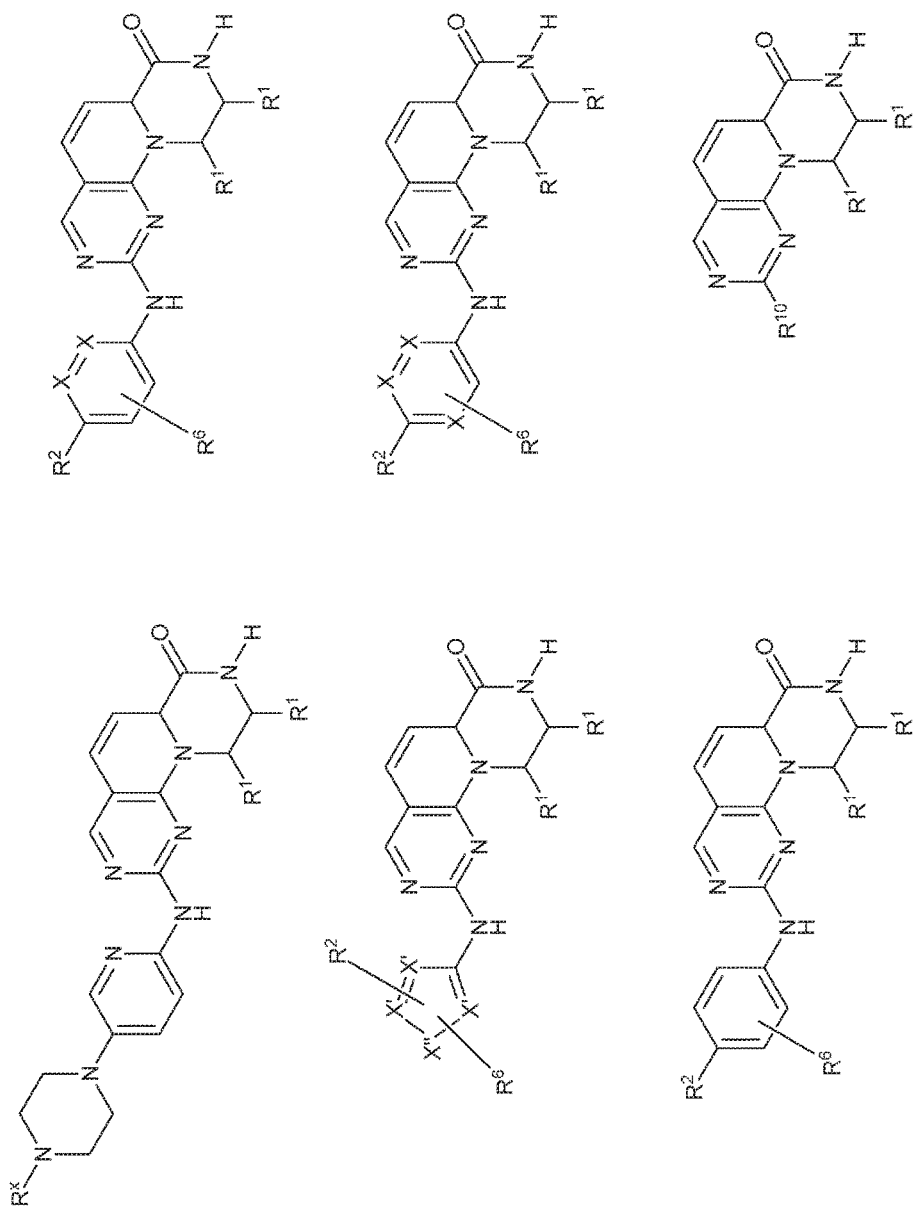
Figure 9C:
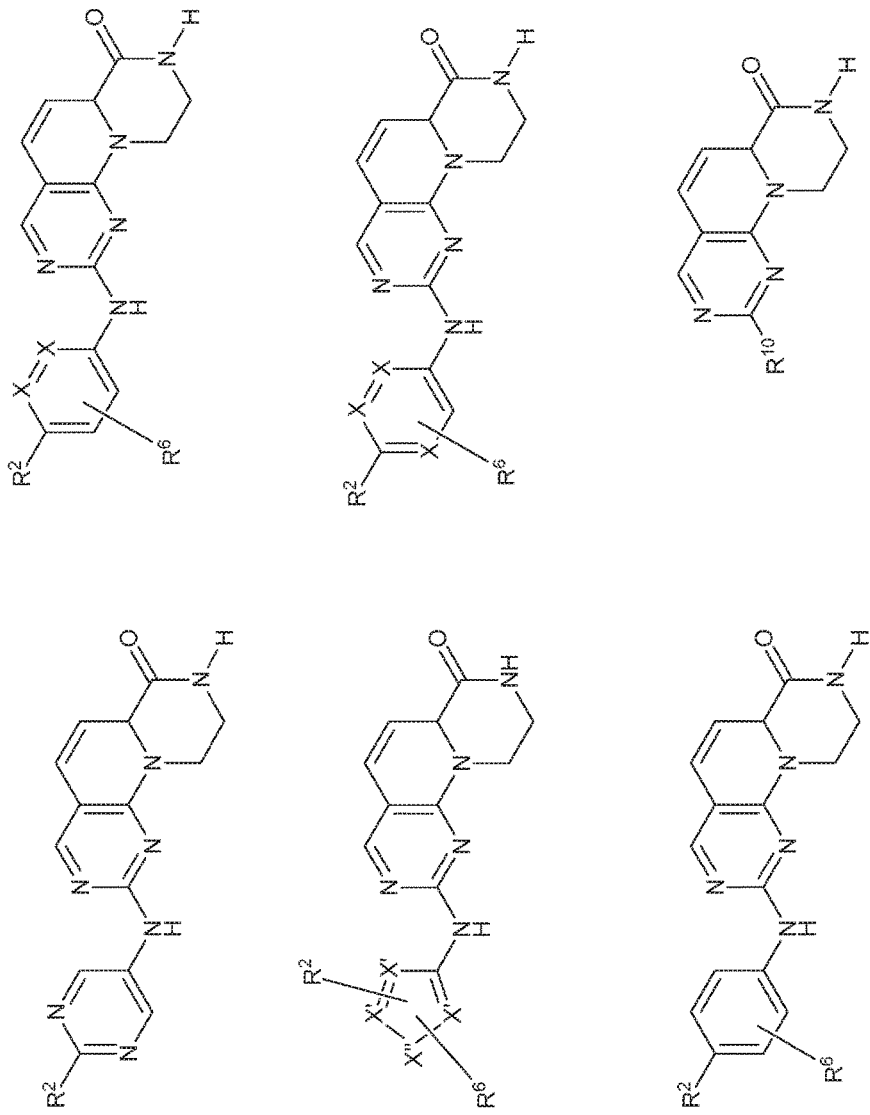
Figure 9D:
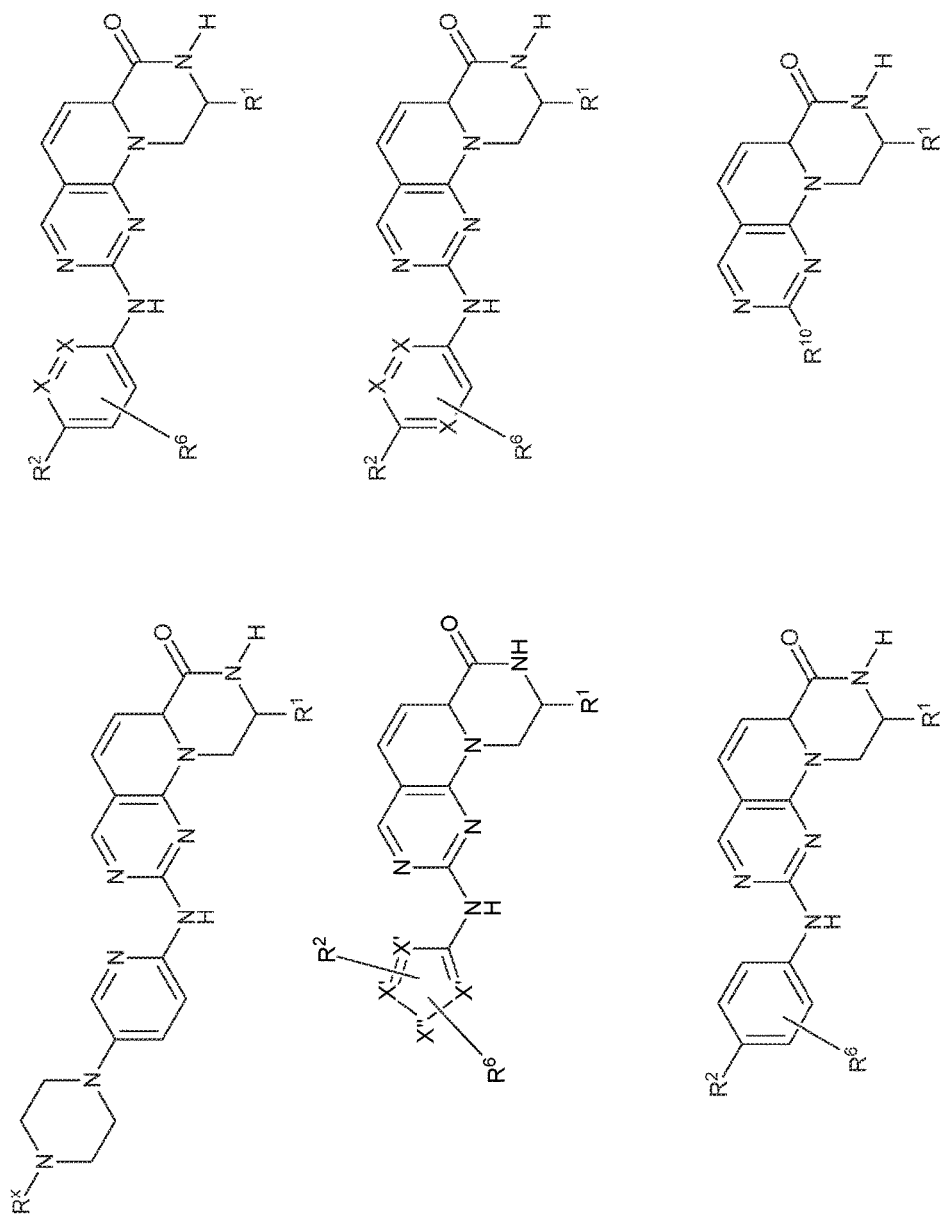
Figure 9E:
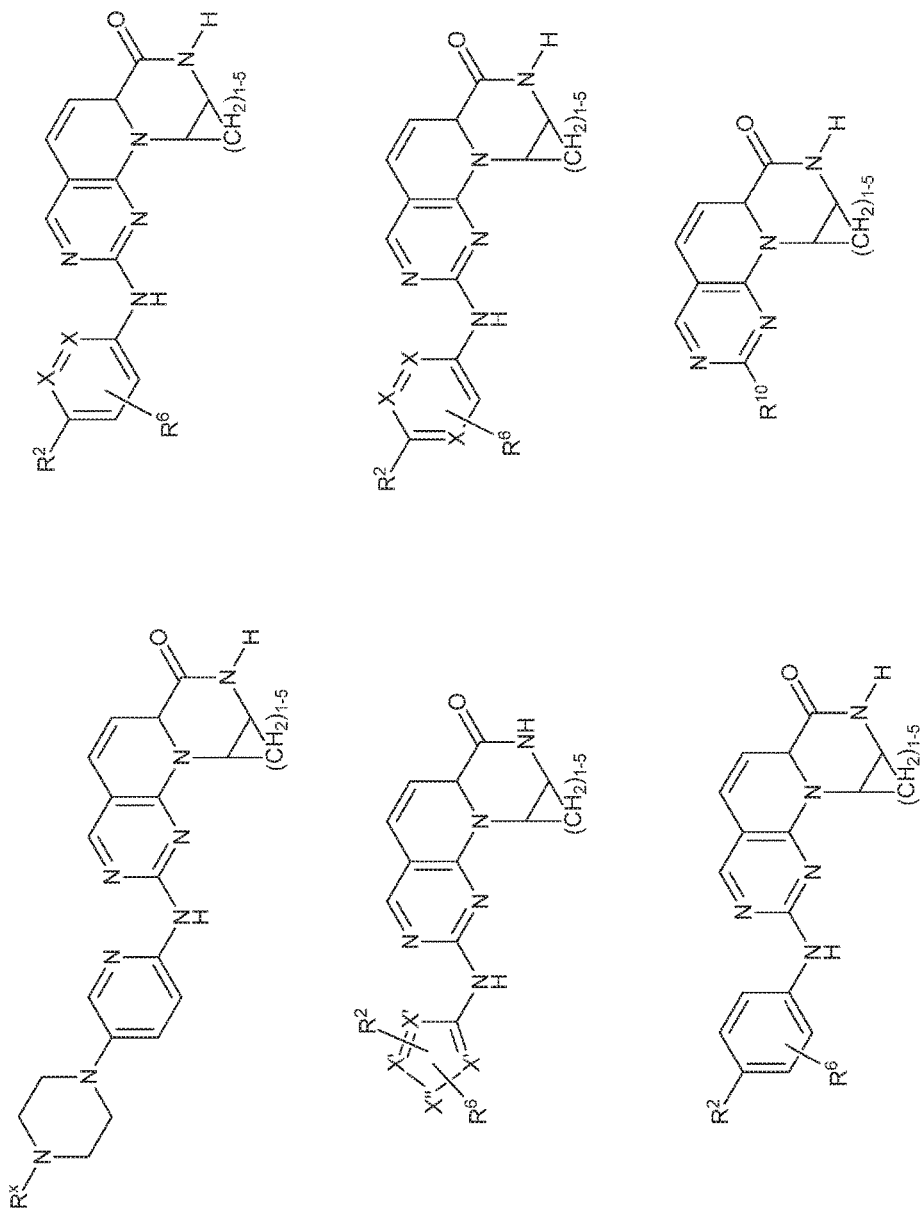
Figure 9F:
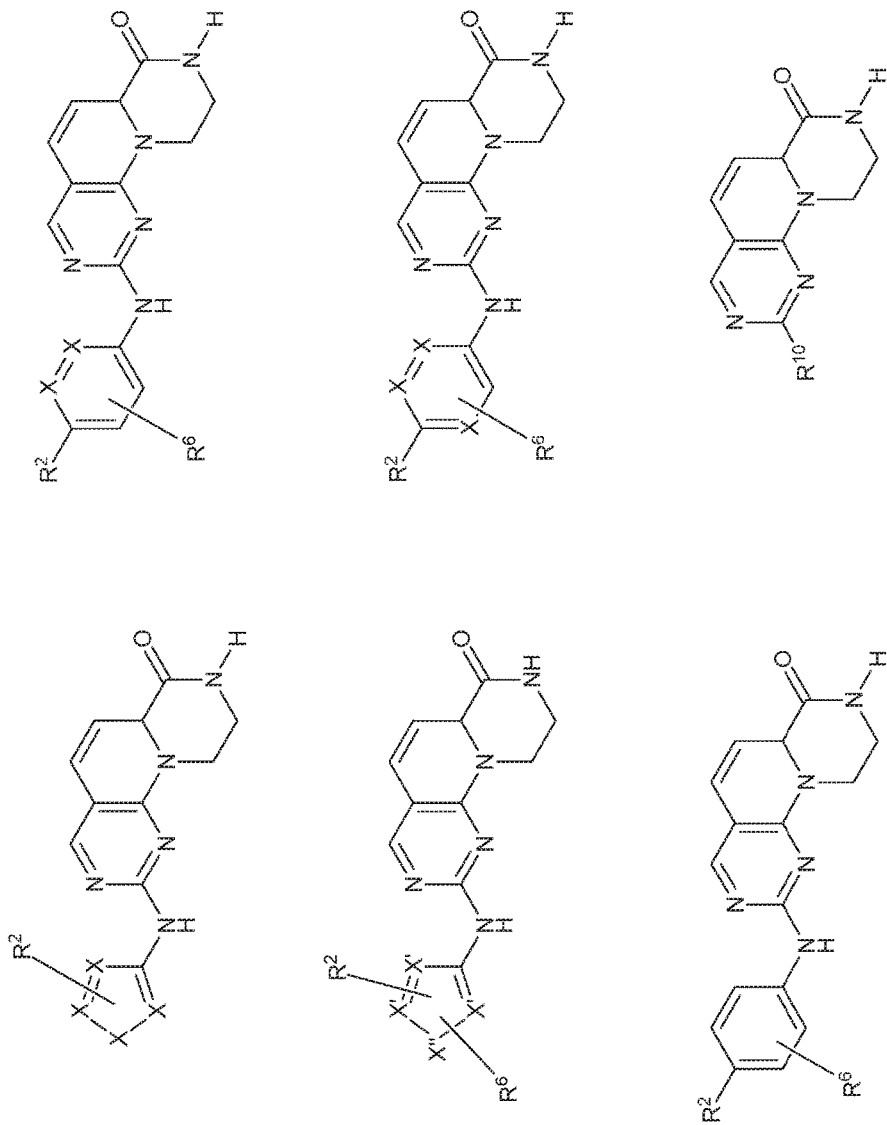

In some aspects, $R^2$ is selected from the structures depicted in FIGS. 2-4.

In some aspects, $R^2$ is

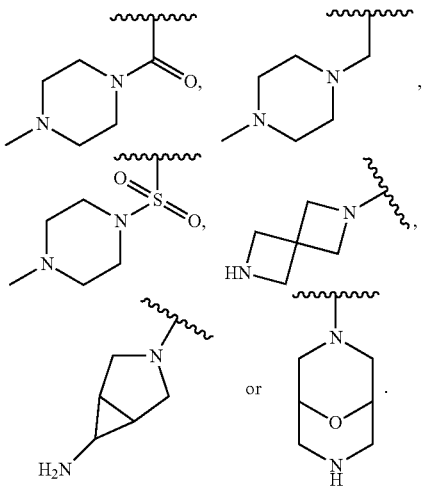

In some aspects, the compound has general Formula I and more specifically one of the general structures disclosed in FIGS. 5A-9F wherein the variables are as previously defined.

In some aspects, the compound has general Formula Ia:

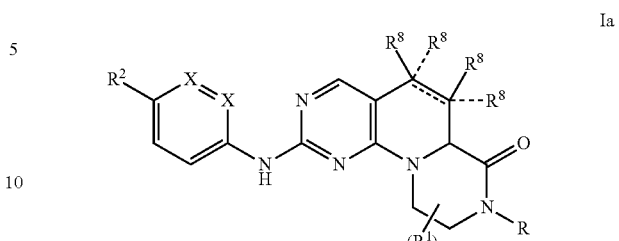

wherein $R^1$, $R^2$, R, $R^8$, X and y are as previously defined.

In some embodiments, the compound has Formula Ia and R is alkyl.

In some embodiments, the compound has Formula Ia and R is H.

In some embodiments, the compound has Formula Ia and $R^2$ is

—R$^{2*}$—N P*—(R$^{x1}$)$_t$ wherein P* is a 4- to 8-membered mono- or bicyclic saturated heterocyclyl group and $R^{2*}$, $R^{x1}$ and t are as previously defined.

In some embodiments, the compound has Formula Ia and $R^2$ is

—R$^{2*}$—N P*—(R$^{x1}$)$_t$ wherein P* is a 4- to 8-membered mono- or bicyclic saturated heterocyclyl group, $R^{x1}$ is hydrogen or unsubstituted $C_1$-$C_4$ alkyl and $R^{2*}$ is as previously defined.

In some embodiments, the compound has Formula Ib:

Ib wherein R, $R^2$ and $R^8$ are as previously defined.

In some embodiments, the compound has Formula Ib and R is alkyl.

In some embodiments, the compound has Formula Ib and R is H.

In some embodiments, the compound has Formula Ib and $R^2$ is

—R$^{2*}$—N P*—(R$^{x1}$)$_t$ wherein P* is a 4- to 8-membered mono- or bicyclic saturated heterocyclyl group and $R^{2*}$, $R^d$ and t are as previously defined.

In some embodiments, the compound has Formula Ib and $R^2$ is

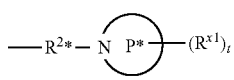

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the compound has Formula Ic:

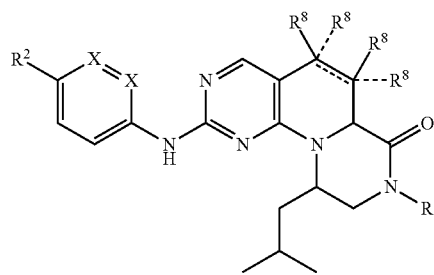

wherein R, $R^2$ and $R^8$ are as previously defined.

In some embodiments, the compound has Formula Ic and R is alkyl.

In some embodiments, the compound has Formula Ic and R is H.

In some embodiments, the compound has Formula Ic and $R^2$ is

wherein P* is a 4- to 8-membered mono- or bicyclic saturated heterocyclyl group and $R^{2*}$, $R^d$ and t are as previously defined.

In some embodiments, the compound has Formula Ic and $R^2$ is

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the compound has Formula Id:

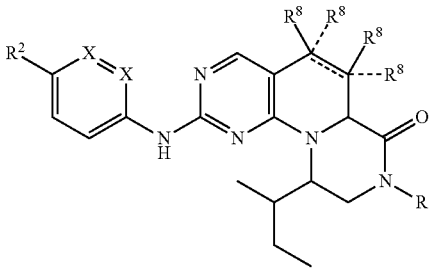

wherein R, $R^2$ and $R^8$ are as previously defined.

In some embodiments, the compound has Formula Id and R is alkyl.

In some embodiments, the compound has Formula Id and R is H.

In some embodiments, the compound has Formula Id and $R^2$ is

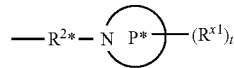

wherein P* is a 4- to 8-membered mono- or bicyclic saturated heterocyclyl group and $R^{2*}$, $R^{x1}$ and t are as previously defined.

In some embodiments, the compound has Formula Id and $R^2$ is

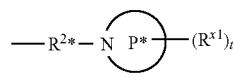

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the compound has Formula Ie:

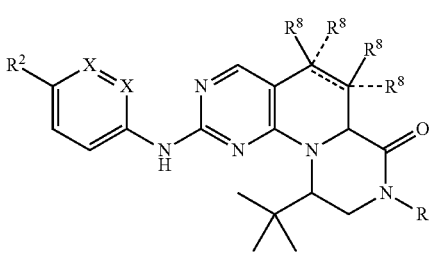

wherein R, $R^2$ and $R^8$ are as previously defined. In some embodiments, the compound has Formula Ie and R is alkyl.

In some embodiments, the compound has Formula Ie and R is H.

In some embodiments, the compound has Formula Ie and $R^2$ is

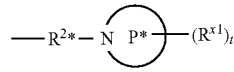

wherein P* is a 4- to 8-membered mono- or bicyclic saturated heterocyclyl group and $R^{2*}$, $R^{x1}$ and t are as previously defined.

In some embodiments, the compound has Formula Ie and $R^2$ is

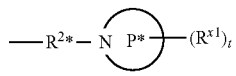

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the compound has Formula If:

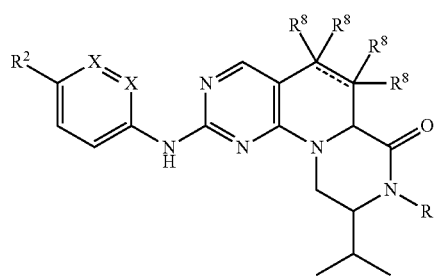

If wherein R, $R^2$ and $R^8$ are as previously defined.

In some embodiments, the compound has Formula If and R is alkyl.

In some embodiments, the compound has Formula If and R is H.

In some embodiments, the compound has Formula If and $R^2$ is

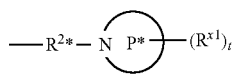

wherein P* is a 4- to 8-membered mono- or bicyclic saturated heterocyclyl group and $R^{2*}$, $Rx^{x1}$ and t are as previously defined.

In some embodiments, the compound has Formula If and $R^2$ is

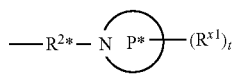

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the compound has Formula Ig:

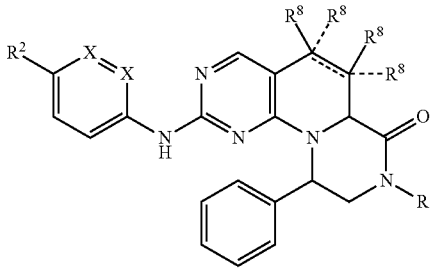

wherein R, $R^2$ and $R^8$ are as previously defined.

In some embodiments, the compound has Formula Ig and R is alkyl.

In some embodiments, the compound has Formula Ig and R is H.

In some embodiments, the compound has Formula Ig and $R^2$ is

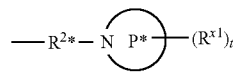

wherein P* is a 4- to 8-membered mono- or bicyclic saturated heterocyclyl group and $R^{2*}$, $R^{x1}$ and t are as previously defined.

In some embodiments, the compound has Formula Ig and $R^2$ is

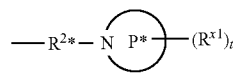

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the compound has Formula Ih:

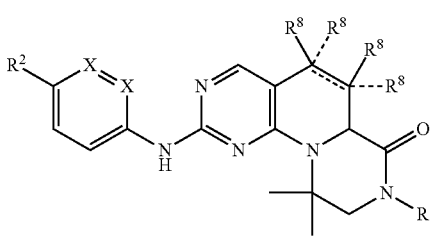

wherein R, $R^2$ and $R^8$ are as previously defined.

In some embodiments, the compound has Formula Ih and R is alkyl.

In some embodiments, the compound has Formula Ih and R is H.

In some embodiments, the compound has Formula Ih and $R^2$ is

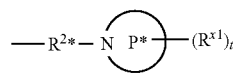

wherein P* is a 4- to 8-membered mono- or bicyclic saturated heterocyclyl group and R²*, R^{x1} and t are as previously defined.

In some embodiments, the compound has Formula Ih and R² is

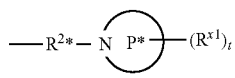

wherein P* is a 4- to 8-membered mono- or bicyclic saturated heterocyclyl group, R^{x1} is hydrogen or $C_1$-$C_4$ alkyl and R²* is as previously defined.

In some embodiments, the compound has Formula Ii:

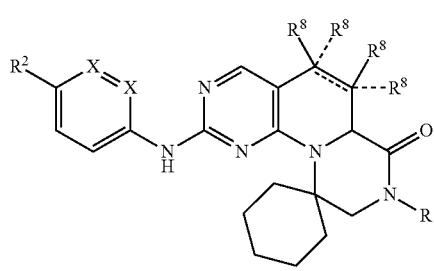

wherein R, R² and R⁸ are as previously defined.

In some embodiments, the compound has Formula Ii and R is alkyl.

In some embodiments, the compound has Formula Ii and R is H.

In some embodiments, the compound has Formula Ii and R² is

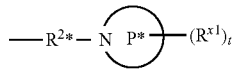

wherein P* is a 4- to 8-membered mono- or bicyclic saturated heterocyclyl group and R²*, R^{x1} and t are as previously defined.

In some embodiments, the compound has Formula Ii and R² is

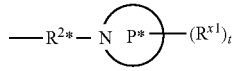

wherein P* is a 4- to 8-membered mono- or bicyclic saturated heterocyclyl group, R^{x1} is hydrogen or $C_1$-$C_4$ alkyl and R²* is as previously defined.

In some embodiments, the compound has Formula Ij:

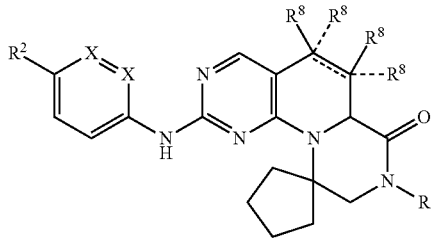

wherein R, R² and R⁸ are as previously defined.

In some embodiments, the compound has Formula Ij and R is alkyl.

In some embodiments, the compound has Formula Ij and R is H.

In some embodiments, the compound has Formula Ij and R² is

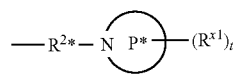

wherein P* is a 4- to 8-membered mono- or bicyclic saturated heterocyclyl group.

In some embodiments, the compound has Formula Ij and R² is

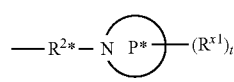

wherein P* is a 4- to 8-membered mono- or bicyclic saturated heterocyclyl group, R^{x1} is hydrogen or $C_1$-$C_4$ alkyl.

In some embodiments, the compound has Formula Ij and R is H, and X is CH and N.

In some embodiments, the compound has the structure:

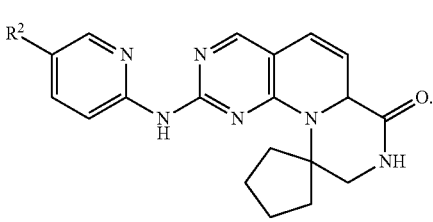

In some embodiments, the compound has the structure Ik:

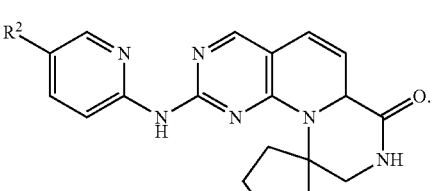

In some embodiments, the compound has Formula Ik and $R^2$ is

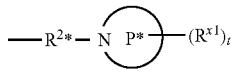

wherein P* is a 4- to 8-membered mono- or bicyclic saturated heterocyclyl group.

In some embodiments, the compound has Formula Ik and $R^2$ is

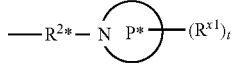

wherein P* is a 4- to 8-membered mono- or bicyclic saturated heterocyclyl group, $R^d$ is hydrogen or $C_1$-$C_4$ alkyl.

In some embodiments, the compound has Formula Il:

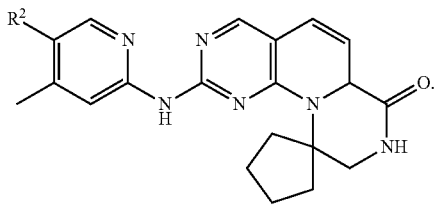

Il

In some embodiments, the compound has Formula Il and $R^2$ is

wherein P* is a 4- to 8-membered mono- or bicyclic saturated heterocyclyl group.

In some embodiments, the compound has Formula Il and $R^2$ is

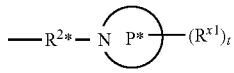

wherein P* is a 4- to 8-membered mono- or bicyclic saturated heterocyclyl group, $R^{x1}$ is hydrogen or $C_1$-$C_4$ alkyl.

In some embodiments, the compound has Formula Im:

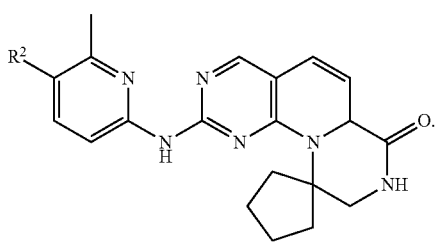

Im

In some embodiments, the compound has Formula Im and $R^2$ is

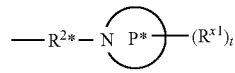

wherein P* is a 4- to 8-membered mono- or bicyclic saturated heterocyclyl group.

In some embodiments, the compound has Formula Im and $R^2$ is

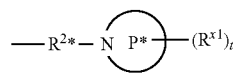

wherein P* is a 4- to 8-membered mono- or bicyclic saturated heterocyclyl group, $R^{x1}$ is hydrogen or $C_1$-$C_4$ alkyl.

In some embodiments, the compound has Formula IIa:

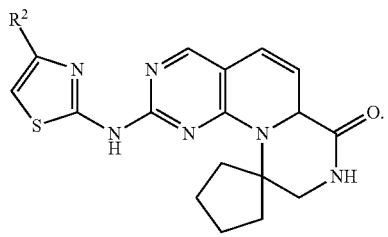

IIa

In some embodiments, the compound has Formula IIa and $R^2$ is

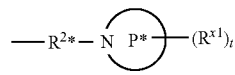

wherein P* is a 4- to 8-membered mono- or bicyclic saturated heterocyclyl group.

In some embodiments, the compound has Formula IIa and $R^2$ is

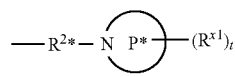

wherein P* is a 4- to 8-membered mono- or bicyclic saturated heterocyclyl group, $R^{x1}$ is hydrogen or $C_1$-$C_4$ alkyl.

In some embodiments, the compound has Formula IIb:

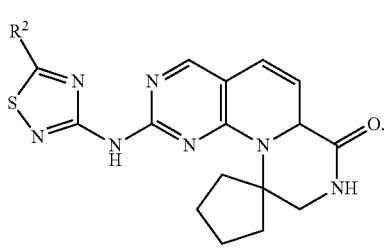

IIb

In some embodiments, the compound has Formula IIb and R² is

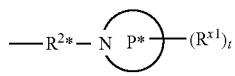

wherein P* is a 4- to 8-membered mono- or bicyclic saturated heterocyclyl group.

In some embodiments, the compound has Formula IIb and R² is

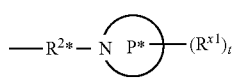

wherein P* is a 4- to 8-membered mono- or bicyclic saturated heterocyclyl group, $R^{1x}$ is hydrogen or $C_1$-$C_4$ alkyl.

In some aspects, the active compound is:

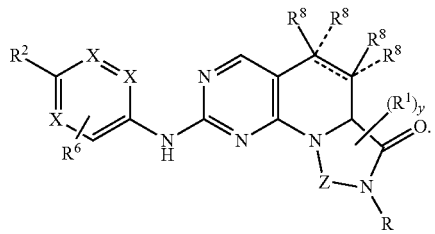

Further specific compounds that fall within the present invention and that can be used in the disclosed methods of treatment and compositions include, but are not limited to, the structures listed in Table 1 below.

TABLE 1

Structures of Tricyclic Lactams

| Structure Reference | Structure |
|---|---|
| A | 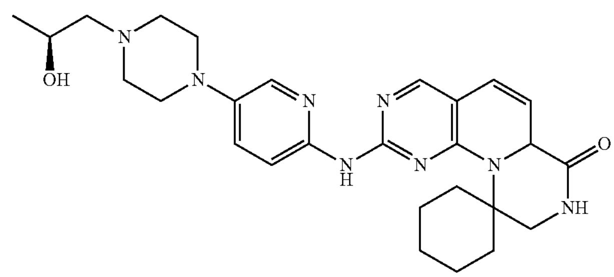 [SMILES: C[C@H](O)CN1CCN(c2ccc(Nc3ncc4c(n3)N3C(C=C4)C(=O)NCC34CCCCC4)nc2)CC1] |
| B | 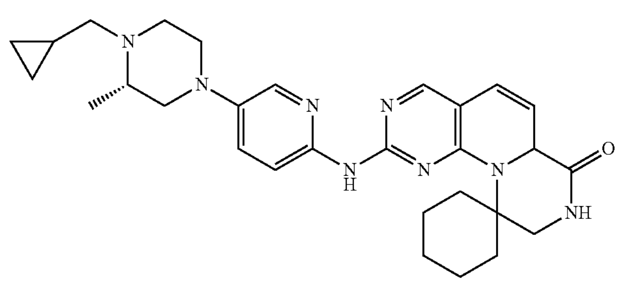 [SMILES: C[C@H]1CN(c2ccc(Nc3ncc4c(n3)N3C(C=C4)C(=O)NCC34CCCCC4)nc2)CCN1CC1CC1] |
| C | 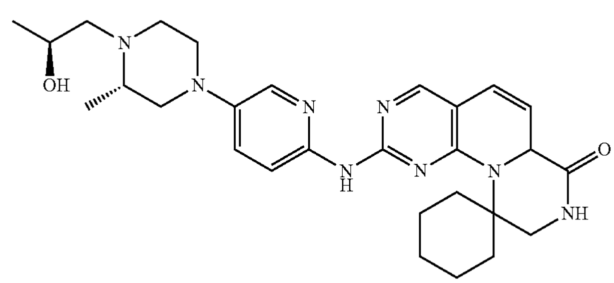 [SMILES: C[C@H](O)CN1CCN(c2ccc(Nc3ncc4c(n3)N3C(C=C4)C(=O)NCC34CCCCC4)nc2)C[C@@H]1C] |

TABLE 1-continued

Structures of Tricyclic Lactams

| Structure Reference | Structure |
|---|---|
| D | 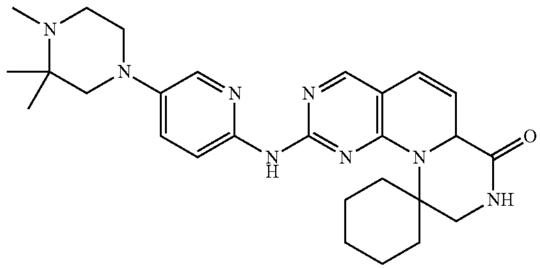 [SMILES: CN1CCN(c2ccc(Nc3ncc4c(n3)N3C(C=C4)C(=O)NCC34CCCCC4)nc2)CC1(C)C] |
| E | 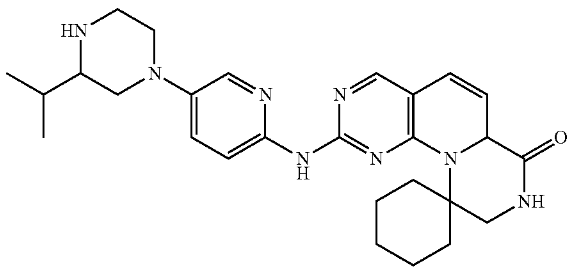 [SMILES: CC(C)C1CN(c2ccc(Nc3ncc4c(n3)N3C(C=C4)C(=O)NCC34CCCCC4)nc2)CCN1] |
| F | 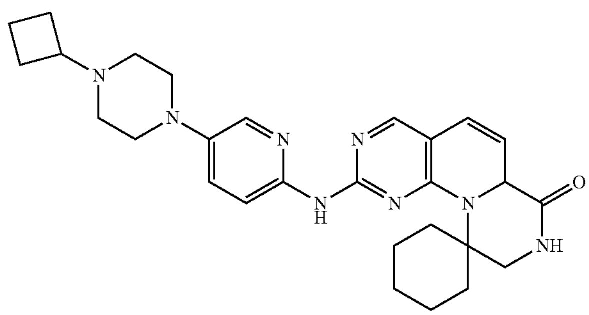 [SMILES: O=C1NCC2(CCCCC2)N2c3nc(Nc4ccc(N5CCN(C6CCC6)CC5)cn4)ncc3C=CC12] |
| G | 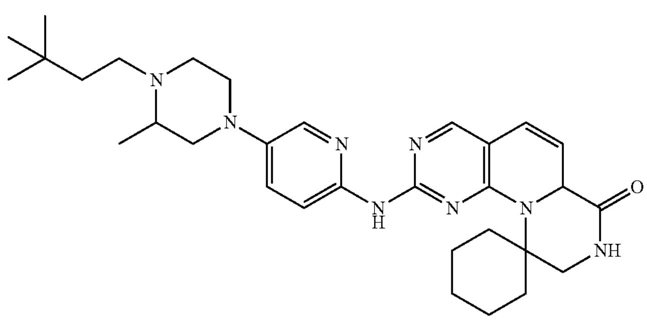 [SMILES: CC1CN(c2ccc(Nc3ncc4c(n3)N3C(C=C4)C(=O)NCC34CCCCC4)nc2)CCN1CCC(C)(C)C] |
| H | 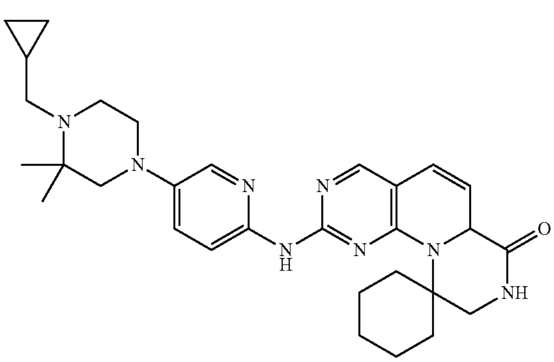 [SMILES: CC1(C)CN(c2ccc(Nc3ncc4c(n3)N3C(C=C4)C(=O)NCC34CCCCC4)nc2)CCN1CC1CC1] |

TABLE 1-continued

Structures of Tricyclic Lactams

| Structure Reference | Structure |
|---|---|
| I | *(chemical structure)* |
| J | *(chemical structure)* |
| K | *(chemical structure)* |
| L | *(chemical structure)* |
| M | *(chemical structure)* |

TABLE 1-continued

Structures of Tricyclic Lactams

| Structure Reference | Structure |
|---|---|
| N | 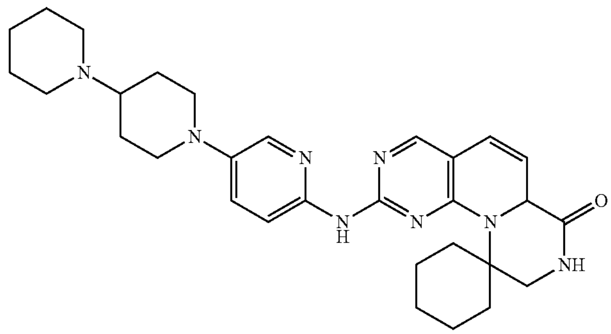 [SMILES: O=C1NCC2(CCCCC2)N2c3nc(Nc4ccc(N5CCC(N6CCCCC6)CC5)cn4)ncc3C=CC12] |
| O | 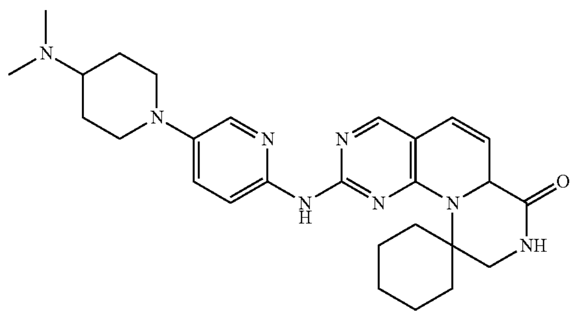 |
| P | 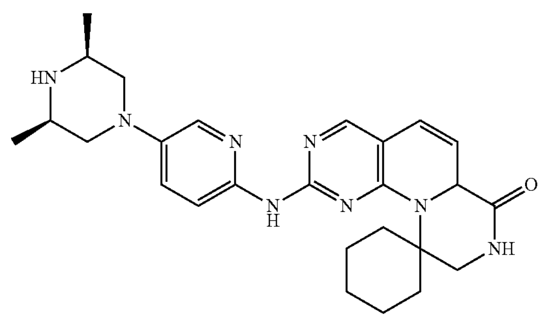 [SMILES: C[C@@H]1CN(c2ccc(Nc3ncc4c(n3)N3C(C=C4)C(=O)NCC34CCCCC4)nc2)C[C@H](C)N1] |
| Q | 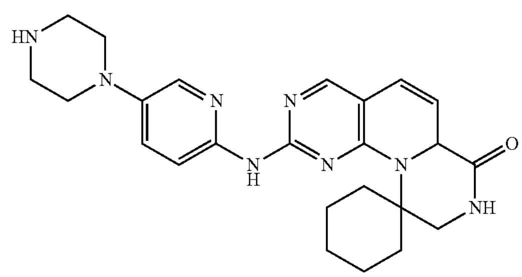 [SMILES: O=C1NCC2(CCCCC2)N2c3nc(Nc4ccc(N5CCNCC5)cn4)ncc3C=CC12] |
| R | 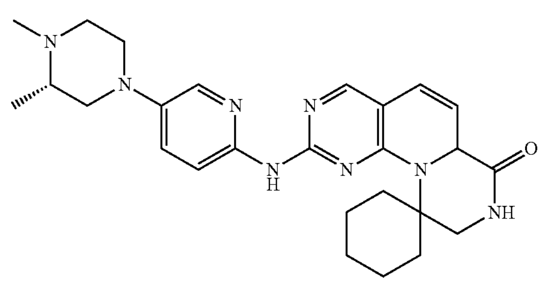 |

TABLE 1-continued

Structures of Tricyclic Lactams

| Structure Reference | Structure |
|---|---|
| S | 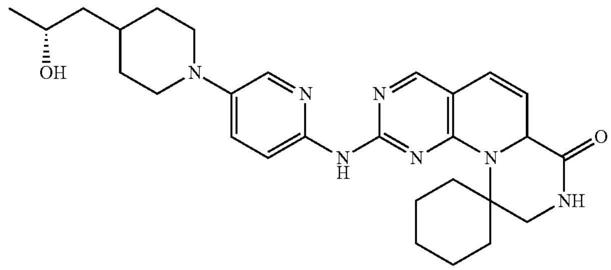 [SMILES: C[C@@H](O)CC1CCN(c2ccc(Nc3ncc4c(n3)N3C(C=C4)C(=O)NCC34CCCCC4)nc2)CC1] |
| T | 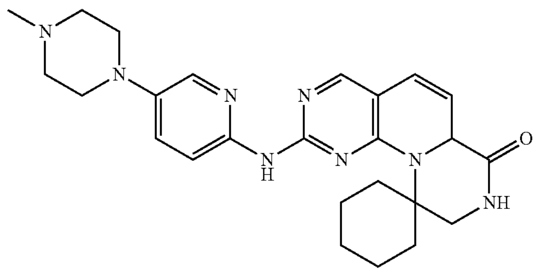 [SMILES: CN1CCN(c2ccc(Nc3ncc4c(n3)N3C(C=C4)C(=O)NCC34CCCCC4)nc2)CC1] |
| U | 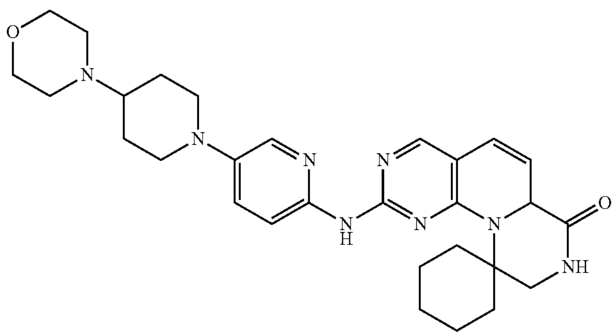 [SMILES: O=C1NCC2(CCCCC2)N2c3nc(Nc4ccc(N5CCC(N6CCOCC6)CC5)cn4)ncc3C=CC12] |
| V | 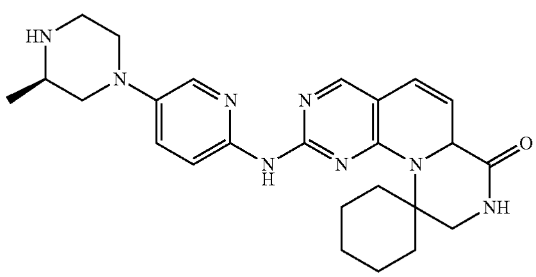 [SMILES: C[C@@H]1CN(c2ccc(Nc3ncc4c(n3)N3C(C=C4)C(=O)NCC34CCCCC4)nc2)CCN1] |
| W | 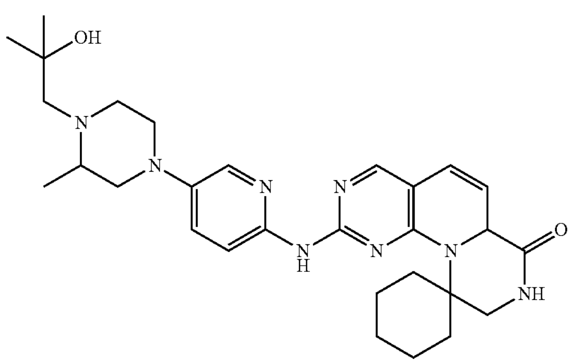 [SMILES: CC1CN(c2ccc(Nc3ncc4c(n3)N3C(C=C4)C(=O)NCC34CCCCC4)nc2)CCN1CC(C)(C)O] |

TABLE 1-continued

Structures of Tricyclic Lactams

| Structure Reference | Structure |
|---|---|
| X | (structure) |
| Y | (structure) |
| Z | (structure) |
| AA | (structure) |

TABLE 1-continued

Structures of Tricyclic Lactams

| Structure Reference | Structure |
|---|---|
| BB | *(chemical structure)* |
| CC | *(chemical structure)* |
| DD | *(chemical structure)* |
| EE | *(chemical structure)* |
| FF | *(chemical structure)* |

TABLE 1-continued
Structures of Tricyclic Lactams
| Structure Reference | Structure |
|---|---|
| GG | 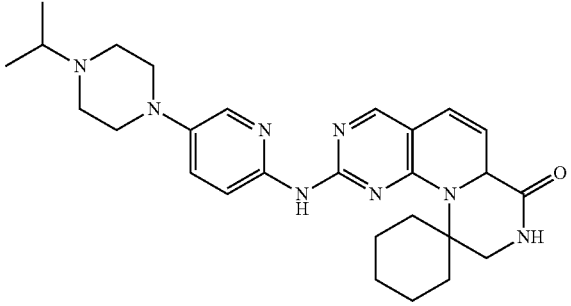 [SMILES: CC(C)N1CCN(c2ccc(Nc3ncc4c(n3)N3C(C=C4)C(=O)NCC34CCCCC4)nc2)CC1] |
| HH | 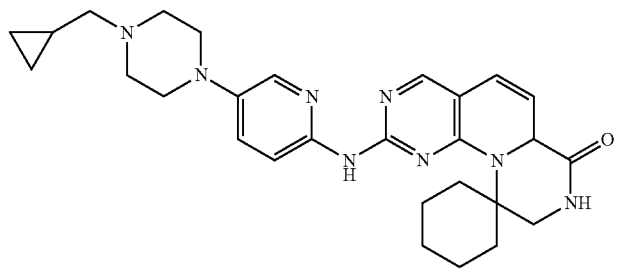 [SMILES: O=C1NCC2(CCCCC2)N2c3nc(Nc4ccc(N5CCN(CC6CC6)CC5)cn4)ncc3C=CC12] |
| II | 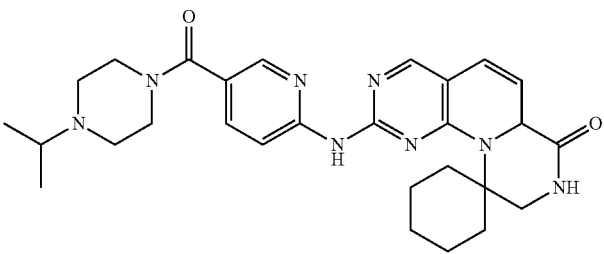 [SMILES: CC(C)N1CCN(C(=O)c2ccc(Nc3ncc4c(n3)N3C(C=C4)C(=O)NCC34CCCCC4)nc2)CC1] |
| JJ | 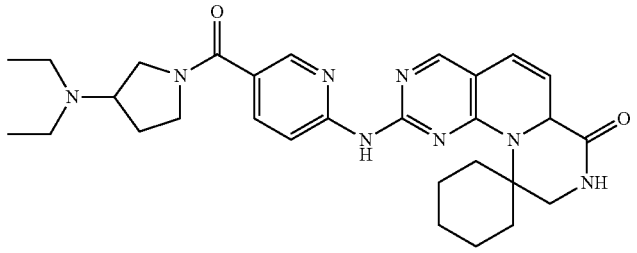 [SMILES: CCN(CC)C1CCN(C(=O)c2ccc(Nc3ncc4c(n3)N3C(C=C4)C(=O)NCC34CCCCC4)nc2)C1] |
| KK | 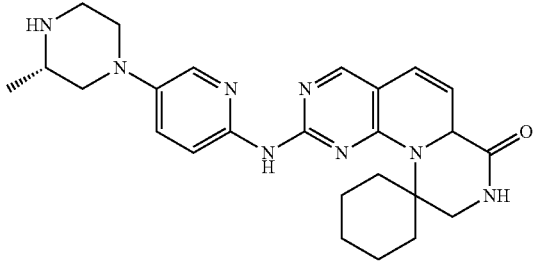 [SMILES: C[C@H]1CN(c2ccc(Nc3ncc4c(n3)N3C(C=C4)C(=O)NCC34CCCCC4)nc2)CCN1] |

TABLE 1-continued
Structures of Tricyclic Lactams
| Structure Reference | Structure |
|---|---|
| LL | 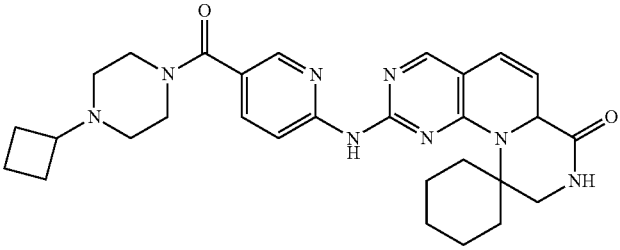 [SMILES: O=C1NCC2(CCCCC2)N2c3nc(Nc4ccc(C(=O)N5CCN(C6CCC6)CC5)cn4)ncc3C=CC12] |
| MM | 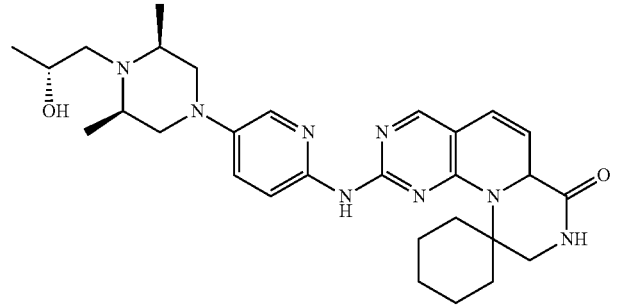 [SMILES: C[C@@H]1CN(c2ccc(Nc3ncc4c(n3)N3C(C=C4)C(=O)NCC34CCCCC4)nc2)C[C@H](C)N1C[C@@H](C)O] |
| NN | 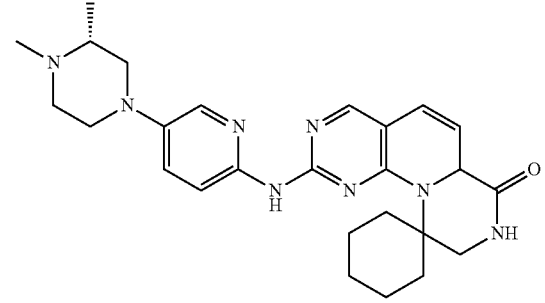 |
| OO | 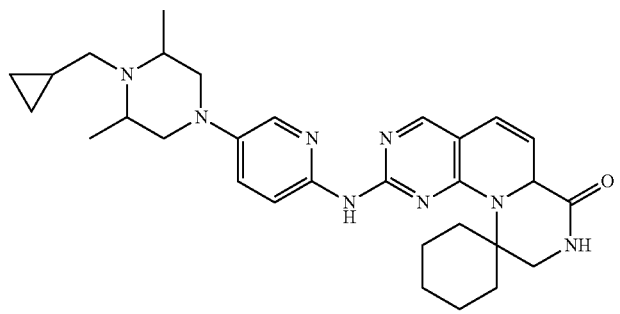 [SMILES: CC1CN(c2ccc(Nc3ncc4c(n3)N3C(C=C4)C(=O)NCC34CCCCC4)nc2)CC(C)N1CC1CC1] |
| PP | 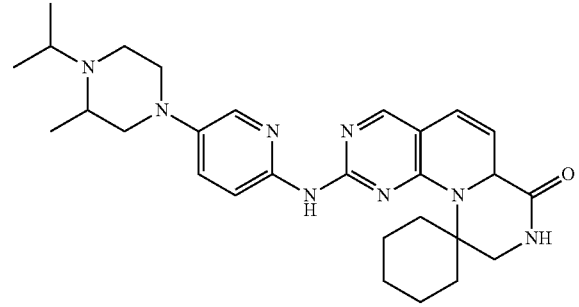 [SMILES: CC(C)N1CCN(c2ccc(Nc3ncc4c(n3)N3C(C=C4)C(=O)NCC34CCCCC4)nc2)CC1C] |

TABLE 1-continued

Structures of Tricyclic Lactams

| Structure Reference | Structure |
|---|---|
| QQ | 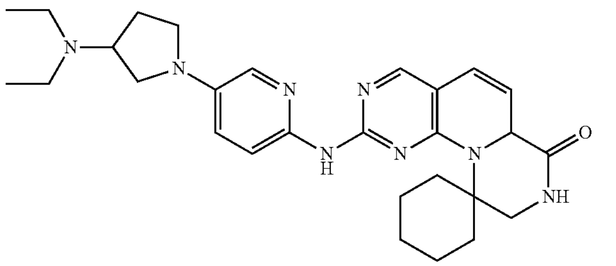 [SMILES: CCN(CC)C1CCN(c2ccc(Nc3ncc4c(n3)N3C(C=C4)C(=O)NCC34CCCCC4)nc2)C1] |
| RR | 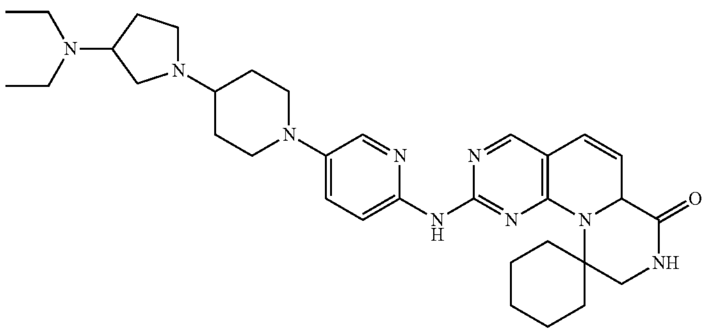 |
| SS | 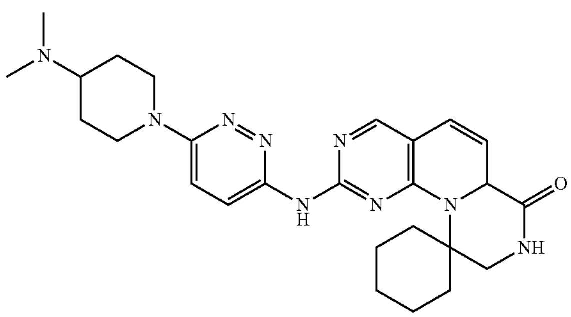 [SMILES: CN(C)C1CCN(c2ccc(Nc3ncc4c(n3)N3C(C=C4)C(=O)NCC34CCCCC4)nn2)CC1] |
| TT | 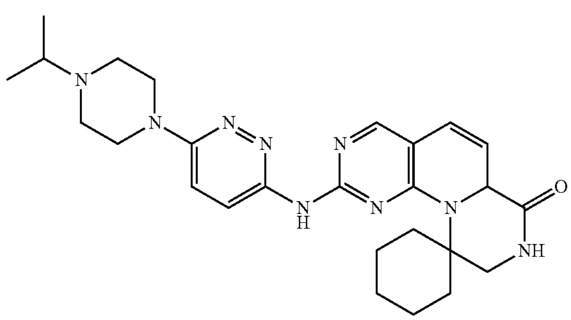 [SMILES: CC(C)N1CCN(c2ccc(Nc3ncc4c(n3)N3C(C=C4)C(=O)NCC34CCCCC4)nn2)CC1] |
| UU | 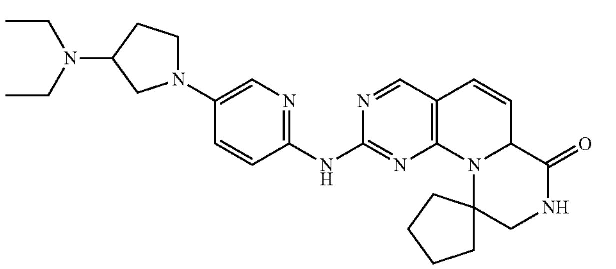 [SMILES: CCN(CC)C1CCN(c2ccc(Nc3ncc4c(n3)N3C(C=C4)C(=O)NCC34CCCC4)nc2)C1] |

TABLE 1-continued

Structures of Tricyclic Lactams

| Structure Reference | Structure |
|---|---|
| VV | 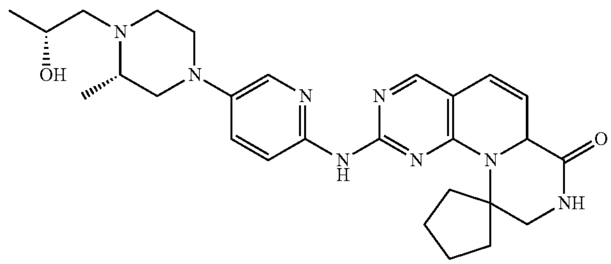 [SMILES: C[C@@H](O)CN1CCN(c2ccc(Nc3ncc4c(n3)N3C(C=C4)C(=O)NCC34CCCC4)nc2)C[C@@H]1C] |
| WW | 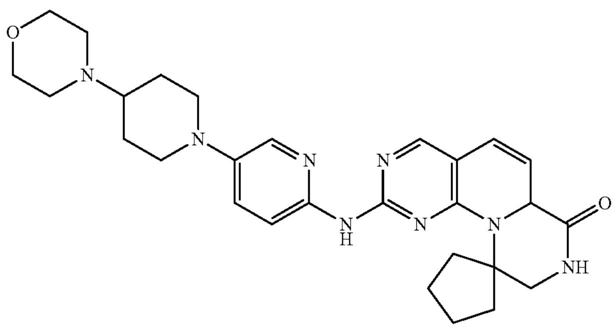 [SMILES: O=C1NCC2(CCCC2)N2c3nc(Nc4ccc(N5CCC(N6CCOCC6)CC5)cn4)ncc3C=CC12] |
| XX | 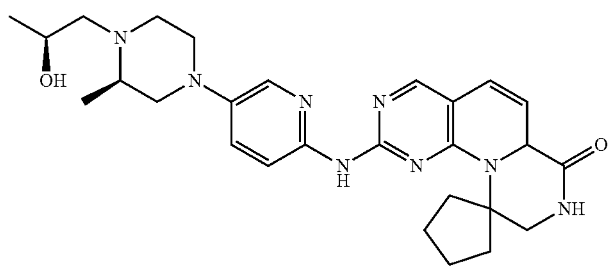 [SMILES: C[C@H](O)CN1CCN(c2ccc(Nc3ncc4c(n3)N3C(C=C4)C(=O)NCC34CCCC4)nc2)C[C@H]1C] |
| YY | 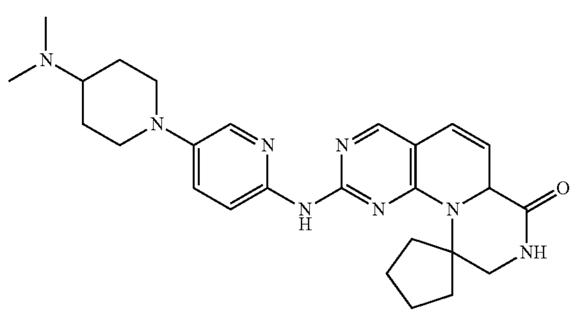 [SMILES: CN(C)C1CCN(c2ccc(Nc3ncc4c(n3)N3C(C=C4)C(=O)NCC34CCCC4)nc2)CC1] |
| ZZ | 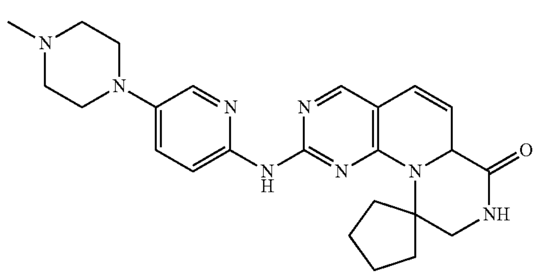 [SMILES: CN1CCN(c2ccc(Nc3ncc4c(n3)N3C(C=C4)C(=O)NCC34CCCC4)nc2)CC1] |

TABLE 1-continued

Structures of Tricyclic Lactams

| Structure Reference | Structure |
|---|---|
| AAA | 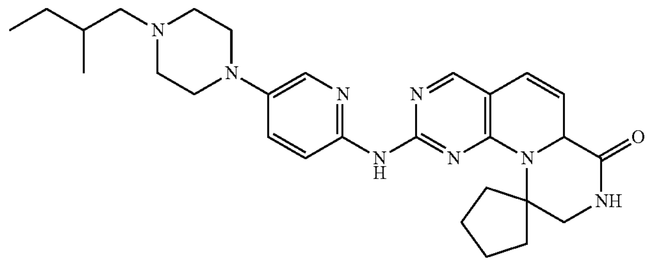 [SMILES: CCC(C)CN1CCN(c2ccc(Nc3ncc4c(n3)N3C(C=C4)C(=O)NCC34CCCC4)nc2)CC1] |
| BBB | 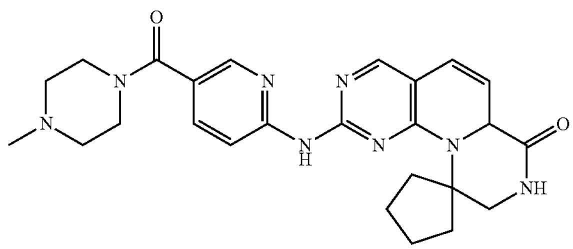 [SMILES: CN1CCN(C(=O)c2ccc(Nc3ncc4c(n3)N3C(C=C4)C(=O)NCC34CCCC4)nc2)CC1] |
| CCC | 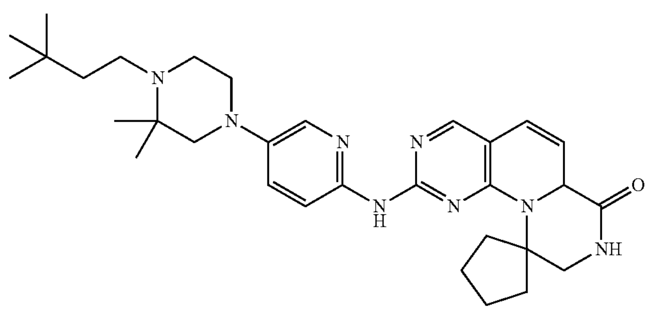 [SMILES: CC(C)(C)CCN1CCN(c2ccc(Nc3ncc4c(n3)N3C(C=C4)C(=O)NCC34CCCC4)nc2)CC1(C)C] |
| DDD | 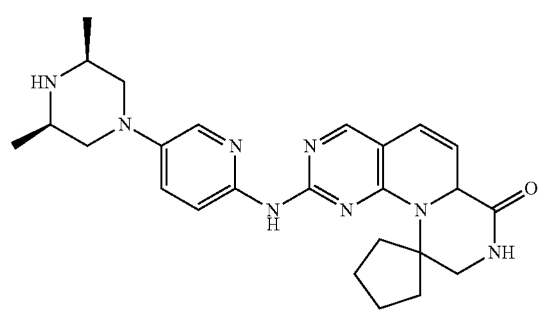 [SMILES: C[C@@H]1CN(c2ccc(Nc3ncc4c(n3)N3C(C=C4)C(=O)NCC34CCCC4)nc2)C[C@H](C)N1] |
| EEE | 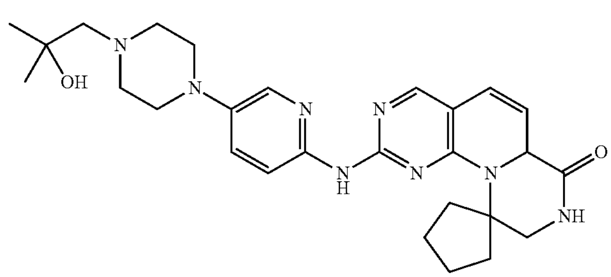 [SMILES: CC(C)(O)CN1CCN(c2ccc(Nc3ncc4c(n3)N3C(C=C4)C(=O)NCC34CCCC4)nc2)CC1] |

TABLE 1-continued

Structures of Tricyclic Lactams

| Structure Reference | Structure |
|---|---|
| FFF | 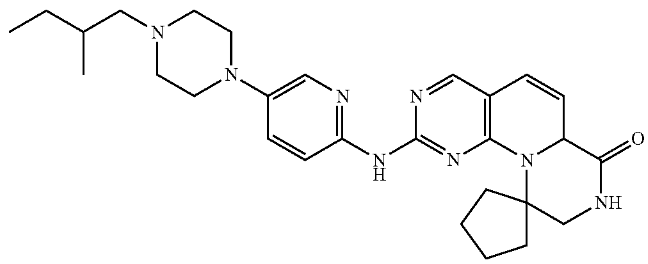 [SMILES: CCC(C)CN1CCN(c2ccc(Nc3ncc4c(n3)N3C(C=C4)C(=O)NCC34CCCC4)nc2)CC1] |
| GGG | 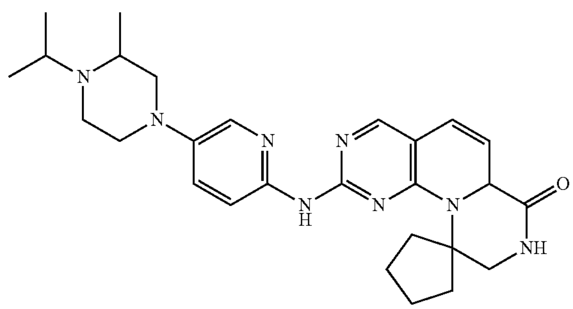 [SMILES: CC(C)N1CCN(c2ccc(Nc3ncc4c(n3)N3C(C=C4)C(=O)NCC34CCCC4)nc2)CC1C] |
| HHH | 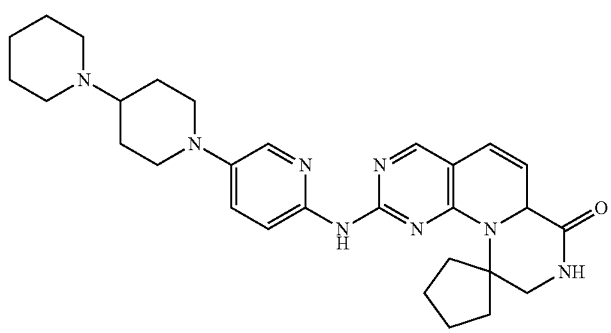 [SMILES: O=C1NCC2(CCCC2)N2c3nc(Nc4ccc(N5CCC(N6CCCCC6)CC5)cn4)ncc3C=CC12] |
| III | 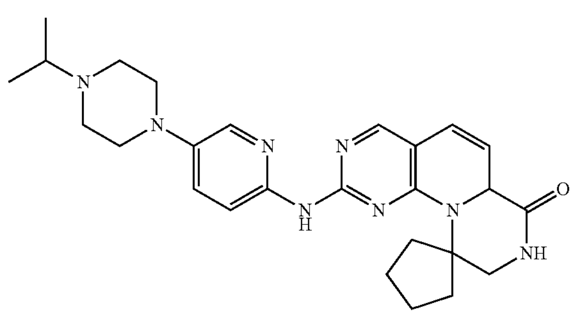 [SMILES: CC(C)N1CCN(c2ccc(Nc3ncc4c(n3)N3C(C=C4)C(=O)NCC34CCCC4)nc2)CC1] |
| JJJ | 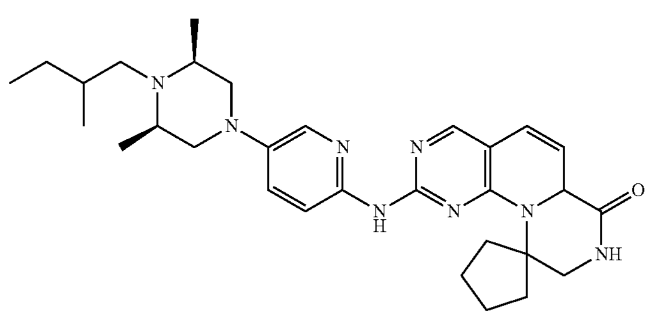 [SMILES: CCC(C)CN1[C@H](C)CN(c2ccc(Nc3ncc4c(n3)N3C(C=C4)C(=O)NCC34CCCC4)nc2)C[C@@H]1C] |

US 10,376,519 B2
TABLE 1-continued
Structures of Tricyclic Lactams
| Structure Reference | Structure |
|---|---|
| KKK | 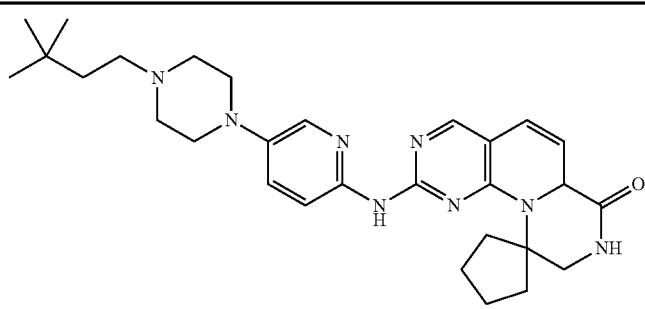 |
| LLL | 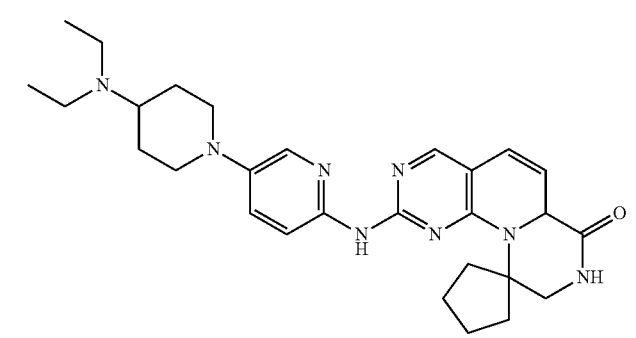 [SMILES: CCN(CC)C1CCN(c2ccc(Nc3ncc4c(n3)N3C(C=C4)C(=O)NCC34CCCC4)nc2)CC1] |
| MMM | 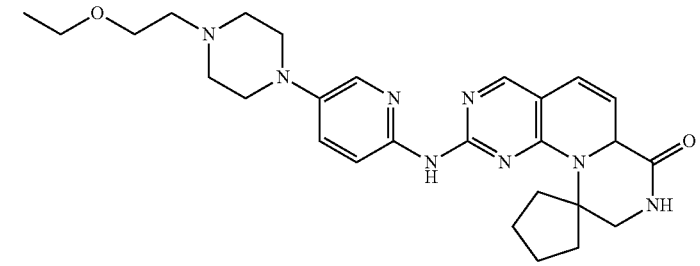 [SMILES: CCOCCN1CCN(c2ccc(Nc3ncc4c(n3)N3C(C=C4)C(=O)NCC34CCCC4)nc2)CC1] |
| NNN | 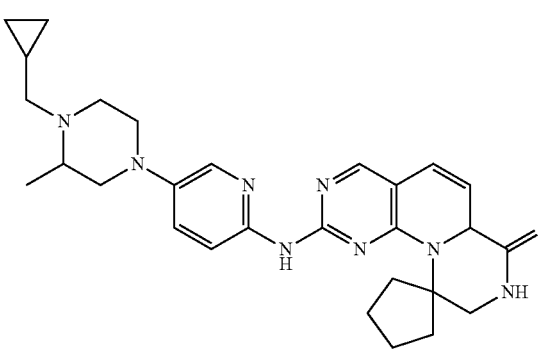 |
| OOO | 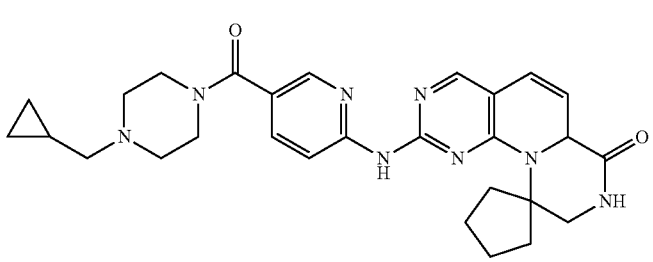 [SMILES: O=C1NCC2(CCCC2)N2c3nc(Nc4ccc(C(=O)N5CCN(CC6CC6)CC5)cn4)ncc3C=CC12] |

TABLE 1-continued
Structures of Tricyclic Lactams
| Structure Reference | Structure |
|---|---|
| PPP | 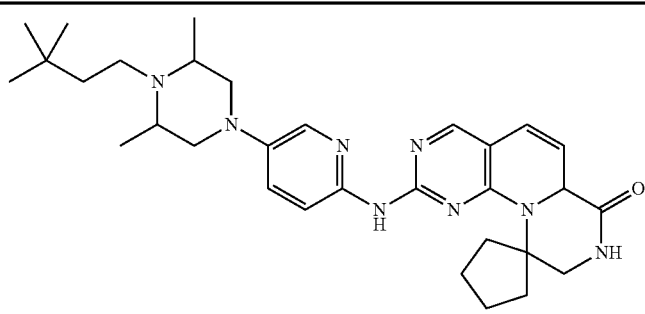 |
| QQQ | 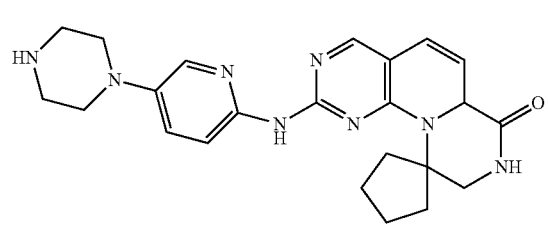 [SMILES: O=C1NCC2(CCCC2)N2c3nc(Nc4ccc(N5CCNCC5)cn4)ncc3C=CC12] |
| RRR | 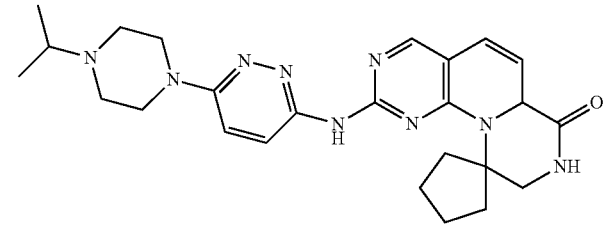 |
| SSS | 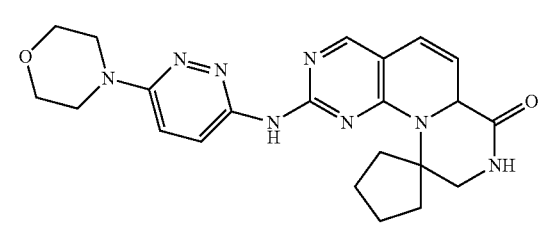 [SMILES: O=C1NCC2(CCCC2)N2c3nc(Nc4ccc(N5CCOCC5)nn4)ncc3C=CC12] |
| TTT | 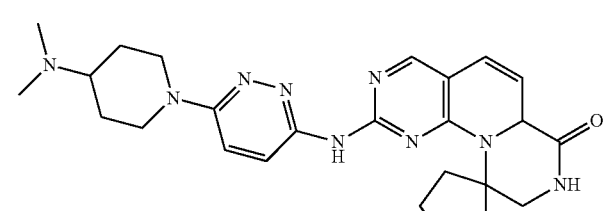 |
| UUU | 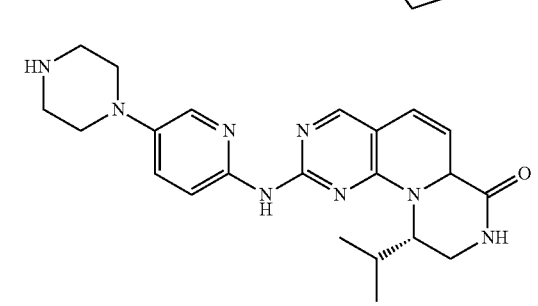 |

TABLE 1-continued

Structures of Tricyclic Lactams

| Structure Reference | Structure |
|---|---|
| VVV | 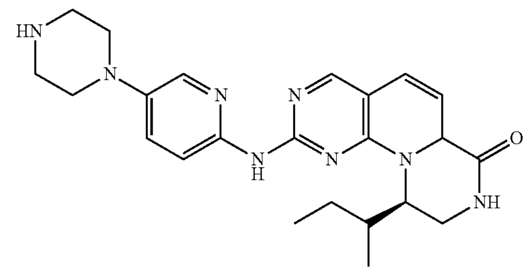 [SMILES: CCC(C)[C@@H]1CNC(=O)C2C=Cc3cnc(Nc4ccc(N5CCNCC5)cn4)nc3N21] |
| WWW | 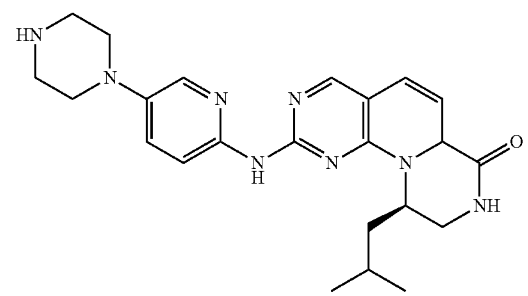 [SMILES: CC(C)C[C@@H]1CNC(=O)C2C=Cc3cnc(Nc4ccc(N5CCNCC5)cn4)nc3N21] |
| XXX | 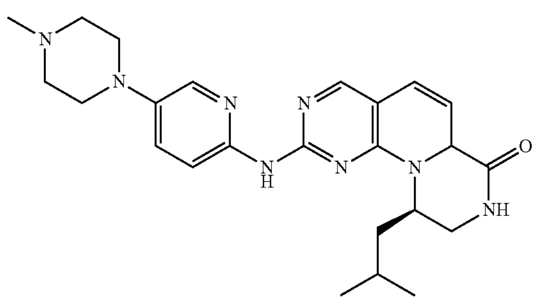 [SMILES: CC(C)C[C@@H]1CNC(=O)C2C=Cc3cnc(Nc4ccc(N5CCN(C)CC5)cn4)nc3N21] |
| YYY | 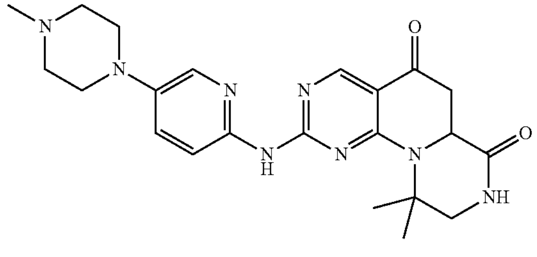 [SMILES: CN1CCN(c2ccc(Nc3ncc4c(n3)N3C(CC4=O)C(=O)NCC3(C)C)nc2)CC1] |
| ZZZ | 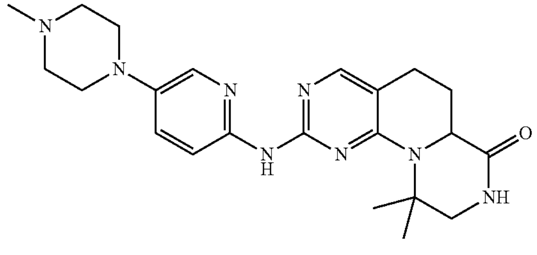 [SMILES: CN1CCN(c2ccc(Nc3ncc4c(n3)N3C(CC4)C(=O)NCC3(C)C)nc2)CC1] |

TABLE 1-continued

Structures of Tricyclic Lactams

| Structure Reference | Structure |
|---|---|
| AAAA | 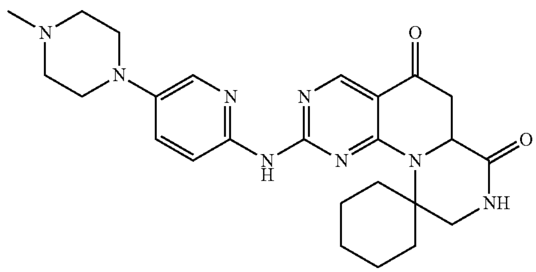 [SMILES: CN1CCN(c2ccc(Nc3ncc4c(n3)N3C(CC4=O)C(=O)NCC34CCCCC4)nc2)CC1] |
| BBBB | 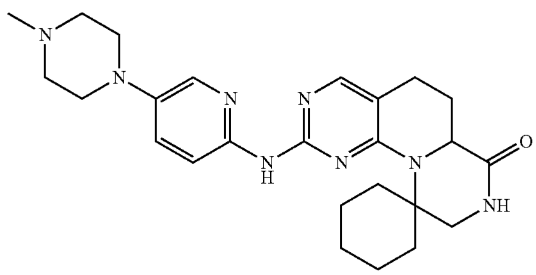 [SMILES: CN1CCN(c2ccc(Nc3ncc4c(n3)N3C(CC4)C(=O)NCC34CCCCC4)nc2)CC1] |
| CCCC | 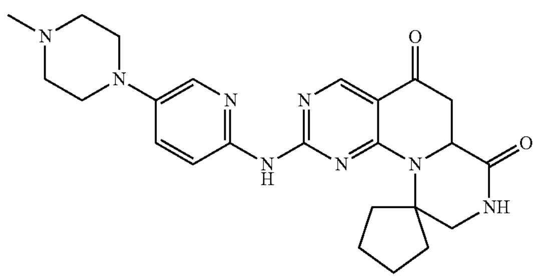 [SMILES: CN1CCN(c2ccc(Nc3ncc4c(n3)N3C(CC4=O)C(=O)NCC34CCCC4)nc2)CC1] |
| DDDD | 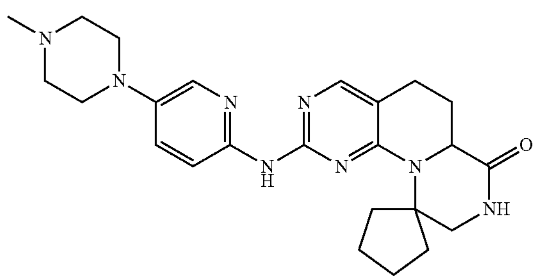 [SMILES: CN1CCN(c2ccc(Nc3ncc4c(n3)N3C(CC4)C(=O)NCC34CCCC4)nc2)CC1] |
| EEEE | 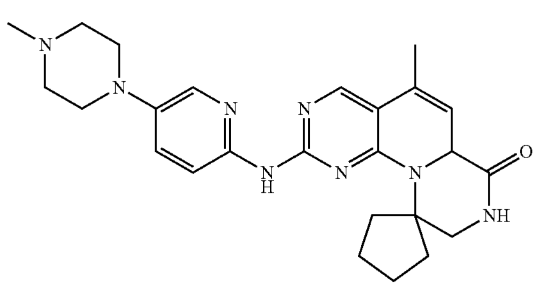 [SMILES: CC1=CC2C(=O)NCC3(CCCC3)N2c2nc(Nc3ccc(N4CCN(C)CC4)cn3)ncc21] |

TABLE 1-continued

Structures of Tricyclic Lactams

| Structure Reference | Structure |
|---|---|
| FFFF | 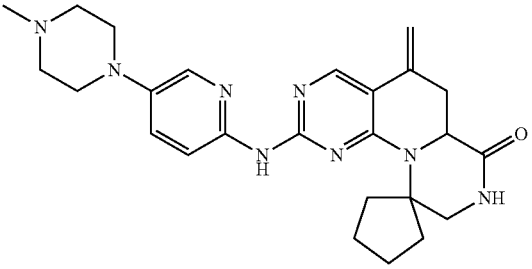 [SMILES: C=C1CC2C(=O)NCC3(CCCC3)N2c2nc(Nc3ccc(N4CCN(C)CC4)cn3)ncc21] |
| GGGG | 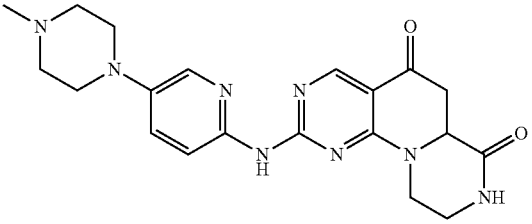 [SMILES: CN1CCN(c2ccc(Nc3ncc4c(n3)N3CCNC(=O)C3CC4=O)nc2)CC1] |
| HHHH | 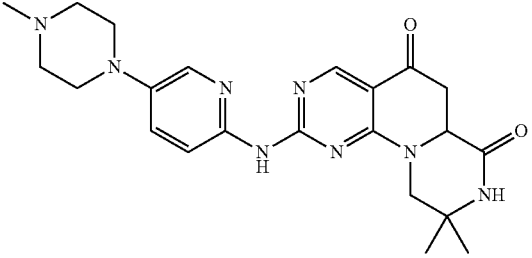 [SMILES: CN1CCN(c2ccc(Nc3ncc4c(n3)N3CC(C)(C)NC(=O)C3CC4=O)nc2)CC1] |

Isotopic Substitution

The present invention includes compounds and the use of compounds with desired isotopic substitutions of atoms, at amounts above the natural abundance of the isotope, i.e., enriched. Isotopes are atoms having the same atomic number but different mass numbers, i.e., the same number of protons but a different number of neutrons. By way of general example and without limitation, isotopes of hydrogen, for example, deuterium ($^2$H) and tritium ($^3$H) may be used anywhere in described structures. Alternatively or in addition, isotopes of carbon, e.g., $^{13}$C and $^{14}$C, may be used. A preferred isotopic substitution is deuterium for hydrogen at one or more locations on the molecule to improve the performance of the drug. The deuterium can be bound in a location of bond breakage during metabolism (an α-deuterium kinetic isotope effect) or next to or near the site of bond breakage (a β-deuterium kinetic isotope effect).

Substitution with isotopes such as deuterium can afford certain therapeutic advantages resulting from greater metabolic stability, such as, for example, increased in vivo half-life or reduced dosage requirements. Substitution of deuterium for hydrogen at a site of metabolic break down can reduce the rate of or eliminate the metabolism at that bond. At any position of the compound that a hydrogen atom may be present, the hydrogen atom can be any isotope of hydrogen, including protium ($^1$H), deuterium ($^2$H) and tritium ($^3$H). Thus, reference herein to a compound encompasses all potential isotopic forms unless the context clearly dictates otherwise.

The term "isotopically-labeled" analog refers to an analog that is a "deuterated analog", a "$^{13}$C-labeled analog," or a "deuterated/$^{13}$C-labeled analog." The term "deuterated analog" means a compound described herein, whereby a H-isotope, i.e., hydrogen/protium ($^1$H), is substituted by a H-isotope, i.e., deuterium ($^2$H). Deuterium substitution can be partial or complete. Partial deuterium substitution means that at least one hydrogen is substituted by at least one deuterium. In certain embodiments, the isotope is 90, 95 or 99% or more enriched in an isotope at any location of interest. In some embodiments it is deuterium that is 90, 95 or 99% enriched at a desired location.

Rb-Positive Cancers and Proliferative Disorders

In particular, the active compounds described herein can be used to treat a subject suffering from an Rb-positive cancer or other Rb-positive abnormal cellular proliferative disorder. In some embodiments, the cancer or cellular proliferation disorder is a CDK4/6-replication dependent cancer or cellular proliferation disorder, which refers to a cancer or cellular proliferation disorder that requires the activity of CDK4/6 for replication or proliferation, or which may be growth inhibited through the activity of a selective CDK4/6 inhibitor. Cancers and disorders of such type can be characterized by (e.g., that has cells that exhibit) the presence of a functional Retinoblastoma protein. Such cancers and disorders are classified as being Rb-positive. Rb-positive abnormal cellular proliferation disorders, and variations of this term as used herein, refer to disorders or diseases caused by uncontrolled or abnormal cellular division which are characterized by the presence of a functional Retinoblastoma protein, which can include cancers. In one aspect of the present invention, the compounds and methods described herein can be used to treat a non-cancerous Rb-positive abnormal cellular proliferation disorder.

Targeted cancers suitable for administration of a compound described herein may include Rb-positive: estrogen-receptor positive, HER2-negative advanced breast cancer, late-line metastatic breast cancer, liposarcoma, non-small cell lung cancer, liver cancer, ovarian cancer, glioblastoma, refractory solid tumors, retinoblastoma positive breast cancer as well as retinoblastoma positive endometrial, vaginal and ovarian cancers and lung and bronchial cancers, adenocarcinoma of the colon, adenocarcinoma of the rectum, central nervous system germ cell tumors, teratomas, estrogen receptor-negative breast cancer, estrogen receptor-positive breast cancer, familial testicular germ cell tumors, HER2-negative breast cancer, HER2-positive breast cancer, male breast cancer, ovarian immature teratomas, ovarian mature teratoma, ovarian monodermal and highly specialized teratomas, progesterone receptor-negative breast cancer, progesterone receptor-positive breast cancer, recurrent breast cancer, recurrent colon cancer, recurrent extragonadal germ cell tumors, recurrent extragonadal non-seminomatous germ cell tumor, recurrent extragonadal seminomas, recurrent malignant testicular germ cell tumors, recurrent melanomas, recurrent ovarian germ cell tumors, recurrent rectal cancer, stage III extragonadal non-seminomatous germ cell tumors, stage III extragonadal seminomas, stage III malignant testicular germ cell tumors, stage III ovarian germ cell tumors, stage IV breast cancers, stage IV colon cancers, stage IV extragonadal non-seminomatous germ cell tumors, stage IV extragonadal seminoma, stage IV melanomas, stage IV ovarian germ cell tumors, stage IV rectal cancers, testicular immature teratomas, testicular mature teratomas. In particular embodiments, the targeted cancers included estrogen-receptor positive, HER2-negative advanced breast cancer, late-line metastatic breast cancer, liposarcoma, non-small cell lung cancer, liver cancer, ovarian cancer, glioblastoma, refractory solid tumors, retinoblastoma positive breast cancer as well as retinoblastoma positive endometrial, vaginal and ovarian cancers and lung and bronchial cancers, metastatic colorectal cancer, metastatic melanoma with CDK4 mutation or amplification, or cisplatin-refractory, unrespectable germ cell tumors.

In one embodiment, the Rb-positive cancer is selected from an Rb-positive carcinoma, sarcoma, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers.

In one embodiment, the Rb-positive cancer is selected from the group consisting of Rb-positive: fibrosarcoma, myxosarcoma, chondrosarcoma, osteosarcoma, chordoma, malignant fibrous histiocytoma, hemangiosarcoma, angiosarcoma, lymphangiosarcoma. Mesothelioma, leiomyosarcoma, rhabdomyosarcoma, squamous cell carcinoma; epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma, Islet cell carcinoma, malignant carcinoid, malignant paraganglioma, melanoma, Merkel cell neoplasm, cystosarcoma phylloide, salivary cancers, thymic carcinomas, bladder cancer, and Wilms tumor.

The presence or normal functioning of the retinoblastoma (Rb) tumor suppressor protein (Rb-positive) can be determined through any of the standard assays known to one of ordinary skill in the art, including but not limited to Western Blot, ELISA (enzyme linked immunoadsorbent assay), IHC (immunohistochemistry), and FACS (fluorescent activated cell sorting). The selection of the assay will depend upon the tissue, cell line or surrogate tissue sample that is utilized e.g., for example Western Blot and ELISA may be used with any or all types of tissues, cell lines or surrogate tissues, whereas the IHC method would be more appropriate wherein the tissue utilized in the methods of the present invention was a tumor biopsy. FACs analysis would be most applicable to samples that were single cell suspensions such as cell lines and isolated peripheral blood mononuclear cells. See for example, US 20070212736 "Functional Immunohistochemical Cell Cycle Analysis as a Prognostic Indicator for Cancer". Alternatively, molecular genetic testing may be used for determination of retinoblastoma gene status. Molecular genetic testing for retinoblastoma includes the following as described in Lohmann and Gallie "Retinoblastoma. Gene Reviews"(2010)
http://www.ncbi.nlm.nih.gov/bookshelf/
br.fcgi?book=gene&part=retinoblastoma or Parsam et al. "A comprehensive, sensitive and economical approach for the detection of mutations in the RB1 gene in retinoblastoma" Journal of Genetics, 88(4), 517-527 (2009).

In some embodiments, the cancer to be treated is selected from estrogen-receptor positive, HER2-negative advanced breast cancer, late-line metastatic breast cancer, liposarcoma, non-small cell lung cancer, liver cancer, ovarian cancer, glioblastoma, refractory solid tumors, retinoblastoma positive breast cancer as well as retinoblastoma positive endometrial, vaginal and ovarian cancers and lung and bronchial cancers.

CDK-Replication Dependent Cells and Cyclin-Dependent Kinase Inhibitors

Tissue-specific stem cells and subsets of other resident proliferating cells are capable of self-renewal, meaning that they are capable of replacing themselves throughout the adult mammalian lifespan through regulated replication. Additionally, stem cells divide asymmetrically to produce "progeny" or "progenitor" cells that in turn produce various components of a given organ. For example, in the hematopoietic system, the hematopoietic stem cells give rise to progenitor cells which in turn give rise to all the differentiated components of blood (e.g., white blood cells, red blood cells, and platelets) (see FIG. 1).

It has been found that certain proliferating cells, such as HSPCs, require the enzymatic activity of the proliferative kinases cyclin-dependent kinase 4 (CDK4) and/or cyclin-dependent kinase 6 (CDK6) for cellular replication. In contrast, the majority of proliferating cells in adult mammals (e.g., the more differentiated blood-forming cells in the bone marrow) do not require the activity of CDK4 and/or CDK6 (i.e., CDK4/6). These differentiated cells can proliferate in the absence of CDK4/6 activity by using other proliferative kinases, such as cyclin-dependent kinase 2 (CDK2) or cyclin-dependent kinase 1 (CDK1).

The present invention includes methods of treating certain cancers, in particular Rb-positive cancers, while minimizing the deleterious effects on CDK4/6-replication dependent healthy cells in a subject, and in particular, hematopoietic cells and/or progenitor cells (HSPCs), by the administration of a compound described herein to treat a specific Rb-positive cancer. In certain embodiments, the compound administered is selected from the group consisting of a compound or composition comprising Formula I, Formula II, Formula III, Formula IV, Formula V, or Formula VI, or a combination thereof. In certain embodiments, the compound administered is selected from the group consisting of a compound selected from Table 1.

In certain aspects, compounds, methods, and compositions are provided as chemotherapeutics which reduce or limit the deleterious effect of CDK4/6 inhibition on CDK4/6-replication dependent healthy cells in a subject undergoing CDK4/6 inhibitory treatment for an Rb-positive cancer. In certain embodiments, the compound administered is selected from the group consisting of the compound or a composition comprising Formula I, Formula II, Formula III, Formula IV, Formula V, or Formula VI, or a pharmaceutically acceptable composition, salt, isotopic analog, or prodrug thereof. In certain embodiments, the compound administered is selected from a compound contained in Table 1, or a pharmaceutically acceptable composition, salt, isotopic analog, or prodrug thereof. In one embodiment, the CDK4/6-replication dependent cells are hematopoietic stem cells and/or progenitor cells (HSPCs).

In certain embodiments, the compound administered is selected from the group consisting of the compound or a composition comprising Formula I, Formula II, Formula III, Formula IV, Formula V, or Formula VI, or a pharmaceutically acceptable composition, salt, isotopic analog, or prodrug thereof, or compound contained in Table 1, or a pharmaceutically acceptable composition, salt, isotopic analog, or prodrug thereof, wherein the effect of the compound is short term and transient in nature, allowing a significant portion of the CDK4/6-replication dependent healthy cells to synchronously renter the cell-cycle quickly, for example within less than about 24, 30, 36, or 40 hours of the last administration of the compound.

In one embodiment, a compound useful in the methods described herein is a selective CDK4/6 inhibitor compound that selectively inhibits at least one of CDK4 and CDK6 or through the inhibition of cellular replication of an Rb-positive cancer. In one embodiment, the tricyclic lactam compounds for use in the described methods are CDK4/6 inhibitors, with minimal CDK2 inhibitory activity. In one embodiment, a compound for use in the methods described herein has a CDK4/CycD1 $IC_{50}$ inhibitory concentration value that is >100, >200, >300, >400, >500, >600, >700, >800, >900, >1000, >1250, >1500 times, >1800 times, >2000 times, >2200 times, >2500 times, >2700 times, >3000 times, >3200 times lower than its respective $IC_{50}$ concentration value for CDK2/CycE inhibition. In one embodiment, a compound for use in the methods described herein has an $IC_{50}$ concentration value for CDK4/CycD1 inhibition that is about <1.50 nM, <1.25 nM, <1.0 nM, <0.90 nM, <0.85 nM, <0.80 nM, <0.75 nM, <0.70 nM, <0.65 nM, <0.60 nM, <0.55 nM, or less. In one embodiment, a tricyclic lactam for use in the methods described herein has an $IC_{50}$ concentration value for CDK2/CycE inhibition that is about >1.0 μM, >1.25 μM, >1.50 μM, >1.75 μM, >2.0 μM, >2.25 μM, >2.50 μM, >2.75 μM, >3.0 μM, >3.25 μM, >3.5 μM or greater. In one embodiment, a compound for use in the methods described herein has an $IC_{50}$ concentration value for CDK2/CycA $IC_{50}$ that is >0.80 μM, >0.85 μM, >0.90 μM, >0.95 μM, >.1.0 μM, >1.25 μM, >1.50 μM, >1.75 μM, >2.0 μM, >2.25 μM, >2.50 μM, >2.75 μM, >3.0 μM or greater.

In one embodiment, the compounds described herein are used in CDK4/6-replication dependent healthy cell cycling strategies wherein a subject is exposed to regular, repeated chemotherapeutic treatments for an Rb-positive cancer. Such cycling allows CDK4/6-replication dependent cells to regenerate damaged blood cell lineages between regular, repeated treatments, and reduces the risk associated with long term CDK4/6 inhibition.

In one embodiment, the use of a compound described herein provides for a rapid, reentry into the cell cycle by CDK4/6-replication dependent healthy cells, for example HSPCs, so that a portion of the cells exhibit a level of cell cycle activity or are capable of entering the cell cycle and proliferate during a continuous treatment regime, for example, a treatment regime wherein the compound is administered for an extended period, for example, 5 continuous days, 7 continuous days, 10 continuous days, 14 continuous days, 18 continuous days, 21 continuous days, 24 continuous days, 28 continuous days, 35 continuous days or more. In one embodiment, a compound useful in a described method is administered for a continuous period, for example, 21, 28, 35 days or more, without the requirement for an off-cycle period or drug holiday. In one embodiment, the use of a compound described herein eliminates the need for an off-cycle period, drug holiday, or reduction in co-administered anti-neoplastic compound concentration during treatment.

According to the present invention, a compound described herein can be administered as a chemotherapeutic to a subject having an Rb-positive proliferation disorder on any treatment schedule and in any dose consistent with the prescribed course of treatment. For instance the compound can be administered once a day, twice a day or three times a day. The compound can be administered on alternating days, or every third day, or every fourth day, or every fifth day, or every sixth day or once a week. The compound can be administered every other week or monthly.

Combination Therapy

In one aspect of the invention, the compounds disclosed herein can be beneficially administered in combination with another therapeutic regimen for beneficial, additive or synergystic effect.

In one embodiment, a compound/method of the present invention is used in combination with another therapy to treat the Rb-positive cancer. The second therapy can be an immunotherapy. As discussed in more detail below, the compound can be conjugated to an antibody, radioactive agent, or other targeting agent that directs the compound to the diseased or abnormally proliferating cell. In another embodiment, the compound is used in combination with another pharmaceutical or a biologic agent (for example an antibody) to increase the efficacy of treatment with a combined or a synergistic approach. In an embodiment, the compound can be used with T-cell vaccination, which typically involves immunization with inactivated autoreactive T cells to eliminate an Rb-positive cancer cell population as described herein. In another embodiment, the compound is used in combination with a bispecific T-cell Engager (BiTE), which is an antibody designed to simultaneously bind to specific antigens on endogenous T cells and Rb-positive cancer cells as described herein, linking the two types of cells.

In one embodiment, the additional therapy is a monoclonal antibody (MAb). Some MAbs stimulate an immune response that destroys cancer cells. Similar to the antibodies produced naturally by B cells, these MAbs "coat" the cancer cell surface, triggering its destruction by the immune system. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs that bind to cell surface growth factor receptors prevent the targeted receptors from sending their normal growth-promoting signals. They may also trigger apoptosis and activate the immune system to destroy tumor cells.

Another group of cancer therapeutic MAbs are the immunoconjugates. These MAbs, which are sometimes called immunotoxins or antibody-drug conjugates, consist of an antibody attached to a cell-killing substance, such as a plant or bacterial toxin, a chemotherapy drug, or a radioactive molecule. The antibody latches onto its specific antigen on the surface of a cancer cell, and the cell-killing substance is taken up by the cell. FDA-approved conjugated MAbs that work this way include ado-trastuzumab emtansine, which targets the HER-2 molecule to deliver the drug DM1, which inhibits cell proliferation, to HER-2 expressing metastatic breast cancer cells.

Immunotherapies with T cells engineered to recognize cancer cells via bispecific antibodies (bsAbs) or chimeric antigen receptors (CARs) are approaches with potential to ablate both dividing and non/slow-dividing subpopulations of cancer cells.

Bispecific antibodies, by simultaneously recognizing target antigen and an activating receptor on the surface of an immune effector cell, offer an opportunity to redirect immune effector cells to kill cancer cells. The other approach is the generation of chimeric antigen receptors by fusing extracellular antibodies to intracellular signaling domains. Chimeric antigen receptor-engineered T cells are able to specifically kill tumor cells in a MHC-independent way.

In some embodiments, the compound can be administered to the subject in combination with other chemotherapeutic agents. If convenient, the compounds described herein can be administered at the same time as another chemotherapeutic agent, in order to simplify the treatment regimen. In some embodiments, the compound and the other chemotherapeutic can be provided in a single formulation. In one embodiment, the use of the compounds described herein is combined in a therapeutic regime with other agents. Such agents may include, but are not limited to, tamoxifen, midazolam, letrozole, bortezomib, anastrozole, goserelin, an mTOR inhibitor, a PI3 kinase inhibitors, dual mTOR-PI3K inhibitors, MEK inhibitors, RAS inhibitors, ALK inhibitors, HSP inhibitors (for example, HSP70 and HSP 90 inhibitors, or a combination thereof), BCL-2 inhibitors, apoptotic inducing compounds, AKT inhibitors, including but not limited to, MK-2206, GSK690693, Perifosine, (KRX-0401), GDC-0068, Triciribine, AZD5363, Honokiol, PF-04691502, and Miltefosine, PD-1 inhibitors including but not limited to, Nivolumab, CT-011 (pidilizumab), MK-3475 (pembrolizumab), BMS936558, MPDL328OA (Roche), and AMP-514 or FLT-3 inhibitors, including but not limited to, P406, Dovitinib, Quizartinib (AC220), Amuvatinib (MP-470), Tandutinib (MLN518), ENMD-2076, and KW-2449, or combinations thereof. Examples of mTOR inhibitors include but are not limited to rapamycin and its analogs, everolimus (Afinitor), temsirolimus, ridaforolimus, sirolimus, and deforolimus. Examples of P13 kinase inhibitors include but are not limited to Wortmannin, demethoxyviridin, perifosine, idelalisib, PX-866, IPI-145, BAY 80-6946, BEZ235, RP6503, TGR 1202 (RP5264), MLN1117 (INK1117), Pictilisib, Buparlisib, SAR245408 (XL147), SAR245409 (XL765), Palomid 529, ZSTK474, PWT33597, RP6530, CUDC-907, and AEZS-136. Examples of MEK inhibitors include but are not limited to Tametinib, Selumetinib, MEK162, GDC-0973 (XL518), and PD0325901. Examples of RAS inhibitors include but are not limited to Reolysin and siG12D LODER. Examples of ALK inhibitors include but are not limited to Crizotinib, AP26113, and LDK378. HSP inhibitors include but are not limited to Geldanamycin or 17-N-Allylamino-17-demethoxygeldanamycin (17AAG), and Radicicol. In a particular embodiment, a compound described herein is administered in combination with letrozole and/or tamoxifen. Other chemotherapeutic agents that can be used in combination with the compounds described herein include, but are not limited to, chemotherapeutic agents that do not require cell cycle activity for their anti-neoplastic effect.

In one embodiment, a CDK4/6 inhibitor described herein can be combined with a chemotherapeutic selected from, but are not limited to, Imatinib mesylate (Gleevac®), Dasatinib (Sprycel®), Nilotinib (Tasigna®), Bosutinib (Bosulif®), Trastuzumab (Herceptin®), Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Tagretin®), Alitretinoin (Panretin®), Tretinoin (Vesanoid®), Carfilizomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

In certain aspects, the additional therapeutic agent is an anti-inflammatory agent, a chemotherapeutic agent, a radiotherapeutic, additional therapeutic agents, or immunosuppressive agents.

Suitable chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™)

Examples of additional suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), anti-mitotic agents, cis-dichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, E. coli L-asparaginase, emetine, epoetin-α, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Additional therapeutic agents that can be administered in combination with a compound disclosed herein can include bevacizumab, sutinib, sorafenib, 2-methoxyestradiol or 2ME2, finasunate, vatalanib, vandetanib, aflibercept, volociximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, and celecoxib.

In one aspect of the present invention, a compound described herein can be combined with at least one immunosuppressive agent. The immunosuppressive agent is preferably selected from the group consisting of a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g.ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA41 g (Abatacept), belatacept, LFA31g, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

In one aspect of the present invention, a compound described herein can be combined with at least one anti-inflammatory agent. The anti-inflammatory agent can be a steroidal anti-inflammatory agent, a nonsteroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lornoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

In one aspect of the present invention, a compound described herein can be combined with at least one immunomodulatory agent. In one embodiment, the immunomodulatory agent is selected from the group consisting of a CTLA-4 inhibitor, PD-1 or anti-PD-1 agent, IFN-alpha, IFN-beta, and a vaccine, for example, a cancer vaccine. In one embodiment, the PD-1 agent is Keytruda® (pembrolizumab). In one embodiment, the PD-1 agent is Opdivo (nivolumab). In one embodiment, the CTLA-4 inhibitor is Yervoy® (ipilimumab).

In certain embodiments, a compound described herein is administered to the subject prior to treatment with another chemotherapeutic agent, during treatment with another chemotherapeutic agent, after administration of another chemotherapeutic agent, or a combination thereof.

In some embodiments, the compound can be administered to the subject such that the other chemotherapeutic agent can be administered either at higher doses (increased chemotherapeutic dose intensity) or more frequently (increased chemotherapeutic dose density). Dose-dense chemotherapy is a chemotherapy treatment plan in which drugs are given with less time between treatments than in a standard chemotherapy treatment plan. Chemotherapy dose intensity represents unit dose of chemotherapy administered per unit time. Dose intensity can be increased or decreased through altering dose administered, time interval of administration, or both.

In one embodiment of the invention, the compounds described herein can be administered in a concerted regimen with another agent such as a non-DNA-damaging, targeted anti-neoplastic agent or a hematopoietic growth factor agent. It has been recently reported that the untimely administration of hematopoietic growth factors can have serious side effects. For example, the use of the EPO family of growth factors has been associated with arterial hypertension, cerebral convulsions, hypertensive encephalopathy, thromboembolism, iron deficiency, influenza like syndromes and venous thrombosis. The G-CSF family of growth factors has been associated with spleen enlargement and rupture, respiratory distress syndrome, allergic reactions and sickle cell complications. By combining the administration of the short-lived selective compounds described herein and methods of the present invention with the timely administration of hematopoietic growth factors, for example, at the time point wherein the affected cells are no longer under growth arrest, it is possible for the health care practitioner to decrease the amount of the growth factor to minimize the unwanted adverse effects while achieving the desired therapeutic benefit. In one embodiment, the growth factor is administered upon cessation of the effect of the compound on the CDK4/6 replication dependent healthy cells, for example HSPCs. Thus, in this embodiment, the use of a selective compound described herein in an anti-neoplastic therapeutic regime may allow the subject to receive a reduced amount of growth factor because the targeted hematopoietic cells will have reentered the cell cycle quicker than treatment with other CDK4/6 inhibitors, for example PD0332991. In addition, rapid cell-cycle reentry following G1 arrest using a compound described herein provides for the ability to time the administration of hematopoietic growth factors to assist in the reconstitution of hematopoietic cell lines to maximize the growth factor effect, that is, when the growth factors will be most effective. As such, in one embodiment, the use of the compounds or methods described herein is combined with the use of hematopoietic growth factors including, but not limited to, granulocyte colony stimulating factor (G-CSF, for example, sold as Neupogen (filgrastin), Neulasta (peg-filgrastin), or lenograstin), granulocyte-macrophage colony stimulating factor (GM-CSF, for example sold as molgramostim and sargramostim (Leukine)), M-CSF (macrophage colony stimulating factor), thrombopoietin (megakaryocyte growth development factor (MGDF), for example sold as Romiplostim and Eltrombopag) interleukin (IL)-12, interleukin-3, interleukin-11 (adipogenesis inhibiting factor or oprelvekin), SCF (stem cell factor, steel factor, kit-ligand, or KL) and erythropoietin (EPO), and their derivatives (sold as for example epoetin-α as Darbopoetin, Epocept, Nanokine, Epofit, Epogin, Eprex and Procrit; epoetin-β sold as for example NeoRecormon, Recormon and Micera), epoetin-delta (sold as for example Dynepo), epoetin-omega (sold as for example Epomax), epoetin zeta (sold as for example Silapo and Reacrit) as well as for example Epocept, EPOTrust, Erypro Safe, Repoeitin, Vintor, Epofit, Erykine, Wepox, Espogen, Relipoeitin, Shanpoietin, Zyrop and EPIAO). In one embodiment, the tricyclic lactam is administered prior to administration of the hematopoietic growth factor. In one embodiment, the hematopoietic growth factor administration is timed so that the compound's effect on HSPCs has dissipated. In one embodiment, the growth factor is administered at least 20 hours after the administration of a compound described herein.

If desired, multiple doses of a compound described herein can be administered to the subject. Alternatively, the subject can be given a single dose of a compound described herein. In some embodiments, the CDK4/6-replication dependent healthy cells can be arrested for longer periods, for example, over a period of hours, days, weeks and/or months, through multiple, limited-time separated administrations of a compound described herein.

The reduction in side effects by the compounds described herein can allow for dose intensification (e.g., more therapy can be given in a fixed period of time), which will translate to better efficacy. Therefore, the presently disclosed methods can result in regimens that are less toxic and more effective. When appropriate, the small molecules can be formulated for oral, topical, intranasal, inhalation, intravenous or any other desired form of administration.

The use of a compound as described herein can induce selective G1 arrest in CDK4/6-dependent cells (e.g., as measured in a cell-based in vitro assay). In one embodiment, the tricyclic lactam is capable of increasing the percentage of CDK4/6-dependent cells in the G1 phase, while decreasing the percentage of CDK4/6-dependent cells in the G2/M phase and S phase. In one embodiment, the compound induces substantially pure (i.e., "clean") G1 cell cycle arrest in the CDK4/6-dependent cells, e.g., wherein treatment with the compound induces cell cycle arrest such that the majority of cells are arrested in G1 as defined by standard methods (e.g. propidium iodide (PI) staining or others) with the population of cells in the G2/M and S phases combined being less than about 30%, about 25%, about 20%, about 15%, about 10%, about 5%, about 3% or less of the total cell population. Methods of assessing the cell phase of a population of cells are known in the art (see, for example, in U.S. Patent Application Publication No. 2002/0224522) and include cytometric analysis, microscopic analysis, gradient centrifugation, elutriation, fluorescence techniques including immunofluorescence, and combinations thereof. Cytometric techniques include exposing the cell to a labeling agent or stain, such as DNA-binding dyes, e.g., PI, and analyzing cellular DNA content by flow cytometry. Immunofluorescence techniques include detection of specific cell cycle indicators such as, for example, thymidine analogs (e.g., 5-bromo-2-deoxyuridine (BrdU) or an iododeoxyuridine), with fluorescent antibodies.

In some embodiments, the use of a tricyclic lactam compound described herein results in reduced or substantially free of off-target effects, for example, related to inhibition of kinases other than CDK4 and or CDK6 such as CDK2. Furthermore, in certain embodiments, the use of the compounds described herein should not induce cell cycle arrest in CDK4/6-independent cells.

In one aspect of the invention, a compound disclosed herein can be beneficially administered in combination with any therapeutic regimen entailing radiotherapy, chemotherapy, or other therapeutic agents. In one embodiment, a tricyclic lactam compound described herein is administered to a subject with an Rb-positive cancer prior to ionizing radiation (IR) treatment, wherein the CDK4/6 inhibitory effect allows the cancer cells to be arrested in G0/G1 replication, and as the CDK4/6 inhibitory effect from the tricyclic lactam wears off prior to IR exposure, released to proliferate in a synchronized way, thus increasing the effectiveness of the IR treatment. In additional embodiments the compounds disclosed herein can be beneficially administered in combination with therapeutic agents targeting autoimmune disorders.

Drug Conjugates

In one embodiment, the activity of an active compound for a purpose described herein can be augmented through conjugation to an agent that targets the diseased or abnormally proliferating cell or otherwise enhances activity, delivery, pharmacokinetics or other beneficial property. For example, the compound can be administered as an antibody-drug conjugates (ADC).

In certain embodiments, a selected compound described herein can be administered in conjugation or combination with an antibody or antibody fragment. Fragments of an antibody can be produced through chemical or genetic mechanisms. The antibody fragment can be an antigen binding fragment. For example, the antigen binding fragment can be selected from an Fab, Fab', (Fab')2, or Fv. The antibody fragment can be a Fab. Monovalent F(ab) fragments have one antigen binding site. The antibody can be a divalent (Fab')2 fragment, which has two antigen binding regions that are linked by disulfide bonds. In one embodiment, the antigen fragment is a (Fab'). Reduction of F(ab')2 fragments produces two monovalent Fab' fragments, which have a free sulfhydryl group that is useful for conjugation to other molecules.

A selected compound described herein can be administered in conjugation or combination with a Fv fragment. Fv fragments are the smallest fragment made from enzymatic cleavage of IgG and IgM class antibodies. Fv fragments have the antigen-binding site made of the VH and VC regions, but they lack the CH1 and CL regions. The VH and VL chains are held together in Fv fragments by non-covalent interactions.

In one embodiment, a selected compound as described herein can be administered in combination with an antibody fragment selected from the group consisting of an ScFv, domain antibody, diabody, triabody, tetrabody, Bis-scFv, minibody, Fab2, or Fab3 antibody fragment. In one embodiment, the antibody fragment is a ScFv. Genetic engineering methods allow the production of single chain variable fragments (ScFv), which are Fv type fragments that include the VH and VL domains linked with a flexible peptide When the linker is at least 12 residues long, the ScFv fragments are primarily monomeric. Manipulation of the orientation of the V-domains and the linker length creates different forms of Fv molecules. Linkers that are 3-11 residues long yield scFv molecules that are unable to fold into a functional Fv domain. These molecules can associate with a second scFv molecule, to create a bivalent diabody. In one embodiment, the antibody fragment administered in combination with a selected compound described herein is a bivalent diabody. If the linker length is less than three residues, scFv molecules associate into triabodies or tetrabodies. In one embodiment, the antibody fragment is a triabody. In one embodiment, the antibody fragment is a tetrabody. Multivalent scFvs possess greater functional binding affinity to their target antigens than their monovalent counterparts by having binding to two more target antigens, which reduces the off-rate of the antibody fragment. In one embodiment, the antibody fragment is a minibody. Minibodies are scFv-CH3 fusion proteins that assemble into bivalent dimers. In one embodiment, the antibody fragment is a Bis-scFv fragment. Bis-scFv fragments are bispecific. Miniaturized ScFv fragments can be generated that have two different variable domains, allowing these Bis-scFv molecules to concurrently bind to two different epitopes.

In one embodiment, a selected compound described herein is administered in conjugation or combination with a bispecific dimer (Fab2) or trispecific dimer (Fab3). Genetic methods are also used to create bispecific Fab dimers (Fab2) and trispecific Fab trimers (Fab3). These antibody fragments are able to bind 2 (Fab2) or 3 (Fab3) different antigens at once.

In one embodiment, a selected compound described herein is administered in conjugation or combination with an rIgG antibody fragment. rIgG antibody fragments refers to reduced IgG (75,000 daltons) or half-IgG. It is the product of selectively reducing just the hinge-region disulfide bonds. Although several disulfide bonds occur in IgG, those in the hinge-region are most accessible and easiest to reduce, especially with mild reducing agents like 2-mercaptoethylamine (2-MEA). Half-IgG are frequently prepared for the purpose of targeting the exposing hinge-region sulfhydryl groups that can be targeted for conjugation, either antibody immobilization or enzyme labeling.

In other embodiments, a selected active compound described herein can be linked to a radioisotope to increase efficacy, using methods well known in the art. Any radioisotope that is useful against Rb-positive cancer cells can be incorporated into the conjugate, for example, but not limited to, $^{131}$I, $^{123}$I, $^{192}$I, $^{32}$P, $^{90}$Sr, $^{198}$Au, $^{226}$Ra, $^{90}$Y, $^{241}$Am, $^{252}$Cf, $^{60}$Co, or $^{137}$Cs.

Of note, the linker chemistry can be important to efficacy and tolerability of the drug conjugates. The thio-ether linked T-DM1 increases the serum stability relative to a disulfide linker version and appears to undergo endosomal degradation, resulting in intra-cellular release of the cytotoxic agent, thereby improving efficacy and tolerability, See, Barginear, M. F. and Budman, D. R., Trastuzumab-DM1: A review of the novel immune-conjugate for HER2-overexpressing breast cancer, The Open Breast Cancer Journal, 1:25-30, 2009.

Examples of early and recent antibody-drug conjugates, discussing drugs, linker chemistries and classes of targets for product development that may be used in the present invention can be found in the reviews by Casi, G. and Neri, D., Antibody-drug conjugates: basic concepts, examples and future perspectives, J. Control Release 161(2):422-428, 2012, Chari, R. V., Targeted cancer therapy: conferring specificity to cytotoxic drugs, Acc. Chem. Rev., 41(1):98-

107, 2008, Sapra, P. and Shor, B., Monoclonal antibody-based therapies in cancer: advances and challenges, Pharmacol. Ther., 138(3):452-69, 2013, Schliemann, C. and Neri, D., Antibody-based targeting of the tumor vasculature, Biochim. Biophys. Acta., 1776(2):175-92, 2007, Sun, Y., Yu, F., and Sun, B. W., Antibody-drug conjugates as targeted cancer therapeutics, Yao Xue Xue Bao, 44(9):943-52, 2009, Teicher, B. A., and Chari, R. V., Antibody conjugate therapeutics: challenges and potential, Clin. Cancer Res., 17(20): 6389-97, 2011, Firer, M. A., and Gellerman, G. J., Targeted drug delivery for cancer therapy: the other side of antibodies, J. Hematol. Oncol., 5:70, 2012, Vlachakis, D. and Kossida, S., Antibody Drug Conjugate bioinformatics: drug delivery through the letterbox, Comput. Math. Methods Med., 2013; 2013:282398, Epub 2013 Jun. 19, Lambert, J. M., Drug-conjugated antibodies for the treatment of cancer, Br. J. Clin. Pharmacol., 76(2):248-62, 2013, Concalves, A., Tredan, O., Villanueva, C. and Dumontet, C., Antibody-drug conjugates in oncology: from the concept to trastuzumab emtansine (T-DM1), Bull. Cancer, 99(12):1183-1191, 2012, Newland, A. M., Brentuximab vedotin: a CD-30-directed antibody-cytotoxic drug conjugate, Pharmacotherapy, 33(1): 93-104, 2013, Lopus, M., Antibody-DM1 conjugates as cancer therapeutics, Cancer Lett., 307(2):113-118, 2011, Chu, Y. W. and Poison, A., Antibody-drug conjugates for the treatment of B-cell non-Hodgkin's lymphoma and leukemia, Future Oncol., 9(3):355-368, 2013, Bertholjotti, I., Antibody-drug conjugate—a new age for personalized cancer treatment, Chimia, 65(9): 746-748, 2011, Vincent, K. J., and Zurini, M., Current strategies in antibody engineering: Fc engineering and pH-dependent antigen binding, bispecific antibodies and antibody drug conjugates, Biotechnol. J., 7(12):1444-1450, 2012, Haeuw, J. F., Caussanel, V., and Beck, A., Immunoconjugates, drug-armed antibodies to fight against cancer, Med. Sci., 25(12):1046-1052, 2009 and Govindan, S. V., and Goldenberg, D. M., Designing immunoconjugates for cancer therapy, Expert Opin. Biol. Ther., 12(7):873-890, 2012.

Pharmaceutical Compositions and Dosage Forms

An active compound described herein, or its salt, isotopic analog, or prodrug can be administered in an effective amount to the host using any suitable approach which achieves the desired therapeutic result. The amount and timing of active compound administered will, of course, be dependent on the host being treated, the instructions of the supervising medical specialist, on the time course of the exposure, on the manner of administration, on the pharmacokinetic properties of the particular active compound, and on the judgment of the prescribing physician. Thus, because of host to host variability, the dosages given below are a guideline and the physician can titrate doses of the compound to achieve the treatment that the physician considers appropriate for the host. In considering the degree of treatment desired, the physician can balance a variety of factors such as age and weight of the host, presence of preexisting disease, as well as presence of other diseases. Pharmaceutical formulations can be prepared for any desired route of administration including, but not limited to, oral, intravenous, or aerosol administration, as discussed in greater detail below.

The therapeutically effective dosage of any active compound described herein will be determined by the health care practitioner depending on the condition, size and age of the patient as well as the route of delivery. In one non-limited embodiment, a dosage from about 0.1 to about 200 mg/kg has therapeutic efficacy, with all weights being calculated based upon the weight of the active compound, including the cases where a salt is employed. In some embodiments, the dosage can be the amount of compound needed to provide a serum concentration of the active compound of up to between about 1 and 5, 10, 20, 30, or 40 µM. In some embodiments, a dosage from about 10 mg/kg to about 50 mg/kg can be employed for oral administration. Typically, a dosage from about 0.5 mg/kg to 5 mg/kg can be employed for intramuscular injection. In some embodiments, dosages can be from about 1 µmol/kg to about 50 µmol/kg, or, optionally, between about 22 µmol/kg and about 33 µmol/kg of the compound for intravenous or oral administration. An oral dosage form can include any appropriate amount of active material, including for example from 5 mg to, 50, 100, 200, or 500 mg per tablet or other solid dosage form.

In accordance with the presently disclosed methods, pharmaceutically active compounds as described herein can be administered orally as a solid or as a liquid, or can be administered intramuscularly, intravenously, or by inhalation as a solution, suspension, or emulsion. In some embodiments, the compounds or salts also can be administered by inhalation, intravenously, or intramuscularly as a liposomal suspension. When administered through inhalation the active compound or salt can be in the form of a plurality of solid particles or droplets having any desired particle size, and for example, from about 0.01, 0.1 or 0.5 to about 5, 10, 20 or more microns, and optionally from about 1 to about 2 microns. Compounds as disclosed in the present invention have demonstrated good pharmacokinetic and pharmacodynamics properties, for instance when administered by the oral or intravenous routes.

The pharmaceutical formulations can comprise an active compound described herein or a pharmaceutically acceptable salt thereof, in any pharmaceutically acceptable carrier. If a solution is desired, water may be the carrier of choice for water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and for illustration by filtration through a 0.22-micron filter. Subsequent to sterilization, the solution can be dispensed into appropriate receptacles, such as depyrogenated glass vials. The dispensing is optionally done by an aseptic method. Sterilized closures can then be placed on the vials and, if desired, the vial contents can be lyophilized.

In addition to the active compounds or their salts, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. An antimicrobial preservative is typically employed when the formulations is placed in a vial designed for multi-dose use. The pharmaceutical formulations described herein can be lyophilized using techniques well known in the art.

For oral administration a pharmaceutical composition can take the form of solutions, suspensions, tablets, pills, capsules, powders, and the like. Tablets containing various excipients such as sodium citrate, calcium carbonate and calcium phosphate may be employed along with various disintegrants such as starch (e.g., potato or tapioca starch) and certain complex silicates, together with binding agents such as polyvinylpyrrolidone, sucrose, gelatin and acacia. Additionally, lubricating agents such as magnesium stearate, sodium lauryl sulfate, and talc are often very useful for tableting purposes. Solid compositions of a similar type may be employed as fillers in soft and hard-filled gelatin capsules. Materials in this connection also include lactose or milk sugar as well as high molecular weight polyethylene glycols. When aqueous suspensions and/or elixirs are desired for oral administration, the compounds of the presently disclosed host matter can be combined with various sweetening agents, flavoring agents, coloring agents, emulsifying agents and/or suspending agents, as well as such diluents as water, ethanol, propylene glycol, glycerin and various like combinations thereof.

In yet another embodiment of the host matter described herein, there are provided injectable, stable, sterile formulations comprising an active compound as described herein, or a salt thereof, in a unit dosage form in a sealed container. The compound or salt is provided in the form of a lyophilizate, which is capable of being reconstituted with a suitable pharmaceutically acceptable carrier to form liquid formulation suitable for injection thereof into a host. When the compound or salt is substantially water-insoluble, a sufficient amount of emulsifying agent, which is physiologically acceptable, can be employed in sufficient quantity to emulsify the compound or salt in an aqueous carrier. Particularly useful emulsifying agents include phosphatidyl cholines and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound can be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques. The liposomal formulations comprising the active compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol by inhalation. These formulations comprise a solution or suspension of a desired compound described herein or a salt thereof, or a plurality of solid particles of the compound or salt. The desired formulations can be placed in a small chamber and nebulized. Nebulization can be accomplished by compressed air or by ultrasonic energy to form a plurality of liquid droplets or solid particles comprising the compounds or salts. The liquid droplets or solid particles may for example have a particle size in the range of about 0.5 to about 10 microns, and optionally from about 0.5 to about 5 microns. In one embodiment, the solid particles provide for controlled release through the use of a degradable polymer. The solid particles can be obtained by processing the solid compound or a salt thereof, in any appropriate manner known in the art, such as by micronization. Optionally, the size of the solid particles or droplets can be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

Pharmaceutical formulations also are provided which provide a controlled release of a compound described herein, including through the use of a degradable polymer, as known in the art.

When the pharmaceutical formulations suitable for administration as an aerosol is in the form of a liquid, the formulations can comprise a water-soluble active compound in a carrier that comprises water. A surfactant can be present, which lowers the surface tension of the formulations sufficiently to result in the formation of droplets within the desired size range when hosted to nebulization.

The term "pharmaceutically acceptable salts" as used herein refers to those salts which are, within the scope of sound medical judgment, suitable for use in contact with hosts (e.g., human hosts) without undue toxicity, irritation, allergic response, and the like, commensurate with a reasonable benefit/risk ratio, and effective for their intended use, as well as the zwitterionic forms, where possible, of the compounds of the presently disclosed host matter.

Thus, the term "salts" refers to the relatively non-toxic, inorganic and organic acid addition salts of the presently disclosed compounds. These salts can be prepared during the final isolation and purification of the compounds or by separately reacting the purified compound in its free base form with a suitable organic or inorganic acid and isolating the salt thus formed. Basic compounds are capable of forming a wide variety of different salts with various inorganic and organic acids. Acid addition salts of the basic compounds are prepared by contacting the free base form with a sufficient amount of the desired acid to produce the salt in the conventional manner. The free base form can be regenerated by contacting the salt form with a base and isolating the free base in the conventional manner. The free base forms may differ from their respective salt forms in certain physical properties such as solubility in polar solvents. Pharmaceutically acceptable base addition salts may be formed with metals or amines, such as alkali and alkaline earth metal hydroxides, or of organic amines. Examples of metals used as cations, include, but are not limited to, sodium, potassium, magnesium, calcium, and the like. Examples of suitable amines include, but are not limited to, N,N'-dibenzylethylenediamine, chloroprocaine, choline, diethanolamine, ethylenediamine, N-methylglucamine, and procaine. The base addition salts of acidic compounds are prepared by contacting the free acid form with a sufficient amount of the desired base to produce the salt in the conventional manner. The free acid form can be regenerated by contacting the salt form with an acid and isolating the free acid in a conventional manner. The free acid forms may differ from their respective salt forms somewhat in certain physical properties such as solubility in polar solvents.

Salts can be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide such as hydrochloric, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts can also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Pharmaceutically acceptable salts can include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. See, for example, Berge et al., J. Pharm. Sci., 1977, 66, 1-19, which is incorporated herein by reference.

Preparation of Active Compounds

Syntheses

The disclosed compounds can be made by the following general schemes.

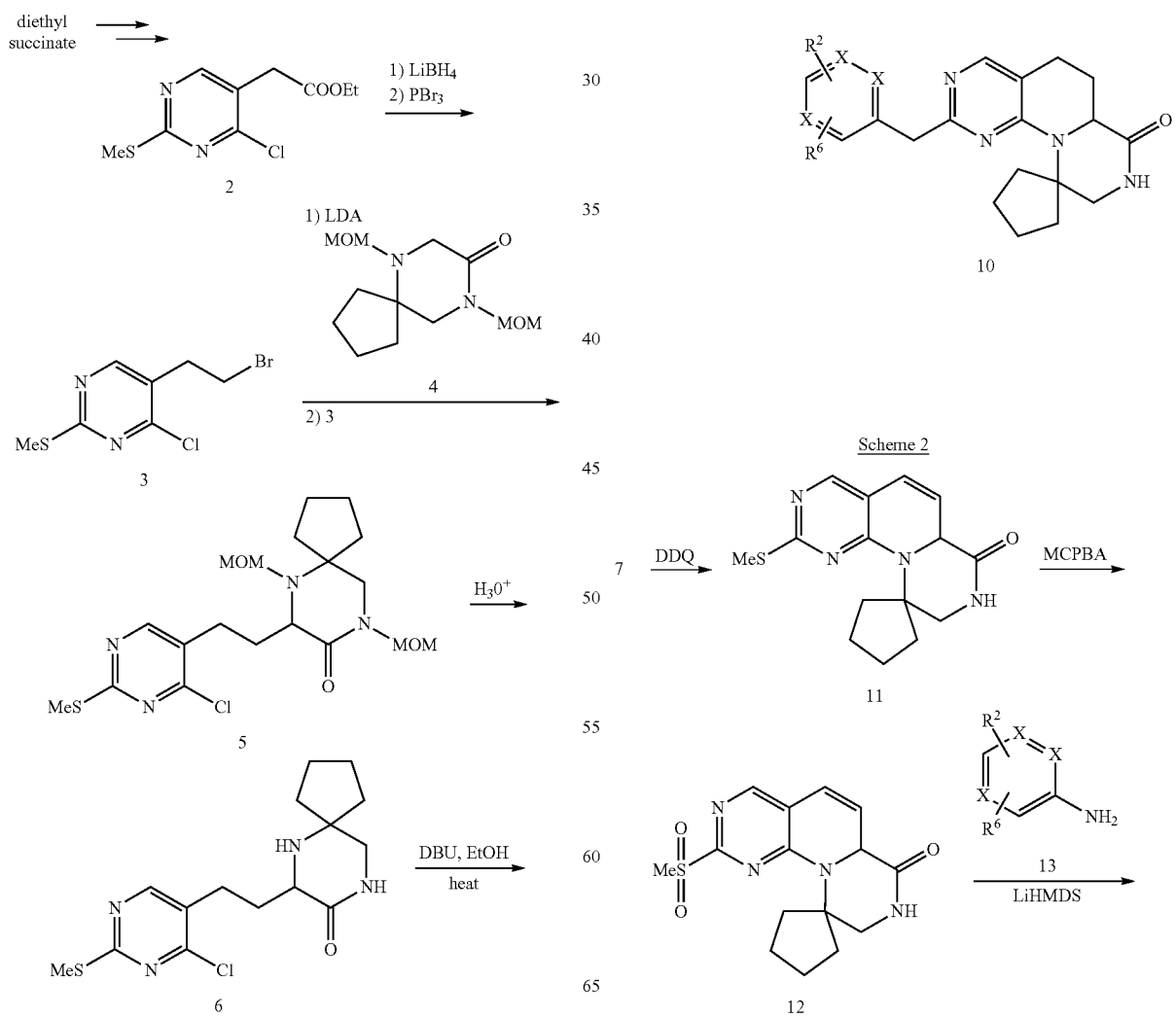

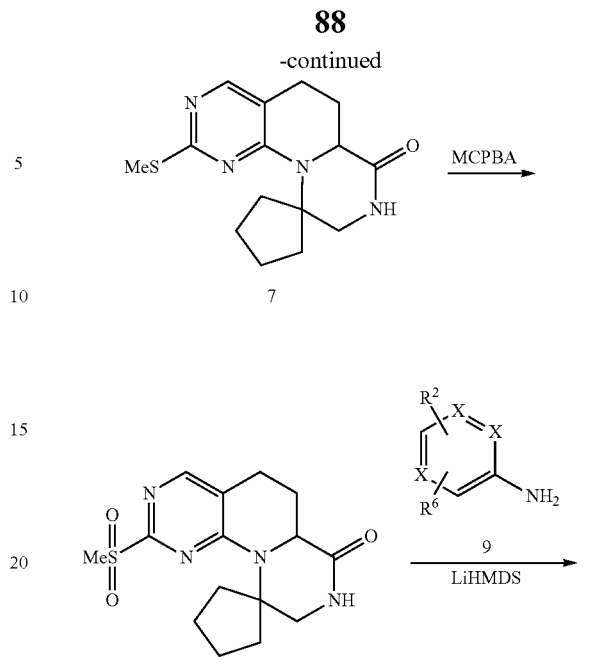

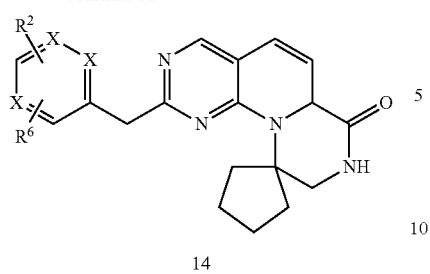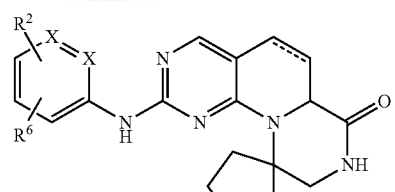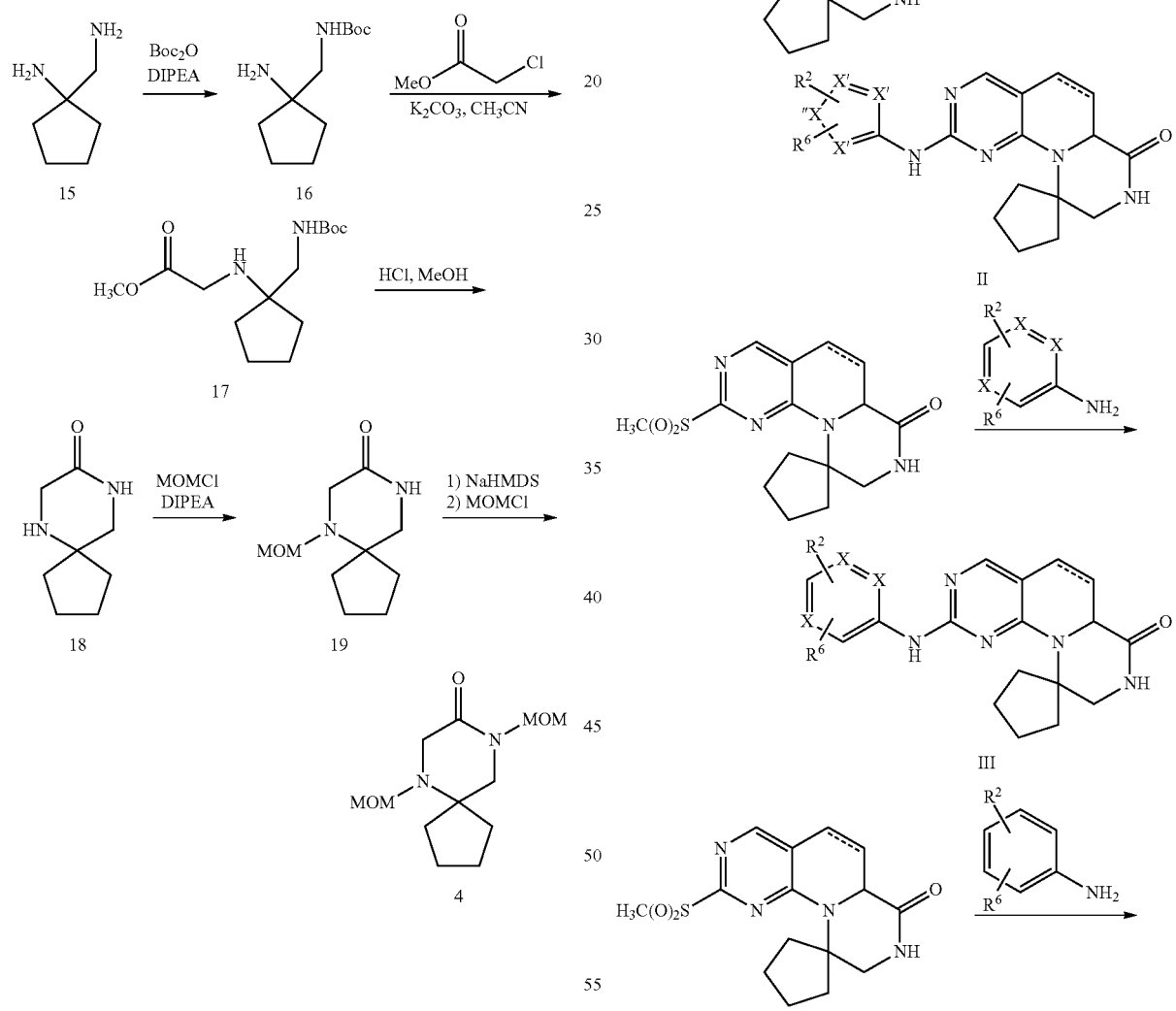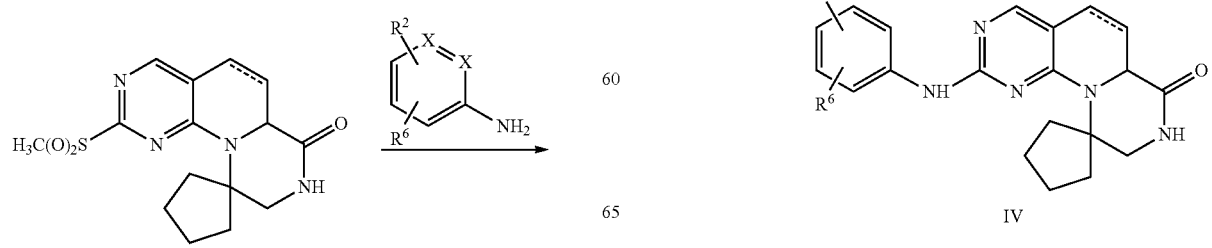

Scheme 5
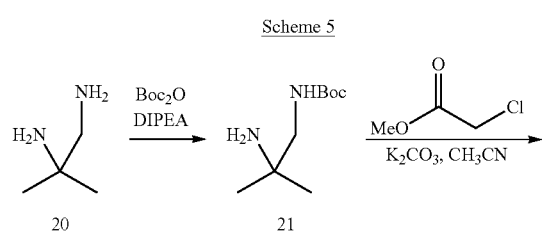
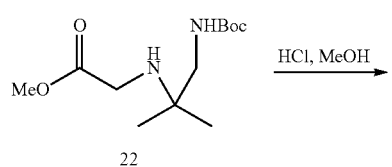
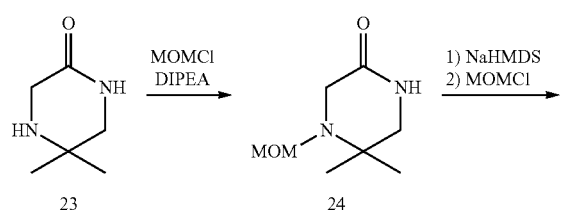
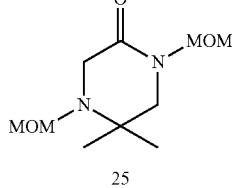
Scheme 6
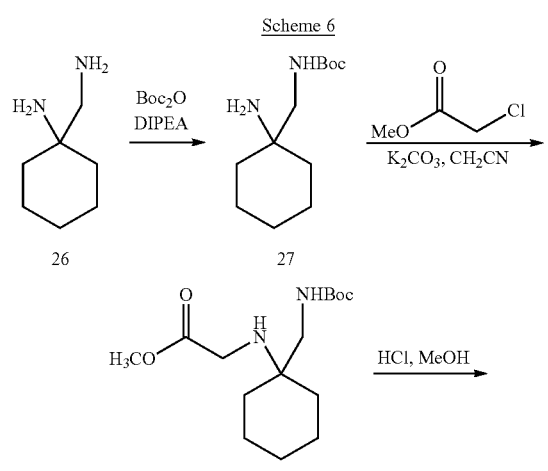
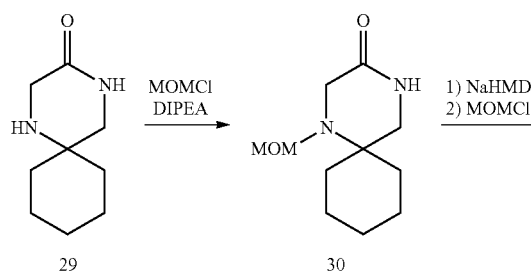
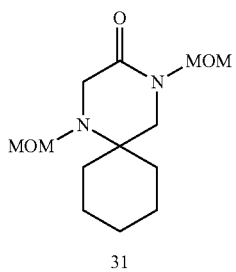
31
Scheme 7
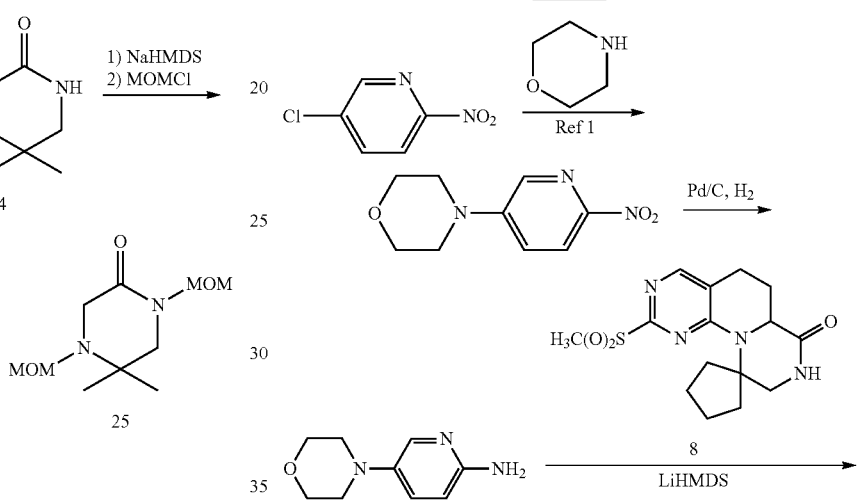
Ref 1 is U.S. Pat. No. 8,598,186
Scheme 8
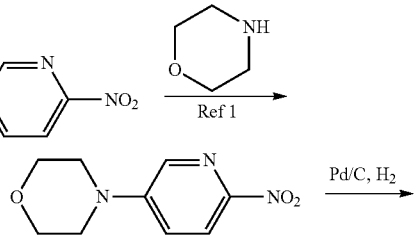

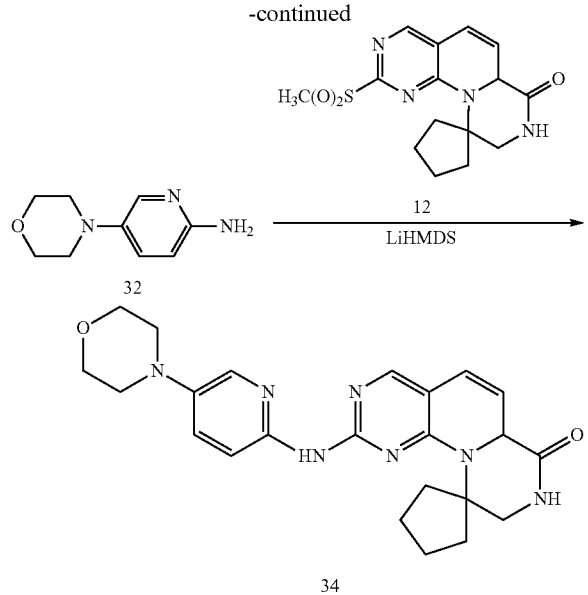

Ref 1 is U.S. Pat. No. 8,598,186

A method for the preparation of substituted tricyclic lactams is provided that includes efficient methods for the preparation of a tricyclic lactam ring system and subsequent displacement of an aryl sulfone with an amine.

In Scheme 1, diethyl succinate is employed to prepare the pyrimidine ester, 2, according to the method of A. Haidle, See, WO 2009/152027 entitled "5,7-dihydro-6H-pyrrolo[2,3-d]pyrimidin-6-one derivatives for MARK inhibition." The ester intermediate 2 can be reduced by directly reacting the ester with a reducing agent such as lithium borohydride in a protic organic solvent such as ethanol to produce the corresponding primary alcohol. The primary alcohol can be reacted with a reagent such as phosphorus tribromide in an organic solvent such as dimethylformamide to produce the primary bromide 3. The primary bromide 3 can be condensed with the lactam 4 optionally at low temperature using a base such as lithium diisopropylamide in an organic solvent such as tetrahydrofuran to produce the lactam 5. Lactam 5 can be deprotected by directly reacting Compound 5 with an aqueous acid such as HCl=pH 1 solution. Lactam 6 can be directly reacted with an organic base such as 1,8-diazabicyclo[5.4.0]undec-7-ene in a protic solvent such as ethanol optionally at high temperature to cyclize Compound 5 to form the tricyclic lactam 7. The thiol moiety can be subsequently oxidized to the sulfone 8 by directly reacting Compound 7 with an oxidizing reagent such as meta-chloroperoxybenzoic acid. The sulfone, 8, can be directly reacted with an amine, 9, in the presence of a strong base such as lithium hexamethyldisilazane to form the tricyclic lactam 10.

In Scheme 2, the tricyclic lactam 7 is directly reacted with an oxidizing reagent such as 2,3-dichloro-5,6-dicyano-1,4-benzoquinone (DDQ) to form the alkene 11. Alkene 11 can be directly reacted with an oxidizing reagent such as meta-chloroperoxybenzoic acid to form the sulfone intermediate 12. The sulfone, 12, can be condensed with an amine, 13, in the presence of a strong base such as lithium hexamethyldisilazane to form the tricyclic lactam 14.

Scheme 3 illustrates the synthesis of a di-protected lactam useful in the preparation of tricyclic lactams. Compound 15 is prepared according to the method of Arigon, J., See, US 2013/0289031 entitled "Pyrimidinone derivatives, preparation thereof and pharmaceutical use thereof." Compound 15 is protected with a suitable protecting group by directly reacting Compound 15 with di-tert-butyl carbonate (Boc anhydride) in the presence of an organic base such as triethylamine or diisopropylethylamine in an organic solvent such as dichloromethane to form the protected amine 16. The protected amine 16 can be directly reacted with methyl chloroacetate in the presence of a base such as potassium carbonate in an organic solvent such as acetonitrile to form the ester 17. The ester 17 can be cyclized by directly reacting the ester with an acid such as hydrochloric acid in a protic solvent such as methanol optionally at a high temperature to form the spirolactam 18. The lactam 18 can be directly reacted with a protecting reagent such as chloromethyl methyl ether (MOM-Cl) in the presence of an organic base such as diisopropylethylamine in an organic solvent such as dichloromethane optionally at a low or at ambient temperature to form the MOM-protected amine 19. The lactam 19 can be protected by directly reacting the lactam with a suitable protecting reagent such as chloromethyl methyl ether (MOM-Cl) in the presence of a base such as sodium bis(trimethylsilyl)amide in an organic solvent such as tetrahydrofuran optionally at a low temperature. Additional lactam intermediates such as Compounds 25 and 31 can be synthesized using analogous chemistry as described for the synthesis of Compound 4. The chemistry for the production of Compounds 25 and 31 is illustrated in Schemes 5 and 6.

Scheme 4 illustrates the coupling of a tricyclic lactam sulfone with an amine to generate compounds of Formula I, II, III, and IV.

Scheme 7 illustrates the preparation of the tricyclic lactam compound 33. Compound 32 is prepared according to the method of Tavares, See, U.S. Pat. No. 8,598,186. Compound 32 is directly reacted with sulfone 8 optionally in the presence of an organic base such as lithium hexamethyldisilazane to form the amine 33. The same chemistry can be employed to produce the alkene compound 34.

In one embodiment a lactam intermediate is treated with BOC-anhydride in the presence of an organic base such as triethylamine in an organic solvent such as dichloromethane. The Boc protected lactam is treated with carbon dioxide in the presence of a nickel catalyst to generate a carboxylic acid. The carboxylic acid is reacted with thionyl chloride in the presence of an organic solvent such as toluene. The resulting acid chloride is treated with an amine to generate an amide that can be deprotected with a strong acid such as trifluoroacetic acid to generate the final target compound.

Alternatively, the lactam can be generated by reacting the carboxylic acid with a protected amine in the presence of a strong acid and a dehydrating agent, which can be together in one moiety as a strong acid anhydride. Examples of strong acid anhydrides include, but are not limited to, trifluoroacetic acid anhydride, tribromoacetic acid anhydride, trichloroacetic acid anhydride, or mixed anhydrides. The dehydrating agent can be a carbodiimide based compound such as but not limited to DCC (N,N-dicyclohexylcarbodiimide), EDC (1-ethyl-3-(3-dimethylaminopropyl)carbodiimide or DIC (N,N-diisopropylcarbodiimide). An additional step may be necessary to take off the N-protecting group and the methodologies are known to those skilled in the art.

Alternatively, the SMe moiety bonded to the pyrimidine ring can be substituted with any leaving group that can be displaced by a primary amine, for example to create an intermediate for a final product such as Br, I, F, $SO_2Me$, SOalkyl, $SO_2$alkyl. See, for Example, PCT/US2013/037878 to Tavares.

Other amine intermediates and final amine compounds can be synthesized by those skilled in the art. It will be appreciated that the chemistry can employ reagents that comprise reactive functionalities that can be protected and de-protected and will be known to those skilled in the art at the time of the invention. See for example, Greene, T. W. and Wuts, P. G. M., Greene's Protective Groups in Organic Synthesis, 4th edition, John Wiley and Sons.
Scheme 9
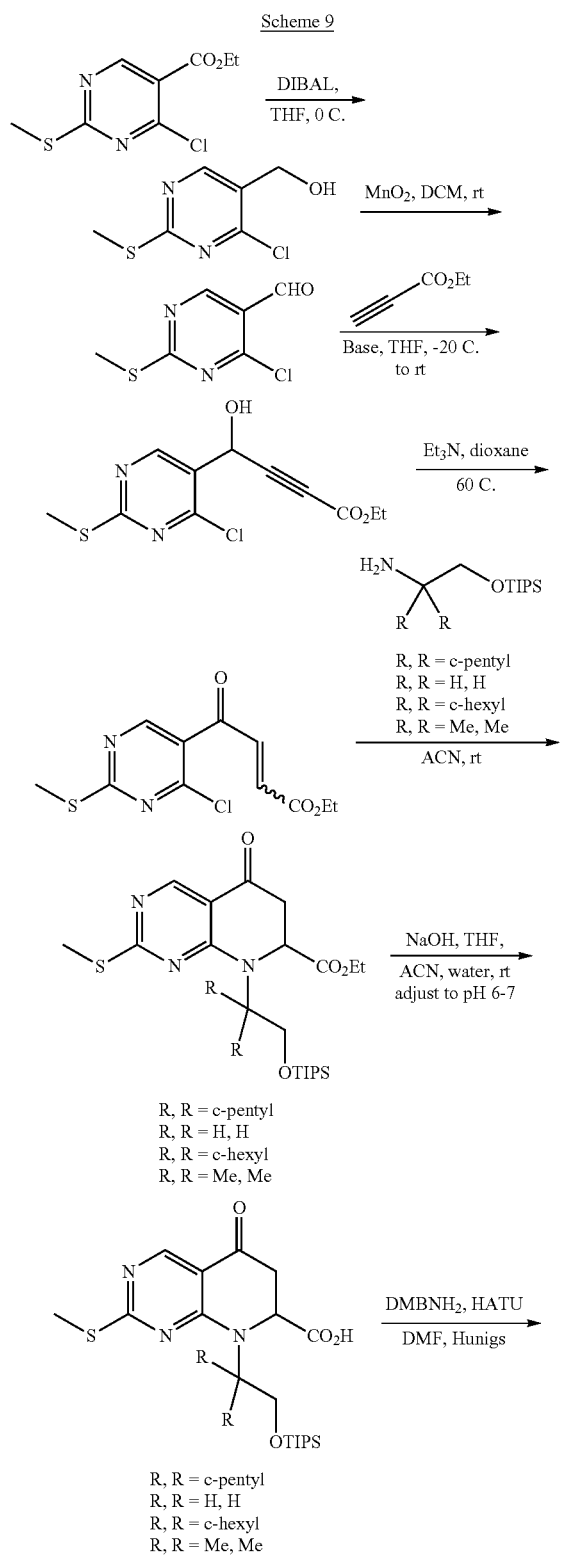
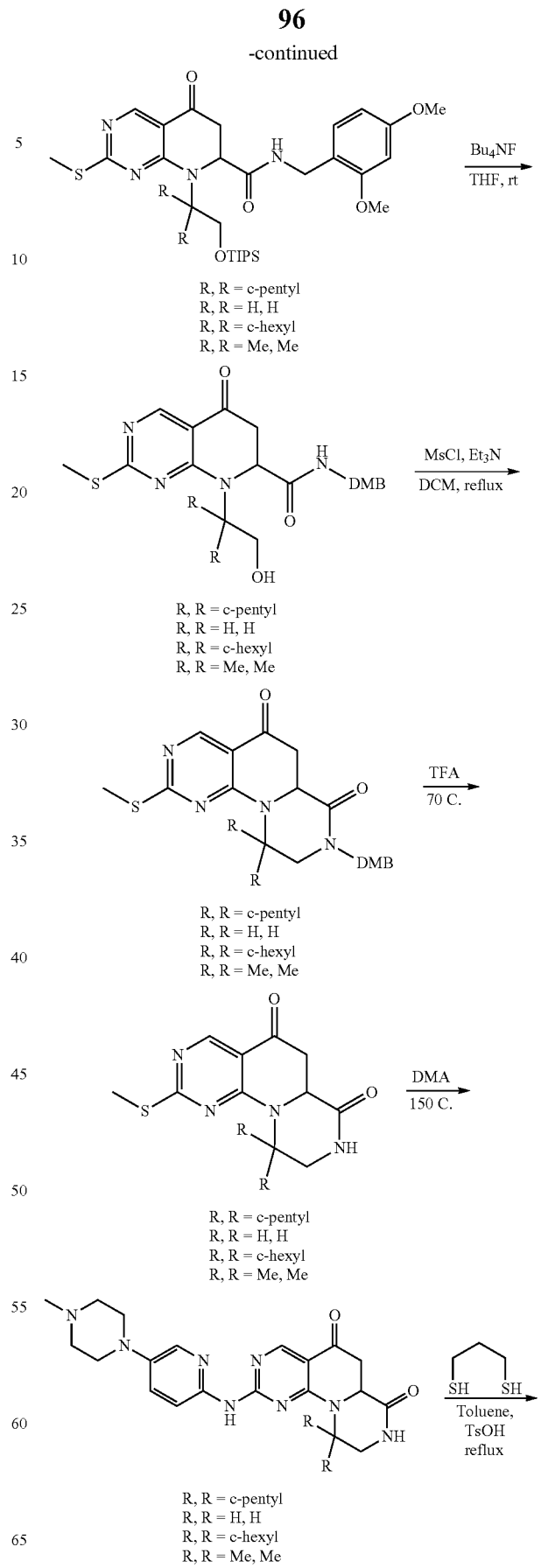

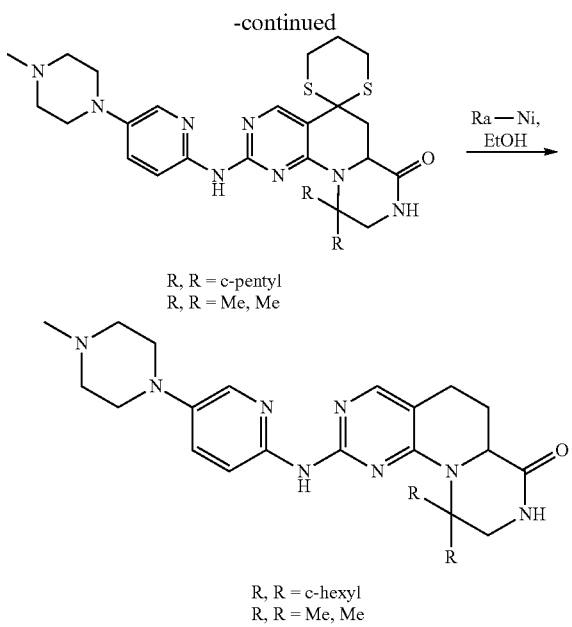

R, R = c-pentyl
R, R = Me, Me

R, R = c-hexyl
R, R = Me, Me

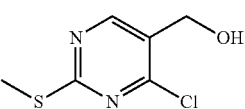

[4-Chloro-2-(methylthio)pyrimidin-5-yl]methanol

4-Chloro-2-methylsulfanyl-5-pyrimidinecarboxylate ethyl ester (62 g, 260 mmol) was dissolved in anhydrous tetrahydrofuran (500 mL) in a 3-necked 5 L round bottomed flask fitted with a mechanical stirrer, addition funnel, temperature probe and nitrogen inlet. The solution was cooled to 0° C. Diisobutylaluminum hydride in tetrahydrofuran (1M solution, 800 mL) was added dropwise over a period of 2 hours. After the addition was complete, the reaction mixture was kept at 0° C. for 0.5 hours. The reaction was quenched at 0° C. by the slow addition of saturated aqueous sodium sulfate (265.3 mL, 530.7 mmol) keeping the internal reaction temperature below 10° C. Ethyl acetate (900 mL) was added and the reaction slowly warmed to room temperature overnight. 6M HCl was added till the reaction mixture was slightly acidic (pH 6). The reaction mixture was filtered thru a pad of Celite® and the aluminum salts were washed with ethyl acetate (1 L). The filtrate was poured into a separatory funnel and washed twice with water (600 mL) and finally with brine (600 mL). The organic layer was dried over sodium sulfate, filtered thru Celite® and the solvent concentrated in vacuo to afford 39.2 g (77% crude yield) of a dark yellow oil. The material was used as is for the next step. NMR (CDCl$_3$) δ8.56 (s, 1H), 4.76 (s, 2H), 2.59 (s, 3H); MS (ESI+) for $C_6H_7ClN_2OS$ m/z 191.0 (M+H)$^+$.

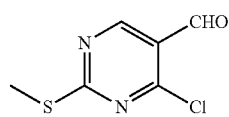

4-Chloro-2-(methylthio)pyrimidine-5-carbaldehyde

[4-Chloro-2-(methylthio)pyrimidin-5-yl]methanol (39.2 g, 206 mmol) was taken up in methylene chloride (520 mL) at room temperature. Manganese(IV) oxide (140 g, 1.60 mol) was added in one portion and the reaction mixture stirred at room temperature overnight. The reaction mixture was filtered through a pad of Celite® and washed with methylene chloride. The filtrate was concentrated under reduced pressure to afford a dark yellow semisolid. The crude product was purified by reverse phase chromatography running a gradient of 1:9 acetonitrile:water (0.1% TFA) to 100% acetonitrile (0.1% TFA). The desired fractions were combined and the acetonitrile was removed under reduced pressure causing precipitation of the desired product. The solids were removed by filtration and the solids washed with water and dried under vacuum at 50° C. Affords 16.6 g (43% yield) of the desired product as a white solid. NMR (CDCl$_3$) δ10.32 (s, 1H), 8.88 (s, 1H), 2.65 (s, 3H); MS (ESI+) for $C_6H_5ClN_2OS$ m/z 189.0 (M+H)$^+$.

General Procedure A.

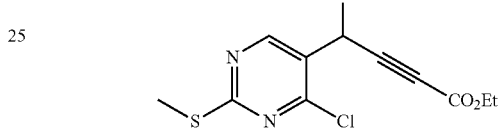

Ethyl 4-[4-chloro-2-(methylthio)pyrimidin-5-yl]-4-hydroxybut-2-ynoate

Isopropylmagnesium chloride:lithium chloride complex (4.43 g, 30.5 mmol, 25.4 mL of a 1.2M solution) was added to tetrahydrofuran (104 mL) in a 500 mL round bottomed flask which had been flame dried and cooled under Argon. The solution was cooled to −15° C. Ethyl propiolate (3.26 mL, 32.1 mmol) was added dropwise affording a yellow solution. Stirring was continued at −15° C. for 30 minutes and then 4-Chloro-2-(methylthio)pyrimidine-5-carbaldehyde (6.06 g, 32.1 mmol) in tetrahydrofuran (52 mL) was added rapidly. After 10 minutes, the reaction was quenched by the addition of saturated aqueous ammonium chloride (40 mL). The reaction mixture was warmed to room temperature and poured into a separatory funnel partitioning between ethyl acetate (200 mL) and water (100 mL). The organic layer removed and the aqueous layer extracted with ethyl acetate (100 mL). The combined organic layers were washed with brine (100 mL), dried over sodium sulfate, filtered and the solvent removed in vacuo to afford a dark red oil. The product was purified by silica gel chromatography using a gradient of 1:4 to 2:3 ethyl acetate:hexanes which afforded 3.76 g (37% yield) of the desired product as a light red oil. NMR (CDCl$_3$) δ8.75 (s, 1H), 5.81 (d, 1H, J=6.0 Hz), 2.72 (bs, 1H), 2.60 (s, 3H), 1.33 (t, 3H, J=7.2 Hz); MS (ESI+) for $C_{11}H_{11}ClN_2O_3S$ m/z 287.9 (M+H)$^+$.

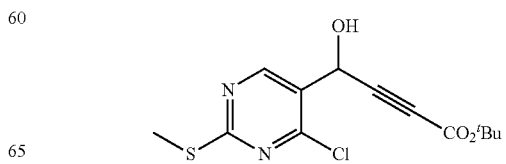

tert-Butyl 4-[4-chloro-2-(methylthio)pyrimidin-5-yl]-4-hydroxybut-2-ynoate

Following General Procedure A and using tert-butyl propiolate affords the desired product in 74% yield as a viscous yellow oil. NMR (CDCl$_3$) δ8.75 (s, 1H), 5.79 (d, 1H, J=5.4 Hz), 4.27 (q, 2H, J=7.2 Hz), 2.97 (d, 1H, J=5.4 Hz), 2.60 (s, 3H), 1.52 (s, 9H); MS (ESI+) for C$_{13}$H$_{15}$ClN$_2$O$_3$S m/z 314.9 (M+H)$^+$.

General Procedure B.

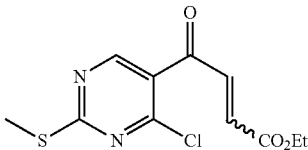 [SMILES: CCOC(=O)C=CC(=O)c1cnc(SC)nc1Cl]

Ethyl 4-[4-chloro-2-(methylthio)pyrimidin-5-yl]-4-oxobut-2-enoate

Ethyl 4-[4-chloro-2-(methylthio)pyrimidin-5-yl]-4-hydroxybut-2-ynoate (3.40 g, 11.8 mmol) was taken up in 1,4-Dioxane (100 mL) at room temperature under argon. Triethylamine (3.3 mL, 24 mmol) was added and the mixture heated to 60° C. for 1 h. The reaction mixture was cooled to room temperature and the solvent removed in vacuo. The resultant dark orange oil was re-evaporated twice with toluene. Affords the desired product (3:1 E:Z double bond isomers) in 99% yield as a dark orange oil. NMR (CDCl$_3$) (major E isomer) δ8.69 (s, 1H), 7.65 (d, 1H, J=18.0 Hz), 6.81 (d, 1H, J=18.0 Hz), 4.32 (q, 2H, J=6.0 Hz), 2.64 (s, 3H), 1.36 (t, 3H, J=6.0 Hz); NMR (CDCl$_3$) (minor Z isomer) δ8.87 (s, 1H), 6.89 (d, 1H, J=12.0 Hz), 6.23 (d, 1H, J=12.0 Hz), 4.14 (q, 2H, J=6.0 Hz), 2.63 (s, 3H), 1.23 (t, 3H, J=6.0 Hz); MS (ESI+) for C$_{11}$H$_{11}$ClN$_2$O$_3$S m/z 287.0 (M+H)$^+$.

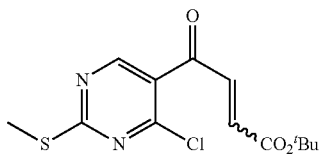 [SMILES: CSc1ncc(C(=O)C=CC(=O)OC(C)(C)C)c(Cl)n1]

tert-Butyl 4-[4-chloro-2-(methylthio)pyrimidin-5-yl]-4-oxobut-2-enoate

Isomerization of tert-butyl 4-[4-chloro-2-(methylthio)pyrimidin-5-yl]-4-hydroxybut-2-ynoate using General Procedure B affords the desired product (5:1 E:Z double bond isomers) in a 99% yield as a viscous dark yellow oil. NMR (CDCl$_3$) (major E isomer) δ8.67 (s, 1H), 7.54 (d, 1H, J=15.6 Hz), 6.72 (d, 1H, J=15.6 Hz), 2.64 (s, 3H), 1.54 (s, 9H); NMR (CDCl$_3$) (minor Z isomer) δ8.86 (s, 1H), 6.76 (d, 1H, J=12.0 Hz), 6.18 (d, 1H, J=12.0 Hz), 2.63 (s, 3H), 1.40 (s, 9H); MS (ESI+) for C$_{13}$H$_{15}$ClN$_2$O$_3$S m/z 314.9 (M+H)$^+$.

General Procedure C.

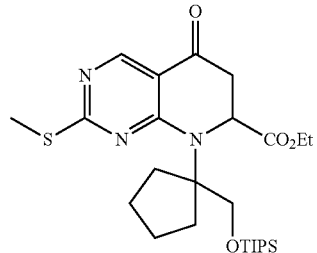

Ethyl 2-(methylthio)-5-oxo-8-(1-{[(triisopropylsilyl)oxy]methyl}cyclopentyl)-5,6,7,8-tetrahydropyrido[2,3-d]pyrimidine-7-carboxylate Ethyl 4-[4-chloro-2-(methylthio)pyrimidin-5-yl]-4-oxobut-2-enoate (3.40 g, 11.8 mmol) was taken up in acetonitrile (20 mL) at room temperature. 1-{[(Triisopropylsilyl)oxy]methyl}cyclopentanamine (3.86 g, 14.2 mmol) was added followed by triethylamine (3.30 mL, 23.7 mmol). The mixture was stirred at room temperature overnight. The reaction mixture was transferred to a separatory funnel transferring with ethyl acetate (250 mL). The organic layer was washed twice with a 10% citric acid (aq) (20 mL)/brine (60 mL) mixture. The organic layer was dried over sodium sulfate, filtered and the solvent removed in vacuo to afford a yellow oil. The product was purified by silica gel chromatography using a gradient from 1:9 to 2:3 ethyl acetate:hexanes which afforded 2.48 g (41% yield) of the desired product as a pale yellow oil. NMR (CDCl$_3$) δ8.58 (s, 1H), 4.72 (m, 1H), 4.46 (m, 1H), 4.16 (q, 2H, J=6.9 Hz), 3.52 (m, 1H), 2.96 (m, 2H), 2.54 (s, 3H), 2.31 (m, 3H), 1.81-1.52 (m, 5H), 1.24 (t, 3H, J=6.9 Hz) 1.08-0.96 (m, 21H); MS (ESI+) for C$_{26}$H$_{43}$N$_3$N$_4$SSi m/z 522.2 (M+H)$^+$.

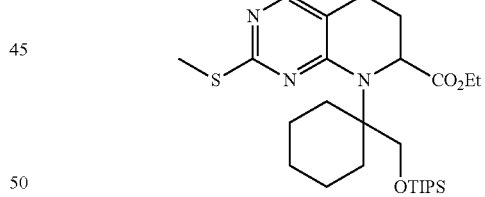

Ethyl 2-(methylthio)-5-oxo-8-(1-{[(triisopropylsilyl)oxy]methyl}cyclohexyl)-5,6,7,8-tetrahydropyrido[2,3-d]pyrimidine-7-carboxylate Cyclization of ethyl 4-[4-chloro-2-(methylthio)pyrimidin-5-yl]-4-oxobut-2-enoate and 1-{[(triisopropylsilyl)oxy]methyl}cyclohexanamine using General Procedure C afforded the desired product in 17% yield as a pale yellow oil. NMR (CDCl$_3$) δ8.63 (s, 1H), 4.83 (m, 1H), 4.73 (m, 1H), 4.14 (q, 2H, J=6.0 Hz), 3.86 (m, 1H), 2.97 (m, 2H), 2.55 (s, 3H), 1.97 (m, 1H), 1.72-1.48 (m, 9H), 1.23 (t, 3H, J=6.0 Hz), 1.13-0.95 (m, 21H); MS (ESI+) for C$_{27}$H$_{45}$N$_3$O$_4$SSi m/z 536.2 (M+H)$^+$

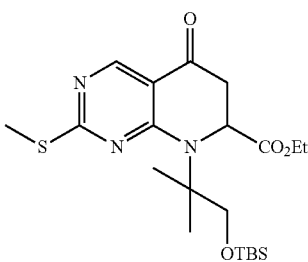 [SMILES: CCOC(=O)C1CC(=O)c2cnc(SC)nc2N1C(C)(C)CO[Si](C)(C)C(C)(C)C]

Ethyl 8-(2-{[tert-butyl(dimethyl)silyl]oxy}-1,1-dimethylethyl)-2-(methylthio)-5-oxo-5,6,7,8-tetrahydropyrido[2,3-d]pyrimidine-7-carboxylate Cyclization of ethyl 4-[4-chloro-2-(methylthio)pyrimidin-5-yl]-4-oxobut-2-enoate and 1-{[tert-butyl(dimethyl)silyl]oxy}-2-methylpropan-2-amine using General Procedure C afforded the desired product in 52% yield as a pale yellow oil. NMR (CDCl$_3$) δ8.62 (s, 1H), 4.94 (m, 1H), 4.18 (m, 3H), 3.63 (m, 1H), 2.93 (m, 2H), 2.57 (s, 3H), 1.71 (s, 3H), 1.55 (s, 3H), 1.23 (t, 3H, J=7.2 Hz), 0.89 (s, 9H), 0.06 (s, 3H), 0.01 (s, 3H); MS (ESI+) for $C_{21}H_{35}N_3O_4SSi$ m/z 454.3 (M+H)$^+$.

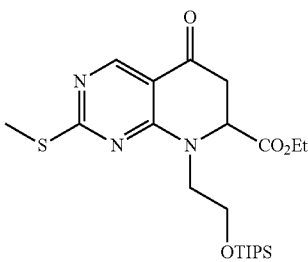

Ethyl 2-(methylthio)-5-oxo-8-{2-[(triisopropylsilyl)oxy]ethyl}-5,6,7,8-tetrahydropyrido[2,3-d]pyrimidine-7-carboxylate Cyclization of ethyl 4-[4-chloro-2-(methylthio)pyrimidin-5-yl]-4-oxobut-2-enoate and 2-[(triisopropylsilyl)oxy]ethanamine using General Procedure C afforded the desired product in 45% yield as a pale yellow oil. NMR (CDCl$_3$) δ8.60 (s, 1H), 4.72 (m, 1H), 4.63 (m, 1H), 4.19 (q, 2H, J=6.0 Hz), 3.97 (m, 2H), 3.22 (m, 1H), 3.01 (m, 2H), 2.54 (s, 3H), 1.28 (t, 3H, J=6.0 Hz), 1.17-1.02 (m, 21H); MS (ESI+) for $C_{22}H_{37}N_3O_4SSi$ m/z 468.1 (M+H)$^+$.

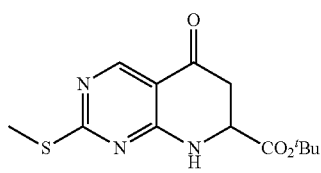 [SMILES: CSc1ncc2c(n1)NC(C(=O)OC(C)(C)C)CC2=O]

tert-Butyl 2-(methylthio)-5-oxo-5,6,7,8-tetrahydropyrido[2,3-d]pyrimidine-7-carboxylate Cyclization of tert-Butyl 4-[4-chloro-2-(methylthio)pyrimidin-5-yl]-4-oxobut-2-enoate and 0.5 M ammonia/dioxane using General Procedure C afforded the desired product in 60% yield as an off-white solid. NMR (CDCl$_3$) δ8.66 (s, 1H), 6.18 (bs, 1H), 4.34 (m, 1H), 3.05-2.80 (m, 2H), 2.56 (s, 3H), 1.51 (s, 9H); MS (ESI+) for $C_{13}H_{17}N_3O_3S$ m/z 296.0 (M+H)$^+$.

General Procedure D.

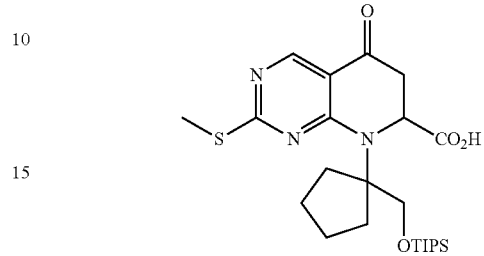

2-(Methylthio)-5-oxo-8-(1-{[(triisopropylsilyl)oxy]methyl}cyclopentyl)-5,6,7,8-tetrahydropyrido[2,3-d]pyrimidine-7-carboxylic acid Ethyl 2-(methylthio)-5-oxo-8-(1-{[(triisopropylsilyl)oxy]methyl}cyclopentyl)-5,6,7,8-tetrahydropyrido[2,3-d]pyrimidine-7-carboxylate (2.48 g, 4.75 mmol) was taken up in tetrahydrofuran (10 mL) and acetonitrile (10 mL) at room temperature. 1M Sodium hydroxide (10 mL, 10 mmol) was added at room temperature for 1 hour. The reaction was quenched by the addition of 10% citric acid till pH ca 6-7. The reaction mixture was transferred to a separatory funnel with water (30 mL) and ethyl acetate (150 mL). The aqueous layer was removed and the organic layer washed with brine (50 mL). The organic layer was dried over sodium sulfate, filtered and the solvent concentrated in vacuo to afford the 2.08 g (89% yield) of the desired product as a dark yellow oil. NMR (CDCl$_3$) δ8.46 (s, 1H), 4.58 (m, 1H), 4.39 (m, 1H), 3.71 (m, 1H), 2.88 (m, 2H), 2.51 (s, 3H), 2.26 (m, 3H), 1.97-1.45 (m, 6H) 1.12-0.92 (m, 21H); MS (ESI+) for $C_{24}H_{39}N_3O_4SSi$ m/z 494.2 (M+H)$^+$.

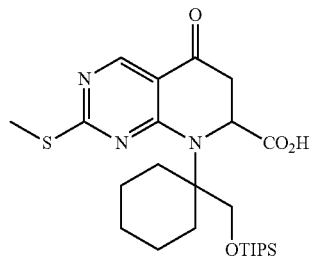

2-(Methylthio)-5-oxo-8-(1-{[(triisopropylsilyl)oxy]methyl}cyclohexyl)-5,6,7,8-tetrahydropyrido[2,3-d]pyrimidine-7-carboxylic acid Saponification of ethyl 2-(methylthio)-5-oxo-8-(1-{[(triisopropylsilyl)oxy]methyl}cyclohexyl)-5,6,7,8-tetrahydropyrido[2,3-d]pyrimidine-7-carboxylate using General Procedure D affords the desired product in 95% yield as a dark yellow oil. NMR (CDCl$_3$) δ8.58 (s, 1H), 4.75 (m, 1H), 4.53 (m, 1H), 3.96 (m, 1H), 2.99 (m, 2H), 2.54 (s, 3H), 1.93-1.48 (m, 10H), 1.13-0.95 (m, 21H); MS (ESI+) for $C_{25}H_{41}N_3O_4SSi$ m/z 508.1 (M+H)$^+$.

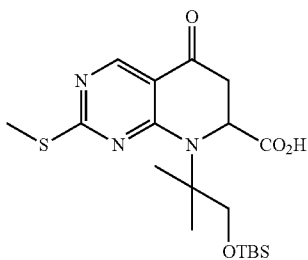 [SMILES: CSc1ncc2c(n1)N(C(C)(C)CO[Si](C)(C)C(C)(C)C)C(C(=O)O)CC2=O]

8-(2-{[tert-Butyl(dimethyl)silyl]oxy}-1,1-dimethylethyl)-2-(methylthio)-5-oxo-5,6,7,8-tetrahydropyrido[2,3-d]pyrimidine-7-carboxylic acid Saponification of ethyl 8-(2-{[tert-butyl(dimethyl)silyl]oxy}-1,1-dimethylethyl)-2-(methylthio)-5-oxo-5,6,7,8-tetrahydropyrido[2,3-d]pyrimidine-7-carboxylate using General Procedure D affords the desired product in 99% yield as a pale yellow foam. NMR (CDCl$_3$) δ8.69 (s, 1H), 4.88 (m, 1H), 4.51 (m, 1H), 3.82 (m, 1H), 3.17 (m, 1H), 2.79 (m, 1H), 2.57 (s, 3H), 1.65 (s, 3H), 1.60 (s, 3H), 0.92 (s, 9H), 0.11 (s, 6H); MS (ESI+) for C$_{19}$H$_{31}$N$_3$O$_4$SSi m/z 426.3 (M+H)$^+$.

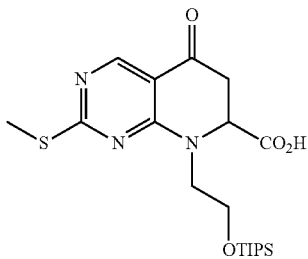

2-(Methylthio)-5-oxo-8-{2-[(triisopropylsilyl)oxy]ethyl}-5,6,7,8-tetrahydropyrido[2,3-d]pyrimidine-7-carboxylic acid Saponification of ethyl 2-(methylthio)-5-oxo-8-{2-[(triisopropylsilyl)oxy]ethyl}-5,6,7,8-tetrahydropyrido[2,3-d]pyrimidine-7-carboxylate using General Procedure D affords the desired product in 98% yield as an orange foam. NMR (CDCl$_3$) δ8.56 (s, 1H), 4.71 (m, 1H), 4.54 (m, 1H), 3.99 (m, 2H), 3.32 (m, 1H), 3.01 (m, 2H), 2.53 (s, 3H), 1.16-0.98 (m, 21H); MS (ESI+) for C$_{20}$H$_{33}$N$_3$O$_4$SSi m/z 440.2 (M+H)$^+$.

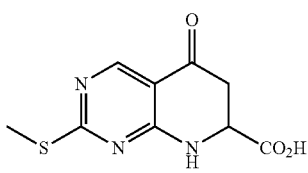 [SMILES: CSc1ncc2c(n1)NC(C(=O)O)CC2=O]

2-(Methylthio)-5-oxo-5,6,7,8-tetrahydropyrido[2,3-d]pyrimidine-7-carboxylic acid tert-Butyl 2-(methylthio)-5-oxo-5,6,7,8-tetrahydropyrido[2,3-d]pyrimidine-7-carboxylate (220 mg, 0.74 mmol) was taken up in trifluoroacetic acid (5 mL) at room temperature under argon. The mixture was stirred at room temperature for 45 minutes. The solvent was removed in vacuo to a pink oil which was re-evaporated first from toluene and finally methanol affording 180 mg (99% yield) of the desired product as an off-white solid. NMR (MeOH-d$_4$) δ8.49 (s, 1H), 4.59 (m, 1H), 3.16-2.91 (m, 2H), 2.63 (s, 3H); MS (ESI+) for C$_9$H$_9$N$_3$O$_3$S m/z 240.0 (M+H)$^+$.

General Procedure E.

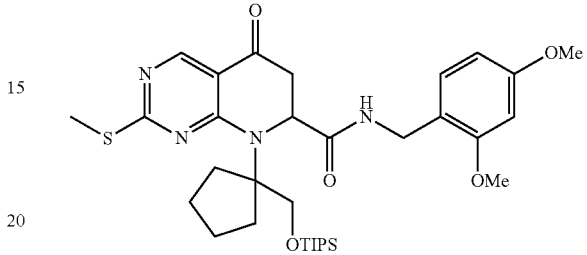

N-(2,4-Dimethoxybenzyl)-2-(methylthio)-5-oxo-8-(1-{[(triisopropylsilyl)oxy]methyl}cyclopentyl)-5,6,7,8-tetrahydropyrido[2,3-d]pyrimidine-7-carboxamide 2-(Methylthio)-5-oxo-8-(1-{[(triisopropylsilyl)oxy]methyl}cyclopentyl)-5,6,7,8-tetrahydropyrido[2,3-d]pyrimidine-7-carboxylic acid (2.08 g, 4.21 mmol) was taken up in N,N-dimethylformamide (30 mL) at room temperature. 1-(2,4-dimethoxyphenyl)methanamine (1.26 mL, 8.42 mmol) was added followed by the addition of N,N,N',N'-tetramethyl-O-(7-azabenzotriazol-1-yl)uranium hexafluoro phosphate (4.80 g, 12.6 mmol) and N,N-diisopropylethylamine (4.40 mL, 25.3 mmol). The reaction mixture was stirred overnight at room temperature. The product was diluted with water (50 mL) and poured into a separatory funnel. The mixture was extracted with twice with ethyl acetate (150 mL) and the combined organic layers were thrice washed with half-saturated aqueous Lice (20 mL). The combined organic layers were dried over sodium sulfate, filtered and the solvent removed in vacuo to afford a dark yellow oil. The product was purified by silica gel chromatography using a gradient from 1:4 to 2:3 ethyl acetate:hexanes which afforded 2.39 g (88% yield) of the desired product as a brown sticky solid. NMR (CDCl$_3$) δ8.58 (s, 1H), 7.07 (m, 1H), 6.62 (m, 1H), 6.39 (m, 2H), 4.56 (m, 1H), 4.38 (m, 2H), 4.20 (m, 1H), 3.80 (s, 3H), 3.66 (s, 3H), 3.48 (m, 1H), 3.02 (m, 2H), 2.55 (s, 3H), 2.35 (m, 2H), 2.06 (m, 1H), 1.70-1.31 (m, 5H), 1.09-0.90 (m, 21H); MS (ESI+) for C$_{33}$H$_{50}$N$_4$O$_5$SSi m/z 643.2 (M+H)$^+$.

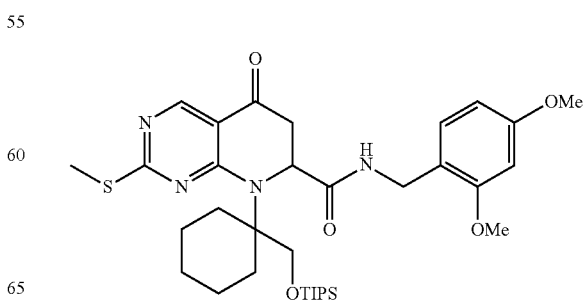

N-(2,4-Dimethoxybenzyl)-2-(methylthio)-5-oxo-8-(1-{[(triisopropylsilyl)oxy]methyl}cyclohexyl)-5,6,7,8-tetrahydropyrido[2,3-d]pyrimidine-7-carboxamide Coupling reaction of 2-(methylthio)-5-oxo-8-(1-{[(triisopropylsilyl)oxy]methyl}cyclohexyl)-5,6,7,8-tetrahydropyrido[2,3-d]pyrimidine-7-carboxylic acid using General Procedure E afforded the desired product in 52% yield as a yellow solid. NMR (CDCl$_3$) δ8.60 (s, 1H), 6.87 (m, 2H), 6.37 (m, 2H), 4.71 (m, 1H), 4.49-4.14 (m, 4H), 3.79 (s, 3H), 3.70 (s, 3H), 3.18 (m, 1H), 2.86 (m, 1H), 2.65 (m, 1H), 2.54 (s, 3H), 2.20 (m, 1H), 1.98 (m, 2H), 1.61-1.48 (m, 6H), 1.08-0.92 (bs, 21H); MS (ESI+) for C$_{34}$H$_{52}$N$_4$O$_5$SSi m/z 657.2 (M+H)$^+$.

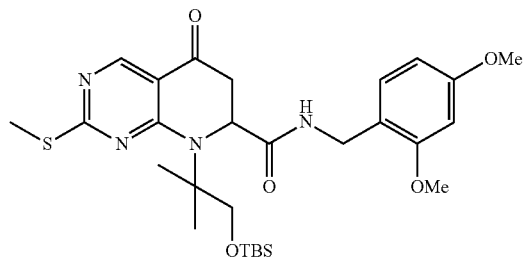 [SMILES: COc1ccc(CNC(=O)C2CC(=O)c3cnc(SC)nc3N2C(C)(C)CO[Si](C)(C)C(C)(C)C)c(OC)c1]

8-(2-{[tert-Butyl(dimethyl)silyl]oxy}-1,1-dimethylethyl)-N-(2,4-dimethoxybenzyl)-2-(methylthio)-5-oxo-5,6,7,8-tetrahydropyrido[2,3-d]pyrimidine-7-carboxamide Coupling reaction of 8-(2-{[tert-butyl(dimethyl)silyl]oxy}-1,1-dimethylethyl)-2-(methylthio)-5-oxo-5,6,7,8-tetrahydropyrido[2,3-d]pyrimidine-7-carboxylic acid using General Procedure E afforded the desired product in 86% yield as a viscous yellow oil. NMR (CDCl$_3$) δ8.58 (s, 1H), 6.95 (m, 1H), 6.80 (m, 1H), 6.37 (m, 2H), 4.71 (m, 1H), 4.27 (m, 2H), 4.13 (m, 1H), 3.84 (m, 1H), 3.79 (s, 3H), 3.70 (s, 3H), 3.15 (m, 1H), 2.77 (m, 1H), 2.56 (s, 3H), 1.64 (s, 3H), 1.58 (s, 3H), 0.85 (s, 9H), 0.02 (s, 3H), -0.03 (s, 3H); MS (ESI+) for C$_{28}$H$_{42}$N$_4$O$_5$SSi m/z 575.4 (M+H)$^+$.

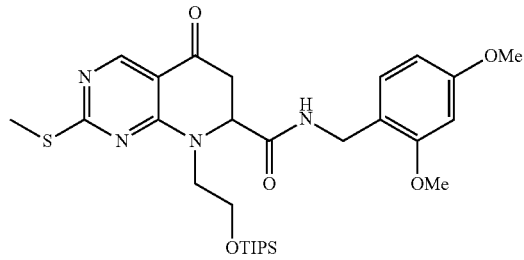

N-(2,4-Dimethoxybenzyl)-2-(methylthio)-5-oxo-8-{2-[(triisopropylsilyl)oxy]ethyl}-5,6,7,8-tetrahydropyrido[2,3-d]pyrimidine-7-carboxamide Coupling reaction of 2-(methylthio)-5-oxo-8-{2-[(triisopropylsilyl)oxy]ethyl}-5,6,7,8-tetrahydropyrido[2,3-d]pyrimidine-7-carboxylic acid using General Procedure E afforded the desired product in 57% yield as a dark yellow solid. NMR (CDCl$_3$) δ8.59 (s, 1H), 7.06 (m, 1H), 6.39 (m, 3H), 4.51 (m, 2H), 4.32 (m, 2H), 3.93 (m, 2H), 3.81 (s, 3H), 3.73 (s, 3H), 3.18 (m, 1H), 3.01 (m, 2H), 2.54 (s, 3H), 1.11-0.95 (m, 21H); MS (ESI+) for C$_{29}$H$_{44}$N$_4$O$_5$SSi m/z 589.4 (M+H)$^+$

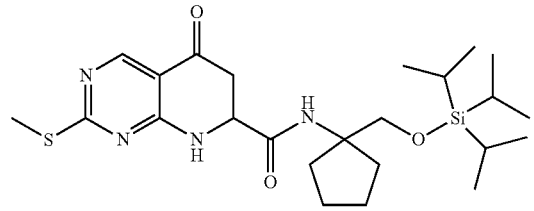 [SMILES: CSc1ncc2c(n1)NC(C(=O)NC1(CO[Si](C(C)C)(C(C)C)C(C)C)CCCC1)CC2=O]

2-(Methylthio)-5-oxo-N-(1-{[(triisopropylsilyl)oxy]methyl}cyclopentyl)-5,6,7,8-tetrahydropyrido[2,3-d]pyrimidine-7-carboxamide Coupling reaction of 2-(methylthio)-5-oxo-5,6,7,8-tetrahydropyrido[2,3-d]pyrimidine-7-carboxylic acid using General Procedure E afforded the desired product in 94% yield as a dark yellow oil. NMR (CDCl$_3$) δ8.64 (s, 1H), 6.09 (bs, 1H), 6.04 (bs, 1H), 4.25 (m, 1H), 3.68 (m, 2H), 2.86 (m, 2H), 2.54 (s, 3H), 2.07-1.54 (m, 8H), 1.33-0.96 (m, 21H); MS (ESI+) for C$_{24}$H$_{40}$N$_4$O$_3$SSi m/z 493.1 (M+H)$^+$.
General Procedure F.

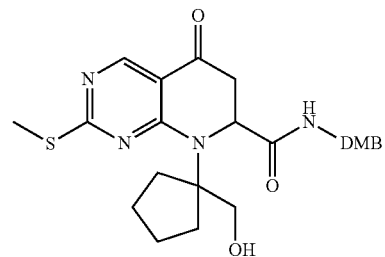

N-(2,4-Dimethoxybenzyl)-8-[1-(hydroxymethyl)cyclopentyl]-2-(methylthio)-5-oxo-5,6,7,8-tetrahydropyrido[2,3-d]pyrimidine-7-carboxamide N-(2,4-Dimethoxybenzyl)-2-(methylthio)-5-oxo-8-(1-{[(triisopropylsilyl)oxy]methyl}cyclopentyl)-5,6,7,8-tetrahydropyrido[2,3-d]pyrimidine-7-carboxamide (2.39 g, 3.72 mmol) was taken up in tetrahydrofuran (42 mL) at room temperature. Tetra-n-butylammonium fluoride (5.6 mL, 5.6 mmol, 1M solution in THF) was added and the reaction stirred for 10 minutes at room temperature. The reaction mixture was concentrated in vacuo to an orange oil and was transferred to a separatory funnel and partitioned between ethyl acetate (200 mL) and water (50 mL). The aqueous layer was removed and the organic layer washed with water (50 mL) and brine (50 mL). The organic layer was dried over sodium sulfate, filtered and the solvent removed in vacuo to afford a dark yellow semi-solid. The product was purified by reverse phase chromatography using a gradient from 1:9 to 3:2 acetonitrile:water (0.1% TFA). Lyophilization of the desired fractions afforded 1.81 g (99% yield) of the desired product as a dark yellow powder. NMR (CDCl$_3$) δ8.59 (s, 1H), 7.21 (m, 1H), 7.02 (m, 1H), 6.39 (m 2H), 4.56 (m, 1H), 4.29 (m, 2H), 3.79 (s, 3H), 3.75 (s, 3H), 3.70 (m, 2H), 3.41 (m, 1H), 3.20 (m, 1H), 2.87 (m, 1H), 2.55 (s, 3H), 2.18 (m, 1H), 1.97-1.59 (m, 7H); MS (ESI+) for $C_{24}H_{30}N_4O_5S$ m/z 487.1 (M+H)$^+$.

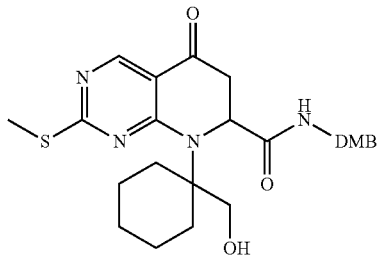

N-(2,4-Dimethoxybenzyl)-8-[1-(hydroxymethyl)cyclohexyl]-2-(methylthio)-5-oxo-5,6,7,8-tetrahydropyrido[2,3-d]pyrimidine-7-carboxamide Desilylation of N-(2,4-dimethoxybenzyl)-2-(methylthio)-5-oxo-8-(1-{[(triisopropylsilyl)oxy]methyl}cyclohexyl)-5,6,7,8-tetrahydropyrido[2,3-d]pyrimidine-7-carboxamide using General Procedure F afforded the desired product in 97% yield as a yellow powder. NMR (CDCl$_3$) δ8.69 (s, 1H), 7.58 (m, 1H), 7.07 (m, 1H), 6.48 (m, 2H), 4.72 (m, 2H), 4.38 (m, 2H), 3.89 (s, 3H), 3.87 (s, 3H), 3.31 (m, 1H), 2.99 (m, 1H), 2.81 (m, 1H), 2.64 (s, 3H), 2.11 (m, 3H), 1.94-1.58 (m, 7H); MS (ESI+) for $C_{25}H_{32}N_4O_5S$ m/z 501.1 (M+H)$^+$.

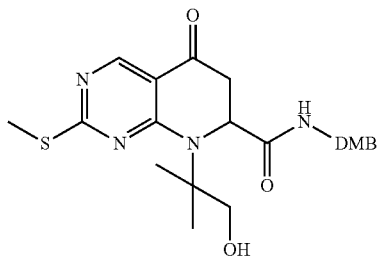

8-(2-Hydroxy-1,1-dimethylethyl)-N-(4-methoxybenzyl)-2-(methylthio)-5-oxo-5,6,7,8-tetrahydropyrido[2,3-d]pyrimidine-7-carboxamide Desilylation of 8-(2-{[tert-butyl(dimethyl)silyl]oxy}-1,1-dimethylethyl)-N-(2,4-dimethoxybenzyl)-2-(methylthio)-5-oxo-5,6,7,8-tetrahydropyrido[2,3-d]pyrimidine-7-carboxamide using General Procedure F afforded the desired product in 98% yield as a yellow powder. NMR (CDCl$_3$) δ8.61 (s, 1H), 7.51 (m, 1H), 7.01 (m, 1H), 6.37 (m, 2H), 4.72 (m, 1H), 4.65 (m, 1H), 4.26 (m, 2H), 3.80 (s, 3H), 3.76 (s, 3H), 3.63 (m, 1H), 3.18 (m, 1H), 2.80 (m, 1H), 2.57 (s, 3H), 1.58 (s, 3H), 1.56 (s, 3H); MS (ESI+) for $C_{22}H_{28}N_4O_5S$ m/z 461.4 (M+H)$^+$.

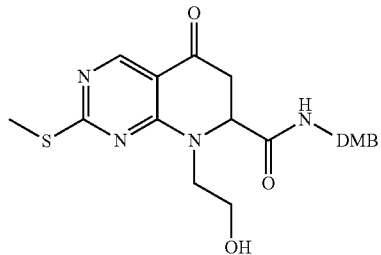

N-(2,4-Dimethoxybenzyl)-8-(2-hydroxyethyl)-2-(methylthio)-5-oxo-5,6,7,8-tetrahydropyrido[2,3-d]pyrimidine-7-carboxamide Desilylation of N-(2,4-dimethoxybenzyl)-2-(methylthio)-5-oxo-8-{2-[(triisopropylsilyl)oxy]ethyl}-5,6,7,8-tetrahydropyrido[2,3-d]pyrimidine-7-carboxamide using General Procedure F afforded the desired product in 97% yield as a pale yellow powder. NMR (CDCl$_3$) δ8.59 (s, 1H), 7.02 (m, 1H), 6.69 (m, 1H), 6.43 (m, 2H), 4.34 (m, 3H), 3.88 (m, 4H), 3.81 (s, 3H), 3.78 (s, 3H), 3.02 (m, 2H), 2.55 (s, 3H); MS (ESI+) for $C_{20}H_{24}N_4O_5S$ m/z 432.9 (M+H)$^+$

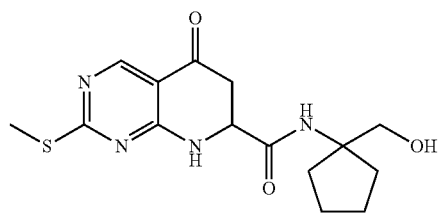 [SMILES: CSc1ncc2c(n1)NC(C(=O)NC1(CO)CCCC1)CC2=O]

N-[1-(Hydroxymethyl)cyclopentyl]-2-(methylthio)-5-oxo-5,6,7,8-tetrahydropyrido[2,3-d]pyrimidine-7-carboxamide Desilylation of 2-(methylthio)-5-oxo-N-(1-{[(triisopropylsilyl)oxy]methyl}cyclopentyl)-5,6,7,8-tetrahydropyrido[2,3-d]pyrimidine-7-carboxamide using General Procedure F afforded the desired product in 31% yield as an off white powder. NMR (CDCl$_3$) δ8.66 (s, 1H), 6.19 (bs, 1H), 5.97 (bs, 1H), 4.31 (m, 1H), 3.69 (s, 2H), 2.92 (m, 2H), 2.56 (s, 3H), 1.95-1.65 (m, 9H); MS (ESI+) for $C_{15}H_{20}N_4O_3S$ m/z 337.0 (M+H)$^+$.

General Procedure G.

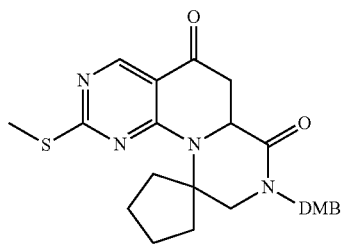

8'-(2,4-Dimethoxybenzyl)-2'-(methylthio)-6',6a',8',9'-tetrahydrospiro[cyclopentane-1,10'-pyrazino[1',2':1,6]pyrido[2,3-d]pyrimidine]-5',7'-dione N-(2,4-Dimethoxybenzyl)-8-[1-(hydroxymethyl)cyclopentyl]-2-(methylthio)-5-oxo-5,6,7,8-tetrahydropyrido[2,3- d]pyrimidine-7-carboxamide (1.81 g, 3.72 mmol) was taken up in methylene chloride (30 mL) at room temperature. Triethylamine (1.3 mL, 9.3 mmol) was added followed by the rapid addition of methanesulfonyl chloride (0.43 mL, 5.6 mmol). The reaction mixture was stirred at room temperature for 30 minutes before being heated at reflux overnight. The solvent was removed in vacuo affording a brown semi-solid. The product was purified by reverse phase chromatography using a gradient from 1:9 to 3:2 acetonitrile:water (0.1% TFA). Lyophilization of the desired fractions gave 764 mg (44% yield) of the desired product as a light brown powder. NMR (CDCl$_3$) δ8.49 (s, 1H), 7.13 (m, 1H), 6.43 (m, 2H), 5.49 (m, 1H), 4.37-4.16 (m, 4H), 3.81 (s, 3H), 3.80 (s, 3H), 3.29 (m, 1H), 2.95 (m, 1H), 2.82 (s, 3H), 2.41 (m, 1H), 1.99-1.52 (m, 7H); MS (ESI+) for C$_{24}$H$_{28}$N$_4$O$_4$S m/z 469.1 (M+H)$^+$.

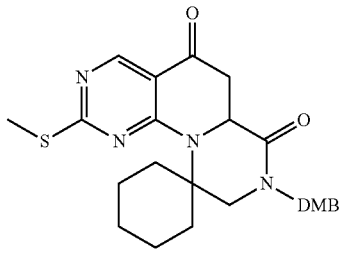

8'-(2,4-Dimethoxybenzyl)-2'-(methylthio)-6',6a',8', 9'-tetrahydrospiro[cyclohexane-1,10'-pyrazino[1',2': 1,6]pyrido [2,3-d]pyrimidine]-5',7'-dione Mesylation and cyclization of N-(2,4-dimethoxybenzyl)-8-[1-(hydroxymethyl)cyclohexyl]-2-(methylthio)-5-oxo-5, 6,7,8-tetrahydropyrido[2,3-d]pyrimidine-7-carboxamide using General Procedure G afforded the desired product in 73% yield as a white powder. NMR (MeOH-d$_4$) δ8.48 (s, 1H), 7.14 (m, 1H), 6.43 (m, 1H), 6.39 (m, 1H), 5.61 (m, 1H), 4.31 (m, 1H), 4.21 (m, 2H), 3.83 (s, 3H), 3.80 (s, 3H), 3.38 (m, 1H), 3.22 (m, 1H), 2.95 (m, 1H), 2.82 (s, 3H), 2.22 (m, 1H), 1.99-1.09 (m, 9H); MS (ESI+) for C$_{25}$H$_{30}$N$_4$O$_4$S m/z 483.1 (M+H)$^+$.

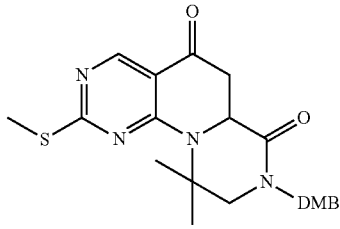

8-(2,4-Dimethoxybenzyl)-10,10-dimethyl-2-(methylthio)-6,6a,9,10-tetrahydro-5H-pyrazino[1',2':1,6] pyrido[2,3-d]pyrimidine-5,7(8H)-dione Mesylation and cyclization of 8-(2-Hydroxy-1,1-dimethylethyl)-N-(4-methoxybenzyl)-2-(methylthio)-5-oxo-5, 6,7,8-tetrahydropyrido[2,3-d]pyrimidine-7-carboxamide using General Procedure G afforded the desired product in 82% yield as a yellow powder. NMR (CDCl$_3$) δ8.45 (s, 1H), 7.14 (m, 1H), 6.40 (m, 2H), 5.56 (m, 1H), 4.40 (m, 1H), 4.31 (m, 2H), 4.13 (m, 1H), 3.81 (s, 3H), 3.79 (s, 3H), 3.28 (m, 1H), 2.88 (m, 1H), 2.79 (s, 3H), 1.80 (s, 3H), 1.45 (s, 3H); MS (ESI+) for C$_{22}$H$_{26}$N$_4$O$_4$S m/z 443.5 (M+H)$^+$.

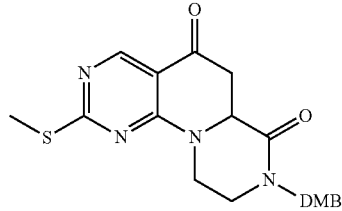

8-(2,4-Dimethoxybenzyl)-2-(methylthio)-6,6a,9,10-tetrahydro-5H-pyrazino[1',2':1,6]pyrido[2,3-d]pyrimidine-5,7(8H)-dione Mesylation and cyclization of N-(2,4-dimethoxybenzyl)-8-(2-hydroxyethyl)-2-(methylthio)-5-oxo-5,6,7,8-tetrahydropyrido[2,3-d]pyrimidine-7-carboxamide using General Procedure G afforded the desired product in 81% yield as a light brown powder. NMR (CDCl$_3$) δ8.52 (s, 1H), 7.11 (m, 1H), 6.44 (m, 2H), 5.31 (m, 1H), 4.68-4.29 (m, 5H), 4.04 (m, 1H), 3.81 (s, 3H), 3.80 (s, 3H), 3.20 (m, 1H), 3.01 (m, 1H), 2.82 (s, 3H); MS (ESI+) for C$_{20}$H$_{22}$N$_4$O$_4$S m/z 415.0 (M+H)$^+$.

General Procedure H.

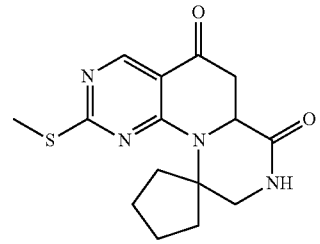 [SMILES: CSc1ncc2c(n1)N1C(CC2=O)C(=O)NCC12CCCC2]

2'-(Methylthio)-6',6a',8',9'-tetrahydrospiro[cyclopentane-1,10'-pyrazino[1',2':1,6]pyrido[2,3-d]pyrimidine]-5',7'-dione 8'-(2,4-Dimethoxybenzyl)-2'-(methylthio)-6',6a', 8',9'-tetrahydrospiro[cyclopentane-1,10'-pyrazino[1',2':1,6]pyrido [2,3-d]pyrimidine]-5',7'-dione (764 mg, 1.63 mmol) was taken up in trifluoroacetic acid (10 mL) at room temperature under argon. The mixture was heated to 75° C. for 6 hours, cooled to room temperature and left to stir overnight. The solvent was removed in vacuo to afford a purple oil. The product was purified by reverse phase chromatography using a gradient from 100% water (0.1% TFA) to 1:1 acetonitrile:water (0.1% TFA). Lyophilization of the desired fractions afforded 117 mg (23% yield) of the desired product as a pale yellow powder. NMR (CDCl$_3$) δ8.52 (s, 1H), 5.58 (m, 2H), 4.34 (bs 2H), 3.29 (m, 1H), 3.06 (m, 1H), 2.84 (s, 3H), 2.48 (m, 1H), 2.31 (m, 1H), 2.11-1.65 (m, 6H); MS (ESI+) for C$_{15}$H$_{18}$N$_4$O$_2$S m/z 319.0 (M+H)$^+$.

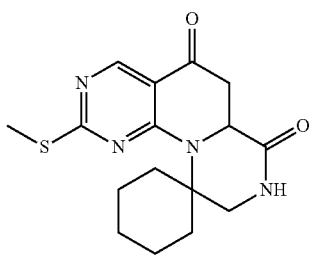 [SMILES: CSc1ncc2c(n1)N1C(CC2=O)C(=O)NCC12CCCCC2]

2'-(Methylthio)-6',6a',8',9'-tetrahydrospiro[cyclohexane-1,10'-pyrazino[1',2':1,6]pyrido[2,3-d]pyrimidine]-5',7'-dione Removal of the dimethoxybenzyl group of 8'-(2,4-Dimethoxybenzyl)-2'-(methylthio)-6',6a',8',9'-tetrahydrospiro[cyclohexane-1,10'-pyrazino[1',2':1,6]pyrido[2,3-d]pyrimidine]-5',7'-dione using General Procedure H afforded the desired product in 23% yield as a white powder. NMR (MeOH-d$_4$) δ8.60 (s, 1H), 4.78 (m, 1H), 4.54 (m, 2H), 3.38 (m, 1H), 2.86 (s, 3H), 2.84 (m, 1H), 2.12-1.30 (m, 10H); MS (ESI+) for $C_{16}H_{20}N_4O_2S$ m/z 333.1 (M+H)$^+$.

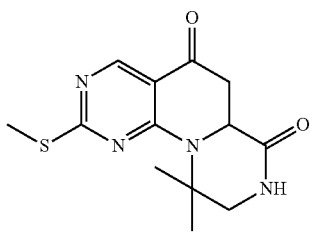 [SMILES: CSc1ncc2c(n1)N1C(CC2=O)C(=O)NCC1(C)C]

10,10-Dimethyl-2-(methylthio)-6,6a,9,10-tetrahydro-5H-pyrazino[1',2':1,6]pyrido[2,3-d]pyrimidine-5,7(8H)-dione Removal of the dimethoxybenzyl group of 8-(2,4-dimethoxybenzyl)-10,10-dimethyl-2-(methylthio)-6,6a,9,10-tetrahydro-5H-pyrazino[1',2':1,6]pyrido[2,3-d]pyrimidine-5,7(8H)-dione using General Procedure H afforded the desired product in 56% yield as a white powder. NMR (CDCl$_3$) δ8.54 (s, 1H), 5.65 (m, 1H), 5.51 (bs, 1H), 4.31 (s, 2H), 3.23 (m, 1H), 3.04 (m, 1H), 2.85 (s, 3H), 1.78 (s, 3H), 1.68 (s, 3H); MS (ESI+) for $C_{13}H_{16}N_4O_2S$ m/z 293.2 (M+H)$^+$.

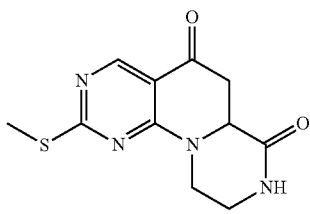 [SMILES: CSc1ncc2c(n1)N1CCNC(=O)C1CC2=O]

2-(Methylthio)-6,6a,9,10-tetrahydro-5H-pyrazino[1',2':1,6]pyrido[2,3-d]pyrimidine-5,7(8H)-dione Removal of the dimethoxybenzyl group of 8-(2,4-dimethoxybenzyl)-2-(methylthio)-6,6a,9,10-tetrahydro-5H-pyrazino[1',2':1,6]pyrido[2,3-d]pyrimidine-5,7(8H)-dione using General Procedure H afforded the desired product in 21% yield as a brown powder. NMR (MeOH-d$_4$) δ8.65 (s, 1H), 4.78-4.05 (m, 5H), 3.32 (m, 2H), 3.01 (m, 1H), 2.87 (s, 3H); MS (ESI+) for $C_{11}H_{12}N_4O_2$ m/z 265.0 (M+H)$^+$.

General Procedure I.

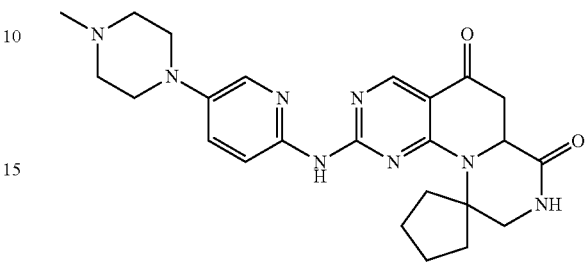

2'-{[5-(4-Methylpiperazin-1-yl)pyridin-2-yl]amino}-6',6a',8',9'-tetrahydrospiro [cyclopentane-1,10'-pyrazino[1',2':1,6]pyrido[2,3-d]pyrimidine]-5',7'-dione 2'-(Methylthio)-6',6a',8',9'-tetrahydrospiro[cyclopentane-1,10'-pyrazino[1',2':1,6]pyrido[2,3-d]pyrimidine]-5',7'-dione (117 mg, 0.367 mmol) was taken up in N,N-dimethylacetamide (4.0 mL, 43 mmol) at room temperature under argon. 5-(4-methylpiperazin-1-yl)pyridin-2-amine (100 mg, 0.55 mmol) was added and the reaction mixture was heated just to 150° C. and then immediately removed from the heat and cooled to room temperature. The product was purified by reverse phase chromatography using a gradient from 100% Water (0.1% TFA) to 1:1 acetonitrile:water (0.1% TFA). Lyophilization of the desired fractions afforded 11 mg (7% yield) of the desired product as an orange powder. NMR (MeOH-d$_4$) δ8.54 (s, 1H); 8.06 (m, 1H), 7.85 (m, 1H), 7.69 (m, 1H), 4.69 (m, 1H), 4.39 (m, 2H), 3.95 (m, 2H), 3.69 (m, 2H), 3.39-3.15 (m, 5H), 3.02 (s, 3H), 2.77 (m, 1H), 2.21 (m, 1H), 2.09-1.67 (m, 7H); MS (ESI+) for $C_{24}H_{30}N_8O_2$ m/z 463.1 (M+H)$^+$.

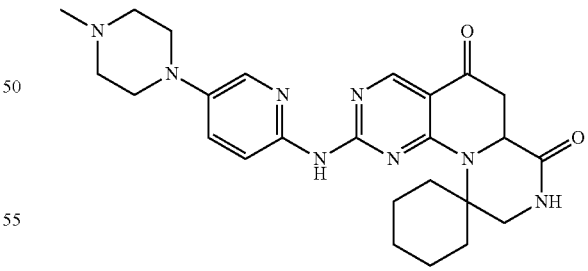

2'-{[5-(4-Methylpiperazin-1-yl)pyridin-2-yl]amino}-6',6a',8',9'-tetrahydrospiro[cyclohexane-1,10'-pyrazino[1',2':1,6]pyrido[2,3-d]pyrimidine]-5',7'-dione SNAr reaction using General Procedure I and 2'-(methylthio)-6',6a',8',9'-tetrahydrospiro[cyclohexane-1,10'- pyrazino[1',2':1,6]pyrido[2,3-d]pyrimidine]-5',7'-dione afforded the desired product in 38% yield as a yellow powder. NMR (MeOH-d$_4$) δ8.52 (s, 1H), 8.07 (m, 1H), 7.89 (bs, 1H), 7.71 (m, 1H), 4.71 (m, 1H), 4.40 (m, 2H), 3.94 (m, 2H), 3.68 (m, 2H), 3.35-3.22 (m, 5H), 3.02 (s, 3H), 2.73 (m, 1H), 2.02-1.25 (m, 10H); MS (ESI+) for C$_{25}$H$_{32}$N$_8$O$_2$ m/z 477.2 (M+H)$^+$.

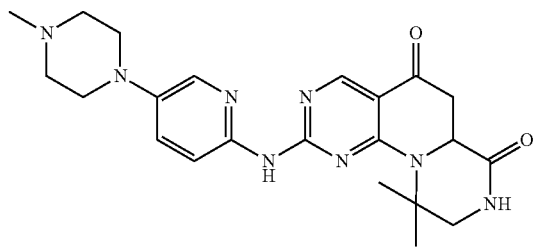 [SMILES: CN1CCN(c2ccc(Nc3ncc4c(n3)N3C(CC4=O)C(=O)NCC3(C)C)nc2)CC1]

10,10-Dimethyl-2-{[5-(4-methylpiperazin-1-yl)pyridin-2-yl]amino}-6,6a,9,10-tetrahydro-5H-pyrazino[1',2':1,6]pyrido[2,3-d]pyrimidine-5,7(8H)-dione SNAr reaction using General Procedure I and 10,10-dimethyl-2-(methylthio)-6,6a,9,10-tetrahydro-5H-pyrazino[1',2':1,6]pyrido[2,3-d]pyrimidine-5,7(8H)-dione afforded the desired product in 10% yield as a yellow powder. NMR (MeOH-d$_4$) δ8.52 (s, 1H), 8.05 (m, 2H), 7.86 (m, 1H), 7.67 (m, 1H), 4.66 (m, 1H), 4.33 (m, 2H), 3.93 (m, 2H), 3.68 (m, 2H), 3.38-3.21 (m, 5H), 3.01 (s, 3H), 2.72 (m, 1H), 1.65 (s, 3H), 1.54 (s, 3H); MS (ESI+) for C$_{22}$H$_{28}$N$_8$O$_2$ m/z 437.4 (M+H)$^+$.

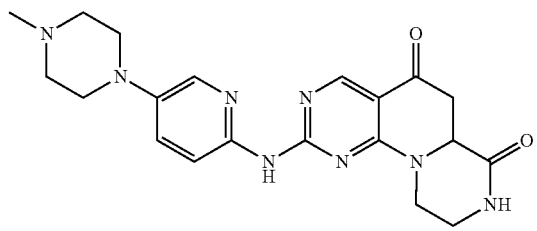 [SMILES: CN1CCN(c2ccc(Nc3ncc4c(n3)N3CCNC(=O)C3CC4=O)nc2)CC1]

2-{[5-(4-methylpiperazin-1-yl)pyridin-2-yl]amino}-6,6a,9,10-tetrahydro-5H-pyrazino[1',2':1,6]pyrido[2,3-d]pyrimidine-5,7(8H)-dione SNAr reaction using General Procedure I and 2-(methylthio)-6,6a,9,10-tetrahydro-5H-pyrazino[1',2':1,6]pyrido[2,3-d]pyrimidine-5,7(8H)-dione afforded the desired product in 15% yield as an orange powder. NMR (DMSO-d$_6$) δ8.41 (s, 1H), 8.05 (m,1H), 7.93 (m, 1H), 7.82 (m, 1H), 4.59-4.34 (m, 3H), 4.03-3.84 (m, 4H), 3.49 (m, 2H), 3.30-3.09 (m, 6H), 2.80 (s, 3H), 2.80-2.67 (m, 2H); MS (ESI+) for C$_{20}$H$_{24}$N$_8$O$_2$ m/z 409.1 (M+H)$^+$.

General Procedure J.

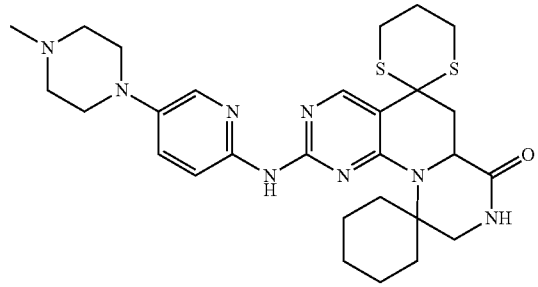 [SMILES: CN1CCN(c2ccc(Nc3ncc4c(n3)N3C(CC45SCCCS5)C(=O)NCC34CCCCC4)nc2)CC1]

2'-{[5-(4-Methylpiperazin-1-yl)pyridin-2-yl]amino}-6',6a',8',9'-tetrahydro-7'H-dispiro[cyclohexane-1,10'-pyrazino[1',2':1,6]pyrido[2,3-d]pyrimidine-5',2"-[1,3]dithian]-7'-one 2'-{[5-(4-Methylpiperazin-1-yl)pyridin-2-yl]amino}-6',6a',8',9'-tetrahydrospiro[cyclohexane-1,10'-pyrazino[1',2':1,6]pyrido[2,3-d]pyrimidine]-5',7'-dione (90.0 mg, 0.189 mmol) and 1,3-propanedithiol (0.0379 mL, 0.378 mmol) were taken up in toluene (5 mL) at room temperature under argon. p-Toluenesulfonic acid (0.02 g, 0.1 mmol) was then added. The reaction vessel was fitted with a condenser and the reaction mixture heated at reflux overnight. The reaction mixture was cooled to room temperature and the solvent removed in vacuo affording a thick dark yellow oil. The product was purified by reverse phase chromatography using a gradient from 100% water (0.1% TFA) to 3:2 acetonitrile:water (0.1% TFA). Lyophilization of the desired fractions afforded 35 mg (33% yield) of the desired product as a pale yellow powder. NMR (MeOH-d$_4$) δ8.52 (s, 1H), 7.90 (m, 1H), 7.84 (m, 1H), 7.52 (m, 1H), 4.64 (m, 1H), 4.53 (m, 1H), 4.16 (m, 1H), 3.60 (m, 2H), 3.41-3.26 (m, 6H), 3.01 (s, 3H), 2.91 (m, 1H), 2.75 (m, 1H), 2.61 (m, 1H), 2.21 (m, 1H), 2.11 (m, 1H), 1.95-1.72 (m, 10H), 1.61 (m, 1H), 1.33 (m 2H); MS (ESI+) for C$_{24}$H$_{38}$N$_8$OS$_2$ m/z 567.1 (M+H)$^+$.

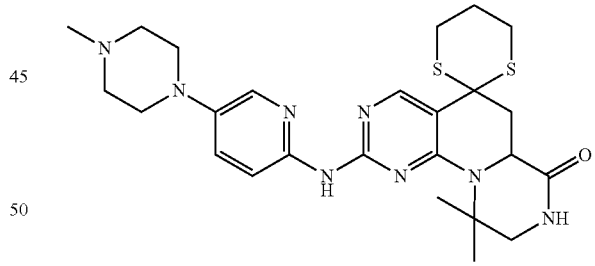

10',10'-Dimethyl-2'-{[5-(4-methylpiperazin-1-yl)pyridin-2-yl]amino}-6',6a',9',10'-tetrahydrospiro[1,3-dithiane-2,5'-pyrazino[1',2':1,6]pyrido[2,3-d]pyrimidin]-7'(8H)-one Dithiane formation using General Procedure J and 10,10-dimethyl-2-{[5-(4-methylpiperazin-1-yl)pyridin-2-yl]amino}-6,6a,9,10-tetrahydro-5H-pyrazino[1',2':1,6]pyrido[2,3-d]pyrimidine-5,7(8H)-dione afforded the desired product in 43% yield as an orange powder. NMR (MeOH-d$_4$) δ8.53 (s, 1H), 7.88 (m, 1H), 7.82 (m, 1H), 7.47 (m, 1H), 4.47 (m, 1H), 4.41 (m, 1H), 4.16 (m, 1H), 3.92-3.15 (m, 11H), 3.00 (s, 3H), 2.90-2.81 (m, 3H), 2.21 (m, 1H), 1.87

(m, 1H), 1.60 (s, 3H), 1.48 (s, 3H); MS (ESI+) for C$_{25}$H$_{34}$N$_8$OS$_2$ m/z 527.1 (M+H)$^+$.

General Procedure K.

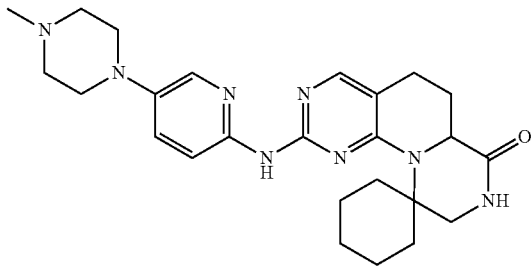 [SMILES: CN1CCN(c2ccc(Nc3ncc4c(n3)N3C(CC4)C(=O)NCC34CCCCC4)nc2)CC1]

2'-{[5-(4-Methylpiperazin-1-yl)pyridin-2-yl]amino}-6',6a',8',9'-tetrahydrospiro[cyclohexane-1,10'-pyrazino[1',2':1,6]pyrido[2,3-d]pyrimidin]-7'(5'H)-one 2'-{[5-(4-Methylpiperazin-1-yl)pyridin-2-yl]amino}-6',6a',8',9'-tetrahydro-7'H-dispiro[cyclohexane-1,10'-pyrazino[1',2':1,6]pyrido[2,3-d]pyrimidine-5',2"-[1,3]dithian]-7'-one (35 mg, 0.062 mmol) in ethanol (1 ml) was added to Raney nickel (1 mL of the aqueous slurry which was washed thrice with ethanol decanting off the ethanol after each washing) in ethanol (3 mL) under argon. The reaction mixture was heated to 45° C. for 30 minutes. After cooling to room temperature, the reaction mixture was filtered through a pad of Celite® washing with ethanol. The solvent was removed in vacuo affording a yellow oil. The product was purified by reverse phase chromatography using a gradient from 100% water (0.1% TFA) to 3:2 acetonitrile:water (0.1% TFA). Lyophilization of the desired fractions afforded 4 mg (14% yield) of the desired product as a pale yellow powder. NMR (CDCl$_3$) δ7.95 (m, 1H), 7.93 (s, 1H), 7.77 (m, 1H), 7.51 (m, 1H), 4.57 (m, 1H), 4.51 (m, 1H), 4.35 (m, 1H), 3.89 (m, 2H), 3.69 (m, 2H), 3.37 (m, 2H), 3.15 (m, 2H), 3.01 (s, 3H), 2.79 (m, 1H), 2.58 (m, 1H), 2.39 (m, 1H), 2.05-1.45 (m, 11H); MS (ESI+) for C$_{25}$H$_{34}$N$_8$O m/z 463.1 (M+H)$^+$.

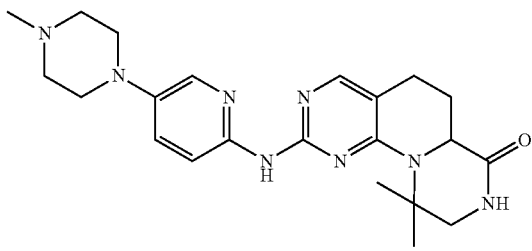 [SMILES: CN1CCN(c2ccc(Nc3ncc4c(n3)N3C(CC4)C(=O)NCC3(C)C)nc2)CC1]

10,10-Dimethyl-2-{[5-(4-methylpiperazin-1-yl)pyridin-2-yl]amino}-6,6a,9,10-tetrahydro-5H-pyrazino[1',2':1,6]pyrido[2,3-d]pyrimidin-7(8H)-one Desulfurization using General Procedure K and 10',10'-dimethyl-2'-{[5-(4-methylpiperazin-1-yl)pyridin-2-yl]amino}-6',6a',9',10'-tetrahydrospiro[1,3-dithiane-2,5'-pyrazino[1',2':1,6]pyrido[2,3-d]pyrimidin]-7'(8H)-one afforded the desired product in 11% yield as a yellow powder. NMR (MeOH-d$_4$) δ7.93 (m, 2H), 7.75 (m, 1H), 7.43 (m, 1H), 4.52 (m, 1H), 4.32 (m, 2H), 3.89 (m, 2H), 3.67 (m, 2H), 3.38 (m, 2H), 3.14 (m, 2H), 3.01 (s, 3H), 2.79 (m, 1H), 2.60 (m, 1H), 2.39 (m, 1H), 2.00 (m, 1H), 1.55 (s, 3H), 1.54 (s, 3H); MS (ESI+) for C$_{22}$H$_{30}$N$_8$O m/z 423.1 (M+H)$^+$.

General Procedure L.

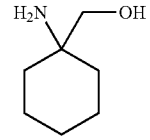

(1-Aminocyclohexyl)methanol

2M Lithium tetrahydroaluminate in tetrahydrofuran (80.0 mL, 160 mmol) was charged into a 500 mL 3-necked round bottomed flask (oven-dried and cooled under argon) fitted with a magnetic stir bar and the solution was cooled to 0° C. under argon. 1-Aminocyclohexanecarboxylic acid (7.64 g, 53.3 mmol) is added portionwise over a period of 1 hour. At the end of the addition, the reaction mixture was diluted with tetrahydrofuran (60 mL), slowly warmed to room temperature, and then heated at reflux for 18 hours. The mixture was cooled to room temperature. The reaction mixture was further diluted with tetrahydrofuran (160 mL) and then cooled to 0° C. Saturated aqueous sodium carbonate (100 ml) was added very slowly keeping the internal temperature below 15° C. After the addition of the carbonate solution is complete, the ice bath was left to expire and the mixture slowly warmed to room temperature overnight. The reaction mixture was filtered thru a pad of Celite® washing with ethyl acetate (400 mL). The solvent was removed in vacuo to afford a wet oil which was taken up in methylene chloride (300 mL) and dried over sodium sulfate. Filtration and concentration of the solvent in vacuo affords 6.89 g (99% yield) of the desired product as a clear colorless oil. NMR (CDCl$_3$) δ3.34 (s, 2H), 1.81 (bs, 3H), 1.51-1.32 (m, 10H); MS (ESI+) for C$_7$H$_{15}$NO m/z 130.0 (M+H)$^+$.

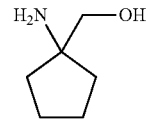

(1-Aminocyclopentyl)methanol

Using General Procedure L on commercially available cycloleucine affords the desired product in 99% yield as a pale yellow oil. NMR (CDCl$_3$) δ3.40 (s, 2H), 1.86-1.61 (m, 9H), 1.46-1.29 (m, 2H); MS (ESI+) for C$_6$H$_{13}$NO m/z 116.1 (M+H)$^+$.

General Procedure M.

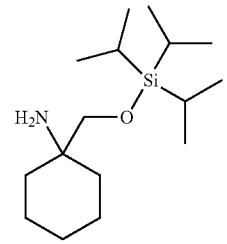 [SMILES: CC(C)[Si](OCC1(N)CCCCC1)(C(C)C)C(C)C]

1-{[(Triisopropylsilyl)oxy]methyl}cycohexanamine (1-Aminocyclohexyl)methanol (3.43 g, 26.5 mmol) was taken up in methylene chloride (80 mL) at room temperature under argon. Triethylamine (5.6 mL, 40 mmol) was added followed by the addition of triisopropylsilyl chloride (5.34 mL, 25.2 mmol). The reaction mixture was stirred at room temperature overnight during which time it became turbid. The reaction mixture was poured into a separatory funnel transferring with methylene chloride (100 mL). The organic layer was washed sequentially with water (40 mL×2) and brine (40 mL). The organic layer was dried over sodium sulfate, filtered and the solvent concentrated in vacuo to afford 6.68 g (93% yield) of the desired product as a clear pale yellow oil. NMR (CDCl$_3$) δ3.49 (s, 2H), 1.75-1.25 (m, 10H), 1.16-1.06 (m, 21H); MS (ESI+) for C$_{11}$H$_{27}$NOSi m/z 203.2 (M+H)$^+$.

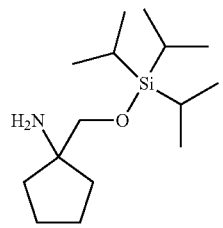 [SMILES: CC(C)[Si](OCC1(N)CCCC1)(C(C)C)C(C)C]

1-{[(Triisopropylsilyl)oxy]methyl}cyclopentanamine

Following General Procedure M and using (1-aminocyclopentyl)methanol the desired product was obtained in 85% yield as a clear dark yellow oil. NMR (CDCl$_3$) δ3.53 (s, 2H), 1.85-1.39 (m, 8H), 1.16-1.07 (m, 21H); MS (ESI+) for C$_{15}$H$_{33}$NOSi m/z 272.2 (M+H)$^+$.

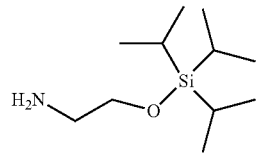

2-[(Triisopropylsilyl)oxy]ethanamine

Following General Procedure M and using commercially available ethanolamine the desired product was obtained in 99% yield as a clear pale yellow oil. NMR (CDCl$_3$) δ3.56 (t, 2H, J=6.0 Hz), 2.94 (t, 2H, J=6.0 Hz), 1.09-0.99 (m, 21H); MS (ESI+) for C$_{11}$H$_{27}$NOSi m/z 217.2 (M+H)$^+$.

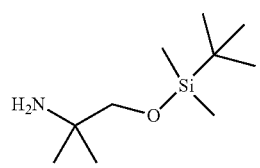

1-{[tert-Butyl(dimethyl)silyl]oxy}-2-methylpropan-2-amine

Following General Procedure M and using commercially available 2-amino-2-methyl-1-propanol and using tert-butyldimethylsilyl chloride the desired product was obtained in 95% yield as a clear colorless oil. NMR (CDCl$_3$) δ3.31 (s, 2H), 0.93 (s, 9H), 0.06 (s, 6H); MS (ESI+) for C$_{10}$H$_{25}$NOSi m/z 204.2 (M+H)$^+$.

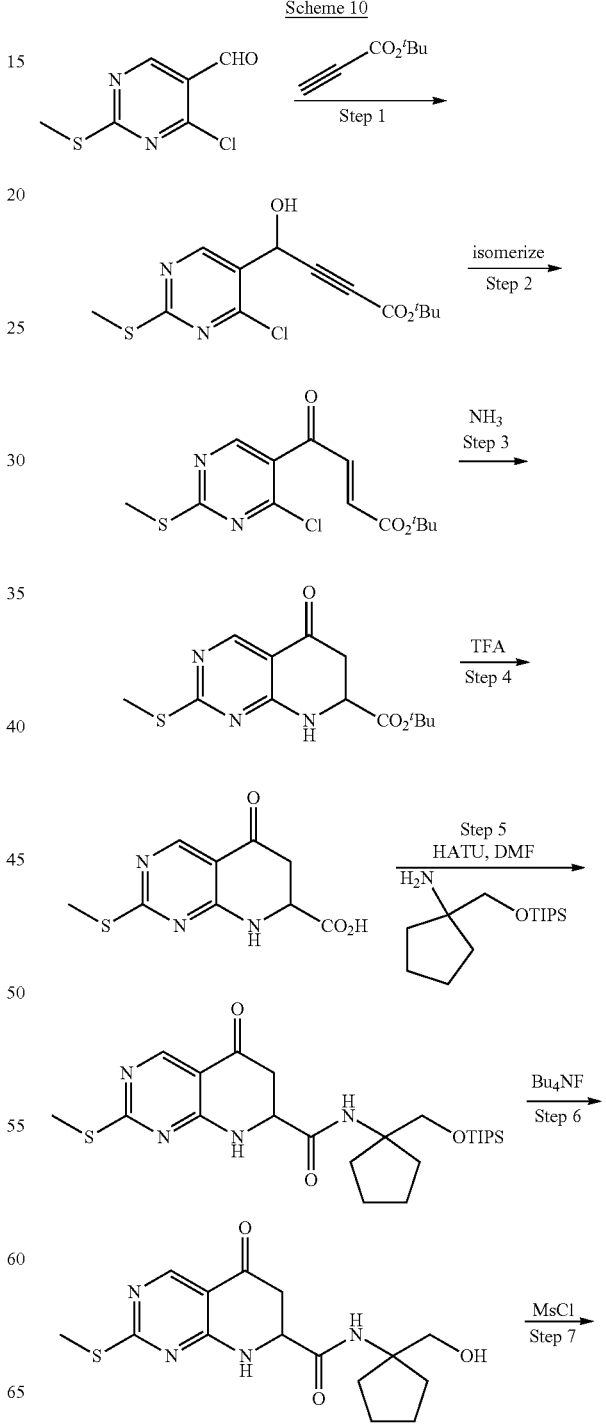

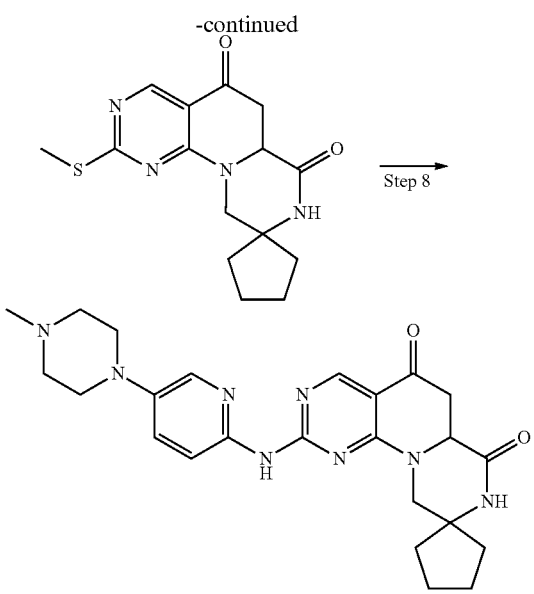

vent, for example, acetonitrile, to generate an alcohol. In step 7, a desired alcohol can be treated with a sulfonyl chloride to generate a desired mesylate according to methods known in the art. For example, an alcohol can be treated with a desired sulfonyl chloride, for example, methanesulfonyl chloride, to generate a mesylate. In one embodiment, an amine spontaneously reacts with said mesylate to generate a cyclic amide. In Step 8, a desired thiol can be treated with a desired amine and an organic solvent at an elevated temperature to generate a desired amine according to methods known in the art. For example, a thiol can be treated with an amine, for example, 5-(4-methylpiperazin-1-yl)pyridin-2-amine, and an organic solvent, for example, N,N-dimethylacetamide, at an elevated temperature of about 150° C. to generate an amine. The compound 5-(4-methylpiperazin-1-yl)pyridin-2-amine can be prepared as disclosed in U.S. Pat. No. 8,598,186 to Tavares and Strum.

As exemplified in Scheme 10, compounds of Formula VI can be synthesized beginning with the aldehyde illustrated above. In Step 1, an alkyne can be treated with an organic solvent, and a base optionally at a reduced temperature and subsequently treated with an aldehyde according to methods known in the art. For example, the aldehyde in Step 1 can be treated with a base, for example, isopropylmagnesium chloride lithium chloride complex in an organic solvent, for example, tetrahydrofuran at about −15° C. and next treated with an aldehyde to generate an alkyne. In Step 2, a desired alkynyl alcohol can be treated with a base in an organic solvent at an elevated temperature to isomerize the desired alkynyl alcohol to a desired alkene. For example, a desired alkynyl alcohol can be treated with a base, such as triethylamine in an organic solvent, for example, 1,4-dioxane at an elevated temperature of about 60° C. to generate an alkene. In Step 3, a desired alkene can be treated with ammonia and a mixture of organic solvents to form a tert-butyl 2-(methylthio)-5-oxo-5,6,7,8-tetrahydropyrido[2,3-d]pyrimidine-7-carboxylate according to methods known in the art. For example, an alkene can be treated with 0.5M ammonia and a mixture of organic solvents, for example, dioxane and acetonitrile to form a tert-butyl 2-(methylthio)-5-oxo-5,6,7,8-tetrahydropyrido[2,3-d]pyrimidine-7-carboxylate. In Step 4, a desired ester can be treated with a desired acid and an organic solvent to generate a desired carboxylic acid according to methods known in the art. For example, a desired ester can be treated with a desired acid, for example, trifluoroacetic acid, to generate a carboxylic acid. In one embodiment, the organic solvent is dichloromethane. In Step 5, a desired acid can be treated with a desired amine, an organic solvent and a coupling reagent to form a desired amide according to methods known in the art. For example, a desired acid can be treated with a desired amine, an organic solvent, for example, N,N-dimethylformamide, and a coupling reagent, for example, 1-[bis(dimethylamino)methylene]-1H-1,2,3-triazolo[4,5-b]pyridinium 3-oxid hexafluorophosphate, to generate an amide. In Step 6, a silyl protected alcohol can be treated with a fluoride reagent and an organic solvent according to methods known in the art to generate a desired alcohol. For example, a silyl protected alcohol can be treated with a fluoride reagent, for example, tetrabutylammonium fluoride, and an organic sol-

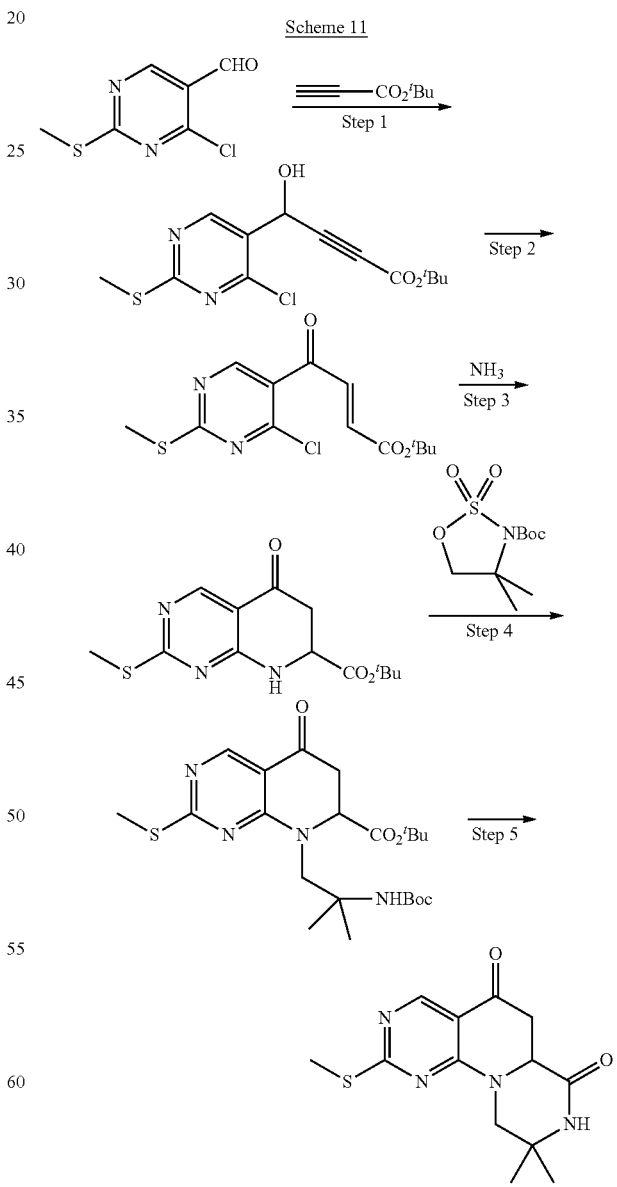

Scheme 11

As exemplified in Scheme 11, compounds of Formula VI can be synthesized beginning with the aldehyde illustrated above. In Step 1, an alkyne can be treated with an organic solvent, and a base optionally at a reduced temperature and subsequently treated with an aldehyde according to methods known in the art. For example, the aldehyde in Step 1 can be treated with a base, for example, isopropylmagnesium chloride lithium chloride complex in an organic solvent, for example, tetrahydrofuran at about −15° C. and next treated with an aldehyde to generate an alkyne. In Step 2, a desired alkynyl alcohol can be treated with a base in an organic solvent at an elevated temperature to isomerize the desired alkynyl alcohol to a desired alkene. For example, a desired alkynyl alcohol can be treated with a base, such as triethylamine in an organic solvent, for example, 1,4-dioxane at an elevated temperature of about 60° C. to generate an alkene. In Step 3, a desired alkene can be treated with ammonia and a mixture of organic solvents to form a tert-butyl 2-(methylthio)-5-oxo-5,6,7,8-tetrahydropyrido[2,3-d]pyrimidine-7-carboxylate according to methods known in the art. For example, an alkene can be treated with 0.5M ammonia and a mixture of organic solvents, for example, dioxane and acetonitrile to form a tert-butyl 2-(methylthio)-5-oxo-5,6,7,8-tetrahydropyrido[2,3-d]pyrimidine-7-carboxylate. In Step 4, an amine can be treated with a base, an organic solvent, and a cyclic sulfamidate to form an amine according to methods known in the art. For example, a desired amine can be treated with a base, for example, triethylamine, an organic solvent, for example, N,N-dimethylformamide, and a cyclic sufamidate to form an amine. In Step 5, a protected amine can be treated with an organic acid to form an amine that can subsequently form a cyclic amide according to methods known in the art. For example, a protected amine can be treated with an organic acid, for example, trifluoroacetic acid, and subsequently react with an ester to form a cyclic amide.

EXAMPLES

The patents WO 2013/148748 entitled "Lactam Kinase Inhibitors" to Tavares, F. X., WO 2013/163239 entitled "Synthesis of Lactams" to Tavares, F. X., and U.S. Pat. No. 8,598,186 entitled "CDK Inhibitors" to Tavares, F. X. and Strum, J. C. are incorporated by reference herein in their entirety.

Example 1

Synthesis of Compound 2 (Scheme 1)

Compound 2 is synthesized according to the method of A. Haidle et al., See, WO 2009/152027 entitled "5,7-dihydro-6H-pyrrolo[2,3-d]pyrimidin-6-one derivatives for MARK inhibition."

Example 2

Synthesis of Compound 3 (Scheme 1)

Step 1: A round-bottomed flask inerted with a nitrogen atmosphere is charged with Compound 2, ethanol, and lithium borohydride at ambient temperature. The reaction is stirred at ambient temperature and monitored by thin layer chromatography (TLC) or high-performance liquid chromatography (HPLC). Once Compound 2 can no longer be detected, the reaction is quenched with an aqueous acid such as aqueous hydrochloric acid, diluted with ethyl acetate and the layers separated. The organic layer is dried over anhydrous magnesium sulfate, filtered and concentrated in vacuo. The product, a primary alcohol, is purified by silica gel column chromatography eluting with a hexane-ethyl acetate gradient and used directly in the next step.

Step 2: A round-bottomed flask inerted with a nitrogen atmosphere is charged with the primary alcohol prepared in step 1, DMF and phosphorus tribromide. The reaction is stirred at ambient temperature and monitored by thin layer chromatography (TLC) or HPLC. Once the primary alcohol can no longer be detected, the reaction is quenched with brine and diluted with toluene. The layers are separated and the toluene layer is dried over anhydrous magnesium sulfate, filtered and concentrated in vacuo. The bromide is purified by silica gel column chromatography eluting with a hexane-ethyl acetate gradient.

Example 3

Synthesis of Compound 5 (Scheme 1)

A round-bottomed flask inerted with a nitrogen atmosphere is charged with tetrahydrofuran and the lactam 4, described below. The reaction is cooled to −78° C. and lithium diisopropylamide solution (2M in THF/heptane/ethyl benzene) is added dropwise. To the resulting enolate is added Compound 3, dropwise, and the reaction is allowed to warm to room temperature overnight. The reaction is diluted with saturated brine and the layers are separated. The organic layer is dried over anhydrous magnesium sulfate, filtered and concentrated in vacuo. The product is purified by silica gel column chromatography eluting with a dichloromethane-methanol gradient.

Example 4

Synthesis of Compound 6 (Scheme 1)

A round-bottomed flask is charged with Compound 5 and an aqueous acid, for example a pH=1 HCl solution. The reaction is allowed to stir at room temperature until starting material is no longer detected by thin layer chromatography or HPLC. The reaction is neutralized with solid $K_2CO_3$ and diluted with dichloromethane. The layers are separated, the organic layer dried over anhydrous magnesium sulfate, filtered and concentrated. Compound 6 is purified by silica gel column chromatography eluting with a dichloromethane-methanol gradient.

Example 5

Synthesis of Compound 7 (Scheme 1)

A round-bottomed flask inerted with a nitrogen atmosphere is charged with Compound 6, ethanol and DBU (10 eq). The reaction is monitored by thin layer chromatography or HPLC. Note: The reaction can be heated at reflux if necessary. Once Compound 6 is no longer detected, the reaction is concentrated in vacuo. The lactam 7 is purified by silica gel column chromatography eluting with a dichloromethane-methanol gradient.

Example 6

Synthesis of Compound 8 (Scheme 1)

A round-bottomed flask inerted with a nitrogen atmosphere is charged with Compound 7, meta-chloroperoxybenzoic acid, an organic solvent and stirred at ambient temperature. The reaction is monitored by thin layer chromatography or HPLC. Once Compound 7 is no longer detected, the reaction is concentrated in vacuo. Compound 8 is purified by silica gel column chromatography eluting with a dichloromethane-methanol gradient.

Example 7

Synthesis of Compound 10 (Scheme 1)

The tricyclic lactam 8 is combined with an amine (9, 0.9 eq) and an organic solvent such as tetrahydrofuran. A strong base such as lithium hexamethyldisilazane is added and the reaction is stirred until lactam 8 is no longer detected by either thin layer chromatography or HPLC. The reaction is concentrated in vacuo. The product is purified by silica gel column chromatography eluting with a dichloromethane-methanol gradient.

Alternatively, a CEM Discovery microwave vessel is charged with the tricyclic lactam 8, N-methyl-2-pyrrolidone (NMP), Hunig's base, and amine 9 (0.9 eq). The reaction is heated at 150° C. for 1-4 hours while being monitored by TLC. Once the tricyclic lactam 8 is no longer detected by TLC or HPLC, the reaction is concentrated in vacuo. The product is purified by silica gel column chromatography eluting with a dichloromethane-methanol gradient.

Example 8

Synthesis of Compound 11 (Scheme 2)

Compound 7 is treated with an oxidizing agent such as 2,3-dichloro-5,6-dicyano-1,4-benzoquinone (DDQ) in an organic solvent to generate the alkene intermediate 12.

Example 9

Synthesis of Compound 14 (Scheme 2)

The sulfone intermediate 12 is combined with an amine (13, 0.9 eq) in an organic solvent such as tetrahydrofuran. An organic base such as lithium hexamethyldisilazane is added and the reaction is stirred until sulfone intermediate 12 can no longer be detected by thin layer chromatography or HPLC. The product is purified by silica gel column chromatography eluting with a dichloromethane-methanol gradient.

Alternatively, a CEM Discovery microwave vessel is charged with the sulfone intermediate 12, N-methyl-2-pyrrolidone (NMP), Hunig's base, and amine 13 (0.9 eq). The reaction is heated at 150° C. for 1-4 hours while being monitored by TLC. Once the sulfone intermediate 12 is no longer detected by TLC or HPLC, the reaction is concentrated in vacuo. The product is purified by silica gel column chromatography eluting with a dichloromethane-methanol gradient.

Example 10

Synthesis of Compound 4

Step 1: Synthesis of Compound 15 (Scheme 3)
Compound 15 is synthesized according to the method of Arigon, J., See, US 2013/0289031, entitled "Pyrimidinone derivatives, preparation thereof and pharmaceutical use thereof."

Step 2: Synthesis of Compound 16 (Scheme 3)
A round-bottomed flask inerted with a nitrogen atmosphere is charged with Compound 15, dichloromethane and triethylamine (1.5 eq). The reaction is cooled to 0° C. and Boc anhydride (1.5 eq) is added. The reaction is allowed to stir at room temperature until Compound 15 is no longer detected by thin layer chromatography or HPLC. The reaction is concentrated in vacuo. The product is purified by silica gel column chromatography eluting with a hexane-ethyl acetate gradient.

Step 3: Synthesis of Compound 17 (Scheme 3)
A round-bottomed flask inerted with a nitrogen atmosphere is charged with Compound 16, acetonitrile and a base such as potassium carbonate. Methyl chloroacetate is added dropwise. The reaction is allowed to stir at room temperature until Compound 16 is no longer detected by thin layer chromatography or HPLC. The reaction is concentrated in vacuo. The product is purified by silica gel column chromatography eluting with a hexane-ethyl acetate gradient.

Step 4: Synthesis of Compound 18 (Scheme 3)
Compound 17 is dissolved in a solution comprising 3M HCl in methanol and the reaction is stirred at ambient temperature. Note: the reaction can be heated at a temperature of about 25° C. to about 60° C. to accelerate the reaction rate. Once the starting material is no longer detected by thin layer chromatography, the reaction is concentrated in vacuo. The product is purified by silica gel column chromatography using a dichloromethane-methanol gradient.

Step 5: Synthesis of Compound 19 (Scheme 3)
A round-bottomed flask inerted with a nitrogen atmosphere is charged with Compound 18, dichloromethane, and diisopropylethylamine (1.2 eq). Chloromethyl methyl ether (MOM-Cl, 1.2 eq) is added dropwise. The reaction is allowed to stir at room temperature and monitored by TLC. Once the starting material is no longer detected by thin layer chromatography, the reaction is quenched with saturated brine solution. The organic layer is separated, dried over anhydrous magnesium sulfate, filtered and concentrated in vacuo. The product is purified by silica gel column chromatography using a dichloromethane-methanol gradient.

Step 6: Synthesis of Compound 4
A round-bottomed flask inerted with a nitrogen atmosphere is charged with anhydrous tetrahydrofuran and Compound 19. The reaction is cooled to −78° C. Sodium bis(trimethylsilyl)amide (1M in THF, 1.1 eq) is added dropwise. Chloromethyl methyl ether (MOM-Cl, 1.2 eq) is added dropwise with stirring and the reaction is allowed to warm to room temperature overnight. The reaction is quenched with saturated brine solution and the layers are separated. The organic layer is dried over anhydrous magnesium sulfate, filtered and concentrated in vacuo. The product is purified by silica gel column chromatography using a dichloromethane-methanol gradient.

Example 11

Synthesis of Compound 25 (Scheme 5)

Compound 20 is commercially available. Compound 25 is synthesized according to the synthetic methodology disclosed in Example 10.

Example 12

Synthesis of Compound 31 (Scheme 6)

Compound 31 is synthesized according to the synthetic methodology disclosed in Example 10.

Example 13

Synthesis of Compound 33 (Scheme 7)

Step 1: Synthesis of Compound 32
Compound 32, 5-morpholinopyrid-2-amine, is synthesized according to Tavares, F. X. and Strum, J. C., See, U.S. Pat. No. 8,598,186, entitled "CDK Inhibitors".
Step 2: Synthesis of Compound 33
The sulfone intermediate 8 is diluted with a suitable solvent such as tetrahydrofuran and an organic base such as lithium hexamethyldisilazane is added. The amine 32 is added and the reaction is stirred until sulfone intermediate 8 can no longer be detected by thin layer chromatography or HPLC. The product is purified by silica gel column chromatography eluting with a dichloromethane-methanol gradient.

Alternatively, a CEM Discovery microwave vessel is charged with the sulfone intermediate 8, N-methyl-2-pyrrolidone (NMP), Hunig's base, and 5-morpholinopyrid-2-amine (0.9 eq). The reaction is heated at 150° C. for 1-4 hours while being monitored by TLC. Once the sulfone intermediate 8 is no longer detected by TLC or HPLC, the reaction is concentrated in vacuo. The product is purified by silica gel column chromatography eluting with a dichloromethane-methanol gradient.

Example 14

Synthesis of Compound 34 (Scheme 8)

Step 1: Synthesis of Compound 32
Compound 32, 5-morpholinopyrid-2-amine, is synthesized according to Tavares, F. X. and Strum, J. C., See, U.S. Pat. No. 8,598,186, entitled "CDK Inhibitors".
Step 2: Synthesis of Compound 34
The sulfone intermediate 12 is combined with a suitable solvent such as tetrahydrofuran and an organic base such as lithium hexamethyldisilazane. The amine 32 is added and the reaction is stirred until sulfone intermediate 12 can no longer be detected by thin layer chromatography or HPLC. The product is purified by silica gel column chromatography eluting with a dichloromethane-methanol gradient.

Alternatively, a CEM Discovery microwave vessel is charged with the sulfone intermediate 12, N-methyl-2-pyrrolidone (NMP), Hunig's base, and 5-morpholinopyrid-2-amine (0.9 eq). The reaction is heated at 150° C. for 1-4 hours while being monitored by TLC. Once the sulfone intermediate 12 is no longer detected by TLC or HPLC, the reaction is concentrated in vacuo. The product is purified by silica gel column chromatography eluting with a dichloromethane-methanol gradient.

Example 15

Preparation of a Formula V Compound

Step 1: Compound 7 is Boc protected according to the method of A. Sarkar et al. (JOC, 2011, 76, 7132-7140).
Step 2: Boc-protected Compound 7 is treated with 5 mol % $NiCl_2(Ph_3)_2$, 0.1 eq triphenylphosphine, 3 eq Mn, 0.1 eq tetraethylammonium iodide, in DMI under $CO_2$ (1 atm) at 25° C. for 20 hours to convert the methyl thiol derivative into the carboxylic acid.
Step 3: The carboxylic acid from Step 2 is converted to the corresponding acid chloride using standard conditions.
Step 4: The acid chloride from Step 3 is reacted with N-methyl piperazine to generate the corresponding amide.

Step 5: The amide from Step 4 is deprotected using trifluoroacetic acid in methylene chloride to generate the target compound. The product is purified by silica gel column chromatography eluting with a dichloromethane-methanol gradient.

Example 16

CDK4/6 Inhibition In Vitro Assay

Selected compounds disclosed herein were tested in CDK4/cyclinD1, CDK6/CycD3, CDK2/CycA, CDK2/cyclinE, CDK5/p25, CDK5/p35, CDK7/CycH/MAT1, and CDK9/CycT kinase assays by Nanosyn (Santa Clara, Calif.) to determine their inhibitory effect on these CDKs. The assays were performed using microfluidic kinase detection technology (Caliper Assay Platform). The compounds were tested in 12-point dose-response format in singlicate at Km for ATP. Phosphoacceptor substrate peptide concentration used was 1.25 µM for all assays (except µM 10 was used for the CKD7/CycH/MAT1 assay and Staurosporine was used as the reference compound for all assays. Specifics of each assay are as described below:

CDK2/CyclinA: Enzyme concentration: 0.2 nM; ATP concentration: 50 µM; Incubation time: 3 hr.
CDK2/CyclinE: Enzyme concentration: 0.2 nM; ATP concentration: 100 µM; Incubation time: 3 hr.
CDK4/CyclinD1: Enzyme concentration: 1 nM; ATP concentration: 200 µM; Incubation time: 3 hr.
CDK6/CyclinD3: Enzyme concentration: 10 nM; ATP concentration: 300 µM; Incubation time: 3 hr.
CDK5/p25: Enzyme concentration: 0.1 nM; ATP concentration: 20 µM; Incubation time: 3 hr.
CDK5/p35: Enzyme concentration: 0.07 nM; ATP concentration: 20 µM; Incubation time: 3 hr.
CDK7/CycH/MAT1: Enzyme concentration: 5 nM; ATP concentration: 50 µM; Incubation time: 3 hr.
CDK9/CycT: Enzyme concentration: 5 nM; ATP concentration: 10 µM; Incubation time: 17 hr.

TABLE 2

Inhibition of CDK kinases by Tricyclic Lactam Compounds

| Compound No. | Cdk2/ CycA | Cdk2/ CycE | Cdk4/ CycD1 | Cdk5/ p25 | Cdk5/ p35 | Cdk6/ CycD3 | Cdk7/ CycH/ MAT1 | Cdk9/ Cyc T |
|---|---|---|---|---|---|---|---|---|
| ZZZ | * | * | * | * | * | * | | * |
| YYY | * | * | *** | * | * | ** | | * |
| BBBB | ** | * | ** | * | * | ** | * | * |
| AAAA | * | * | * | * | * | * | * | * |
| CCCC | * | * | * | * | * | * | * | * |
| GGGG | * | * | ** | * | * | ** | * | * |

*>100 µM
**10 µM < X > 100 µM
***<10 µM

Example 17

G1 Arrest (Cellular G1 and S-phase) Assay

For determination of cellular fractions in various stages of the cell cycle following various treatments, HS68 cells (human skin fibroblast cell line (Rb-positive)) are stained with propidium iodide staining solution and run on Dako Cyan Flow Cytometer. The fraction of cells in G0-G1 DNA cell cycle versus the fraction in S-phase DNA cell cycle is determined using FlowJo 7.2.2 analysis.

Example 18

Inhibition of Cellular Proliferation

Cellular proliferation assays are conducted using the following cancer cell lines: MCF7 (breast adenocarcinoma—Rb-positive), ZR-75-1 (breast ductal carcinoma—Rb-positive), H69 (human small cell lung cancer—Rb-negative) cells, or A2058 (human metastatic melanoma cells—Rb-negative). These cells are seeded in Costar (Tewksbury, Mass.) 3093 96 well tissue culture treated white walled/clear bottom plates. Cells are treated with the compounds of Table 1 as nine point dose response dilution series from 10 uM to 1 nM. Cells are exposed to compounds and then cell viability is determined after either four (H69) or six (MCF7, ZR75-1, A2058) days as indicated using the Cell-Titer-Glo® luminescent cell viability assay (CTG; Promega, Madison, Wis., United States of America) following the manufacturer's recommendations. Plates are read on BioTek (Winooski, Vt.) Syngergy2 multi-mode plate reader. The Relative Light Units (RLU) are plotted as a result of variable molar concentration and data is analyzed using Graphpad (LaJolla, Calif.) Prism 5 statistical software to determine the $EC_{50}$ for each compound.

Example 19

Pharmacokinetic and Pharmacodynamic Properties of Tricyclic Lactam Compounds Tricyclic lactam compounds are dosed to mice at 30 mg/kg by oral gavage or 10 mg/kg by intravenous injection. Blood samples are taken at 0, 0.25, 0.5, 1.0, 2.0, 4.0, and 8.0 hours post dosing and the plasma concentration of compounds are determined by HPLC.

Example 20

Cellular Wash-Out Experiment

HS68 cells are seeded out at 40,000 cells/well in 60 mm dish on day 1 in DMEM containing 10% fetal bovine serum, 100 U/ml penicillin/streptomycin and 1x Glutamax (Invitrogen) as described (Brookes et al. EMBO J, 21(12)2936-2945 (2002) and Ruas et al. Mol Cell Biol, 27(12)4273-4282 (2007)). 24 hrs post seeding, cells are treated with a tricyclic lactam compound or DMSO vehicle alone at 300 nM final concentration of test compounds. On day 3, one set of treated cell samples are harvested in triplicate (0 Hour sample). Remaining cells are washed two times in PBS-CMF and returned to culture media lacking test compound. Sets of samples were harvested in triplicate at 24, 40, and 48 hours.

Alternatively, the same experiment is done using normal Renal Proximal Tubule Epithelial Cells (Rb-positive) obtained from American Type Culture Collection (ATCC, Manassas, Va.). Cells are grown in an incubator at 37° C. in a humidified atmosphere of 5% $CO_2$ in Renal Epithelial Cell Basal Media (ATCC) supplemented with Renal Epithelial Cell Growth Kit (ATCC) in a 37° C. humidified incubator.

Upon harvesting cells, samples are stained with propidium iodide staining solution and samples run on Dako Cyan Flow Cytometer. The fraction of cells in G0-G1 DNA cell cycle versus the fraction in S-phase DNA cell cycle is determined using FlowJo 7.2.2 analysis.

Example 21

Bone Marrow Proliferation as Evaluated Using EdU Incorporation and Flow Cytometry Analysis For hematopoietic stem cell and/or hematopoietic progenitor cell (HSPC) proliferation experiments, young adult female FVB/N mice are dosed with a single dose of compound by oral gavage. Mice are then sacrificed at 0, 12, 24, 36, or 48 hours following compound administration, and bone marrow is harvested, as previously described (Johnson et al. J. Clin. Invest. (2010) 120(7), 2528-2536). Four hours before the bone marrow is harvested, mice are treated with 100 μg of EdU by intraperitoneal injection (Invitrogen). Bone marrow mononuclear cells are harvested and immunophenotyped using previously described methods and percent EdU positive cells are then determined (Johnson et al. J. Clin. Invest. (2010) 120(7), 2528-2536). In brief, HSPCs are identified by expression of lineage markers (Lin-), Scal (S+), and c-Kit (K+).

Example 22

Metabolic Stability

The metabolic stability of tricyclic lactam compounds can be determined in human, dog, rat, monkey, and mouse liver microsomes. Human, mouse, and dog liver microsomes are purchased from Xenotech, and Sprague-Dawley rat liver microsomes are prepared by Absorption Systems. The reaction mixture comprising 0.5 mg/mL of liver microsomes, 100 mM of potassium phosphate, pH 7.4, 5 mM of magnesium chloride, and 1 uM of test compound is prepared. The test compound is added into the reaction mixture at a final concentration of 1 uM. An aliquot of the reaction mixture (without cofactor) is incubated in a shaking water bath at 37° C. for 3 minutes. The control compound, testosterone, is run simultaneously with the test compound in a separate reaction. The reaction is initiated by the addition of cofactor (NADPH), and the mixture is then incubated in a shaking water bath at 37° C. Aliquots (100 μL) are withdrawn at 0, 10, 20, 30, and 60 minutes for the test compound and 0, 10, 30, and 60 minutes for testosterone. Test compound samples are immediately combined with 100 μL of ice-cold acetonitrile containing internal standard to terminate the reaction. Testosterone samples are immediately combined with 800 μL of ice cold 50/50 acetonitrile/$dH_2O$ containing 0.1% formic acid and internal standard to terminate the reaction. The samples are assayed using a validated LC-MS/MS method. Test compound samples are analyzed using the Orbitrap high resolution mass spectrometer to quantify the disappearance of parent test compound and detect the appearance of metabolites. The peak area response ration (PARR) to internal standard is compared to the PARR at time 0 to determine the percent of test compound or positive control remaining at time-point. Half-lives are calculated using GraphPad software, fitting to a single-phase exponential decay equation. Half-life is calculated based on t1/2=0.693k, where k is the elimination rate constant based on the slope plot of natural logarithm percent remaining versus incubation time.

Example 23

Efficacy of Tricyclic Lactams in HER2-Driven Breast Tumors

A HER2-driven model (Rb-positive) of breast cancer (Muller W J, Sinn E, Pattengale P K, Wallace R, Leder P. Single-step induction of mammary adenocarcinoma in transgenic mice bearing the activated c-neu oncogene. Cell 1988; 54: 105-15), that expresses c-neu (the mouse ortholog of human HER2) driven by the MMTV promoter is used in the following example. This model is chosen because previous studies in murine (Yu Q, Geng Y, Sicinski P. Specific protection against breast cancers by cyclin D1 ablation. Nature 2001; 411: 1017-21; Landis M W, Pawlyk B S, Li T, Sicinski P, Hinds P W. Cyclin D1-dependent kinase activity in murine development and mammary tumorigenesis. Cancer Cell 2006; 9: 13-22; Reddy H K, Mettus R V, Rane S G, Grana X, Litvin J, Reddy E P. Cyclin-dependent kinase 4 expression is essential for neu-induced breast tumorigenesis. Cancer Res 2005; 65: 10174-8; Yu Q, Sicinska E, Geng Y, Ahnstrom M, Zagozdzon A, Kong Y, et al. Requirement for CDK4 kinase function in breast cancer. Cancer Cell 2006; 9: 23-32.) and human HER2-positive breast cancer (An H X, Beckmann M W, Reifenberger G, Bender H G, Niederacher D. Gene amplification and overexpression of CDK4 in sporadic breast carcinomas is associated with high tumor cell proliferation. Am J Pathol 1999; 154: 113-8; Samady L, Dennis J, Budhram-Mahadeo V, Latchman D S. Activation of CDK4 gene expression in human breast cancer cells by the Brn-3b POU family transcription factor. Cancer Biol Ther 2004; 3: 317-23; Takano Y, Takenaka H, Kato Y, Masuda M, Mikami T, Saegusa M, et al. Cyclin D1 overexpression in invasive breast cancers: correlation with cyclin-dependent kinase 4 and oestrogen receptor overexpression, and lack of correlation with mitotic activity. J Cancer Res Clin Oncol 1999; 125: 505-12) suggest that these tumors require CDK4/6 and CCND1 for progression and maintenance.

MMTV-neu mice are generated and observed post-lactation, with tumors observed with a median latency of approximately 25 weeks. Mice are enrolled in therapy studies when tumors reach a standard size (50-60 mm3) that permitted easy serial assessment. Tumor-bearing mice are continuously treated with a tricyclic lactam compound added to their chow (100 mg/kg/d or 150 mg/kg/d). MMTV-c-neu mice are examined weekly to assess tumor development by palpation. Tumor volumes are calculated by the formula, Volume=$[(width)^2 \times length]/2$. Tumor-bearing mice are euthanized at the indicated times due to predefined morbidity, tumor ulceration, or a tumor size of more than 1.5 cm in diameter.

Example 24

Efficacy of Tricyclic Lactams in HER2-Driven Breast Tumors

The in vivo efficacy of the tricyclic lactams is tested in the genetically engineered mouse model of luminal breast cancer. Tumors are serially assessed weekly using caliper measurements. Therapeutic intervention begins once tumors reach 40-64 $mm^3$. Tumor volume is calculated using the formula $((Width^2) \times Length)/2$. Compounds are administered orally via medicated diets (100 mg/kg/d). Medicated diets are administered for 28 consecutive days and then stopped. RECIST criteria are used to assess objective response rates.

Example 25

Cell Cycle Arrest by Tricyclic Lactams in CDK4/6-Dependent Cells

To test the ability of tricyclic lactams to induce a clean G1-arrest, a cell based screening method is used consisting of two CDK4/6-dependent cell lines (tHS68 and WM2664; Rb-positive) and one CDK4/6-independent (A2058; Rb-negative) cell line. Twenty-four hours after plating, each cell line is treated with a tricyclic lactam compound in a dose dependent manner for 24 hours. At the conclusion of the experiment, cells are harvested, fixed, and stained with propidium iodide (a DNA intercalator), which fluoresces strongly red (emission maximum 637 nm) when excited by 488 nm light. Samples are run on a Dako Cyan flow cytometer and >10,000 events are collected for each sample. Data are analyzed using FlowJo 2.2 software developed by TreeStar, Inc.

Example 26

Inhibition of RB Phosphorylation

The CDK4/6-cyclin D complex is essential for progression from G1 to the S-phase of the DNA cell cycle. This complex phosphorylates the retinoblastoma tumor suppressor protein (Rb). To demonstrate the impact of tricyclic lactams on Rb phosphorylation (pRb), compounds are exposed to three cell lines, two CDK4/6 dependent (tHS68, WM2664; Rb-positive) and one CDK4/6 independent (A2058; Rb-negative). Twenty four hours after seeding, cells are treated with a tricyclic lactam compound at 300 nM final concentration for 4, 8, 16, and 24 hours. Samples are lysed and protein is assayed by western blot analysis. Rb phosphorylation is measured at two sites targeted by the CDK4/6-cyclin D complex, Ser780 and Ser807/811 using species specific antibodies.

Example 27

Preparation of Drug Product

The active compounds of the present invention can be prepared for intravenous administration using the following procedure. The excipients hydroxypropyl-beta-cyclodextrin and dextrose can be added to 90% of the batch volume of USP Sterile Water for Injection or Irrigation with stirring; stir until dissolved. The active compound in the hydrochloride salt form is added and stirred until it is dissolved. The pH is adjusted with 1N NaOH to pH 4.3+0.1 and 1N HCl can be used to back titrate if necessary. USP sterile water for injection or irrigation can be used to bring the solution to the final batch weight. The pH is next re-checked to ensure that the pH is pH 4.3+0.1. If the pH is outside of the range add 1N HCl or 1N NaOH as appropriate to bring the pH to 4.3+0.1. The solution is next sterile filtered to fill 50 or 100 mL flint glass vials, stopper, and crimped.

This specification has been described with reference to embodiments of the invention. The invention has been described with reference to assorted embodiments, which are illustrated by the accompanying Examples. The invention can, however, be embodied in different forms and should not be construed as limited to the embodiments set forth herein. Given the teaching herein, one of ordinary skill in the art will be able to modify the invention for a desired purpose and such variations are considered within the scope of the invention.

We claim:

1. A method for treating retinoblastoma (Rb)-positive breast cancer in a host comprising administering an effective amount to a host in need thereof, of a compound selected from:

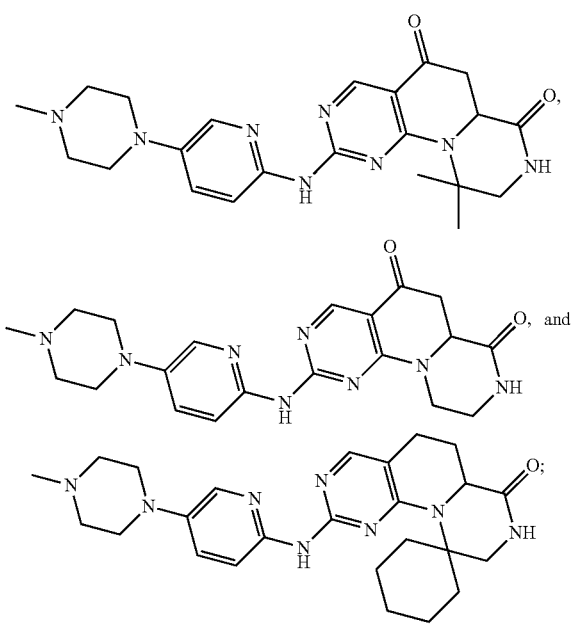

or a pharmaceutically acceptable salt thereof.

2. The method of claim 1, wherein the host is a human.

3. The method of claim 1, wherein the compound is administered in combination with another chemotherapeutic agent.

4. The method of claim 3, wherein the chemotherapeutic agent does not rely on cellular proliferation for its anti-cancer activity.

5. The method of claim 2, wherein the compound is

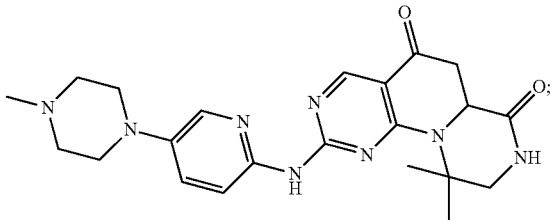 [SMILES: CN1CCN(c2ccc(Nc3ncc4c(n3)N3C(CC4=O)C(=O)NCC3(C)C)nc2)CC1]

or a pharmaceutically acceptable salt thereof.

6. The method of claim 5, wherein the compound is administered in combination with another chemotherapeutic agent.

7. The method of claim 2, wherein the compound is

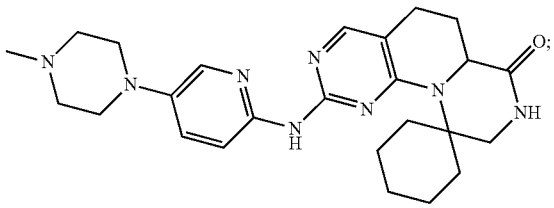 [SMILES: CN1CCN(c2ccc(Nc3ncc4c(n3)N3C(CC4)C(=O)NCC34CCCCC4)nc2)CC1]

or a pharmaceutically acceptable salt thereof.

8. The method of claim 7, wherein the compound is administered in combination with another chemotherapeutic agent.

9. The method of claim 2, wherein the compound is

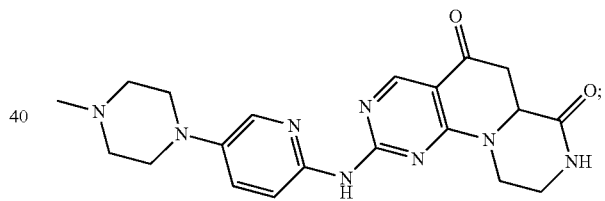

or a pharmaceutically acceptable salt thereof.

10. The method of claim 9, wherein the compound is administered in combination with another chemotherapeutic agent.

* * * * *